(12) United States Patent
De Haard et al.

(10) Patent No.: US 10,040,870 B2
(45) Date of Patent: Aug. 7, 2018

(54) HIGHLY DIVERSE COMBINATORIAL ANTIBODY LIBRARIES

(71) Applicant: argenx BVBA, Zwijnaarde (BE)

(72) Inventors: Johannes Joseph Wilhelmus De Haard, Breda (NL); Christophe Frederic Jerome Blanchetot, Breda (NL); Alex Klarenbeek, IJsselstein (NL); Ikbel Achour, Chicago, IL (US); Khalil El Mazouari, Vinderhoute (BE); Jurgen Del Favero, Tienen (BE)

(73) Assignee: argenx BVBA, Zwijnaarde (BE)

( * ) Notice: Subject to any disclaimer, the term of this patent is extended or adjusted under 35 U.S.C. 154(b) by 339 days.

(21) Appl. No.: 14/419,881

(22) PCT Filed: Sep. 2, 2013

(86) PCT No.: PCT/EP2013/068110
§ 371 (c)(1),
(2) Date: Feb. 5, 2015

(87) PCT Pub. No.: WO2014/033304
PCT Pub. Date: Mar. 6, 2014

(65) Prior Publication Data
US 2015/0166680 A1     Jun. 18, 2015

Related U.S. Application Data

(60) Provisional application No. 61/695,819, filed on Aug. 31, 2012.

(51) Int. Cl.
*C07K 16/00* (2006.01)
*C07K 16/46* (2006.01)

(52) U.S. Cl.
CPC .......... *C07K 16/461* (2013.01); *C07K 16/005* (2013.01); *C07K 2317/22* (2013.01); *C07K 2317/24* (2013.01)

(58) Field of Classification Search
None
See application file for complete search history.

(56) References Cited

U.S. PATENT DOCUMENTS

2011/0165621 A1    7/2011   Dreier et al.
2011/0300140 A1   12/2011   Dreier et al.

FOREIGN PATENT DOCUMENTS

JP        2010-195798 A    9/2010
WO     1999/020749 A1    4/1999
(Continued)

OTHER PUBLICATIONS

Glanville et al (2009) "Precise determination of the diversity of a combinatorial antibody library gives insight into the human immunoglobulin repertoire" Proc. Natl. Acad. Sci. 106(48):20216-20221.*

(Continued)

*Primary Examiner* — Karen S. Weiler
(74) *Attorney, Agent, or Firm* — Lathrop Gage LLP; James H. Velema, Esq.

(57) ABSTRACT

Disclosed is an immune library obtained from a Camelid species containing at antibody chains belonging to at least 7 human germline antibody chains. The presence of a large number of human germline antibody chain families in the library contributes to the usefulness of the library in producing antibodies to human target antigens. The antibodies produced from the library have low inherent immunogenicity.

4 Claims, 38 Drawing Sheets

| | Vk1 | Vk2 | Vk3 | Vk4 | Vk5 | Vk6 | V lambda 1 | V lambda 2 | V lambda 3 | V lambda 4 | V lambda 5 | V lambda 6 | V lambda 7 | V lambda 8 | V lambda 9 | V lambda 10 | no VL match | Total VHs | Percentage | Number clones | Colour code |
|---|---|---|---|---|---|---|---|---|---|---|---|---|---|---|---|---|---|---|---|---|---|
| Vh1 | 344 | 209 | 170 | 51 | 6 | 0 | 259 | 124 | 230 | 0 | 3 | 305 | 6 | 0 | 0 | 6 | 0 | 1713 | 33.7 | 0 | |
| Vh2 | 8 | 11 | 1 | 1 | 0 | 0 | 3 | 1 | 6 | 0 | 0 | 11 | 0 | 0 | 0 | 1 | 0 | 43 | 0.85 | 1-25 | |
| Vh3 | 547 | 192 | 180 | 92 | 11 | 0 | 289 | 285 | 357 | 0 | 3 | 601 | 3 | 1 | 1 | 2 | 1 | 2565 | 50.5 | 26-50 | |
| Vh4 | 30 | 13 | 6 | 1 | 0 | 0 | 1 | 1 | 3 | 0 | 0 | 4 | 0 | 0 | 0 | 0 | 0 | 59 | 0.1 | 51-100 | |
| Vh5 | 35 | 7 | 31 | 4 | 2 | 0 | 20 | 10 | 51 | 0 | 0 | 39 | 0 | 0 | 0 | 0 | 0 | 199 | 3.9 | 101-200 | |
| Vh6 | 57 | 64 | 32 | 23 | 6 | 2 | 40 | 7 | 6 | 0 | 1 | 21 | 0 | 0 | 0 | 1 | 0 | 260 | 5.1 | 201-300 | |
| Vh7 | 6 | 3 | 1 | 4 | 0 | 0 | 13 | 1 | 6 | 0 | 0 | 10 | 0 | 0 | 0 | 1 | 0 | 45 | 0.9 | 301-400 | |
| no VH match | 16 | 1 | 10 | 0 | 0 | 0 | 57 | 6 | 69 | 1 | 0 | 27 | 7 | 0 | 0 | 0 | 0 | 194 | 3.8 | 401-500 | |
| Total VLs | 1043 | 500 | 431 | 176 | 25 | 2 | 682 | 435 | 728 | 1 | 7 | 1018 | 16 | 1 | 1 | 11 | 1 | 5078 | | 501+ | |
| Percentage | 20.5 | 9.8 | 8.5 | 3.5 | 0.5 | <0.1 | 13 | 8.6 | 14 | <0.1 | 0.1 | 20 | 0.3 | <0.1 | <0.1 | 0.2 | <0.1 | | | | |

(56) References Cited

FOREIGN PATENT DOCUMENTS

WO     WO 2010001251 A2 *   1/2010    ............ C07K 16/00
WO     2011/080350 A1     7/2011

OTHER PUBLICATIONS

Mazor et al. 2010 "Selection of full-length IgGs by tandem display on filamentous phage particles and *Escherichia coli* fluorescence-activated cell sorting screening." FEBS Journal 277(10):2291-303.*

Haard et al., "A Large Non-Immunized Human Fab Fragment Phage Library That Permits Rapid Isolation and Kinetic Analysis of High Affinity Antibodies." Journal of Biological Chemistry. 1999, 274(26):18218-18230.

Schofield et al., "Application of Phage Display to High Throughput Antibody Generation and Characterization." Genome Biology. 2007, 8(11):R254.

International Search Report and Written Opinion received in PCT/EP2013/068110 dated Mar. 5, 2014.

* cited by examiner

| | Vκ1 | Vκ2 | Vκ3 | Vκ4 | Vκ5 | Vκ6 | V lambda 1 | V lambda 2 | V lambda 3 | V lambda 4 | V lambda 5 | V lambda 6 | V lambda 7 | V lambda 8 | V lambda 9 | V lambda 10 | no VL match | Total VHs | Percentage | Number clones | Colour code |
|---|---|---|---|---|---|---|---|---|---|---|---|---|---|---|---|---|---|---|---|---|---|
| Vh1 | 344 | 209 | 170 | 51 | 6 | 0 | 259 | 124 | 230 | 0 | 3 | 305 | 6 | 0 | 0 | 6 | 0 | 1713 | 33.7 | 0 | |
| Vh2 | 8 | 11 | 1 | 1 | 0 | 0 | 3 | 1 | 6 | 0 | 0 | 11 | 0 | 0 | 0 | 1 | 0 | 43 | 0.85 | 1-25 | |
| Vh3 | 547 | 192 | 180 | 92 | 11 | 0 | 289 | 285 | 357 | 0 | 3 | 601 | 3 | 1 | 1 | 2 | 1 | 2565 | 50.5 | 26-50 | |
| Vh4 | 30 | 13 | 6 | 1 | 0 | 0 | 1 | 1 | 3 | 0 | 0 | 4 | 0 | 0 | 0 | 0 | 0 | 59 | 0.1 | 51-100 | |
| Vh5 | 35 | 7 | 31 | 4 | 2 | 0 | 20 | 10 | 51 | 0 | 0 | 39 | 0 | 0 | 0 | 0 | 0 | 199 | 3.9 | 101-200 | |
| Vh6 | 57 | 64 | 32 | 23 | 6 | 2 | 40 | 7 | 6 | 0 | 1 | 21 | 0 | 0 | 0 | 1 | 0 | 260 | 5.1 | 201-300 | |
| Vh7 | 6 | 3 | 1 | 4 | 0 | 0 | 13 | 1 | 6 | 0 | 0 | 10 | 0 | 0 | 0 | 1 | 0 | 45 | 0.9 | 301-400 | |
| no VH match | 16 | 1 | 10 | 0 | 0 | 0 | 57 | 6 | 69 | 1 | 0 | 27 | 7 | 0 | 0 | 0 | 0 | 194 | 3.8 | 401-500 | |
| Total VLs | 1043 | 500 | 431 | 176 | 25 | 2 | 682 | 435 | 728 | 1 | 7 | 1018 | 16 | 1 | 1 | 11 | 1 | 5078 | | 501+ | |
| Percentage | 20.5 | 9.8 | 8.5 | 3.5 | 0.5 | <0.1 | 13 | 8.6 | 14 | <0.1 | 0.1 | 20 | 0.3 | <0.1 | <0.1 | 0.2 | <0.1 | | | | |

IGHV1 Family
Group1: CDR1-2 (1-2)

| | | FR Identity(%) | FR1 | CDR1 | FR2 | CDR2 | FR3 | CDR3 | SEQ ID NO: |
|---|---|---|---|---|---|---|---|---|---|
| Human | IGHV1-2*02 | Ref | QVQLVQSGAEVKKPGASVKVSCKASGYTFT | GYYMH | WVRQAPGQGLEWMG | WINPNSGGTNYAQKFQG | RVTMTRDTSISTAYMELSRLRSDDTAVYYC | AR | 70 |
| Lpacos | IGHV1-2 | 91.89 | .............LRN............. | S..ID | R............. | ..........K...... | .F..................V........ | .. | 71 |
| Lpacos | IGHV1-3*01 | 81.08 | .............LRN............. | S..ID | R............. | .................. | .F..................V........ | C.L.* | 72 |
| Lpacos | IGHV1-3*02 | 81.08 | .............LRN............. | S..ID | R............. | .................. | .F..................V........ | .C.C | 73 |
| Lpacos | IGHV1-3*03 | 82.43 | ..........P..LRN............. | S..ID | R............. | .................. | .L..................V........ | EG... | 74 |
| Lpacos | IGHV1-1*01 | 81.08 | ..........P..LRK....LL....... | S..ID | R............. | ..........K...... | .L..................V........ | .VCY | 75 |
| Lpacos | IGHV1-1*02 |  | AGPAGAARG*AEEAMGFAEGLLQGFWIHLH | QLLHA | ...........G.V | ................. | .L..................V........ | .CY. | 76 |
| Camel | IGHV1-1 |  | VQMVQPGLS*GSLGLQ*RSPARLPDTPSPA | TT*TG | CD.PL....W.V | RT...........E.K. | .L..M...........V...E...... | .CY. | 77 |
| Camel | IGHV1-2 |  | AGPAGAAR..LR.................. | R..ID | ...........W.V | RT...........E.K. | .L......................E... | .CY. | 78 |
| Lpacos | IGHV1-4 | 86.49 | ....LR.....A...Y...*.....A | S.NVH | .E......EE..S.. | *T.FK.A.SC.E..... | .L.K......TD.K.P.I.K.M.M.SR | .... | 79 |
| Camel | IGHV1-3 |  | ....LR.....A...Y...*.....A | S.NVH | .E......EE..S.. | *T.FK.A.S...E.... | .L.K......ID.KV.P.I.K.M.M.S. | .... | 80 |

IGHV3 VH3 Family
Group1: CDR1-2 (1-3)

| | | FR Identity(%) | FR1 | CDR1 | FR2 | CDR2 | FR3 | CDR3 | SEQ ID NO: |
|---|---|---|---|---|---|---|---|---|---|
| | | Group1a | | | | | | | |
| Human | IGHV3-23*04 | Ref | EVQLVESGGGLVQPGGSLRLSCAASGFTFS | SYAMS | WVRQAPGKGLEWVS | AISGSGGSTYYADSVKG | RFTISRDNSKNTLYLQMNSLRAEDTAVYYC | AK | 81 |
| Lpacos | IGHV3-1*01 | 94.59 | ............................. | .D... | ............... | ...W............. | .........A................KS.G. | .. | 82 |
| Lpacos | IGHV3-1*02 | 93.24 | ..V.......................... | .D... | ............... | ...W............. | .........A................KS.G. | .. | 83 |
| Lpacos | IGHV3-S17 | 86.49 | QL........................... | .D.G. | .........HS... | ...W.........E.M. | .........A.....V..........KP.G. | .. | 84 |
| | | Group1b | | | | | | | |
| Human | IGHV3-23*04 | Ref | EVQLVESGGGLVQPGGSLRLSCAASGFTFS | SYAMS | WVRQAPGKGLEWVS | AISGSGGSTYYADSVKG | RFTISRDNSKNTLYLQMNSLRAEDTAVYYC | AK | 81 |
| Lpacos | IGHV3-2*01 | 91.89 | Q.........................L.. | .Y... | ...........S.. | S..YSYSS......... | .........A................KP... | .T | 85 |
| Lpacos | IGHV3-2*02 | 90.54 | Q.........................L.. | .Y... | ...........S.. | S..YSYSS......... | .........A................KP...L. | .. | 86 |
| Lpacos | IGHV3-S4 | 89.19 | Q....V....D.................. | .S... | ...........S.. | S..YSYSS......... | .........A................KP.G. | .T | 87 |
| Lpacos | IGHV3-S11 | 93.24 | Q............................ | ..... | ...........S.. | S..YSYSS......... | .........A................KS.M. | .. | 88 |
| Lpacos | IGHV3-S12 | 91.89 | Q............................ | ..... | ...........S.. | S..YSYSS......... | .........A................KS.G. | .. | 89 |
| Lpacos | IGHV3-3 |  | ............................. | .S... | ........L..... | S..YSYSS......... | .........A................KP..V. | AA | 90 |
| Lpacos | IGHV3-S2 | 94.59 | ..R.......................... | .S... | ............... | S..YSYSS......... | .T.A......................KS... | .. | 91 |
| Lpacos | IGHV3-S3 | 89.19 | ............................. | ..... | R....V......... | S..YSYSS......... | .T.A......................KS.G. | .. | 92 |
| Lpacos | IGHV3-4*01 | 90.54 | Q............................ | ..... | ............... | S..YSYSS.....VE.L. | .TE.A.....................KS... | .. | 93 |
| Lpacos | IGHV3-4*02 |  | ............................. | .Y.D. | ............... | S..YSYSS......... | .TE.A.....................KS... | .. | 94 |
| | | Group1c | | | | | | | |
| Human | IGHV3-23*04 | Ref | EVQLVESGGGLVQPGGSLRLSCAASGFTFS | SYAMS | WVRQAPGKGLEWVS | AISGSGGSTYYADSVKG | RFTISRDNSKNTLYLQMNSLRAEDTAVYYC | AK | 81 |
| Lpacos | IGHV3-5 | 94.59 | ............................. | ..... | ..........P.. | .NSG.........S... | .........A................KP... | .. | 95 |
| Lpacos | IGHV3-S44 | 93.24 | ............................. | ..... | ............... | .N.GD........S... | .S.......A................KP.G. | .. | 96 |
| Lpacos | IGHV3-6*01 |  | Q...........F................ | .Y... | .........HS... | .NSG.........S.M. | .........A.....T..........KP... | VR | 97 |
| Lpacos | IGHV3-6*02 | 89.19 | Q............................ | ..... | .........HS... | .NSG.........S.M. | .........A................KP.G...* | .. | 98 |
| Lpacos | IGHV3-S27 | 86.49 | QL........................... | ..... | ............... | .NSG.........S.M. | .........A.....AR.........KP.G. | .. | 99 |
| Lpacos | IGHV3-S26 | 91.89 | Q.........................G.. | .W... | ............... | .NSG.........S... | .........A................KP.G. | .. | 100 |
| Lpacos | IGHV3-7*01 |  | RCSWWSL.EAWCRL................ | ..... | ........CHS... | .NSG.........S... | .........A.....V..........KP... | VR | 101 |
| Lpacos | IGHV3-7*02 |  | ..........................G.. | .VL.. | ........CHS... | .NSC.........S... | .........A.....V..........KP.G. | .. | 102 |
| Lpacos | IGHV3-8*01 | 87.84 | ..........................G.. | .VL.. | ............... | D.NSG.........*.. | .........A................KP.G. | .T | 103 |
| Lpacos | IGHV3-8*02 | 93.24 | Q............................ | .D... | ............... | D.NSG............ | .........A................KP.G. | .. | 104 |
| Lpacos | IGHV3-S40 | 94.59 | Q............................ | .N... | ............... | .NSG............. | .........A.....V..........KP... | .. | 105 |
| Lpacos | IGHV3-S25 | 90.54 | QL........................... | .D... | .........P.... | .NSG............. | .........A.....V..........KP.G. | .. | 106 |
| Lpacos | IGHV3-S33 | 91.89 | Q............................ | .D... | ............... | D.NSG............ | .........A................KP.G. | .. | 107 |
| Lpacos | IGHV3-S32 | 91.89 | Q............................ | ..... | .........P.... | .NSG............. | .........A................KP.G. | .. | 108 |
| Lpacos | IGHV3-S45 | 85.14 | .........A......KH........L.G | .D... | ............... | .NSG............. | .........A................KP.G. | .. | 109 |

IGHV4 Family

Group1: CDR1-2 (3-1)

| | | FR Identity(%) | FR1 | CDR1 | FR2 | CDR2 | FR3 | CDR3 | SEQ ID NO: |
|---|---|---|---|---|---|---|---|---|---|
| Human | IGHV4-30-4*01 | Ref | QVQLQESGPGLVKPSQTLSLTCTVSGGSIS | SGDYYWS | WIRQPPGKGLEWIG | YIYYSGSTYYNPSLKS | RVTISVDTSKNQFSLKLSSVTAADTAVYYC | AR | 138 |
| Lpacos | IGHV4-1*01 | 89.18 | ............................. | T TSY.A. | .............. | .M. V.A.D....S.. | .TS..R..................Q....PE. | .. | 139 |
| Lpacos | IGHV4-1*02 | 86.48 | .............D............... | T TSY.A. | .............. | .M. V.A.D....S.. | .TS..R..................Q...PEG. | .. | 140 |
| Lpacos | IGHV4-2 | 89.18 | ............................. | T TSY.. | .............. | .M. V.A.D....S.. | .TS..R..................Q....PE. | .. | 141 |
| Lpacos | IGHV4-3 | | ............................. | T TNY.. | .............. | .M. V.G.E....S.. | HTS..R..................Q....PE. | .. | 142 |
| Lpacos | IGHV4-4 | 87.83 | ............................. | T TSY.. | .............. | .M. A.A......S.. | .TS..R.......................... | .. | 143 |
| Lpacos | IGHV4-5 | 79.72 | E........G.L................. | .A.Y... | .............. | .M. A.A.D....S.. | .TS..R..................Q...PEG. | .. | 144 |
| Lpacos | IGHV4-6 | 81.08 | ........................M.... | .A...NT TSY.A. | .............. | .M. A.A.D....S.. | HTS..R..................Q...PEG. | .. | 145 |
| Lpacos | IGHV4-7 | 79.72 | E.R...A...................... | .A...NT TSY.A. | .............. | .M. A.A.D....S.. | HTS..R..................Q...PEG. | .. | 146 |
| Lpacos | IGHV4-8 | 81.08 | E.V........................... | .A.....NT TSY.A. | .............. | .M. A.A......S.. | .TS..R..................Q...PEG. | .. | 147 |
| Lpacos | IGHV4-9 | 79.72 | E............................. | T TSY.A. | .............. | .M. A.A......S.. | .TS..R..N...............Q...PEG. | .. | 148 |
| Camel | IGHV4-1 | 86.48 | ............................. | T TSY.G. | .............. | .M. A.A......S.. | .TS..R..N...............Q...PED. | .. | 149 |
| Lpacos | IGHV4-10 | | ...........M.S............... | T TSC.A. | .C............ | .M. A.AL.QN*LIILKVKHL | TNCLFYI*TKLDSKFSIDDNVSKHAICITD | -- | 150 |
| Camel | IGHV4-2 | | ............P................. | T TSYCA* | IX............ | .M. A.AL.QN*LIILKVKHL | TNCLFYI*TKLDSKFSIDDNVSKHAICITD | -- | 151 |
| Camel | IGHV4-3 | | ............P................. | T TSYCA* | .............. | | | | 151 |
| Lpacos | IGHV4-11 | | ............................. | T TSY.. | .............. | | | | 152 |

Group2: CDR1-2 (3-x)

| | | | FR1 | CDR1 | FR2 | CDR2 | FR3 | CDR3 | |
|---|---|---|---|---|---|---|---|---|---|
| Human | IGHV4-30-4*01 | Ref | QVQLQESGPGLVKPSQTLSLTCTVSGGSIS | SGDYYWS | WIRQPPGKGLEWIG | YIYYSGSTYYNPSLKS | RVTISVDTSKNQFSLKLSSVTAADTAVYYC | AR | 138 |
| Lpacos | IGHV4-12 | 82.43 | ..........................A...NT | TSY.A. | .............. | .M. A.-.......S.. | .TS..R..N...............Q...PEG. | -- | 153 |
| Lpacos | IGHV4-13 | 81.08 | E..........M.....L.D..T.R..... | TSC.A. | .............. | .M. A.-.......S.. | .TS..R..K...............Q...PEG. | -- | 154 |
| Lpacos | IGHV4-14*01 | 77.02 | ...................A.Y........T | TSC.A. | C.C......E.... | .MA A.-..........| HTS..R..K...............Q....PE. | -- | 155 |
| Lpacos | IGHV4-14*02 | 77.02 | ...................A.Y........T | TSC.A. | .C.......E.... | .MA A.-..........| HTS..R.M.K...............Q....PE. | -- | 156 |
| Lpacos | IGHV4-15 | 78.37 | ...............................T | TSC.A. | .H............ | *M. A.-.......S.. | HTS..R..K...............Q....PE. | -- | 157 |

IGHV5 Family
CDR1-2 (1-2)

| | | FR Identity(%) | FR1 | CDR1 | FR2 | CDR2 | FR3 | CDR3 | SEQ ID NO: |
|---|---|---|---|---|---|---|---|---|---|
| Human | IGHV5-51 | Ref | EVQLVQSGAEVKKPGESLKISCKGSGYSFT | SYWIG | WVRQMPGKGLEWMG | IIYPGDSDTRYSPSFQG | HVTISADSSSTAYLQWSLKASDAAMYC | VR | 158 |
| Camel | IGHV5-1 | 77.02 | Q...E.PV.L.M...A.R...T........ | ...... | .............. | ..............A. | I......K.T.........ST.SAV....AK | | 159 |
| Lpacos | IGHV5-1 | | Q.K.E.PA.L.R...T.R....T........ | ...... | .............. | ..............A. | .T...T.NPPALPTCGGAA*SPRTQPCITV | QR | 160 |

IGHV7 Family
CDR1-2 (1-2)

| | | FR Identity(%) | FR1 | CDR1 | FR2 | CDR2 | FR3 | CDR3 | SEQ ID NO: |
|---|---|---|---|---|---|---|---|---|---|
| Human | IGHV7-4 | Ref | QVQLVQSGSELKKPGASVKVSCKASGYTFT | SYAMN | WVRQAPGQGLEWMG | WINTNTGNPTYAQGFTG | RFVFSLDTSVSTAYLQICSLKAEDTAVYYC | AR | 161 |
| Camel | IGHV7-1 | | ......AA..RA................... | .CAEL | G.TGPWKGTGVYGMDQHRHWEANICPGLLGPMCLLHGHFHQYSLSADQQPEV*GHGHTLLCERQCX | | | | 162 |
| Lpacos | IGHV7-1 | | ......P.A..RA..............L.. | .CAEL | GATGPWKGTGVYGMDQHRHWEANICPGLLGPMCLLHGHFHQHSLSADQQPEV*GHGHVLLCERHSX | | | | 163 |

FIG. 10A

IGLV1 Family Functional

```
Group1:CDR1-2(13-7)
                          %identity(FR)   FR1                          CDR1              FR2                CDR2      FR3                                              CDR3            SEQ ID NO:
Human  IGLV1-47*02        Ref             QSVLTQPPSASGTPGQRVTISC       SGSSSNIGSNYVY     WYQQLPGTAPKLLIY    SNNQRPS   GVPDRFSGSKSGTSASLAISGLRSEDEADYYC                 AAWDDSLSG       164
Camel  IGLV1-1            81.15           .......M..SLR.S.....         T.......WG...N    ...H..........     D.SK.A.   ...E.....................QA...G.....             .S........      165
Lpacos IGV1l-1*01         85.50           .......V..S...KF....         T.......D...N     ...H..........     ..SN.A.   .........S.....T.T..QA..........                 SS........      166
Lpacos IGLV1-1*02         85.50           .......V..S...KF....         T.......D...N     ...H..........     ..SN.A.   .........S.....T.T..QA..........                 SS........      167
Llama  IGLV1-1            84.04           .......V..S...KF....         T.......G...N     ...H..........     G.SN.A.   ...E.....S.....T.T..QA..........                 ----------      168

Group2:CDR1-2(14-7)       %identity(FR)   FR1                          CDR1              FR2                CDR2      FR3                                              CDR3            SEQ ID NO:
Human  IGLV1-40*01        Ref             QSVLTQPPSVSGAPGQRVTISC       TGSSSNIGAGYDVH    WYQQLPGTAPKLLIY    GNSNRPS   GVPDRFSGSKSGTSASLAITGLQAEDEADYYC                 QSYDSSLSG       169
Camel  IGLV1-2            88.40           .......F..SL..I.....         ......G.S.Q       ..K.........I..    ....A..   .........S.....T...............C......           G.........      170
Lpacos IGLV1-2*01         89.85           .......L..S...K.....         ......G.S.Q       ...F.........P.    ....A..   .........S.....T...............                  EC.N......      171
Lpacos IGVl1-2*02         89.85           .......L..S...K.....         ......G.S.Q       ...F.........P.    ....A..   .........S.....T...............                  EC.N......      172
Llama  IGLV1-2            89.85           .......L..S...K.....         ......G.S.Q       ...F.........P.    ....A..   .........S.....T...............                  EC.N......      173

Group3: CDR1-2(14-7)
Human  IGLV1-40*01        Ref             QSVLTQPPSVSGAPGQRVTISC       TGSSSNIGAGYDVH    WYQQLPGTAPKLLIY    GNSNRPS   GVPDRFSGSKSGTSASLAITGLQAEDEADYYC                 QSYDSSLSG       169
Camel  IGLV1-3            86.95           .......M..SL...G....         ......G.G.Q       ..F............    .....A.   .........N..........T...F..D...                  GR.N......      174
Camel  IGLV1-4            85.50           .......T..S...T...T.         ......G..YLS      .................  NAH..A.   .........S..........T..........                  GC......A.      175
Lpacos IGLV1-3            84.05           ......LS.M.S...T....         ......G..YLS      ............V..    NAN..A.   .........T.SL.......T..........                  GC........T     176
Llama  IGLV1-3            84.05           ......LS.M.S...T....         ......G..YLS      .................  NAN..A.   .........T.SL.......T..........                  ----------      177

Group4: CDR1-2(14-7)
Human  IGLV1-40*01        Ref             QSVLTQPPSVSGAPGQRVTISC       TGSSSNIGAGYDVH    WYQQLPGTAPKLLIY    GNSNRPS   GVPDRFSGSKSGTSASLAITGLQAEDEADYYC                 QSYDSSLSG       169
Camel  IGLV1-5            86.95           .......F..SL..A.....         ......H.NY.N      ................    HVK..A.   ....P....N....S................                  ADW.N.....      178
Lpacos IGLV1-4*01         84.05           ...........SL.H.....         ......K.RS.NY.N   L..H.....C.R...    HVK..A.   ....P....SN...S................                  VDW.N.....      179
Lpacos IGLV1-4*02         84.05           ...........SL.H.....         ......K.RS.NY.N   L..H.....C.R...    HVK..A.   ....P....SN...S................                  VDW.N...S.      180
Llama  IGLV1-4            84.05           ...........SL.H.....         ......K.RS.NY.N   L..H.....C.R...    HVK..A.   ....P....SN...S................                  ----------      181

Group5: CDR1-2(14-7)
Human  IGLV1-40*01        Ref             QSVLTQPPSVSGAPGQRVTISC       TGSSSNIGAGYDVH    WYQQLPGTAPKLLIY    GNSNRPS   GVPDRFSGSKSGTSASLAITGLQAEDEADYYC                 QSYDSSLSG       169
Camel  IGLV1-6            86.95           P......S..S...A.....         ......R.NY.E      ..K...........     DVN..A.   .........N.V..T........K........                  EDWGN.N...      182
Lpacos IGLV1-5*01         86.95           -..PI..S..S.........         ......R.NY.S      ..K............    NVN..A.   .........N....T........Q........                  EDWEN.N...      183
Lpacos IGLV1-5*02         86.95           -..PI..S..S.........         ......R.NY.S      ..K............    NVN..A.   .........N....T........Q........                  EDWEN.N...      184
Llama  IGLV1-5            91.30           .......S............         ......H.NY.S      ..K............    NVN..A.   .........N....T.................                  ----------      185

Group6: CDR1-2(14-7)
Human  IGLV1-40*01        Ref             QSVLTQPPSVSGAPGQRVTISC       TGSSSNIGAGYDVH    WYQQLPGTAPKLLIY    GNSNRPS   GVPDRFSGSKSGTSASLAITGLQAEDEADYYC                 QSYDSSLSG       169
Lpacos IGLV1-6            86.95           ......S.M.S...T.....         ......R..SIQ      .LF.........C..    .....A.   .........S.....T................                  GC........      186
Llama  IGLV1-6            88.40           ......S.M.S.........         ......R..SIQ      .LF.........C..    .....A.   .........S.....T................                  ----------      187
```

FIG. 10B

Group7: CDR1-2(14-7)

```
Human  IGLV1-40*02  Ref    QSVVTQPPSVSGAPGQRVTISC TGSSNIGAGYDVH WYQQLPGTAPKLLIY GNSNRPS GVPDRFSGSKSGTSASLAITGLQAEDEADYC QSYDSSLSG  188
Camel  IGLV1-7      66.66  .T....E..L.VS..GT..LT. GL..GSVSSNYFG  .I..T..QV.RT... ST..S.. .I........I..NK.T.T...A.P........ ALYPGSYLD  189
```

IGLV1 Family Pseudogene (Stop condon or out of frame)

SEQ
                                                                                                                                         ID
                                                                                                                                         NO:

GroupPseudo-1
```
Llama   IGLV1-7    QSVPTQPPFVSGSPGQRVTLSC TGSSSNIGRGCYVR WFQQLPGTAPRLLIY DVNY*AS GGPD*VFGSKSATWSP*TSLGSSQRMRLLIITV   190
Lpacos  WGS IGLV1-7 KSVPTQLPFVYGSPGQRVTLSC TGSSSNIGRGCYVR WFQQLPGTAPRLLIY DVNY*AS GGPD*VFGSKSATWSP*TSLGSSQRMRLLIITV   191
Camel   IGLV1-8    PSVST*PPSVSGSSGQRVTMSC TGSSSNIGCGNYVH WFQQLPGTAPRLLIY DVNCRAS GVPDRFGSESSNTVSLNISGLQPEDEVDYYC     192
```

GroupPseudo-2
```
Llama   IGLV1-8    QSVLSQPPSMSGSPCGKVTVSC TGSAATILGVVIMCNGTNSSQEWPPNE*STMLTIEPWGSPTDSLAPSLAALPP*PSLGSRLETRLTITV   193
Llama   IGLV1-9    QSVLTQSPSMSGSPGQRVTISC TGSATILGVVIMCSGTNSSHEWPPNE*STMLTVMPQASPTDSLAPSLGTRPP*PSLGSRLRTRLTITV   194
Llama   IGLV1-10   QSVLTQPPSMSGSPGQKVTVSC TGSAKILGVVIMCNGTNSSQEWPPNF*STMLTIEPWGSRTVSLAPSLAALPP*PSLGSRLRTRLTITV   195
Llama   IGLV1-11   QPVLTQELAVWESLGDGHTISY SGNANKIKSCECLDVPQ*LPEMCPPLGISRVKNGASGVPHLFWGSKYSTPPP*GSVRSTLKKTLSITV     196
```

GroupPseudo-3
```
Camel   IGLV1-9        QSGLTQEASESGAVGQKITLSC T*NSNSVGANPMGWYQHSSRHTPKLMLRSSWPSGIPDRFLGSKSGNMASLAISDLQPEDEAEHYGSTLDSSTSG   197
Lpacos  WGS IGLV1-8    QSGLTQEASVSGAVGQKITLSC T*NSNNVGANPMGWYQHSSRHTPKLMLRSSWPSGIPDRFSGSKSGNMASLAISDFQPEDEAEHYGSTLDSSTSG   198
```

GroupPseudo-4
```
Camel   IGLV1-10       PAITQPEALLVFPGCVAQLSC MLSPRYATVGDYGVS WYQQRAGGSAPRYLIY YRSEEDYHRPDIPDRFSAATDKAHNACILITISPVQPEDEADYCSVG  199
Lpacos  WGS IGLV1-9    PAITQPEALLVFPGGVAQLSC MLSPRYATVGDYGVS WYQQRAGGSAPRYLIY YRSEEDYHRPDIPDRFSAATDKAHNACILITISPVQPEDEADYCSVG  200
```

GroupPseudo-5
```
Camel   IGLV1-11       QSVLTQRASVPECLGCTVTRFRTRSSSNFWGMSQTGSSVCQVPRVLTYKRNSQPLGVPAVFSGSTLGNPAFLAIAGLRAEDKTSRYCPLYDTTVEP    201
Lpacos  WGS IGLV1-10   QSVLTQLASVPGSLGYTVTRFCTRSSSNFRGMFQTGSSVCQVPSVLTYEKNSRPLGVPAGFSGSTLGNPASLTTAGLRAEDKTSRYCDTTVRPTPP    202
```

GroupPseudo-6
```
Camel   IGLV1-12       PSLC*LSRPLCLDPRARGSPTPAKDQQHTGSGYYVQNYQQLPGMAPKLLIYNANSRALGVPECFSGSKSGSSASLIITGLQAEDEADCYCGSYDSSLS   203
Camel   IGLV1-13    --SLC*LSRPLCLDPRARGSPTPAKDQQHIGSGYYVQNYQQLPGMAPKLLIYNANSRALGVPECFSGSKSGSSASLIITGLQAEDEADCYCGSYDSSLS   204
```

GroupPseudo-7
```
Lpacos  WGS IGLV1-11   SVLT*PPSVLDPRARGSPSPALEAAATLG*LSELVPTAPRIGPQITPDLW*QQ*RLRG-PEHFSGFKSGSSASLTTITGLQAEDEADYCSWDDRL      205
Llama   IGLV1-12       SLLTXPPSVLDPRARGSPSPALEAAATLGXLSELVPTAPRIGPQITPDLWXQQXRLRGPXALLMLQVWQLGLPDH-HWAPGXGXL--               206
```

GroupPseudo-8
```
Camel   IGLV1-14       ISLCRLSRPLCLDPRARRSPSALEAAATLGVVVMCAGSNSSQELLIYDVNYRASGGPD*FFDSKSGNTVSLIITGLQPEDEADNYCAVEMSSHLYAV   207
Camel   IGLV1-15       PGLC*LSRPLCWI-PEPEGHHILLHWKQQQHCG*LSELVPTAPRIAPKLLIYGNSNRDSGVPEHFSGFKSGSSASLIITGLQAEDEGDYCASWDDSL    208
```

FIG. 10C

IGLV2 Family Functional

FIG. 10D

Group8: CDR1-2 (14-7)

```
                              FR1                                 CDR1           FR2                    CDR2    FR3                                CDR3                    SEQ ID NO:
Human   IGLV2-18*02   QSALTQPPSVSGSPGQSVTISC TGTSSDVGSYNRVS WYQQPPGTAPKLMIY EVSNRPS GVPDRFGSKSGNTASLTISGLQAEDEADYC SSYTSSST                         228
Lpacos  IGLV2-8       .........L...T.*.T..... A......A.G.Y...L........L.. D.S.S..IT.................T....S....A.R.NN                                 233
Lpacos  IGLV2-9       .........L...T.*.T..... A......A.G.Y...V.R.......L...NK.A..IS..................V....SI....S.K..CS..A...T...                          234
Camel   IGLV2-7       ....................... A......G.Y...H..L......FL..Q.NK.A..IS..................I....SA......A.G.YN                                235
Llama   IGLV2-7       H..V.........TLGKT..... A.......YG.Y...L........L..A..Y.A..vI.................I....S....                                          236
```

Group9:

```
Human   IGLV2-18*02   QSALTQPPSVSGSPGQSVTISC TGTSSDVGSYNRVS WYQQPPGTAPKLMIY EVSNRPS GVPDRFGSKSGNTASLTISGLQAEDEADYC SSYTSSST                         228
Camel   IGLV2-8       ..................... ---SVS WYQQLPGMAPKLLIY AVSYRAS VIA.H......E..................SANK....A.vR.NN                                    237
Camel   IGLV2-9       --------------------- ------------- --------------- ------- R..S...Q......P...........VWDG.LS                                    238
Lpacos  IGLV2-10      --------------------- ------------- --------------- ------- .................V...WS.........A..R.GGP                          239
Lpacos  IGLV2-11      --------------------- ------------- --------------- ------- .TS.D...S.K.T.VP.LRS.D..........A..R.GP                           240
```

IGLV3 Family Functional

```
                                            FR1                         CDR1          FR2                      CDR2    FR3                                CDR3         SEQ ID NO:
Group1: CDR1-2 (11-7)   Identity(%)
Human   IGLV3-9*01     Ref      SYELTQPLSVSVALGQTARITC GGNNIGSKNVI WYQQKPGQAPVLVIY RDSNRPS GIPERFSGSNSGNTATLTISRAQAGDEADYYC QVWDSSTA                         241
Camel   IGLV3-1        91.30    .........SP......R..K...  .D.........S.. ...............A.NS.... ..........................G....E....     .......S.               242
Lpacos  IGLV3-1        91.30    .........TP......R..K...  .D........SAQ. ...............A..R.... ..........................G....E....     ........AN              243
Llama   IGLV3-1        88.40    .........SP......R.A.K..  .D..A..YAN.... ................K....... ..........................V.G...E....     .......H...AN           244
Lpacos  IGLV3-2        86.95    .........SP......R.A.K..  .D..A..YA..... ................K....... ..........................V.G...E....     .......QV...AN          245
Llama   IGLV3-1*01     88.40    .........SP......R.A.K..  .D..A..YAN.... ................K....... ..........................V.G...E....     -------                 246
Llama   IGLV3-1*02     86.95    .........TP......R..K...  .D......YA.... ................K....... ..........................V.G.R.E....     -------                 247
Llama   IGLV3-2        88.40    ........G.SP.....R..K...  .D........A... ...............E........ ..........................G..VE.....     -------                 248
Llama   IGLV3-3        86.95    .........TP......R..K...  .D...N.YAY.... ...................... ....G.....................V.G.L.E....     -------                 249
Lpacos  IGLV3-3        86.95    .........QA....D.Q....S.  S.DLLDK.YTQ... ................K.E..... ............S..K..........G....E....     HSA...DN                250
                                ** *** **** * *:* ***     *:* .*:*  ********* *:*******  *. *** *** ****** **:***  *. * ********

Group2: CDR1-2 (11-7)
Human   IGLV3-25*03    Ref      SYELTQPPSVSVSPGQTARITC SGDALPKQYAY WYQQKPGQAPVLVIY KDSERPS GIPRFSGSSSGTTVLTITISGVQAEDEADYYC QSADSSG                          251
Camel   IGLV3-2        88.40    .SA.......SA....L.........  Q.GN.GSS.VH ................ G.DS.... ............G.A....A........A......     .......Y...S            252
Lpacos  IGLV3-4        84.05    .SA.......SAL...L.........  Q.GNFGSS...F .......I.......G.DS.... ............G.A....A..Q......A......     .......GS..A            253
Camel   IGLV3-3        85.50    .SA.......ST....L.........  Q.GNFGSS...F .......M.......R..N..... ............D.A....A....N....A......     .......HAS...           254
Lpacos  IGLV3-5        85.50    .SA.......SA....L.........  Q.GNFGSY.GS .....S..........F....... ............D.A....A.........A......     .......L.YE...          255
Lpacos  IGLV3-6        86.95    .SA.......SA....L.........  Q.GN.GSY.GS ................GN.N.... ............G.A....A.........AP.....     .......YE...            256
Llama   IGLV3-4        82.60    .SA.......ST....L....G....  Q.GNIGSY...  ...........Q....GN.N.... .......W....A.S.A..A.........A......     -------                 257
Camel   IGLV3-4        86.95    .SA.......SA....L.E.......  Q.GNVGSN...S ................G.DS.... ............G.A....A.........A......     .......Y....            258
Llama   IGLV3-5        84.05    .SA.......SA....L.........  Q.GNFGSY.P.. ................R....... ...........RL.G.A..........A.T......     -------                 259
Llama   IGLV3-6        84.05    .SA.......SA....L.........  Q.GNFGGY.P.. ................QCNN.... ........S....TK.D.A........A........     -------                 260
```

FIG. 10E

Group3: CDR1-2 (11-7)

```
                                                                                                                                                                   SEQ ID NO:
Human  IGLV3-25*02   Ref     SYELTQPPSVSVSPGQTARITC SGDALPKQYAY WYQQKPGQAPVLVIY KDSERPS GIPERFSGSSSGTTVTLTISGVQAEDEADYYC QSADSSGTYP    261
Lpacos IGLV3-7       86.95   .SA....SA....L.....     Q.GS.GSY.GS  .R..........    GNNN..  ........D.A....A......            .GS..D-NA    262
Lpacos IGLV3-8       78.26   ASSV...SA....L.....S.   QFGS.GSY..H  .L......S...    N.NS..  ......R.D.A..V..S......           .VW....YNA   263
Camel  IGLV3-5       82.60   .SAV...ST....L.....S.   QFGS.GSY.SH  .L..........    N.NS..  ......R.D.A............           .VW....YNA   264
Camel  IGLV3-6       81.15   PSA....ST....L.....K..  Q.GS.RSY..H  ............    ...N..  ......R.G.A.........RT.           L......DYNA  265
Lpacos IGLV3-9       84.05   .SA....ST....L..M...    Q.GS.ESY..H  .........D..    R..N..  ......R.G.A..........I.           L......DYNA  266
Lpacos IGLV3-10      84.05   .SA....ST....L..M...    Q.GS.GSYD.H  ..........H     D.NS..  ......R.G.A............           .Y..A-NA     267
Lpacos IGLV3-11      82.60   .SA....SM....L.....T..  Q.GS.GSYG.N  .R..........    E..K..  ......K.GPA............           .VW....YNA   268
Llama  IGLV3-7       85.50   .SA....SA....L.....K..  Q.GS.GSS..H  ............    D.DS..  ........GRA............            ............  269
Lpacos IGLV3-12      81.15   .SA....SAL.TL..L.....   Q.GS.GSS..H  ............    D.DS..  ........GRA..........G.            ............-NA 270
Lpacos IGLV3-13      86.95   .SA....SA....L.....     Q.GS.GSS..H  ........M...    R....   ........G.A............            .D-NA        271
Llama  IGLV3-8       86.95   .SA....SA....L.....     Q.SS.GSS..H  ........M...    R....   ........G.A............                         272
```

Group4: CDR1-2 (11-7)

```
Human  IGLV3-25*02   Ref     SYELTQPPSVSVSPGQTARITC SGDALPKQYAY WYQQKPGQAPVLVIY KDSERPS GIPERFSGSSSGTTVTLTISGVQAEDEADYYC ..ADSSG  261
Llama  IGLV3-9       84.05   .SA....SA....L.....     R..S..ERYG.N ..........Q.    G.DI..  ......RL.G.A............                  273
Lpacos IGLV3-14      84.05   .SA....SA....L.....     R..S..ERYG.N ..........Q.    G.DI..  ......RL.G.A............      .S....    274
Lpacos IGLV3-10      86.95   .SA....SA....L..M...    Q..S..ESYG.N ..........P.   H G.DS..  ........G.A............                  275
Lpacos IGLV3-15      85.50   .SA....SA....L.....     Q..S..ESYG.N ..........P.    G.DS..  ........G.A..........G.                  276
Llama  IGLV3-11      81.15   .SA....SA....L..M...    Q..S.GSYG.N  .H........P.L.. G.NS..  ......K.G.A............      ..E...V   277
```

IGLV3 Pseudogene

```
                            FR1                              CDR1           FR2                    CDR2      FR3                                    CDR3      SEQ ID NO:
Human  IGLV3-25*01          SYELTQPPSVSVSPGQTARITC           SGDALPKQYAY    WYQQKPGQAPVLVIY        KDSERPS   GIPERFSGSSSGTTVTLTISGVQAEDEADYYC        QSADSS    278
Human  IGLV3-19*01          SSELTQDPAVSVALGQTVRITC           QGDSLRSYYAS    WYQQKPGQAPVLVIY        GKNNRPS   GIPDRFSGSSSGNTASLTITGAQAEDEADYYC        NSRDSS    279
Human  IGLV3-32*01          SSGPTQVPAVSVALGQMARITC           QGDSMEGSYEH    WYQQKPGQAPVLVIY        DSSDRPS   RIPERFSGSKSGNTTTLTITGAQAEDEADYYY        QLIDN-    280
Lpacos IGLV3-16             SSALTQPSAVSVSLGQTARITC           QGGSIESYAAH    WYQQKPGQFPVLVIY        GDDRRPS   GIPERFSGSSSGGTATLTISGPRPRTRPTITV        -TQQTA    281
Lpacos IGLV3-17             SYELTQSP*VSANPR*MAKFTC           GRDSIGNKYAY    WYQQKPGQAPVLVIY        RDSERSL   GSQTSIHAPTRGTWPP*PSAGPRPRTRLTIIV        SHDSS-    282
Lpacos IGLV3-18             SFELTQSP*VSVNPG*MAKLTC           GRNSIGNKYAY    WYQQKPGQAPVLVIY        RDSERSL   GSQTSTHAPTRGTWPP*PSAGPRPRTSLIITV        SHMTAV    283
Lpacos IGLV3-19             SYGLTQSPSVSVNPG*PAKLTC           GRDSIGNKYAY    WYQQKPGQAPVLVIY        RDSKRPL   GSQTSTHAPTRGTRPP*PSAGPWPRTRLTITV        SHMTA-    284
Camel  IGLV3-7               SYELT*SPSVSVNLGQMAKITC           GGDNIGSKSAP    WCCQKPGQAPVLVIC        GDNSRPS   GIPEWFSGSNSKNTATLTIISGAQAKDKANYYC        QVWDRS    285
Camel  IGLV3-8               KN*LSHPRCQ*IRDRWTAKIIC           VGDNIGSKSAY    WYQKKTGQATVLVIY        GDNNQAL   GIPD*FSGSNSGNTATLTISRAQAKGEADHYC        QVWDSS    286
Lpacos IGLV3-20             ------------------------        -----------    KPGQAPVLVMY            DDDSGHS   GIPEWFSGSHSGNTVLTNISAQVEDEADYYC        QSYD--    287
Lpacos IGLV3-21             ------------------------        -----------    SPAQAPVLVIY            DDNGHS    GIPEWFSGSHSGNTVLTNISAQVEDEAGYYS        QSYDSN    288
Lpacos IGLV3-22             ------------------------        -----------    KPGQAPVLVIY            DDNTGHS   GIPEWFSGSHSGNTVTLNISAQVEDEADYY-        -        289
Camel  IGLV3-9               ------------------------        -----------    KPGQAPVLVIY            DDNSGHS   GIPEWFSGSDSGYTVLTISRTQVEDEADYYC        QSYDSS    290

Lpacos IGLV3-23             SYELTQSPSVSVKLGQTAKITYGRKELEIIHMLTGTSRSRARPLCWSSTEIANGPQGSRAGSQAPTPGTRPP*PSAGPRPRTRPTTTVKCGTAA            291
Camel  IGLV3-10             SSALTQPSAVSVSLGQMARITCQGGSLGSSYAYWYQQKTG------ISKL*NR*TRLYCIA-------QGNIHKMF**LTEKKI*--                   292
S      IGLV3-24             S-------DSVTLGVGEPG--------IESQDHLMQGQH--WK*ICLLVPAQARSGPCSGHLQR*RTALGIPDQYGGSNSGNMATLITISGAEAE          293
Lpacos IGLV3-25             SSALTQPSMVSVSLGQTARITCQGGSLGSYGANWY----------                                                             294
```

FIG. 10F
IGLV4 Family

```
                                   FR1                   CDR1              FR2              CDR2           FR3                                      CDR3    SEQ ID NO:
Group1: CDR1-2 (12-11) Identity(%)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSN   295
Camel   IGVL4-1      69.57%   ...S.PP........T.A....  ....Y....SVD  .Y.V....S..F..R  VGT..VGS..D  .I....VLG..LN.....K.I.E....S..H. GADHGS   296
Lpacos  IGVL4-1      68.11%   ...S.PP...............  ....Y....SVD  .Y.V....S.WF..R  VGS..VGS..D  .I....VLG..LN.....K.I.E....S..H. GADHGS   297
Llama   IGVL4-1      75.36%   ...S.PP........A.A....  ....Y....SVD  .Y.V....S.WF..R  VGS..VGS...          .S..............Q.V.E........   298
Llama   IGVL4-2      69.57%   ...S.PP........A.A....  ....Y....SVD  .Y.V....S.WF..R  VGS..VGS...          .S..............LE...Q.V.EDE.E.V.   299

Group2: CDR1-2 (12-11) Identity(%)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Camel   IGVL4-2      73.91%   A......PP.......TA.R.P.  .G.E..THY.Q  .FR.RS.QT.SF..  VTSD.TVT..D  .L.G..........V..I..K.K.E....   GVNYKSD  300
Lpacos  IGVL4-2               A......PP.......TA....P.  ...E..THY.Q  .FR.RS.QT.*C..  VTSN.TVT..D  .L.G................V..SI.......*   301
Llama   IGVL4-3               A......PP.......TA....P.  ...E..THY.Q  .FR.RS.QT.*C..  GTSN.TVT..D  .L.G................V..SI.......   GVNYKSD  302

Group3: CDR1-2 (12-11)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Llama   IGVL4-4               E......P.G.......MA....P.  ...EH...YLQ .FR.RS.QT.*C..E  VTSN.TVT..D  .L.G................V..SI........   303
Llama   IGVL4-5               E......P.G.......MA....P.  ...EH...YLQ .FR.RS.T.*C..  VTSD.TVT..D  .L.GH..A...R.GC..V..I........   304
Lpacos  IGVL4-3               A......PP..S....TG....R.  ...EH..HY.Q  .F..RS.QT.*C..  VTSD.TVT..D  .L.SC................V..I........   GVNYKTD  305

Group4: CDR1-2 (12-11)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Llama   IGVL4-6               A......PP..S....TG....R.  ....E..THY.Q  .F..RSGQT....  VTSD.TVT..D  .L.SC................V..I........   306

Group5: CDR1-2 (12-11)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Lpacos  IGVL4-4               A......PP........TV....P.  ....E..THY.Q  LFR.RS.QTSYC..  VTSD.RVT..N  .L..VTSQAPAP.LVAT*PSPTSSPRTRLTNTV ESTIKVM 307
Lpacos  IGVL4-5               V......PP........TA....P.  ....E..THY.Q  WFR.RS.QTP*C..  VTNN.TVN..D  .S..VAS*APAP.LTAT*PSPTSSPRMRLTNTV ESTIKVM 308

Group6: CDR1-2 (12-11)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Lpacos  IGVL4-6               .T......PP....TQRPWA.V.C  ....Y.V..SVD .*..VS..G..F..*  VGT..GDT.ED  .LSNS....G..LE.....Q.F.EDE..E.V.   GANHGSG  309
Lpacos  IGVL4-7               .......PP....TQRPWA.V.C  ....Y.V..SVD .*..VS..G..F..*  VGT..GDT.ED  .LSNS....G..LE.....Q.F.EDE..E.V.   GANHGSG  310
Llama   IGVL4-7               .T......PP....TQRPWA.V.C  ....Y.V..SVD .*..VS..G..F..*  VGT..GDT.ED  .LSNS....G..LE.....Q.F.EDE..E.V.           311
Camel   IGVL4-3               SRPCICLPGSLSQAELYPEQWL QWL..Y..YSVD .Y..VP....C..F..R  VSI..VGS.VD  .VS..H....G..LEH.....Q.FRE.D..E.I* THGADHG  312

Group7: CDR1-2 (12-11)
Human   IGLV4-60*03  Ref      QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Camel   IGVL4-4               .E.....PP....T.*A.A...   ....Y.G..SVD .Y..V..NG..QF..R  VGT..DES.WV  .SLIVSQAQVLVWTDT*PSRTSRRKTRLNTSV GQTMAVG  313
Camel   IGVL4-5               ..E.....PP....T.*A.A...  ....Y.G..SVD .Y..V..NG..QF..R  VGT..DES.WV  .SLIVSQAQVLVWTDT*PSRTSRRKTRLNTSV GQTMAVG  314

Group8
Human   IGLV4-60*03           QPVLTQSSSASASLGSSVKLTC TLSSGHSSYIIA WHQQQPGKAPRYLMK LEGSGSYNKGS GVPDRFSGSSSGADRYLTISNLQSEDEADYYC ETWDSNT  295
Camel   IGVL4-6               ....R.PP....T.L.ALA...   ....DY....SVD .Y..V...GPWFLSQ XVPVVLAPRQV RSLIPSQARALAWSTLXPSRTSGRRSRLTTSV GQTMAAT  315
```

FIG. 10G

IGlV5 Family Functional

```
Group1: CDR1-2 (14-11)
                           %identity  FR1                           CDR1                   FR2                       CDR2            FR3                                              CDR3        SEQ ID NO:
Human  IGLV5-39*01         Ref        QPVLTQPTSLSASPGASARFTC        TLRSGINVGTYRIY         WYQQKPGSLPRYLLR           YKSDSDKQQGS     GVPSRFSGSKDASTNAGLLLISGLQSEDEADYYC               AIWYSST     316
Camel  ICLV5-1             85.91      .........P......L......LN.   ..S..TV.C.H.N          .F.K.A..P....             FY...N.H...     ......A..............................            CTYHGN.     317
Camel  IGLV5-2             85.91      .........P......L......LN.   ..S..TV.G.H.N          .F.K.A..P....             FY...N.H...     ......A..............................            GTYHGN.     318
Lpacos IGLV5-1*01          90.14      .........P............LT.    S.S..TI.G.H.N          .......A..P....           FY...N.H...     ......A..............................            GTYH.N.     319
Lpacos IGVL5-1*02          91.54      .........P............L.     S.S..TI.G.H.N          .......A..P....           FY...N.H...     ......A..............................            GTYH.N.     320
Llama  IGLV5-1             90.14      .........LP...........L.     S.S..TI.G.H.N          .......A..P....           FY...N.H...     ......A..............................            ------      321

Group2: CDR1-2 (14-11)
Human  IGLV5-52*01         Ref        QPVLTQPSSHSASSGASVRLTC        MLSSGFSVGDFWIR         WYQQKPGNPPRXLLY           YHSDSNKGQQGS    GVPSRFSGSNDASANAGILRISGLQPEDEADYYC               GTWHSNSK    322
Camel  IGLV5-3             85.91      .....P..L.V.L..A......       T......K......         ..H...........            ..T..........   ...........S......L.L.................            A.Y.G..     323
Lpacos IGLV5-2*01          84.50      .....L..L.AL..A......        T......K......         ..Y.........              ..T..........   ...........S......L.L..........H......           A.Y.G..     324
Lpacos IGVL5-2*02          84.50      .....L..L.AL..A......        T......K......         ..Y.........              ..T..........   ...........S......L.L..........H......           A.Y.G..     325
Llama  IGLV5-2             84.50      .....L..L.AL..A......        T.............         ..Y.........              ..T..........   ...........S......L.L...........H......          ------      326

Group3: CDR1-2 (14-11)
Human  IGLV5-37*01         Ref        QPVLTQPPSSSASPGESARLIC        TLPSDINVGSYNIY         WYQQKPGSPPRYILY           YYSDSDKGQGS     GVPSRFSGSKDASANTGILLISGLQSEDEADYYC                MIMPSNAS    327
Camel  IGLV5-4             81.69      .T.G....A.F....L.A....        ..S.G.S........D.S     S.S........A...           ....Y.H....     ............L.....R......A.L..........P......    AA.DGSSE    328
Lpacos IGLV5-3*01          83.09      ...G..L..F..F..PL.A...        ..S.G.S........D.S     ..H.A.......              ..T......Q..    .....................S.L..........PD.........    VA.D.SSE    329
Lpacos IGVL5-3*02          83.09      ...G..L..F..F..PL.A...        ..S.G.S........D.S     ..H.A.......              ..T......Q..    .....................S.L..........PD.........    VA.D.SSE    330
Llama  IGLV5-3             83.09      ...G..L..F..F..PL.A...        ..S.G.S........D.S     ..H.A.......              ..T......Q..    .....................S.L......V..P...........    ------      331

Group4: CDR1-2 (14-11)
Human  IGLV5-45*01         Ref        QAVLTQPASLSASPGASASLIC        TLRSGINVGTYRIY         WYQQKPGSPPQYLLRY          KSDSDKQQGS      GVPSRFSGSKDASANAGILLISGLQSEDEADYYC                MIWHSSAS    332
Camel  IGLV5-5             78.87      .P.....PF.AE..S..TR....      .SN.NSA.SCI.S          C...A....R...S.           Y..PI.R...      .............................L......P......D.   SAVS..GN    333
Lpacos IGLV5-4*01          80.28      .P.....LPF.AE.....TR...       .SN.NSA.SCI.S          ....H.A....R....S.        Y.GAI.R...      .............................L......P..........  SAVS..SN    334
Lpacos IGLV5-4*02          80.28      .L.V...PF.AE.....TR....       .SN.NSA.SCI.S          ....H.A....R....S.        Y.GPI.R...      .............................L......P..........  SAVS..SN    335

Group5: CDR1-2 (14-11)
Human  IGLV5-45*01         Ref        QAVLTQPASLSASPGASASLIC        TLRSGINVGTYRIY         WYQQKPGSPPQYILR           YKSDSDKQQGS     GVPSRFSGSKDASANAGILLISGLQSEDEADYYC                MIWH       332
Camel  IGLV5-6                        .L.E..LPFV.EF....SI....       ..T..KS..SHY.S         .Y.........               ...Y....S.H.    ........Q.H....R.........L........P.....ITAL     H.RA       336
Lpacos IGLV5-5                        .L.E..LSFV.EF....SI....       ..T..NS..SHY.S         *N...A.....               ...Y....S.H.    ........Q.C..............L........P.....ITAL     H.RA       337
Llama  IGLV5-4                        .L.E..LSFV.EF....SI....       ..T..NS..SHY.S         .N...A.....               ...Y....S.H.    ........Q.C..............L........P............  ------     338
```

FIG. 10H

```
Group6: CDR1-2 (14-11)
Human   IGLV5-37*01  Ref     QPVLTQPPSSSASPGESARLTC TLPSDINVGSYNIY WYQQKPGSPPRYLLY YYSDSDKGQGS GVPSRFSGSKDASANTGILLISGLQSEDEADYYC MIWPSNS        327
Lpacos  IGLV5-6      88.73   .......L.G.L.A........ ..S.GNS...YA.S  .........A....D .....S.H... .................A..........P.... ............... 339
Llama   IGLV5-5      88.73   .H.V...L...L.S........ ..S.GNS...YA.S  .........A...... .....S.H... .................A..........P.... ............... 340
Llama   IGLV5-6      88.73   .......L.G.L.A........ ..S.GNS...YA.S  .........A....D .....S.H... .................A..........P.... ............... 341
Lpacos  IGLV5-7      81.69   .H...L..L.E..EA....... ..S.GNS...SA.S  ...R.A....W..... .H...S.H... ................LT.A.........P.... VA.DG.N        342
Camel   IGLV5-8      85.91   .L...L.ET..A.......... ..S.GNS...YA.S  .....TA.......... .........Q. .................A..........PK.... AAVD.S.        343
Camel   IGLV5-9      85.91   .L...L.ET..A.......... ..S.CNS...A.S   .....TA.......... .........Q. .................A..........PK.... AAVD.S.        344

FR1                    CDR1            FR2            CDR2         FR3                                   CDR3
Group7: CDR1-2 (14-11)
Human   IGLV5-37*01  Ref     QPVLTQPPSSSASPGESARLTC TLPSDINVGSYNIY WYQQKPGSPPRYLLY YYSDSDKGQGS GVPSRFSGSKDASANTGILLISGLQSEDEADYYC MIWPSNS        327
Camel   IGLV5-10     85.91   .......L.G.L.S........ ..S.GN..G.TV.   .NA......VY..... .....S.H... .....C...........A..........P.... GTLHG.G        345
Camel   IGLV5-11             .......*.............. ..S.GNS...DLS   ..G.A........... .....S.H... .L..S.L.H........A..........P..C. FAYKNH.        346
Lpacos  IGLV5-7      85.91   ..V....L...P.S.V...... ..S.GNS....D.S  .......A........ .....S.H... .R..C............A..........P.... SAYK.GY        347
Llama   IGLV5-7      87.32   .L.V...L...P.S.V...... ..S.GNS....D.S  .......A........ .........D.H .................A..........P.... ............... 348
Lpacos  IGLV5-8*01   85.91   .L.....L...P.S.V...... ..S.GNS....Y.S  .......A........ .........N. .................A..........P.... ............... 349
Llama   IGLV5-8*02   85.91   .L.V.A.L...P.S.V...... ..S.GNS....Y.S  .......A........ .........D.Q .................A..........P.... ............... 350
Llama   IGLV5-9      85.91   .L.....L...P.S.V...... ..S.GNS....Y.S  .......A....Q...S ........Y.H .................A..........P.... ............... 351
Llama   IGLV5-8      85.91   .L.....L...L.S.V...... ..S.GNS....Y.S  .......A....Q...S ........Y.Q .................A..........P.... ............... 352
Lpacos  IGLV5-9*01   87.32   .H.V...L...L.S.V...... ..S.GNS....Y.S  .......A......... ........Y.Q .................A..........P.... VAYK.KY        353
Lpacos  IGLV5-9*01   87.32   .H.V...L...L.S.V...... ..S.GNS....Y.S  .......A......... ........Y.Q .................A..........P.... ............... 354
Llama   IGLV5-10*01  87.32   .H.V...L...L.S........ ..S.GNS....Y.S  .......A......... ........Y.Q .................A..........P.... ............... 355
Llama   IGLV5-10*02  88.73   .L.....L...P.S.V...... ..S.GNS....Y.S  .......A......... ........Y.Q .................A..........P.... ............... 356
```

IGLV7 Family

CDR1-2 (14-7)

| | | FR1 | CDR1 | FR2 | CDR2 | FR3 | CDR3 | SEQ ID NO: |
|---|---|---|---|---|---|---|---|---|
| Human IGLV7-46*01 | Ref | QAVVTQEPSLTVSPGGTVTLTC | GSSTGAVTSGHYPY | WFQQKPGQAPRTLIY | DTSNKHS | WTPARFSGSLLGGKAALTLSGAQPEDEAEYYC | LLSYSGAR | 388 |
| Camel IGLV7-1 | 79.71 | .T........S........... | .L.S.S.TSN..G | .Y............. | S.NSR.. | GV.N......IS.K.....IT.......D... | A.DTGSGG | 389 |
| Llama IGLV7-1 | 84.05 | .T........S........... | .L.S.S...SN..G | .Y............. | N.NSRY. | GV.N......IS.N.....IT........... | | 390 |

IGLV8 Functional

Group1: CDR1-2 (14-7)

| | | FR1 | CDR1 | FR2 | CDR2 | FR3 | CDR3 | SEQ ID NO: |
|---|---|---|---|---|---|---|---|---|
| Human IGLV8-61*01 | Ref | QTVVTQEPSFSVSPGGTVTLTC | GLSSGSVSTSYYPS | WYQQTPGQAPRTLIY | STNTRSS | GVPDRFSGSILGNKAALTITGAQADDESDYYC | VLYMGSGIS | 391 |
| Lpacos IGLV8-1 | 91.30 | ..........L........... | ...TS.N..G | .F............. | N..S.Y. | ..N........S........PE..A....... | AV.I...SY | 392 |
| Camel IGLV8-1 | 86.95 | ..........L........... | ...T..TS.N.. | ..........S.QL. | K..S.H. | ...........S........PE..D....... | A......SY | 393 |
| Lpacos IGLV8-2*01 | 85.50 | ..........L........... | ...TS.N..G | .F............. | ...S.H. | ...........S.....T..PE..A.F..... | A.SRV..TY | 394 |
| Lpacos IGLV8-3 | 82.60 | ..........L........... | ...T..N..G | .F......T...... | ...S.H. | ..SS........S.......PK..AN.D.... | S..P..YPD | 395 |
| Camel IGLV8-2 | 86.95 | ..........L........... | ...TS.N..R | ............T.. | N..S.H. | ..SSC...............PE..D....... | A..VS..SY | 396 |
| Llama IGLV8-1 | 88.40 | ..........L........... | ...T..N..G | .F............. | N..S.H. | ............S.......PE..AE...... | | 397 |
| Camel IGLV8-3 | 86.95 | ..........L........... | ...T..N..G | ...........A... | N..S.P. | ...S.K..............PE..AE...... | A......SY | 398 |
| Lpacos IGLV8-2*02 | 85.50 | ..........L........... | ...TS.N..G | ...........A... | N..S.H. | ...........S.....T..S..PE..A.F.. | A.SRV..TY | 399 |
| Lpacos IGLV8-4 | 86.95 | ..........L........... | ...TS.N..G | ...........A... | N..S.H. | ...S.Y..............EPE..A...... | A.HK..YTD | 400 |

Group2: CDR1-2 (14-7)

| | | FR1 | CDR1 | FR2 | CDR2 | FR3 | CDR3 | SEQ ID NO: |
|---|---|---|---|---|---|---|---|---|
| Human IGLV8-61*01 | Ref | QTVVTQEPSFSVSPGGTVTLTC | GLSSGSVSTSYYPS | WYQQTPGQAPRTLIY | STNTRSS | GVPDRFSGSILGNKAALTITGAQADDESDYYC | VLYMGSGIS | 391 |
| Lpacos IGLV8-5 | 86.95 | ..........M........... | | .F............. | R.SN.L. | ...........S........M..PE..AE... | AV.V...SY | 401 |
| Llama IGLV8-2 | 86.95 | ..........M........... | ...T..N..G | .F............. | R.SN.L. | ...........S........M..PE..AE... | | 402 |
| Lpacos IGLV8-6 | 86.95 | ..........M........... | ...T..N..G | .F............. | R.SN.L. | ...........S........M..PE..AE... | AV.V...SY | 403 |
| Camel IGLV8-4 | 86.95 | ..........M........... | ...T..N..G | ...........S... | R.SN.L. | ...........S.....T..T..PE..A.... | AV.....SY | 404 |

Group3: CDR1-2 (14-7)

| | | FR1 | CDR1 | FR2 | CDR2 | FR3 | CDR3 | SEQ ID NO: |
|---|---|---|---|---|---|---|---|---|
| Human IGLV8-61*01 | Ref | QTVVTQEPSFSVSPGGTVTLTC | GLSSGSVSTSYYPS | WYQQTPGQAPRTLIY | STNTRSS | GVPDRFSGSILGNKAALTITGAQADDESDYYC | VLYMGSGIS | 391 |
| Camel IGLV8-5 | 85.50 | ..........L........... | ...T...N..G | ......R..A..... | ..SS.Y. | ...S................PKE.A...D... | S.YH..YPD | 405 |
| Lpacos IGLV8-7 | 88.40 | ..........L.A......... | ...T..N..G | .F............. | ..SS.H. | ...S................PE..A....... | A.DI..YTD | 406 |
| Camel IGLV8-6 | 81.15 | ..........L........... | ..S.N..G | ........V...... | ..SS.P. | I.S.AGT.S....T......PE..A....... | A.YP..YLD | 407 |
| Camel IGLV8-7 | 81.15 | P.........L....W...... | ...T..ND.G | ........V...... | R.SSHL. | ...S.FR..S..........M...PK..A... | A.DM..SY | 408 |

Group4: CDR1-2 (14-7)

| | | FR1 | CDR1 | FR2 | CDR2 | FR3 | CDR3 | SEQ ID NO: |
|---|---|---|---|---|---|---|---|---|
| Human IGLV8-61*01 | Ref | QTVVTQEPSFSVSPGGTVTLTC | GLSSGSVSTSYYPS | WYQQTPGQAPRTLIY | STNTRSS | GVPDRFSGSILGNKAALTITGAQADDESDYYC | VLYMGSGIS | 391 |
| Lpacos IGLV8-8 | 89.85 | ..........L........... | ...TS.N..D | ............L.. | N..S.H. | ...........S........PE..A....... | A......SN | 409 |
| Llama IGLV8-3 | 88.40 | ..........L........... | ...TS.N..D | ............L.. | N..S.H. | ...........S........PE..AE...... | | 410 |
| Lpacos IGLV8-9 | | ..........L........... | ...TS.N..D | ............L.. | N..S.H. | ...........S........*PE..A...... | | 411 |
| Llama IGLV8-4 | 88.40 | ..........L........... | ...TS.N..D | ...........A... | S..S.H. | ...........N........PE..AE...... | | 412 |

FIG. 10K

Group5: CDR1-2 (14-7)

```
                          FR1                        CDR1             FR2            CDR2    FR3                                CDR3                SEQ ID NO:
Human    IGLV8-61*01  Ref  QTVVTQEPSFSVSPGGTVTLTC GLSSGSVSTSYYPS WYQQTPGQAPRTLIY STNTRSS GVPDRFSGSILGNKAALTITGAQADDESDYC VLYMGSGIS   391
Lpacos   IGLV8-10*01  81.15 ......K.l.............  .......T.SN..G .I......VLH....  .TSSCL. ......S......TT.....PE..A..... AV.IWVVAV   413
Lpacos   IGVL8-10*02  81.15 ......K.l.............  .......T.SN..G .I......VLH....  .TSSCL. ......S......TT.....PE..A..... AV.IWVVAV   414
```

IGLV8 Pseudogenes

Group6: CDR1-2 (14-7)

```
                           FR1                        CDR1             FR2            CDR2    FR3                                CDR3           SEQ ID NO:
Human    IGLV8-61*01   QTVVTQEPSFSVSPGGTVTLTC GLSSGSVSTSYYPS WYQQTPGQAPRTLIY STNTRSS GVPDRFSGSILGNKAALTITGAQADDESDYC VLYMGSG        391
Camel    IGLV8-8       K........L...........F.    ..P...TI.D.HS  ........*A....  .SSHY.  ...NQ......S............PE..A.D. A.HT..Y        415
Camel    IGLV8-9       K........G...F.            ..P...TI.D.HS  ........P*A...  .SSHY.  ...NQ......S............PE..A..D. A.HT..Y        416
Lpacos   IGVL8-11*01   .....QSFLK....QG.F....     ..P.T.T..N.PC  F....R....L*L.. .S.S.PT ...SRS..TVS...........R..PE.KA... A.E...Y        417
Lpacos   IGVL8-11*02   .....QSFLK....QG.F....     ..P.T.T..N.PC  F....R....L*L.. .S.S.PT ...SRS..TVS...........R..PE.KA... A.E...Y        418
```

Group7: CDR1-2 (14-7)

```
Human    IGLV8-61*01   QTVVTQEPSFSVSPGGTVTLTC GLSSGSVSTSYYPS WYQQTPGQAPRTLIY STNTRSS GVPDRFSGSILGNKAALTITGAQADDESDYC VLYMGSG        391
Camel    IGLV8-12      .....VS.L..FLR........     ...N....T..K.S. .....R.Q......* ...SCL. ..LN.L...T.S....S............SE..AD... A.DT..Y        419
Llama    IGLV8-5       .....VS.L..FLR........     ...N....T..K.S. .....R.Q......* ...SCL. ..LN.L...T.S....S............SE...AE...                420
Llama    IGLV8-6       .....VS.L..FLL........     ...N....T..K...  ....RMQ.......* ...SCL. ..LN.L...T.S....S...F........SE...AE...                421
Llama    IGLV8-7       .....L..VS.L..FLL.....     ...N....T..K...  ....RMQ.......* R..SCL. ..LS....TVC.....A..SI..S.SE..AE...                422
```

Group8: CDR1-2 (14-7)

```
Human    IGLV8-61*01   QTVVTQEPSFSVSPGGTVTLTC GLSSGSVSTSYYPS WYQQTPGQAPRTLIY STNTRSS GVPDRFSGSILGNKAALTITGAQADDESDYC VLYMGSG        391
Lpacos   IGVL8-13*01   ...M.....L.G......K..      .......T..N..G  .....R.Q......L.* ...SCL. ..LNC........TVC...............SE..AEYC ARDT..C        423
Lpacos   IGVL8-13*02   ...M.....L.G......K..      .......T..N..G  .....R.Q......L.* ...SCL. ..LNC........TVC...............SE..AEYC ARDT..C        424
Llama    IGLV8-8       ...M.....L.G......K..      .......T..N..G  .....R.Q......L.* R..SCL. ..LNC........TVCR..............SE..AE            425
```

Group9: CDR1-2 (14-7)

```
Human    IGLV8-61*01   QTVVTQEPSFSVSPGGTVTLTC GLSSGSVSTSYYPS WYQQTPGQAPRTL-IY STNTRSS GVPDRFSGSILGNKAALTITGAQADDESDYC VLYMGSG        391
Camel    IGLV8-10      ...DS.L.A.............     .......T..N....  ........RL..-I*  ...SCP. ..NLN....TSPRMRPSIIVLWTQVVTITQ*-. N.TGKCF        426
Camel    IGLV8-11      ..I.NS.ITL...E........     .?..............  ....QV.PIA EAAEGPQS ...PS.L..S.S.I..T..N.E.LPK.KA... A.YP..         427
Lpacos   IGVL8-14*01   .....L.....EM.........     .?......T..N....  ....QV.SIA EAA.ILRS P.ACLDPSLGSKPFPSPPLRPCPRTRPTTIVL T.VVTV         428
Lpacos   IGVL8-14*02   .....L.....EM.........     .?......T..N....  ....QV.SIA EAA.ILRS P.ACLDPSLGSKPFPSPPLRPCPRTRPTTIVL T.VVTV         429
```

FIG. 10L

IGLV9 family

Group1: CDR1-2 (12-12)

```
                       FR1                      CDR1                 FR2                 CDR2               FR3                                       CDR3      SEQ ID NO:
Human   IGLV9-49*01  Ref     QPVLTQPPSASASLGASVTLTC  TLSSGYSNYKVD  WYQQRPGKGPRFVMR  VGTGGIVGSKGD  GIPDRFSVLGSGLNRYLTIKNIQEEDESDYHC  GADHGS    430
Lpacos  IGVL9-1      65.21%  ...M..................  .LRT..IC.Y..  ....D..N....E.G  AA.S.G......  VS.H..SV....EHSVN.Q.VR...K...I.   ......    431
Llama   IGVL9-1      68.12%  ...M..................  .PRT..IC.Y..  ....D..N....E.G  A..S.G......  VS.....G....EHSVN.Q.VR...K...I.   ......    432
Llama   IGVL9-2      65.21%  ...M..................  .LRT..IC.Y..  ....D..N....E.G  AA.S.G......  VS.H..SV....EHSVN.Q.VR...K...I.   ......    433
```

Group2: CDR1-2 (12-12)

```
Human   IGLV9-49*01  Ref     QPVLTQPPSASASLGASVTLTC  TLSSGYSNYKVD  WYQQRPGKGPRFVMR  VGTGGIVGSKGD  GIPDRFSVLGSGLNRYLTIKNIQEEDESDYHC  GADHGS    430
Lpacos  IGVL9-3              ..P.S........SK.......  ......H.G*Y.  *...D..N.S*.EMG  ..SSVLE.....  .VS.S.SGS..*PE....Q.VL....A.DI.   ......    434
Lpacos  IGVL9-4              ..M...S...............  ......GFYM..  *...D..K.TQ.EMG  .IS.V.E.MR..  .VS.....GS.P.PEHD....VL....A.I.   .P....    435
Lpacos  IGVL9-5              .......T......GSSPA   P*AVATVFTWT STSKTQ.K..Q.EVG  ...V.E.*RY  RVS.....GS.P.PEC....*.VL....A.I.   .P....    436
Camel   IGVL9-2              .........S..R..AKF.*  ...N...GCY.D  ....D..N..Q.EMG  ...S.V.E..E.  .VS.....AGS..CPEC.....Q.VW...AKT.I.   ...R..    437
Camel   IGVL9-3              .........S..R..AKF.*  ...N...GCY.D  ....D..N..Q.EMG  ...S.V.E..E.  .DSN.....S...RE....QMFQ.DDRLTTSV  .QTMAA    438
Camel   IGVL9-4              ..M.L.F.........AK..  ...S....G.Y.D  .E.D..N.SQ.EMG  GS.S..T.Y.E.  .VS.H..GS..S.EH....*.V*...KAG.I.   .T....    439
```

IGLV10 family

Group1: CDR1-2 (13-7)

```
                       FR1                      CDR1                 FR2                 CDR2          FR3                                  CDR3      SEQ ID NO:
Human   IGLV10-54*02  Ref     QAGLTQPPSVSKGLRQTATLTC  TGNSNIVGNQGAA  WLQHQGHPPKLLSY  RNNNRPS  GISERFSASSGNTASLTITGLQPEDEADYC  SALDSSLS  440
Camel   IGLV10-2      70.79%  ..W....Q..TGS.G.......  ..NVHSI..E.P.  .....QA.R..TL.  ...HQ..  .L....LG....SM.T.SIS...A........  .W......  441
Lpacos  IGLV10-1*01   71.91%  ..R....R..TASPG.......  ...D.HS....E..  .....P.QA.R..TL  ...Q...  .V......G....S..T.SIS...A........  .W......  442
Llama   IGLV10-1*01   69.66%  ..W....Q..TASPG.......  ...DGHS....E..  .....P.QA.R..TL  G..Q...  .V......G....S..T.SIS...........  ........  443
```

FIG. 11A

IGLV1 Family
Group1: CDR1-2 (2-1)

| | Identity(%) | FR1 | CDR1 | FR2 | CDR2 | FR3 | CDR3 | SEQ ID NO: |
|---|---|---|---|---|---|---|---|---|
| Human IGKV1-39*01 | Ref | DIQMTQSPSSLSASVGDRVTITC | RASQSISSYLN | WYQQKPGKAPKLLIY | AASSLQS | GVPSRFSGSGSGTDFTLTISSLQPEDFATYYC | QQSYSTPP | 444 |
| Lpacos IGKV1-1 | 84.29 | AT.V......... | Q......... | ....A....... | G.R.T | ....S........G.EA..AG.... | L.HKLPSH | 445 |
| Camel IGKV1-1 | 80.00 | AT........L..T... | Q......... | ....A...H...Q.... | G.R.T | ....S........GVEA..VG.... | L.HN.Y.. | 446 |
| Lpacos IGKV1-2 | 85.71 | AT......L..... | Q......... | ....A........ | G.R.T | ....S........G.EA..AG.... | ..Y..A.. | 447 |
| Camel IGKV1-2 | 80.00 | AT.V.....L..T... | Q......... | ....A.....QV... | D...YT | ....S........GVEA..VG.... | ..YN.A.. | 448 |

Group2: CDR1-2 (2-1)

| | Identity(%) | FR1 | CDR1 | FR2 | CDR2 | FR3 | CDR3 | SEQ ID NO: |
|---|---|---|---|---|---|---|---|---|
| Human IGKV1-27*01 | Ref | DIQMTQSPSSLSASVGDRVTITC | RASQGISNYLA | WYQQKPGKVPKLLIY | AASTLQS | GVPSRFSGSGSGTDFTLTISSLQPEDVATYYC | QKYNSAPP | 449 |
| Lpacos IGKV1-3*01 | 80.00 | AT......S....L.... | Q..S....E.S | .H......QT.... | G.R.T | ....S........G.EA..AG.... | ..Q.Y... | 450 |
| Lpacos IGKV1-3*02 | 81.43 | AT......S....L.... | Q..S....E.S | .H......QT.... | G.R.T | ....S........G.EA..AG.... | ..Q.Y... | 451 |
| Llama IGKV1-4 | 81.43 | AT..........L.... | Q..S....E.S | .H......QT.... | G.R.T | ....S........G.EA..AG.... | -------- | 452 |
| Lpacos IGKV1-4 | 85.71 | AT..........L.... | Q..S....TE.S | .........QT.... | G.R.T | ....S........G.EA..L..... | LQDY.W.. | 453 |
| Camel IGKV1-2 | 80.00 | AT..........L.... | ....S....E.S | .........QA.... | D..S.HT | ....S........GVEA..AG...S | ..Q.YR.. | 454 |

Group3:

| | Identity(%) | FR1 | CDR1 | FR2 | CDR2 | FR3 | CDR3 | SEQ ID NO: |
|---|---|---|---|---|---|---|---|---|
| Human IGKV1-39*01 | Ref | DIQMTQSPSSLSASVGDRVTITC | RASQSISSYLN | WYQQKPGKAPKLLIY | AASSLQS | GVPSRFSGSGSGTDFTLTISSLQPEDFATYYC | | 444 |
| Camel IGKV1-4 | | AT........L..T... | Q......... | ....A...H....... | G...HT | .F...........S........RDR**TNKIAAAV | | 455 |
| Camel IGKV1-5 | | AT........L..T... | Q......... | ....A...H....... | G...HT | .F...........S........RDR**TNKIAAAV | | 456 |
| Lpacos IGKV1-5*01 | | E.VL.....A.KAV.Q.E | S..S.V.TCYL | TLVPTEAQS.SQA? | F*HIQPG | FWGPIPLQWQMIWDLL.SHHQQRGG*RCCRLL | | 457 |
| Lpacos IGKV1-5*02 | | E.VL.....A.KAV.QEE | S..S.V.TCYL | TLVPTEAQS.SQA? | F*HIQPG | FWGPIPLQWQMIWDLL.SHHQQRGG*RCCRLL | | 458 |
| Camel IGKV1-6 | | E.VL.....A.KAV.Q.E | S..S.V.TCYL | TLLPTEARS.SQA? | L*HIQPG | LWGPIPLQWQMIWDLL.SHHQQRGG*RYCRLL | | 459 |

IGLV2 Family
Group1: CDR1-2 (4-1)

| | Identity(%) | FR1 | CDR1 | FR2 | CDR2 | FR3 | CDR3 | SEQ ID NO: |
|---|---|---|---|---|---|---|---|---|
| Human IGKV2D-29*02_1 | REF | DIVMTQTPLSLSVTPGQPASISC | KSSQSLLHSDGKTYLY | WYLQKPGQSPQLLIY | EVSNRFS | GVPDRFSGSGSGTDFTLKISRVEAEDVGVYYC | MQSIQLP | 460 |
| Lpacos IGKV2-2 | 82.86 | .V.L......G.....V..ES... | .A.....V.T...... | ....L......... | ....Q... | ....G........T........G.K....A... | A.A.YD. | 461 |
| Lpacos IGKV2-3 | 82.86 | .V.L......G.....I..ES... | .A.....V........ | ....L......... | ....Q... | ....G........T........G.K....A... | A.A.YD. | 462 |
| Lpacos IGKV2-4 | 82.86 | .V.L......G.....V..ES... | .A.....V........ | ....L......... | ....R... | ....G........T........G.K....A... | A.A.Y-- | 463 |
| Lpacos IGKV2-1*01 | 82.86 | .V.L......G.....V..ES... | .A.....V........ | ....L......... | ....R... | ....G........T........G.K....A... | A.A.Y-- | 464 |
| Llama IGKV2-2*01 | 82.86 | .V.L......G.....V..ES... | .A.....V........ | ....L......... | ....R... | ....G........T........G.K....A... | -------- | 465 |
| Camel IGKV2-1 | 82.86 | EV.L......G.....V..ES... | .A.....V........ | ....L......... | ....Q... | ....G........T........G.K....A... | A.ATRDR | 466 |
| Camel IGKV2-3 | | .V.L......G.....V..ES... | .A.....V........ | ....LR........ | ....*... | ....G........T........G.K....A..H | A.AT.S. | 467 |
| Llama IGKV2-3*01 | 82.86 | .V.L......G.....V..ES... | .A.....V.T...... | ....L......... | ....R... | ....G........T........G.K....A... | -------- | 468 |
| Lpacos IGKV2-5 | 82.86 | .V.L......G.....V..ES... | .A.....I.T...... | ....L......... | ....Q...HE | ....G........T........G.K....A... | A.AT.-- | 469 |
| Llama IGKV2-4*01 | 82.86 | .V.L......G.....V..ES... | .A.....I.T...... | ............. | ....R... | ....Q...HE | ........ | 470 |
| Lpacos IGKV2-1 | 82.86 | .L.L......G.....V..ES... | R.TEN.ED.E.D...S | ....M.F | AG.S.AP | .I........T........G.K....A... | A..LPTV | 471 |

Group2: CDR1-2 (3-1)

| | Identity(%) | FR1 | CDR1 | FR2 | CDR2 | FR3 | CDR3 | SEQ ID NO: |
|---|---|---|---|---|---|---|---|---|
| Human IGKV2-40*01_1 | REF | DIVMTQTPLSLPVTPGEPASISC | RSSQSLLDSDDGNTYLD | WYLQKPGQSPQLLIY | TLSYRAS | GVPDRFSGSGSGTDFTLKISRVEAEDVGVYYC | MQRIEFP | 472 |
| Lpacos IGKV2-6*01 | 61.43 | N..L.RFLA.VIAS.....L.T... | .A.RRVSGILGIIIIVN | .CK.....P.K...C | AATR..P | ....A........T.HP....D.AEEDF..... | QHSK.D. | 473 |
| Lpacos IGKV2-6*02 | 60.00 | N..L.RFLA.VIAS....L.T... | .A.RRVSVILGIIIIVN | .CK.....P.K...C | AATR..P | ....A.R......T.HP....D.AEEDF..... | QHSK.-- | 474 |
| Camel IGKV2-4 | | N..L.RFLA.VIAS...*.T... | .A.RRVSGILGIIIIVN | .CK.....P.K...C | AATC..P | ....A.C......T.HP....D.AEEDF..... | QHSK.D. | 475 |
| Llama IGKV2-5 | 60.00 | N..L.RFLA.VIAS.....L.T... | .A.RRVSGILGIIIIVN | .CK.....P.K...C | AAIRL.P | ....A.R......T.HP....D.AEEDF..... | -------- | 476 |

FIG. 11B

IGLV3 Family

Group1: CDR1-2 (2-1) Identity(%)

|  |  | FR1 | CDR1 | FR2 | CDR2 | FR3 | CDR3 | SEQ ID NO: |
|---|---|---|---|---|---|---|---|---|
| Human IGKV3-11*01 | REF | EIVLTQSPATLSLSPGERATLSC | RASQSVSSYLA | WYQQKPGQAPRLLIY | DASNRAT | GIPARFSGSGSGTDFTLTITSSLEPEDFAVYYC | QQRSNWPP | 477 |
| Camel IGKV3-1 | 62.86 | SA...T..I..V.LR.SISIT. | T.NE...D.VS | ................ | .DD.YP | .V.D..V.LQ...Q.I...NKV.AD.A.S... | ..GYTV.. | 478 |
| LpacosIGKV3-1*01 | 61.43 | SAE...I..V.LR.SISIT. | T.SE...D.VS | ................ | .TDD.YS | .V.D..V.LQ...Q.I...NNV.AD.T.S.. | .FHDYTV.. | 479 |

Group2: CDR1-2 (2-1) Identity(%)

|  |  | FR1 | CDR1 | FR2 | CDR2 | FR3 | CDR3 | SEQ ID NO: |
|---|---|---|---|---|---|---|---|---|
| Human IGKV3-11*01 | REF | EIVLTQSPATLSLSPGERATLSC | RASQSVSSYLA | WYQQKPGQAPRLLIY | DASNRAT | GIPARFSGSGSGTDFTLTISSLEPEDFAVYYC | QQRSNWPP | 477 |
| Camel IGKV3-2 | 60.00 | Q.A...F.ES.AA.H.SLVSIT. | .S.IE.GTSM. | .......KE...... | F G.A.S | .T.S..........S..S.A.HGV.A..VG... | ..HASL.L | 480 |
| LpacosIGKV3-2*01 | 60.00 | Q.A...F.ES.AA.H.SLVSIT. | .S.ME.GTSM. | .......KE...... | F G.A.S | .T.S..........S..S.A.HGV.A..VG... | ..HISL.L | 481 |

IGLV4 Family

Group1: CDR1-2 (3-1) Identity(%)

|  |  | FR1 | CDR1 | FR2 | CDR2 | FR3 | CDR3 | SEQ ID NO: |
|---|---|---|---|---|---|---|---|---|
| Human IGKV4-1*01 | REF | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | QQYYSTPP | 482 |
| Lpacos IGKV4-2 | 78.57 | ......S.VTA.A..KV.... | ..........Q...... | ......R....... | ......R.. | .......S..T.......IS..F.P..... | ..A..A.. | 483 |
| Llama IGKV4-1 | 81.43 | ......S.VTA.A..KV.... | ..........Q...... | ......RL....... | ......R.. | .........T..........F.P........ | ..A..A.. | 484 |

Group2: CDR1-2 (3-1) Identity(%)

|  |  | FR1 | CDR1 | FR2 | CDR2 | FR3 | CDR3 | SEQ ID NO: |
|---|---|---|---|---|---|---|---|---|
| Human IGKV4-1*01 | REF | DIVMTQSPDSLAVSLGERATINC | KSSQSVLYSSNNKNYLA | WYQQKPGQPPKLLIY | WASTRES | GVPDRFSGSGSGTDFTLTISSLQAEDVAVYYC | QQYYSTPP | 482 |
| Camel IGKV4-2 | 80.00 | ......S.VTA.V..KV.... | .........S...Q.S.. | .......R...S.R.. | Y...... | .........T.I......V....A.... | ..A..A.S | 485 |
| Camel IGKV4-1 | 78.57 | ......S.VTA.V..KV.... | ......FS..SQ.SL.. | ..H..RN...RR.... | Y....A. | .........T.........V....A.... | ..A..A.. | 486 |
| Lpacos IGKV4-1*01 | 80.00 | ......S.VTA.V..KV.... | ......VSG..Q.S..N | .......R...S.R.. | Y...Q.. | .........I.........V....A.... | ..A..A.S | 487 |
| Lpacos IGKV4-1*02 | 80.00 | ......S.VTA.V..KV.... | ......VSG..Q.S..N | .......R...S.R.. | Y...Q.L | .........I.........V....A.... | ..A..A.S | 488 |

IGLV5 Family

Group1: CDR1-2 (2-1) Identity(%)

|  |  | FR1 | CDR1 | FR2 | CDR2 | FR3 | CDR3 | SEQ ID NO: |
|---|---|---|---|---|---|---|---|---|
| Human IGKV5-2*01 | REF | ETTLTQSPAFMSATPGDKVNISC | KASQDIDDDMN | WYQQKPGEAAIFIIQ | EATTLVP | GIPPRFSGSGYGTDFTLTNNIESDAAYFC | LQHDNFPL | 489 |
| Camel IGKV5-1 | 77.14 | ..V......LV......T.T. | ...........I...... | .......Q.PRL..K | YVS..IS | .V.S............N...D.MK....... | Q.D..T.. | 490 |
| Lpacos IGKV5-1 | 75.71 | ..V......LA.......TLT. | .V...T...I...... | .......Q.PRL.TK | YDS.VIS | .L.S....................D.MK....... | Q.D..I.. | 491 |
| Llama IGKV5-1 | 72.86 | ..VPI....LA.......TLT. | .....T...I...... | .......Q.PRL.TK | YDS..IS | .V.S....................D.MK....... |  | 492 |

FIG. 11C

IGLV6 Family

| Group1: CDR1-2 (2-1) | Identity (%) | FR1 | CDR1 | FR2 | CDR2 | FR3 | CDR3 | SEQ ID NO: |
|---|---|---|---|---|---|---|---|---|
| Human IGKV6-? | REF | DVVMTQSPAFLSVTPGEKVTITC | QASEGIGNYLY | WYQQKPDQAPKLLIK | YASQSIS | GVPSRFSGSGSGTDFTFTISSLEAEDAATYYC | QQGNKHP | 493 |
| Camel IGKV6-1 | 77.14 | AT.L.....L..KA..D.A.... | R..QSVS...R | ..K...N.P..... | Q .T..TF. | ...A..I.............L........... | Q...YSSS | 494 |
| Lpacos IGKV6-1 | 77.14 | ATML.....L..KA..D.A.... | R..QS.STS.H | .....N.P..... | Q H...TF. | ....T..............L........KC.. | Q...YSYS | 495 |
| Llama IGKV6-1 | 77.14 | ATML.....L..KA..D.A.... | R..QS.STS.H | .....N.P..... | Q H...TF. | ....T..............L........KC.. | | 496 |

FIG. 12A

| | | Germline VH name | Primer name | Primer size (23-25bp) | SEQ ID NO: |
|---|---|---|---|---|---|
| Lama pacos | VH1 | IGHV1-1*01 | VH1-primer2 | GAGGTCCAGCTGGTGCAGCCAGG | 2 |
| | | IGHV1-1*02 | N/A | N/A | |
| | | IGHV1-2 | VH1-primer1 | CAGGTCCAGCTGSTGCAGTCAGG | 1 |
| | | IGHV1-3*01 | VH1-primer1 | CAGGTCCAGCTGSTGCAGTCAGG | 1 |
| | | IGHV1-3*02 | VH1-primer1 | CAGGTCCAGCTGSTGCAGTCAGG | 1 |
| | | IGHV1-3*03 | VH1-primer2 | GAGGTCCAGCTGGTGCAGCCAGG | 2 |
| | | IGHV1-4 | VH1-primer1 | CAGGTCCAGCTGSTGCAGTCAGG | 1 |
| | | IGHV1-5 | N/A | N/A | |
| | VH3 | IGHV3-1*01 | VH3-primer1 | GAGGTGCAGSTGGTGGAGTCTGGG | 3 |
| | | IGHV3-1*02 | VH3-primer1 | GAGGTGCAGSTGGTGGAGTCTGGG | 3 |
| | | IGHV3-S17 | VH3-primer2 | CAGGTGCAGCTGGTGGAGTCTGGG | 4 |
| | | IGHV3-2*01 | VH3-primer2 | CAGGTGCAGCTGGTGGAGTCTGGG | 4 |
| | | IGHV3-2*02 | VH3-primer1 | GAGGTGCAGSTGGTGGAGTCTGGG | 3 |
| | | IGHV3-S4 | VH3-primer2 | CAGGTGCAGCTGGTGGAGTCTGGG | 4 |
| | | IGHV3-S11 | VH3-primer1 | GAGGTGCAGSTGGTGGAGTCTGGG | 3 |
| | | IGHV3-S12 | VH3-primer2 | CAGGTGCAGCTGGTGGAGTCTGGG | 4 |
| | | IGHV3-3 | N/A | N/A | |
| | | IGHV3-S2 | VH3-primer1 | GAGGTGCAGSTGGTGGAGTCTGGG | 3 |
| | | IGHV3-S3 | VH3-primer1 | GAGGTGCAGSTGGTGGAGTCTGGG | 3 |
| | | IGHV3-4*01 | VH3-primer1 | GAGGTGCAGSTGGTGGAGTCTGGG | 3 |
| | | IGHV3-4*02 | N/A | N/A | |
| | | IGHV3-5 | VH3-primer1 | GAGGTGCAGSTGGTGGAGTCTGGG | 3 |
| | | IGHV3-s44 | VH3-primer1 | GAGGTGCAGSTGGTGGAGTCTGGG | 3 |
| | | IGHV3-6*01 | VH3-primer2 | CAGGTGCAGCTGGTGGAGTCTGGG | 4 |
| | | IGHV3-6*02 | VH3-primer2 | CAGGTGCAGCTGGTGGAGTCTGGG | 4 |
| | | IGHV3-s27 | VH3-primer2 | CAGGTGCAGCTGGTGGAGTCTGGG | 4 |
| | | IGHV3-s26 | VH3-primer2 | CAGGTGCAGCTGGTGGAGTCTGGG | 4 |
| | | IGHV3-7*01 | VH3-primer1 | GAGGTGCAGSTGGTGGAGTCTGGG | 3 |
| | | IGHV3-7*02 | VH3-primer1 | GAGGTGCAGSTGGTGGAGTCTGGG | 3 |
| | | IGHV3-8*01 | VH3-primer1 | GAGGTGCAGSTGGTGGAGTCTGGG | 3 |
| | | IGHV3-8*02 | VH3-primer2 | CAGGTGCAGCTGGTGGAGTCTGGG | 4 |
| | | IGHV3-S40 | VH3-primer1 | GAGGTGCAGSTGGTGGAGTCTGGG | 3 |
| | | IGHV3-S25 | VH3-primer2 | CAGGTGCAGCTGGTGGAGTCTGGG | 4 |
| | | IGHV3-S33 | VH3-primer2 | CAGGTGCAGCTGGTGGAGTCTGGG | 4 |
| | | IGHV3-S32 | VH3-primer1 | GAGGTGCAGSTGGTGGAGTCTGGG | 3 |
| | | IGHV3-S45 | VH3-primer2 | CAGGTGCAGCTGGTGGAGTCTGGG | 4 |
| | | IGHV3-S34 | VH3-primer2 | CAGGTGCAGCTGGTGGAGTCTGGG | 4 |
| | | IGHV3-S38 | VH3-primer2 | CAGGTGCAGCTGGTGGAGTCTGGG | 4 |
| | | IGHV3-S37 | VH3-primer2 | CAGGTGCAGCTGGTGGAGTCTGGG | 4 |
| | | IGHV3-S35 | VH3-primer1 | GAGGTGCAGSTGGTGGAGTCTGGG | 3 |
| | | IGHV3-S36 | VH3-primer1 | GAGGTGCAGSTGGTGGAGTCTGGG | 3 |
| | | IGHV3-S30 | VH3-primer2 | CAGGTGCAGCTGGTGGAGTCTGGG | 4 |
| | | IGHV3-9 | VH3-primer2 | CAGGTGCAGCTGGTGGAGTCTGGG | 4 |
| | | IGHV3-10*01 | VH3-primer1 | GAGGTGCAGSTGGTGGAGTCTGGG | 3 |
| | | IGHV3-10*02 | VH3-primer2 | CAGGTGCAGCTGGTGGAGTCTGGG | 4 |
| | | IGHV3-S20 | VH3-primer2 | CAGGTGCAGCTGGTGGAGTCTGGG | 4 |
| | | IGHV3-S29 | VH3-primer2 | CAGGTGCAGCTGGTGGAGTCTGGG | 4 |
| | | IGHV3-S28 | VH3-primer2 | CAGGTGCAGCTGGTGGAGTCTGGG | 4 |
| | | IGHV3-S13 | VH3-primer1 | GAGGTGCAGSTGGTGGAGTCTGGG | 3 |
| | | IGHV3-S14 | VH3-primer2 | CAGGTGCAGCTGGTGGAGTCTGGG | 4 |
| | | IGHV3-11 | N/A | N/A | |
| | | IGHV3-12 | VH3-primer2 | CAGGTGCAGCTGGTGGAGTCTGGG | 4 |
| | | IGHV3-13 | VH3-primer2 | CAGGTGCAGCTGGTGGAGTCTGGG | 4 |
| | | IGHV3-14 | VH3-primer2 | CAGGTGCAGCTGGTGGAGTCTGGG | 4 |
| | | IGHV3-15 | VH3-primer2 | CAGGTGCAGCTGGTGGAGTCTGGG | 4 |
| | | IGHV3-17*01 | VH3-primer1 | GAGGTGCAGSTGGTGGAGTCTGGG | 3 |
| | | IGHV3-17*02 | VH3-primer1 | GAGGTGCAGSTGGTGGAGTCTGGG | 3 |

FIG. 12B

| | | | | | |
|---|---|---|---|---|---|
| | VH4 | IGHV4-1*01 | VH4-primer1 | CAGGTGCAGCTGCAGGAGTCGGG | 5 |
| | | IGHV4-1*02 | VH4-primer1 | CAGGTGCAGCTGCAGGAGTCGGG | 5 |
| | | IGHV4-2 | VH4-primer1 | CAGGTGCAGCTGCAGGAGTCGGG | 5 |
| | | IGHV4-3 | N/A | N/A | |
| | | IGHV4-4 | N/A | N/A | |
| | | IGHV4-5 | VH4-primer1 | CAGGTGCAGCTGCAGGAGTCGGG | 5 |
| | | IGHV4-6 | VH4-primer1 | CAGGTGCAGCTGCAGGAGTCGGG | 5 |
| | | IGHV4-7 | VH4-primer1 | CAGGTGCAGCTGCAGGAGTCGGG | 5 |
| | | IGHV4-8 | VH4-primer1 | CAGGTGCAGCTGCAGGAGTCGGG | 5 |
| | | IGHV4-9 | VH4-primer1 | CAGGTGCAGCTGCAGGAGTCGGG | |
| | | IGHV4-10 | VH4-primer1 | CAGGTGCAGCTGCAGGAGTCGGG | 5 |
| | | IGHV4-11 | VH4-primer1 | CAGGTGCAGCTGCAGGAGTCGGG | 5 |
| | | IGHV4-12 | VH4-primer1 | CAGGTGCAGCTGCAGGAGTCGGG | 5 |
| | | IGHV4-13 | VH4-primer1 | CAGGTGCAGCTGCAGGAGTCGGG | 5 |
| | | IGHV4-14*01 | VH4-primer1 | CAGGTGCAGCTGCAGGAGTCGGG | 5 |
| | | IGHV4-14*02 | VH4-primer1 | CAGGTGCAGCTGCAGGAGTCGGG | 5 |
| | | IGHV4-15 | N/A | N/A | |
| | VH5 | IGHV5-1 | VH5-primer1 | CAGGTGMAGCTGGAGCAGCCTGTGG | 6 |
| | VH7 | IGHV7-1 | VH7-primer2 | CAAGTGCAGCTGGTGCAGCCAGGG | 8 |
| Camel ferus | VH1 | IGHV1-1 | VH1-primer2 | GAGGTCCAGCTGGTGCAGCCAGG | 2 |
| | | IGHV1-2 | N/A | N/A | |
| | | IGHV1-3 | VH1-primer1 | CAGGTCCAGCTGSTGCAGTCAGG | 1 |
| | | IGHV1-4 | VH1-primer1 | CAGGTCCAGCTGSTGCAGTCAGG | 1 |
| | VH3 | IGHV3-1 | VH3-primer1 | GAGGTGCAGSTGGTGGAGTCTGGG | 3 |
| | | IGHV3-2 | VH3-primer1 | GAGGTGCAGSTGGTGGAGTCTGGG | 3 |
| | | IGHV3-3 | VH3-primer1 | GAGGTGCAGSTGGTGGAGTCTGGG | 3 |
| | | IGHV3-4 | VH3-primer1 | GAGGTGCAGSTGGTGGAGTCTGGG | 3 |
| | | IGHV3-5 | VH3-primer1 | GAGGTGCAGSTGGTGGAGTCTGGG | 3 |
| | | IGHV3-6 | VH3-primer1 | GAGGTGCAGSTGGTGGAGTCTGGG | 3 |
| | VH4 | IGHV4-1 | VH4-primer1 | CAGGTGCAGCTGCAGGAGTCGGG | 5 |
| | | IGHV4-2 | VH4-primer1 | CAGGTGCAGCTGCAGGAGTCGGG | 5 |
| | | IGHV4-3 | VH4-primer1 | CAGGTGCAGCTGCAGGAGTCGGG | 5 |
| | VH5 | IGHV5-1 | VH5-primer1 | CAGGTGMAGCTGGAGCAGCCTGTGG | 6 |
| | VH7 | IGHV7-1 | VH7-primer1 | CAGGTGCAGCTGGTGCAGTCTGCG | 7 |

FIG. 13A

VL1-primers

| | Germline VL1 name | Primer name | Primer sequences | SEQ ID NO: |
|---|---|---|---|---|
| Lama pacos | Lpacos IGLV1-1*01 | VL1-primer1 | CAGTCTGTGCTGACTCAGCYGCCCTC | 9 |
| | Lpacos IGLV1-1*02 | VL1-primer1 | CAGTCTGTGCTGACTCAGCYGCCCTC | 9 |
| | Lpacos IGLV1-2*01 | VL1-primer1 | CAGTCTGTGCTGACTCAGCYGCCCTC | 9 |
| | Lpacos IGLV1-2*02 | VL1-primer1 | CAGTCTGTGCTGACTCAGCYGCCCTC | 9 |
| | Lpacos IGLV1-3 | VL1-primer2 | CAGTCTGTGCTGACTCAGCYGTCCTC | 10 |
| | Lpacos IGLV1-4*01 | VL1-primer1 | CAGTCTGTGCTGACTCAGCYGCCCTC | 9 |
| | Lpacos IGLV1-4*02 | VL1-primer1 | CAGTCTGTGCTGACTCAGCYGCCCTC | 9 |
| | Lpacos IGLV1-5*01 | VL1-primer5 | CAGTCTGTGCCGATTCAGCCGTCCTC | 13 |
| | Lpacos IGLV1-5*02 | VL1-primer5 | CAGTCTGTGCCGATTCAGCCGTCCTC | 13 |
| | Lpacos IGLV1-6 | VL1-primer2 | CAGTCTGTGCTGACTCAGCYGTCCTC | 10 |
| | Lpacos IGLV1-7 | VL1-primer6 | AAGTCTGTGCCGACTCAGCTGCCCTT | 14 |
| | Lpacos IGLV1-8 | VL1-primer4 | CAGTCTGGGCTGACACAGGAAGCCTC | 12 |
| | Lpacos IGLV1-9 | N/A | N/A | |
| | Lpacos IGLV1-10 | VL1-primer3 | CAGTCTGTGCTGACCCAGCKGGCCTC | 11 |
| | Lpacos IGLV1-11 | N/A | N/A | |
| Camel ferus | Camel IGLV1-1 | VL1-primer1 | CAGTCTGTGCTGACTCAGCYGCCCTC | 9 |
| | Camel IGLV1-2 | VL1-primer1 | CAGTCTGTGCTGACTCAGCYGCCCTC | 9 |
| | Camel IGLV1-3 | VL1-primer1 | CAGTCTGTGCTGACTCAGCYGCCCTC | 9 |
| | Camel IGLV1-4 | VL1-primer2 | CAGTCTGTGCTGACTCAGCYGTCCTC | 10 |
| | Camel IGLV1-5 | VL1-primer1 | CAGTCTGTGCTGACTCAGCYGCCCTC | 9 |
| | Camel IGLV1-6 | VL1-primer1 | CAGTCTGTGCTGACTCAGCYGCCCTC | 9 |
| | Camel IGLV1-7 | VL1-primer7 | CAGACTGTGGTGACCCAGGAGCCGTC | 15 |
| | Camel IGLV1-8 | N/A | N/A | |
| | Camel IGLV1-9 | VL1-primer4 | CAGTCTGGGCTGACACAGGAAGCCTC | 12 |
| | Camel IGLV1-10 | N/A | N/A | |
| | Camel IGLV1-11 | VL1-primer3 | CAGTCTGTGCTGACCCAGCKGGCCTC | 11 |
| | Camel IGLV1-12 | VL1-primer1 | CAGTCTGTGCTGACTCAGCYGCCCTC | 9 |
| | Camel IGLV1-13 | VL1-primer1 | CAGTCTGTGCTGACTCAGCYGCCCTC | 9 |
| | Camel IGLV1-14 | N/A | N/A | |
| | Camel IGLV1-15 | N/A | N/A | |
| Lama glama | Llama IGLV1-1 | VL1-primer1 | CAGTCTGTGCTGACTCAGCYGCCCTC | 9 |
| | Llama IGLV1-2 | VL1-primer1 | CAGTCTGTGCTGACTCAGCYGCCCTC | 9 |
| | Llama IGLV1-3 | VL1-primer2 | CAGTCTGTGCTGACTCAGCYGTCCTC | 10 |
| | Llama IGLV1-4 | VL1-primer1 | CAGTCTGTGCTGACTCAGCYGCCCTC | 9 |
| | Llama IGLV1-5 | VL1-primer1 | CAGTCTGTGCTGACTCAGCYGCCCTC | 9 |
| | Llama IGLV1-6 | VL1-primer2 | CAGTCTGTGCTGACTCAGCYGTCCTC | 10 |
| | Llama IGLV1-7 | VL1-primer6 | AAGTCTGTGCCGACTCAGCTGCCCTT | 14 |
| | Llama IGLV1-8 | VL1-primer1 | CAGTCTGTGCTGACTCAGCYGCCCTC | 9 |
| | Llama IGLV1-9 | N/A | N/A | |
| | Llama IGLV1-10 | N/A | N/A | |
| | Llama IGLV1-11 | VL1-primer4 | CAGTCTGGGCTGACACAGGAAGCCTC | 12 |
| | Llama IGLV1-12 | N/A | N/A | |

FIG. 13B

VL2-primers

| | Germline VL2 name | Primer name | Primer sequences | SEQ ID NO: |
|---|---|---|---|---|
| Lama pacos | Lpacos IGLV2-1 | IGLV2-primer2 | CAGTCTGCCSTGACTCAGCCTYCCTC | 17 |
| | Lpacos IGLV2-2*01 | IGLV2-primer2 | CAGTCTGCCSTGACTCAGCCTYCCTC | 17 |
| | Lpacos IGLV2-2*02 | IGLV2-primer1 | AACTCTGCCCTGACTCAGCCTCCATC | 16 |
| | Lpacos IGLV2-3 | IGLV2-primer2 | CAGTCTGCCSTGACTCAGCCTYCCTC | 17 |
| | Lpacos IGLV2-4 | IGLV2-primer2 | CAGTCTGCCSTGACTCAGCCTYCCTC | 17 |
| | Lpacos IGLV2-5 | IGLV2-primer2 | CAGTCTGCCSTGACTCAGCCTYCCTC | 17 |
| | Lpacos IGLV2-6 | IGLV2-primer1 | AACTCTGCCCTGACTCAGCCTCCATC | 16 |
| | Lpacos IGLV2-7 | IGLV2-primer3 | CAGTCTGCCYTGACTCAGCCTCCCTT | 18 |
| | Lpacos IGLV2-8 | N/A | N/A | |
| | Lpacos IGLV2-9 | IGLV2-primer3 | CAGTCTGCCYTGACTCAGCCTCCCTT | 18 |
| | Lpacos IGLV2-10 | N/A | N/A | |
| | Lpacos IGLV2-11 | N/A | N/A | |
| Camel ferus | Camel IGLV2-1 | IGLV2-primer2 | CAGTCTGCCSTGACTCAGCCTYCCTC | 17 |
| | Camel IGLV2-2 | IGLV2-primer2 | CAGTCTGCCSTGACTCAGCCTYCCTC | 17 |
| | Camel IGLV2-3 | IGLV2-primer3 | CAGTCTGCCYTGACTCAGCCTCCCTT | 18 |
| | Camel IGLV2-4 | IGLV2-primer3 | CAGTCTGCCYTGACTCAGCCTCCCTT | 18 |
| | Camel IGLV2-5 | IGLV2-primer2 | CAGTCTGCCSTGACTCAGCCTYCCTC | 17 |
| | Camel IGLV2-6 | IGLV2-primer4 | CAGTCTGCCCTGATTCAGCCTCTCTC | 19 |
| | Camel IGLV2-7 | IGLV2-primer3 | CAGTCTGCCYTGACTCAGCCTCCCTT | 18 |
| | Camel IGLV2-8 | IGLV2-primer2 | CAGTCTGCCSTGACTCAGCCTYCCTC | 17 |
| | Camel IGLV2-9 | N/A | N/A | |
| Lama glama | Llama IGLV2-1 | IGLV2-primer2 | CAGTCTGCCSTGACTCAGCCTYCCTC | 17 |
| | Llama IGLV2-2*01 | IGLV2-primer1 | AACTCTGCCCTGACTCAGCCTCCATC | 16 |
| | Llama IGLV2-2*02 | IGLV2-primer1 | AACTCTGCCCTGACTCAGCCTCCATC | 16 |
| | Llama IGLV2-3 | IGLV2-primer2 | CAGTCTGCCSTGACTCAGCCTYCCTC | 17 |
| | Llama IGLV2-4 | IGLV2-primer2 | CAGTCTGCCSTGACTCAGCCTYCCTC | 17 |
| | Llama IGLV2-5*01 | IGLV2-primer2 | CAGTCTGCCSTGACTCAGCCTYCCTC | 17 |
| | Llama IGLV2-5*02 | IGLV2-primer2 | CAGTCTGCCSTGACTCAGCCTYCCTC | 17 |
| | Llama IGLV2-6 | IGLV2-primer1 | AACTCTGCCCTGACTCAGCCTCCATC | 16 |
| | Llama IGLV2-7 | IGLV2-primer2 | CAGTCTGCCSTGACTCAGCCTCCCTC | 17 |

VL3-primers

| | Germline VL3 name | Primer name | Primers 25-26bp | SEQ ID NO: |
|---|---|---|---|---|
| Lama pacos | Lpacos IGLV3-1 | IGLV3-primer3 | TCCTACGAACTGACTCAGWCACCCTC | 22 |
| | Lpacos IGLV3-2 | IGLV3-primer3 | TCCTACGAACTGACTCAGWCACCCTC | 22 |
| | Lpacos IGLV3-3 | IGLV3-primer5 | TCCTATGAGCTGACCCAGCAGGCTTC | 24 |
| | Lpacos IGLV3-4 | IGLV3-primer1 | TCTTCTGCACTGACTCAGCCCTCCGC | 20 |
| | Lpacos IGLV3-5 | IGLV3-primer1 | TCTTCTGCACTGACTCAGCCCTCCGC | 20 |
| | Lpacos IGLV3-6 | IGLV3-primer1 | TCTTCTGCACTGACTCAGCCCTCCGC | 20 |
| | Lpacos IGLV3-7 | IGLV3-primer1 | TCTTCTGCACTGACTCAGCCCTCCGC | 20 |
| | Lpacos IGLV3-8 | IGLV3-primer4 | GCCTCTTCAGTGACTCAGCCCTCCGC | 23 |
| | Lpacos IGLV3-9 | IGLV3-primer2 | TCTTCTGCASTGACTCAGCCCTCCA | 21 |
| | Lpacos IGLV3-10 | IGLV3-primer2 | TCTTCTGCASTGACTCAGCCCTCCA | 21 |
| | Lpacos IGLV3-11 | IGLV3-primer2 | TCTTCTGCASTGACTCAGCCCTCCA | 21 |
| | Lpacos IGLV3-12 | IGLV3-primer1 | TCTTCTGCACTGACTCAGCCCTCCGC | 20 |
| | Lpacos IGLV3-13 | IGLV3-primer1 | TCTTCTGCACTGACTCAGCCCTCCGC | 20 |
| | Lpacos IGLV3-14 | IGLV3-primer1 | TCTTCTGCACTGACTCAGCCCTCCGC | 20 |
| | Lpacos IGLV3-15 | IGLV3-primer1 | TCTTCTGCACTGACTCAGCCCTCCGC | 20 |
| | Lpacos IGLV3-16 | IGLV3-primer1 | TCTTCTGCACTGACTCAGCCCTCCGC | 20 |
| | Lpacos IGLV3-17 | N/A | N/A | |
| | Lpacos IGLV3-18 | N/A | N/A | |
| | Lpacos IGLV3-19 | N/A | N/A | |
| | Lpacos IGLV3-20 | N/A | N/A | |
| | Lpacos IGLV3-21 | N/A | N/A | |

FIG. 13C

| | Germline VL3 name | Primer name | Primer sequences | SEQ ID NO: |
|---|---|---|---|---|
| | Lpacos IGLV3-22 | N/A | N/A | |
| | Lpacos IGLV3-23 | IGLV3-primer3 | TCCTACGAACTGACTCAGWCACCCTC | 22 |
| | Lpacos IGLV3-24 | N/A | N/A | |
| | Lpacos IGLV3-25 | IGLV3-primer2 | TCTTCTGCASTGACTCAGCCCTCCA | 21 |
| Camel ferus | Camel IGLV3-1 | IGLV3-primer3 | TCCTACGAACTGACTCAGWCACCCTC | 22 |
| | Camel IGLV3-2 | IGLV3-primer1 | TCTTCTGCACTGACTCAGCCCTCCGC | 20 |
| | Camel IGLV3-3 | IGLV3-primer2 | TCTTCTGCASTGACTCAGCCCTCCA | 21 |
| | Camel IGLV3-4 | IGLV3-primer1 | TCTTCTGCACTGACTCAGCCCTCCGC | 20 |
| | Camel IGLV3-5 | IGLV3-primer2 | TCTTCTGCASTGACTCAGCCCTCCA | 21 |
| | Camel IGLV3-6 | IGLV3-primer2 | TCTTCTGCASTGACTCAGCCCTCCA | 21 |
| | Camel IGLV3-7 | N/A | N/A | |
| | Camel IGLV3-8 | N/A | N/A | |
| | Camel IGLV3-9 | N/A | N/A | |
| Lama glama | Llama IGLV3-1 | IGLV3-primer3 | TCCTACGAACTGACTCAGWCACCCTC | 22 |
| | Llama IGLV3-2 | IGLV3-primer3 | TCCTACGAACTGACTCAGWCACCCTC | 22 |
| | Llama IGLV3-3 | IGLV3-primer3 | TCCTACGAACTGACTCAGWCACCCTC | 22 |
| | Llama IGLV3-4 | IGLV3-primer2 | TCTTCTGCASTGACTCAGCCCTCCA | 21 |
| | Llama IGLV3-5 | IGLV3-primer1 | TCTTCTGCACTGACTCAGCCCTCCGC | 20 |
| | Llama IGLV3-6 | IGLV3-primer1 | TCTTCTGCACTGACTCAGCCCTCCGC | 20 |
| | Llama IGLV3-7 | N/A | N/A | |
| | Llama IGLV3-8 | IGLV3-primer1 | TCTTCTGCACTGACTCAGCCCTCCGC | 20 |
| | Llama IGLV3-9 | IGLV3-primer1 | TCTTCTGCACTGACTCAGCCCTCCGC | 20 |
| | Llama IGLV3-10 | IGLV3-primer1 | TCTTCTGCACTGACTCAGCCCTCCGC | 20 |

VL4-primers

| | Germline VL4 name | Primer name | Primer sequences | SEQ ID NO: |
|---|---|---|---|---|
| Lama pacos | Lpacos IGLV4-1 | IGLV4-primer1 | CAGCCTGTGCTGTCGCAGCCACCC | 25 |
| | Lpacos IGLV4-2 | IGLV4-primer5 | GCGCCTGTGCTGACCCAGCCCCCG | 29 |
| | Lpacos IGLV4-3 | IGLV4-primer5 | GCGCCTGTGCTGACCCAGCCCCCG | 29 |
| | Lpacos IGLV4-4 | IGLV4-primer5 | GCGCCTGTGCTGACCCAGCCCCCG | 29 |
| | Lpacos IGLV4-5 | IGLV4-primer6 | GAGCCTGTGCTGACCCAGCCCYCG | 30 |
| | Lpacos IGLV4-6 | N/A | N/A | |
| | Lpacos IGLV4-7 | IGLV4-primer3 | CAGACTGTGCTGACGCAGCCGCCC | 27 |
| Camel ferus | Camel IGLV4-1 | IGLV4-primer1 | CAGCCTGTGCTGTCGCAGCCACCC | 25 |
| | Camel IGLV4-2 | IGLV4-primer5 | GCGCCTGTGCTGACCCAGCCCCCG | 29 |
| | Camel IGLV4-3 | N/A | N/A | |
| | Camel IGLV4-4*01 | IGLV4-primer4 | CAGCCTGAGCTGACACAGCCGCCC | 28 |
| | Camel IGLV4-4*02 | IGLV4-primer4 | CAGCCTGAGCTGACACAGCCGCCC | 28 |
| | Camel IGLV4-5 | N/A | N/A | |
| | Camel IGLV4-6 | N/A | N/A | |
| | Camel IGLV4-7 | IGLV4-primer2 | CAGCCTGTGCTGATGCAGCTGCCC | 26 |
| Lama glama | Llama IGLV4-1 | IGLV4-primer1 | CAGCCTGTGCTGTCGCAGCCACCC | 25 |
| | Llama IGLV4-2 | IGLV4-primer1 | CAGCCTGTGCTGTCGCAGCCACCC | 25 |
| | Llama IGLV4-3 | IGLV4-primer5 | GCGCCTGTGCTGACCCAGCCCCCG | 29 |
| | Llama IGLV4-4 | IGLV4-primer6 | GAGCCTGTGCTGACCCAGCCCYCG | 30 |
| | Llama IGLV4-5 | IGLV4-primer6 | GAGCCTGTGCTGACCCAGCCCYCG | 30 |
| | Llama IGLV4-6 | IGLV4-primer5 | GCGCCTGTGCTGACCCAGCCCCCG | 29 |
| | Llama IGLV4-7 | IGLV4-primer3 | CAGACTGTGCTGACGCAGCCGCCC | 27 |

FIG. 13D
VL5-primers

| | Germline VL5 name | Primer name | Primer sequences | SEQ ID NO: |
|---|---|---|---|---|
| Lama pacos | Lpacos IGLV5- | VL5-primer6 | CAGCCTGTGCTGACTCAGCYGCCCTC | 36 |
| | Lpacos IGLV5- | VL5-primer6 | CAGCCTGTGCTGACTCAGCYGCCCTC | 36 |
| | Lpacos IGLV5- | VL5-primer5 | CAGCCTGTGCTGACTCAGCTGTCCTC | 35 |
| | Lpacos IGLV5- | VL5-primer5 | CAGCCTGTGCTGACTCAGCTGTCCTC | 35 |
| | Lpacos IGLV5- | VL5-primer7 | CAGCCTGTGGGGACTCAGCTGCCCTC | 37 |
| | Lpacos IGLV5- | VL5-primer7 | CAGCCTGTGGGGACTCAGCTGCCCTC | 37 |
| | Lpacos IGLV5- | VL5-primer6 | CAGCCTGTGCTGACTCAGCYGCCCTC | 36 |
| | Lpacos IGLV5- | VL5-primer2 | CAGCTTGTGSTGACTCAGCCGCCCTC | 32 |
| | Lpacos IGLV5-5 | VL5-primer8 | CAGCTTGTGGAGACTCAGCTGTCTTT | 38 |
| | Lpacos IGLV5-6 | VL5-primer6 | CAGCCTGTGCTGACTCAGCYGCCCTC | 36 |
| | Lpacos IGLV5-7 | N/A | N/A | |
| | Lpacos IGLV5-8 | VL5-primer2 | CAGCTTGTGSTGACTCAGCCGCCCTC | 32 |
| | Lpacos IGLV5- | VL5-primer1 | CAGCATGTGGTGACTCAGCCGCCCTC | 31 |
| | Lpacos IGLV5- | VL5-primer1 | CAGCATGTGGTGACTCAGCCGCCCTC | 31 |
| | Lpacos IGLV5-10 | VL5-primer4 | CAGCTTGTGCWGACTCAGCTGCCCTC | 34 |
| | Lpacos IGLV5- | N/A | N/A | |
| | Lpacos IGLV5- | VL5-primer3 | CAGCTTCTGCTGACTCAGCCGCCCTC | 33 |
| | Lpacos IGLV5-12 | VL5-primer2 | CAGCTTGTGSTGACTCAGCCGCCCTC | 32 |
| | Lpacos IGLV5-13 | VL5-primer2 | CAGCTTGTGSTGACTCAGCCGCCCTC | 32 |
| | Lpacos IGLV5-14 | VL5-primer6 | CAGCCTGTGCTGACTCAGCYGCCCTC | 36 |
| | Lpacos IGLV5-15 | VL5-primer2 | CAGCTTGTGSTGACTCAGCCGCCCTC | 32 |
| | Lpacos IGLV5-16 | N/A | N/A | |
| | Lpacos IGLV5-17 | N/A | N/A | |
| Camel ferus | Camel IGLV5-1 | VL5-primer6 | CAGCCTGTGCTGACTCAGCYGCCCTC | 36 |
| | Camel IGLV5-2 | VL5-primer6 | CAGCCTGTGCTGACTCAGCYGCCCTC | 36 |
| | Camel IGLV5-3 | VL5-primer5 | CAGCCTGTGCTGACTCAGCTGTCCTC | 35 |
| | Camel IGLV5-4 | VL5-primer9 | CAGACTGTGGGGACTCAGCCAGCCTC | 39 |
| | Camel IGLV5-5 | VL5-primer6 | CAGCCTGTGCTGACTCAGCYGCCCTC | 36 |
| | Camel IGLV5-6 | VL5-primer8 | CAGCTTGTGGAGACTCAGCTGTCTTT | 38 |
| | Camel IGLV5-7 | VL5-primer4 | CAGCTTGTGCWGACTCAGCTGCCCTC | 34 |
| | Camel IGLV5-8 | VL5-primer2 | CAGCTTGTGSTGACTCAGCCGCCCTC | 32 |
| | Camel IGLV5-9 | VL5-primer2 | CAGCTTGTGSTGACTCAGCCGCCCTC | 32 |
| | Camel IGLV5-10 | VL5-primer6 | CAGCCTGTGCTGACTCAGCYGCCCTC | 36 |
| | Camel IGLV5-11 | N/A | N/A | |
| | Camel IGLV5-12 | VL5-primer2 | CAGCTTGTGSTGACTCAGCCGCCCTC | 32 |
| | Camel IGLV5-13 | VL5-primer3 | CAGCTTCTGCTGACTCAGCCGCCCTC | 33 |
| | Camel IGLV5-14 | VL5-primer6 | CAGCCTGTGCTGACTCAGCYGCCCTC | 36 |
| | Camel IGLV5-15 | VL5-primer6 | CAGCCTGTGCTGACTCAGCYGCCCTC | 36 |
| | Camel IGLV5-16 | VL5-primer2 | CAGCTTGTGSTGACTCAGCCGCCCTC | 32 |
| | Camel IGLV5-17 | VL5-primer2 | CAGCTTGTGSTGACTCAGCCGCCCTC | 32 |
| | Camel IGLV5-18 | N/A | N/A | |
| | Camel IGLV5-19 | N/A | N/A | |
| Lama glama | Llama IGLV5-1 | VL5-primer6 | CAGCCTGTGCTGACTCAGCYGCCCTC | 36 |
| | Llama IGLV5-2 | VL5-primer5 | CAGCCTGTGCTGACTCAGCTGTCCTC | 35 |
| | Llama IGLV5-3 | VL5-primer7 | CAGCCTGTGGGGACTCAGCTGCCCTC | 37 |
| | Llama IGLV5-4 | VL5-primer8 | CAGCTTGTGGAGACTCAGCTGTCTTT | 38 |
| | Llama IGLV5-5 | VL5-primer1 | CAGCATGTGGTGACTCAGCCGCCCTC | 31 |
| | Llama IGLV5-6 | VL5-primer6 | CAGCCTGTGCTGACTCAGCYGCCCTC | 36 |
| | Llama IGLV5-7 | VL5-primer2 | CAGCTTGTGSTGACTCAGCCGCCCTC | 32 |
| | Llama IGLV5-8*01 | VL5-primer2 | CAGCTTGTGSTGACTCAGCCGCCCTC | 32 |
| | Llama IGLV5-8*02 | VL5-primer2 | CAGCTTGTGSTGACTCAGCCGCCCTC | 32 |
| | Llama IGLV5-9 | VL5-primer2 | CAGCTTGTGSTGACTCAGCCGCCCTC | 32 |
| | Llama IGLV5- | VL5-primer1 | CAGCATGTGGTGACTCAGCCGCCCTC | 31 |
| | Llama IGLV5- | VL5-primer2 | CAGCTTGTGSTGACTCAGCCGCCCTC | 32 |
| | Llama IGLV5-11 | VL5-primer4 | CAGCTTGTGCWGACTCAGCTGCCCTC | 34 |
| | Llama IGLV5-12 | VL5-primer4 | CAGCTTGTGCWGACTCAGCTGCCCTC | 34 |
| | Llama IGLV5-13 | VL5-primer2 | CAGCTTGTGSTGACTCAGCCGCCCTC | 32 |

FIG. 13E

| | Llama IGLV5-14 | VL5-primer2 | CAGCTTGTGSTGACTCAGCCGCCCTC | 32 |
|---|---|---|---|---|
| | Llama IGLV5-15 | VL5-primer6 | CAGCCTGTGCTGACTCAGCYGCCCTC | 36 |
| | Llama IGLV5-16 | VL5-primer2 | CAGCTTGTGSTGACTCAGCCGCCCTC | 32 |
| | Llama IGLV5-17 | VL5-primer6 | CAGCCTGTGCTGACTCAGCYGCCCTC | 36 |
| | Llama IGLV5-18 | VL5-primer3 | CAGCTTCTGCTGACTCAGCCGCCCTC | 33 |
| | Llama IGLV5-19 | VL5-primer3 | CAGCTTCTGCTGACTCAGCCGCCCTC | 33 |
| | Llama IGLV5-20 | VL5-primer3 | CAGCTTCTGCTGACTCAGCCGCCCTC | 33 |

VL6-primers

| Germline VL6 name | Primer name | Primer sequences | SEQ ID NO: |
|---|---|---|---|
| Lpacos IGLV6-1*01 | VL6-primer1 | GAGGTTGTGCTGACTCAGCCCAGCTC | 40 |
| Lpacos IGLV6-1*02 | VL6-primer1 | GAGGTTGTGCTGACTCAGCCCAGCTC | 40 |
| Camel IGLV6-1 | VL6-primer1 | GAGGTTGTGCTGACTCAGCCCAGCTC | 40 |
| Llama IGLV6-1*01 | VL6-primer1 | GAGGTTGTGCTGACTCAGCCCAGCTC | 40 |
| Llama IGLV6-1*02 | VL6-primer1 | GAGGTTGTGCTGACTCAGCCCAGCTC | 40 |

VL7-primers

| Germline VL7 name | Primer Name | Primer sequence | SEQ ID NO: |
|---|---|---|---|
| Camel IGLV7-1 | IGLV7-primer1 (IGLV1- | CAGACTGTGGTGACCCAGGAGCCGTC | 41 |
| Llama IGLV7-1 | IGLV7-primer1 (IGLV1- | CAGACTGTGGTGACCCAGGAGCCGTC | 41 |

VL8-primers

| | Germline VL8 name | Primer name | Primer sequences | SEQ ID NO: |
|---|---|---|---|---|
| Lama pacos | Lpacos IGLV8-1 | VL8-primer2 | CAGACTGTGRTGACCCAGGAGCCATC | 43 |
| | Lpacos IGLV8-2*01 | VL8-primer2 | CAGACTGTGRTGACCCAGGAGCCATC | 43 |
| | Lpacos IGLV8-2*02 | VL8-primer2 | CAGACTGTGRTGACCCAGGAGCCATC | 43 |
| | Lpacos IGLV8-3 | VL8-primer1 (VL1- | CAGACTGTGGTGACCCAGGAGCCGTC | 15 |
| | Lpacos IGLV8-4 | VL8-primer2 | CAGACTGTGRTGACCCAGGAGCCATC | 43 |
| | Lpacos IGLV8-5 | VL8-primer3 | CAGACTGTGGTGACCCAGRAGCCGTC | 44 |
| | Lpacos IGLV8-6 | VL8-primer3 | CAGACTGTGGTGACCCAGRAGCCGTC | 44 |
| | Lpacos IGLV8-7 | VL8-primer1 (VL1- | CAGACTGTGGTGACCCAGGAGCCGTC | 15 |
| | Lpacos IGLV8-8 | VL8-primer1 (VL1- | CAGACTGTGGTGACCCAGGAGCCGTC | 15 |
| | Lpacos IGLV8-9 | VL8-primer1 (VL1- | CAGACTGTGGTGACCCAGGAGCCGTC | 15 |
| | Lpacos IGLV8-10*01 | VL8-primer3 | CAGACTGTGGTGACCCAGRAGCCGTC | 44 |
| | Lpacos IGLV8-10*02 | VL8-primer3 | CAGACTGTGGTGACCCAGRAGCCGTC | 44 |
| | Lpacos IGLV8-11*01 | VL8-primer5 | CAGACTGTGGTGACCCAACAGTCGTT | 46 |
| | Lpacos IGLV8-11*02 | VL8-primer5 | CAGACTGTGGTGACCCAACAGTCGTT | 46 |
| | Lpacos IGLV8-12 | VL8-primer4 | CAGACTGTGGTGACCCAGGTTTCATC | 45 |
| | Lpacos IGLV8-13*01 | VL8-primer2 | CAGACTGTGRTGACCCAGGAGCCATC | 43 |
| | Lpacos IGLV8-13*02 | VL8-primer2 | CAGACTGTGRTGACCCAGGAGCCATC | 43 |
| | Lpacos IGLV8-14*01 | VL8-primer2 | CAGACTGTGRTGACCCAGGAGCCATC | 43 |
| | Lpacos IGLV8-14*02 | VL8-primer2 | CAGACTGTGRTGACCCAGGAGCCATC | 43 |
| Camel ferus | Camel IGLV8-1 | VL8-primer1 (VL1- | CAGACTGTGGTGACCCAGGAGCCGTC | 15 |
| | Camel IGLV8-2 | VL8-primer1 (VL1- | CAGACTGTGGTGACCCAGGAGCCGTC | 15 |
| | Camel IGLV8-3 | VL8-primer1 (VL1- | CAGACTGTGGTGACCCAGGAGCCGTC | 15 |
| | Camel IGLV8-4 | VL8-primer2 | CAGACTGTGRTGACCCAGGAGCCATC | 43 |
| | Camel IGLV8-5 | VL8-primer1 (VL1- | CAGACTGTGGTGACCCAGGAGCCGTC | 15 |
| | Camel IGLV8-6 | VL8-primer1 (VL1- | CAGACTGTGGTGACCCAGGAGCCGTC | 15 |
| | Camel IGLV8-7 | VL8-primer2 | CAGACTGTGRTGACCCAGGAGCCATC | 43 |

FIG. 13F

| | Camel IGLV8-8 | VL8-primer3 | CAGACTGTGGTGACCCAGRAGCCGTC | 44 |
|---|---|---|---|---|
| | Camel IGLV8-9 | VL8-primer3 | CAGACTGTGGTGACCCAGRAGCCGTC | 44 |
| | Camel IGLV8-10 | N/A | N/A | |
| | Camel IGLV8-11 | N/A | N/A | |
| Lama glama | Llama IGLV8-1 | VL8-primer1 (VL1- | CAGACTGTGGTGACCCAGGAGCCGTC | 15 |
| | Llama IGLV8-2 | VL8-primer3 | CAGACTGTGGTGACCCAGRAGCCGTC | 44 |
| | Llama IGLV8-3 | VL8-primer1 (VL1- | CAGACTGTGGTGACCCAGGAGCCGTC | 15 |
| | Llama IGLV8-4 | VL8-primer1 (VL1- | CAGACTGTGGTGACCCAGGAGCCGTC | 15 |
| | Llama IGLV8-5 | VL8-primer4 | CAGACTGTGGTGACCCAGGTTTCATC | 45 |
| | Llama IGLV8-6 | VL8-primer4 | CAGACTGTGGTGACCCAGGTTTCATC | 45 |
| | Llama IGLV8-7 | N/A | N/A | |
| | Llama IGLV8-8 | VL8-primer2 | CAGACTGTGRTGACCCAGGAGCCATC | 43 |

VL9-primers

| | Germline VL9 name | Primer name | Primer sequences | SEQ ID NO: |
|---|---|---|---|---|
| lama pacos | Lpacos IGLV9-1*01 | VL9-primer1 | CAGCCTGTGCTGATGCAGCCGCCCTC | 47 |
| | Lpacos IGLV9-1*02 | VL9-primer1 | CAGCCTGTGCTGATGCAGCCGCCCTC | 47 |
| | Lpacos IGLV9-2 | VL9-primer5 | CAGCCTGTGCCGACACAGTCACCATC | 51 |
| | Lpacos IGLV9-3 | VL9-primer3 | CAGCCTATGCTGACACAGTCGTCCCC | 49 |
| | Lpacos IGLV9-4 | VL9-primer4 | CAGCCTGTGCTGACACAGACGCCCTC | 50 |
| | Lpacos IGLV9-5 | N/A | N/A | |
| Camel Ferus | Camel IGLV9-1 | VL9-primer2 | CAGCCTGTGCTGACACAGTCGCCCTC | 48 |
| | Camel IGLV9-2 | VL9-primer2 | CAGCCTGTGCTGACACAGTCGCCCTC | 48 |
| | Camel IGLV9-3 | VL9-primer1 | CAGCCTGTGCTGATGCAGCCGCCCTC | 47 |
| Lama glama | Llama IGLV9-1 | VL9-primer1 | CAGCCTGTGCTGATGCAGCCGCCCTC | 47 |
| | Llama IGLV9-2 | VL9-primer1 | CAGCCTGTGCTGATGCAGCCGCCCTC | 47 |
| | Llama IGLV9-3 | VL9-primer1 | CAGCCTGTGCTGATGCAGCCGCCCTC | 47 |

VL10-primers

| Germline VL10 name | Primers name | Primer sequences | SEQ ID NO: |
|---|---|---|---|
| Lpacos IGLV10-1*01 | IGLV10-primer1 | CAGGCAWGGCTGACTCAGCCCCRGTC | 52 |
| Lpacos IGLV10-1*02 | IGLV10-primer1 | CAGGCAWGGCTGACTCAGCCCCRGTC | 52 |
| Camel IGLV10-1 | IGLV10-primer1 | CAGGCAWGGCTGACTCAGCCCCRGTC | 52 |
| Camel IGLV10-2 | IGLV10-primer1 | CAGGCAWGGCTGACTCAGCCCCRGTC | 52 |
| Llama IGLV10-1*01 | IGLV10-primer1 | CAGGCAWGGCTGACTCAGCCCCRGTC | 52 |
| Llama IGLV10-1*02 | IGLV10-primer1 | CAGGCAWGGCTGACTCAGCCCCRGTC | 52 |

Figure 14

| | | Germline VK name | Primer name | Primer sequence | SEQ ID NO: |
|---|---|---|---|---|---|
| Lama pacos | VK1 | IGKV1-1 | Vk1-Primer1 | GCTACCCAGRTGACCCAGTCTYCCTCC | 53 |
| | | IGKV1-2 | Vk1-Primer1 | GCTACCCAGRTGACCCAGTCTYCCTCC | 53 |
| | | IGKV1-3*01 | Vk1-Primer1 | GCTACCCAGRTGACCCAGTCTYCCTCC | 53 |
| | | IGKV1-3*02 | Vk1-Primer1 | GCTACCCAGRTGACCCAGTCTYCCTCC | 53 |
| | | IGKV1-4 | Vk1-Primer1 | GCTACCCAGRTGACCCAGTCTYCCTCC | 53 |
| | | IGKV1-5*01 | Vk1-Primer2 | GAAATTGTGCTGACCCAGTCTCCGGCC | 54 |
| | | IGKV1-5*02 | Vk1-Primer2 | GAAATTGTGCTGACCCAGTCTCCGGCC | 54 |
| | VK2 | IGKV2-1 | Vk2-Primer1 | GATTTWGTGCTGACCCAGAYCCCAGGC | 55 |
| | | IGKV2-2 | Vk2-Primer2 | GACGTTGTGCTGACCCAGACCCCAGGC | 56 |
| | | IGKV2-3 | Vk2-Primer2 | GACGTTGTGCTGACCCAGACCCCAGGC | 56 |
| | | IGKV2-4 | Vk2-Primer2 | GACGTTGTGCTGACCCAGACCCCAGGC | 56 |
| | | IGKV2-5 | Vk2-Primer2 | GACGTTGTGCTGACCCAGACCCCAGGC | 56 |
| | | IGKV2-6*01 | Vk2-Primer3 | AACATTGTACTGACCCGTTTTCTAGCC | 57 |
| | | IGKV2-6*02 | Vk2-Primer3 | AACATTGTACTGACCCGTTTTCTAGCC | 57 |
| | VK3 | IGKV3-1 | Vk3-Primer1 | AGCGCTGAGCTGACCCAGACTCCAGCC | 58 |
| | | IGKV3-2*01 | Vk3-Primer2 | CAGATCGCCCTGACTCAGTTTCCAGAA | 59 |
| | | IGKV3-2*02 | Vk3-Primer2 | CAGATCGCCCTGACTCAGTTTCCAGAA | 59 |
| | | IGKV3-3 | Vk3-Primer3 | GGAGAGAATGTGGAGCAGAGTCCTCCC | 60 |
| | | IGKV3-4 | Vk3-Primer3 | GGAGAGAATGTGGAGCAGAGTCCTCCC | 60 |
| | VK4 | IGKV4-1*01 | Vk4-Primer1 | GACATCGTGATGACCCAGTCTCCCAGC | 61 |
| | | IGKV4-1*02 | Vk4-Primer1 | GACATCGTGATGACCCAGTCTCCCAGC | 61 |
| | | IGKV4-2 | Vk4-Primer1 | GACATCGTGATGACCCAGTCTCCCAGC | 61 |
| | VK5 | IGKV5-1 | Vk5-Primer1 | GAAACAGTCCCCACCCAATCTCCAGCA | 62 |
| | VK6 | IGKV6-1 | Vk6-Primer1 | GCGACCRTGCTGACCCAGTCCCCAGCC | 63 |
| Camel ferus | V1 | IGKV1-1 | Vk1-Primer1 | GCTACCCAGRTGACCCAGTCTYCCTCC | 53 |
| | | IGKV1-2 | Vk1-Primer1 | GCTACCCAGRTGACCCAGTCTYCCTCC | 53 |
| | | IGKV1-3 | Vk1-Primer1 | GCTACCCAGRTGACCCAGTCTYCCTCC | 53 |
| | | IGKV1-4 | Vk1-Primer1 | GCTACCCAGRTGACCCAGTCTYCCTCC | 53 |
| | | IGKV1-5 | Vk1-Primer1 | GCTACCCAGRTGACCCAGTCTYCCTCC | 53 |
| | | IGKV1-6 | Vk1-Primer2 | GAAATTGTGCTGACCCAGTCTCCGGCC | 54 |
| | V2 | IGKV2-1 | Vk2-Primer2 | GACGTTGTGCTGACCCAGACCCCAGGC | 54 |
| | | IGKV2-2 | Vk2-Primer1 | GATTTWGTGCTGACCCAGAYCCCAGGC | 55 |
| | | IGKV2-3 | Vk2-Primer2 | GACGTTGTGCTGACCCAGACCCCAGGC | 56 |
| | | IGKV2-4 | Vk2-Primer3 | AACATTGTACTGACCCGTTTTCTAGCC | 57 |
| | V3 | IGKV3-1 | Vk3-Primer1 | AGCGCTGAGCTGACCCAGACTCCAGCC | 58 |
| | | IGKV3-2 | Vk3-Primer2 | CAGATCGCCCTGACTCAGTTTCCAGAA | 59 |
| | V4 | IGKV4-1 | Vk4-Primer1 | GACATCGTGATGACCCAGTCTCCCAGC | 61 |
| | | IGKV4-2 | Vk4-Primer1 | GACATCGTGATGACCCAGTCTCCCAGC | 61 |
| | V5 | IGKV5-1 | Vk5-Primer1 | GAAACAGTCCCCACCCAATCTCCAGCA | 62 |
| | V6 | IGKV6-1 | Vk6-Primer1 | GCGACCRTGCTGACCCAGTCCCCAGCC | 63 |
| Lama glama | V1 | IGKV1-1 | Vk1-Primer1 | GCTACCCAGRTGACCCAGTCTYCCTCC | 53 |
| | V2 | IGKV2-1*01 | Vk2-Primer2 | GACGTTGTGCTGACCCAGACCCCAGGC | 56 |
| | | IGKV2-1*02 | Vk2-Primer2 | GACGTTGTGCTGACCCAGACCCCAGGC | 56 |
| | | IGKV2-1*03 | Vk2-Primer2 | GACGTTGTGCTGACCCAGACCCCAGGC | 56 |
| | | IGKV2-2*01 | Vk2-Primer2 | GACGTTGTGCTGACCCAGACCCCAGGC | 56 |
| | | IGKV2-2*02 | Vk2-Primer2 | GACGTTGTGCTGACCCAGACCCCAGGC | 56 |
| | | IGKV2-3*01 | Vk2-Primer2 | GACGTTGTGCTGACCCAGACCCCAGGC | 56 |
| | | IGKV2-3*02 | Vk2-Primer2 | GACGTTGTGCTGACCCAGACCCCAGGC | 56 |
| | | IGKV2-4*01 | Vk2-Primer2 | GACGTTGTGCTGACCCAGACCCCAGGC | 56 |
| | | IGKV2-4*02 | Vk2-Primer2 | GACGTTGTGCTGACCCAGACCCCAGGC | 56 |
| | | IGKV2-4*03 | Vk2-Primer2 | GACGTTGTGCTGACCCAGACCCCAGGC | 56 |
| | | IGKV2-5 | Vk2-Primer3 | AACATTGTACTGACCCGTTTTCTAGCC | 57 |
| | V4 | IGKV4-1 | Vk4-Primer1 | GACATCGTGATGACCCAGTCTCCCAGC | 61 |
| | V5 | IGKV5-1 | Vk5-Primer1 | GAAACAGTCCCCACCCAATCTCCAGCA | 62 |
| | V6 | IGKV6-1*01 | Vk6-Primer1 | GCGACCRTGCTGACCCAGTCCCCAGCC | 63 |
| | | IGKV6-1*02 | Vk6-Primer1 | GCGACCRTGCTGACCCAGTCCCCAGCC | 63 |

Figure 15

```
VH1-primer1        CAG GTC CAG CTG STG CAG TCA GG     SEQ ID NO: 1
Lpacos-IGHV1-2     ... ... ... ... G.. ... ... ..    SEQ ID NO: 497
Lpacos-IGHV1-3*01  ... ... ... ... G.. ..G ... ..    SEQ ID NO: 497
Camel_IGHV1-4      ... ... ... ... G.. ..G ..T ..    SEQ ID NO: 498
Camel_IGHV1-3      ... ... ... ... C.. ..G ..T ..    SEQ ID NO: 499
Lpacos_IGHV1-4     ... ... ... ... C.. ..G ..T ..    SEQ ID NO: 499
```

HIGHLY DIVERSE COMBINATORIAL ANTIBODY LIBRARIES

RELATED APPLICATIONS

This application is a 371 filing of International Application No. PCT/EP2013/068110, filed Sep. 2, 2013, which claims priority to U.S. Patent Application No. 61/695,819, filed Aug. 31, 2012, the contents of each of which are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 564678AGX5-020US_SL.txt. The text file is 405,504 bytes, was created on Mar. 28, 2017, and is being submitted electronically via EFS-Web.

BACKGROUND OF THE INVENTION

1. Field of the Invention

The invention relates generally to antibody libraries obtained from Camelid species, and more in particular to Camelid antibody libraries containing families of chains corresponding to those used in wild type human antibodies.

2. Description of the Related Art

With the advent of display methods, such as ribosome display, phage display and cell surface display, antibody libraries have become increasingly important resources for antibody research and development. Antibody libraries differ in design and means of construction. The most important libraries are those that were developed for the identification and isolation of therapeutic antibodies. An overview is provided by Ponsel et al., "*High Affinity, Developability and Functional Size: The Holy Grail of Combinatorial Antibody Library Generation*," Molecules 2011, 16, 3675-3700.

Nature uses somatic hypermutation (SHM) to create high-affinity antibodies. A number of affinity maturation techniques have been developed to mimic SHM. Maturation techniques generally aim to introduce a certain degree of diversity into selected, moderate affinity candidates, followed by repeated selection under progressively increased selective pressure. It is desirable to provide a library that offers antibodies with high pre-maturation affinities. According to Perelson et al., affinities that can be obtained directly (i.e., without affinity maturation) from a combinatorial antibody library correlate generally with the size of the library (Perelson, A. S.; Oster, G. F. Theoretical studies of clonal selection: Minimal antibody repertoire size and reliability of self-non-self discrimination. *J. Theor. Biol.* 1979, 81, 645-670).

The affinity/library size correlation can be easily understood from the perspective of probabilities: the larger the library, the greater the probability that it can generate a high-affinity antibody from its available building blocks. Size alone is not the answer, however; quality of the library is at least as important. As stated by Ponsel et al., "Functional library size . . . matters more than absolute library size." (Ponsel et al., supra, at page 3676).

Nature relies on random combinations of antibody building blocks, in particular heavy chains ($V_H$) and light chains ($V_L$). Human antibody generation, for example, uses 7 $V_H$ families and 16 $V_L$ families (10 lambda families and 6 kappa families), which greatly contributes to the diversity of human antibodies. It is desirable for antibody libraries to contain significant numbers of antibody families so as to approach the diversity encountered in nature.

Naïve antibody libraries constructed from antibodies obtained from healthy human donors in principle contain the full contingent of human antibody chains. As compared to immune libraries, naïve libraries are less suitable for the development of high-affinity therapeutic antibodies. Moreover, it has been found that an important portion of the chain diversity of naïve libraries is lost under the selective pressures of standard screening and enrichment protocols.

Immune libraries constructed from antibodies obtained from infected human beings have the potential of producing high-affinity therapeutic antibodies. Such libraries might be expected to contain the full contingent of human antibody chains. However, the immune systems of infected human donors are often severely impaired, resulting in low quality immune libraries. Indeed, therapeutic antibodies of interest almost by definition deal with diseases that are characterized by weakened immune systems in the patients.

In many cases it is not possible to obtain antigen-specific antibodies through immunization of healthy human donors. Immunization with life threatening or toxic antigens is ethically not possible. Other antigens do not trigger a robust immune response in humans, or no immune response at all.

Antigen-specific antibodies can be obtained via immunization of laboratory animals, such as mice or rats. Such animals tend to be heavily inbred, however, which reduces the diversity of the immune response. Moreover, murine antibodies share only a limited number of antibody chain families with the human germline.

Dreier et al., U.S. Patent Application Publication No. 2011/0300140, Dec. 8, 2011, disclose a method for generating high-affinity antibodies via immunization of a Camelid species, *Lama glama*. The document reports isolation of Vλ chains in the families lambda 3, 5, and 8. No Vκ chains are reported.

Dreier et al, U.S. Patent Application Publication No. 2011/0165621, Jul. 7, 2011 discloses methods for humanization of antibodies obtained via immunization of Camelid species. The document proposes humanization protocols for chains of the following families: heavy chains: VH1, VH3, and VH4; Vlambda chains: Vλ1, Vλ2, Vλ3, Vλ5, and Vλ8; and Vkappa chains Vκ1, Vκ2, and Vκ4.

Schofield et al., "*Application of Phage Display to High Throughput Antibody Generation and Characterization*," Genome Biol. (2007), reports on a high quality phage display library containing over 1010 human antibodies. The publication provides an overview of the usage frequencies of the various antibody chains. Vκ1 and Vλ6 are the most frequently used light chains.

Thus, there is a need for antibody libraries from non-human animals in which a large number of human antibody chain families are represented.

There is a particular need for antibody libraries from non-human animals in which the human antibody chain Vλ6 is represented.

BRIEF SUMMARY OF THE INVENTION

The present invention relates to an antibody library derived from a Camelid species, which library contains antibody chains belonging to at least one of the following human antibody chain families: VH6; Vκ3; and Vλ6. Preferred are antibody libraries, which contain antibody chains belonging to the human Vλ6 family.

BRIEF DESCRIPTION OF THE FIGURES

Figure 8B:
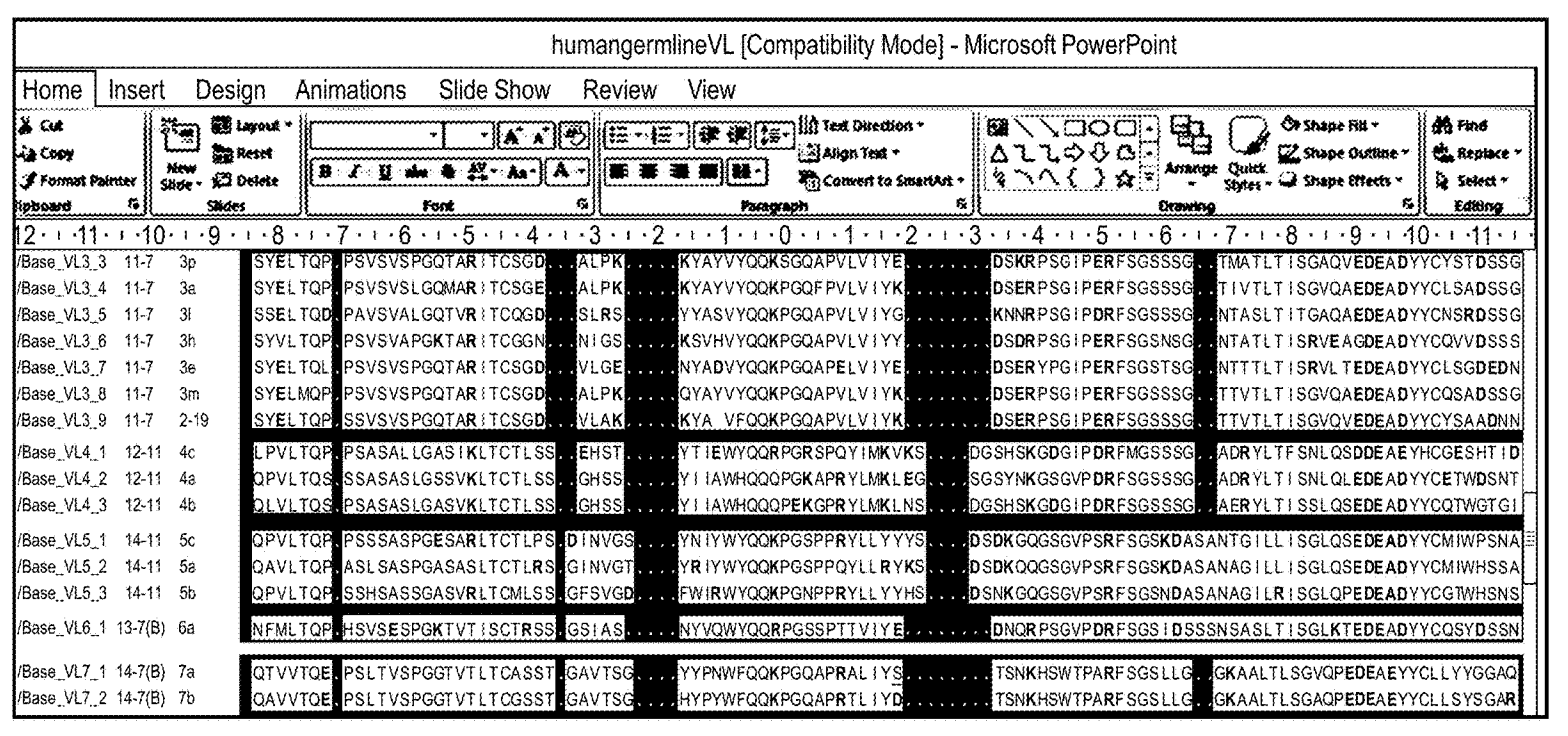

FIGS. 8A and 8B are a representation of Vλ germline6. The four sequences shown in FIG. 8A correspond, from top to bottom, to SEQ ID NOs: 500-503, respectively. The sixteen sequences shown in FIG. 8B correspond, from top to bottom, to SEQ ID NOs: 504-518 and 388, respectively.

FIG. 9A-9C is an alignment of camelid VH germlines genes per VH family (VH1, VH3, VH4, VH5 and VH7) referred to human VH family and germline gene counterparts. % Identity illustrates the percentage of identical amino acids (dots) of each of the Camel (Camel ferus) and Llama (Lama pacos or lama vicugna) frameworks (FR1+FR2+FR3) of the VH germline shared with a reference FR amino acid sequences (ref), here human VH germline counterpart.

FIG. 10A-10L is an alignment of camelid Vλ germlines genes per Vλ family (Vλ1, Vλ2, Vλ3, Vλ4, Vλ5, Vλ6, Vλ7, Vλ8, Vλ9 and Vλ10) referred to human Vλ family and germline gene counterparts. % identity illustrates the percentage of identical amino acids (dots) of each of the Camel (Camel ferus) and Llama (Lama pacos or lama vicugna) frameworks (FR1+FR2+FR3) of the Vλ germline shared with a reference FR amino acid sequences (ref), here human Vλ germline counterpart.

FIG. 11A-11C is an alignment of the camelid Vκ families with the corresponding human germline % Identity illustrates the percentage of identical amino acids (dots) of each of the Camel (Camel ferus) and Llama (Lama pacos or vicugna) frameworks (FR1+FR2+FR3) Vκ germline shared with a reference FR amino acid sequences (ref), here a human Vκgermline counterpart.

FIG. 12A-12B shows camelid (Lama pacos and Camelus ferus) VH genes and the corresponding primers.

FIG. 13A-13F shows camelid (Lama pacos, Camelus ferus and Lama glama) Vλ genes and the corresponding primers.

FIG. 14 shows camelid (Lama pacos, Camelus ferus and Lama glama) Vκgenes and the corresponding primers.

FIG. 15 shows an example of alignment of VH1-primer1 with the first 23 bp of VH1 FR1. This example of alignment illustrates how primers, specific for a V family amplification are designed. A V family specific primer is generated by aligning all Framework 1, FR1, of V germline genes belonging to the same family (here an example for VH1 family) All the FR1 family V specific are extracted from all found V germline sequences collected and annotated from Lama pacos WGS and HTG, Camel ferus WGS, and any available sequence database or unpublished or published literature. WGS stands for Whole Genome Shotgun sequencing projects and HTG or HTGS stand for High-Throughput Genomic Sequences. Dots represent identical nucleotide compared to a reference sequence, here in this example represented by VH1-primer1. Here the VH1-primer1 is a degenerated primer allowing at the position 13 to anneal with G or C; S represents G/C for primer synthesis.

DETAILED DESCRIPTION OF THE INVENTION

Figure 1:
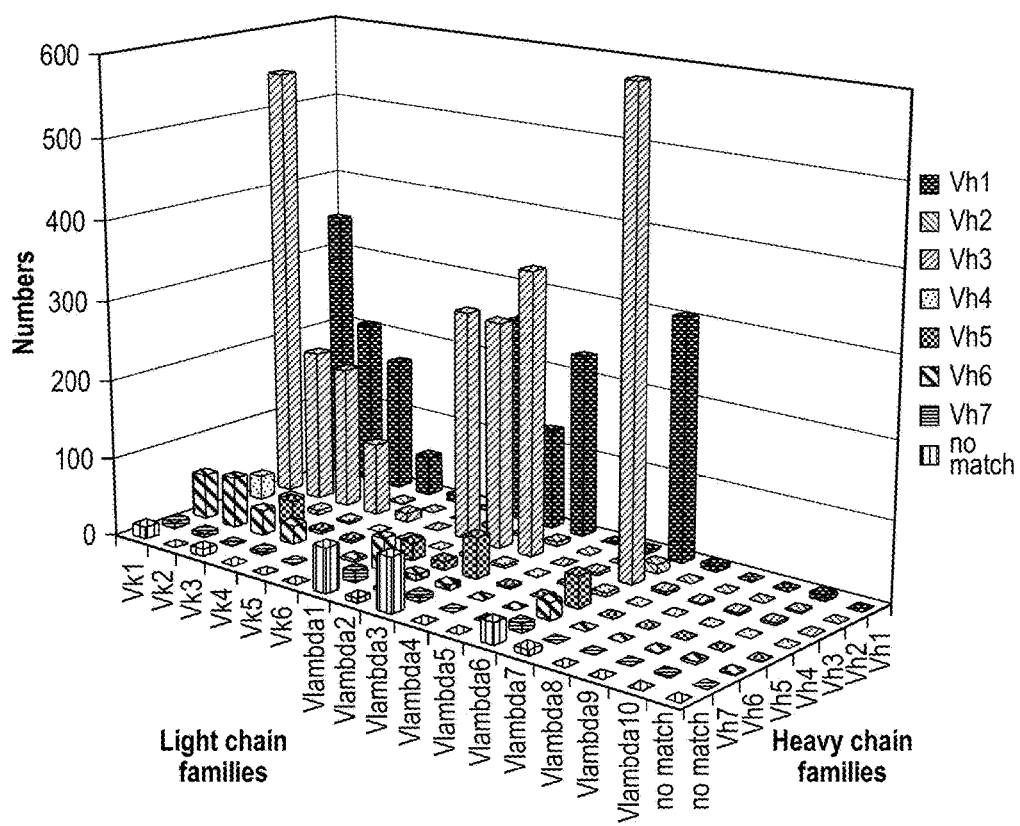
FIG. 1 is a graphic representation of usage frequencies of human chain families present in the library of Schofield et al., supra. Source: openi.nlm.nih.gov/detailedresult.php?img=2258204_gb-2007-8-11-r254-3&query=the&fields=all&favor=none&it=none&sub=none&uniq=0&sp=none&req=4&simCollection=2583049_pone.0003793.g005&npos=35&prt=3.
Figure 2:
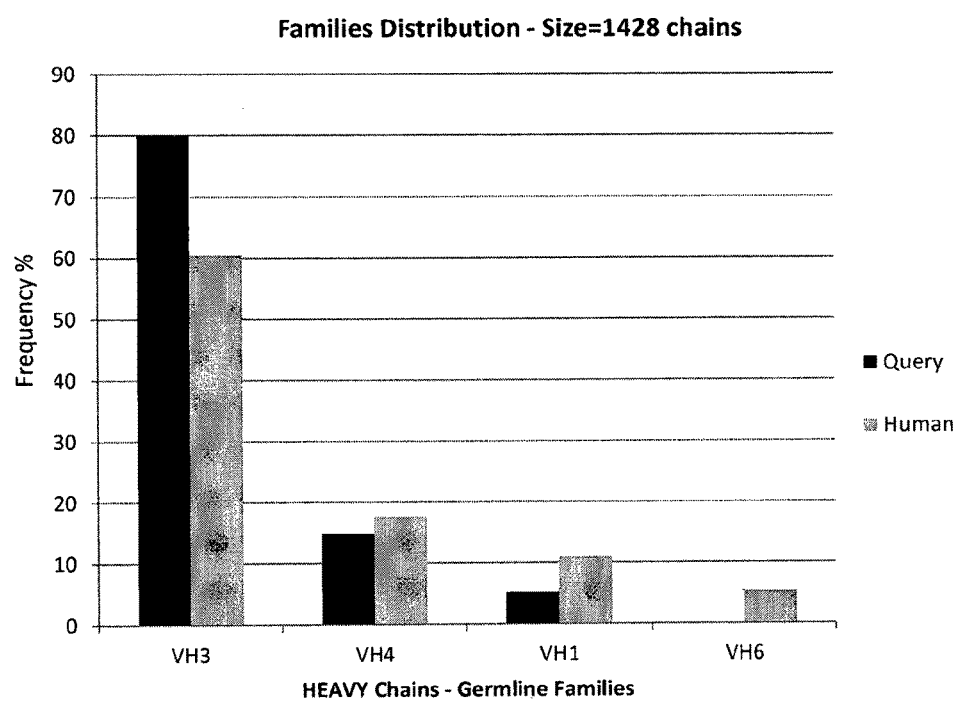
FIG. 2 is a graphic representation of the usage of human heavy chain families in a Camelid antibody library of the present invention (left hand bar of each pair), compared to the usage of the heavy chain families in human antibodies (right hand bar of each pair).
Figure 3:
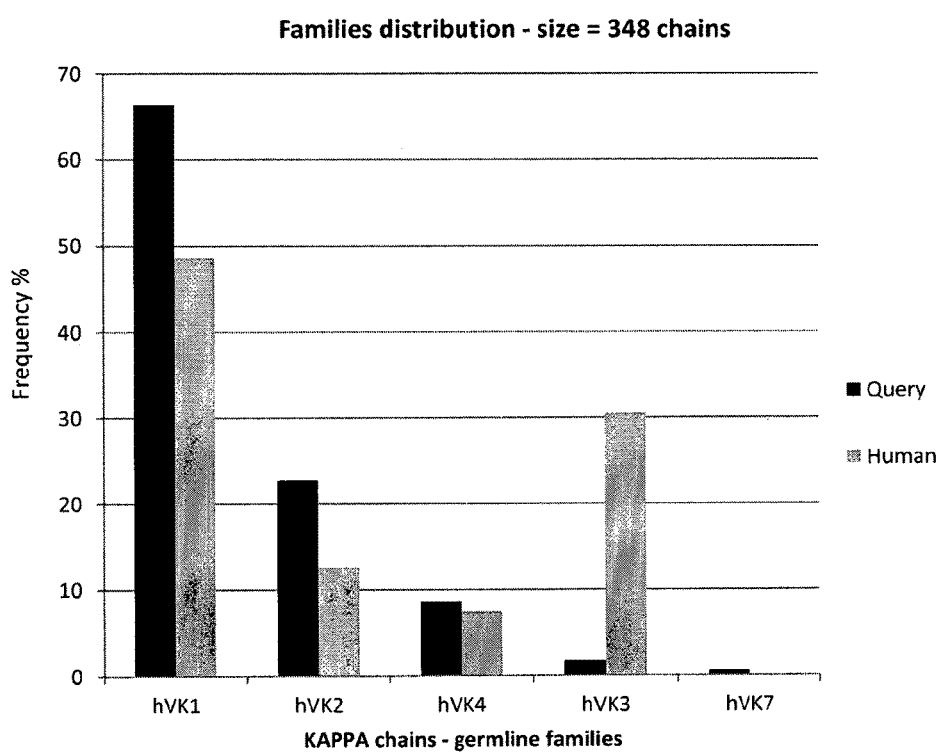
FIG. 3 is a graphic representation of the usage of human kappa chain families in a Camelid antibody library of the present invention (left hand bar of each pair), compared to the usage of the kappa chain families in human antibodies (right hand bar of each pair).
Figure 4:
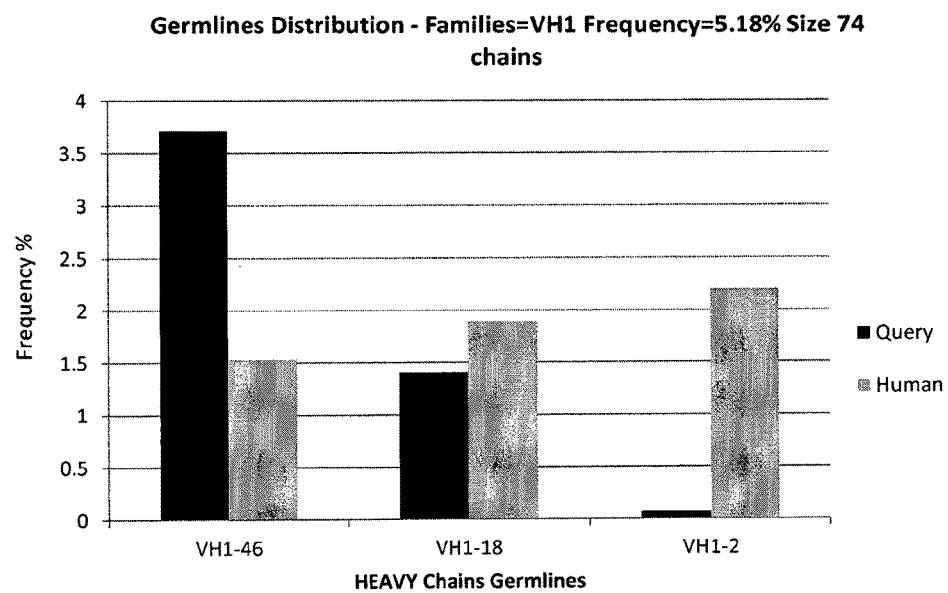
FIG. 4 is a graphic representation of the usage of human VH1 chain families in a Camelid antibody library of the present invention (left hand bar of each pair), compared to the usage of the lambda chain families in human antibodies (right hand bar of each pair).
Figure 5:
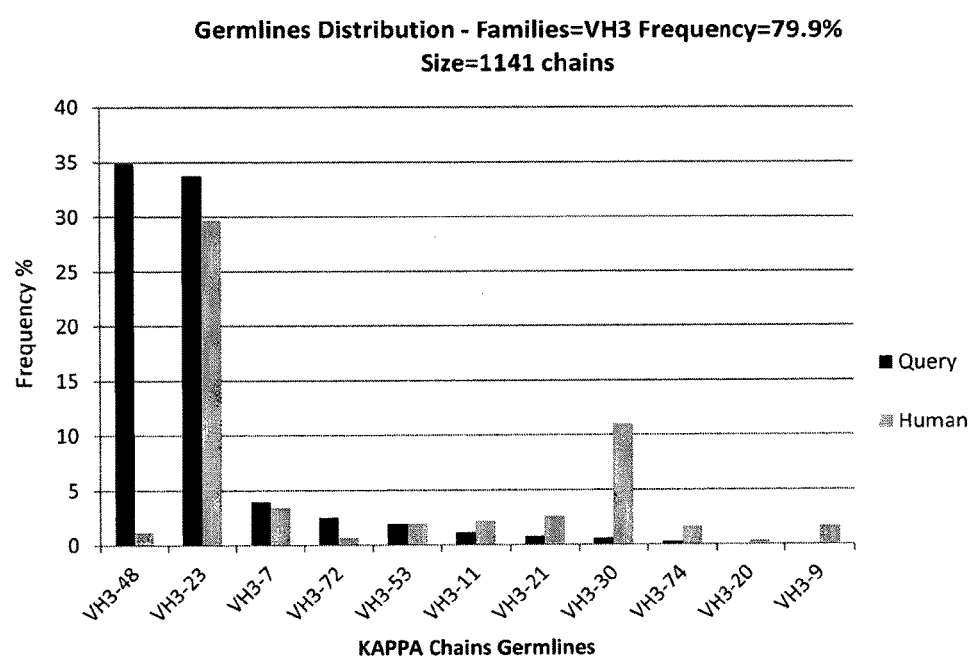
FIG. 5 is a graphic representation of the usage of human VH3 chain families in a Camelid antibody library of the present invention (left hand bar of each pair), compared to the usage of the lambda chain families in human antibodies (right hand bar of each pair).
Figure 6:
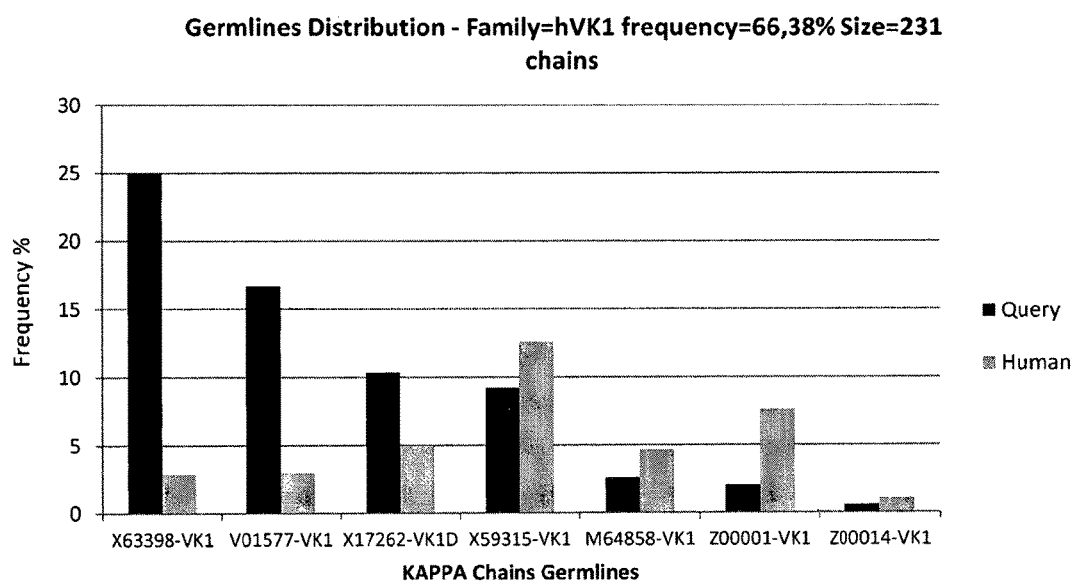
FIG. 6 is a graphic representation of the usage of human Vκ1 chain families in a Camelid antibody library of the present invention (left hand bar of each pair), compared to the usage of the lambda chain families in human antibodies (right hand bar of each pair).
Figure 7:
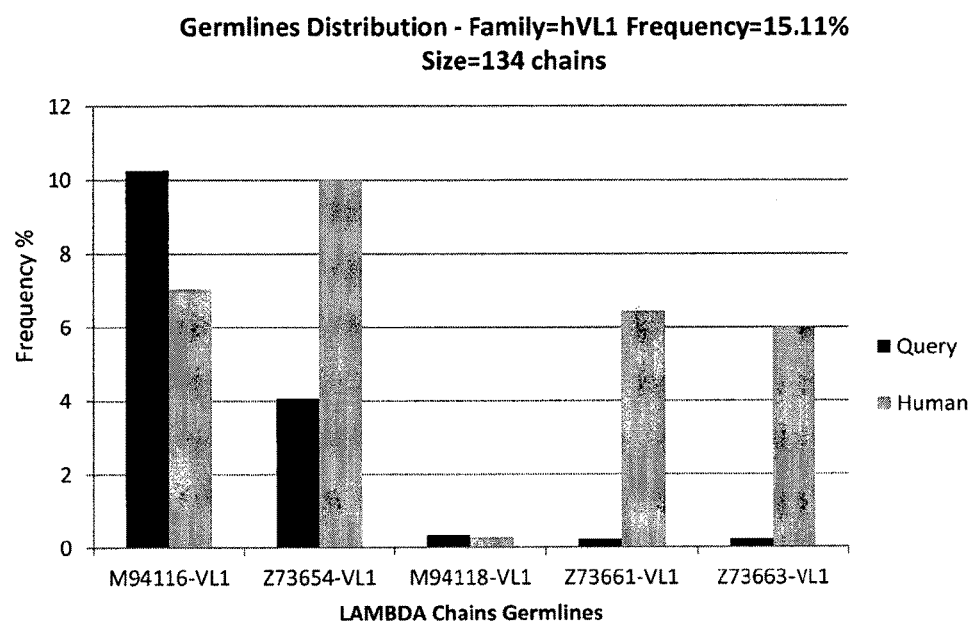
FIG. 7 is a graphic representation of the usage of human Vλ1 chain families in a Camelid antibody library of the present invention (left hand bar of each pair), compared to the usage of the lambda chain families in human antibodies (right hand bar of each pair).
Figure 8A:
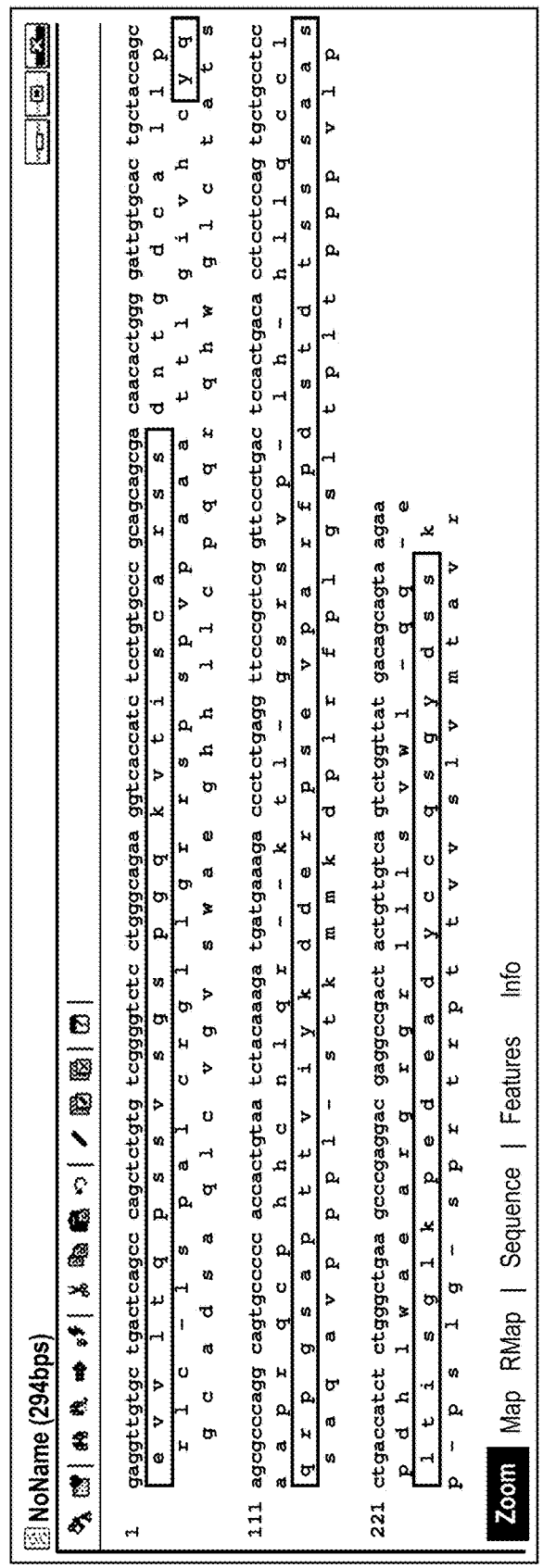

The following is a detailed description of the invention.

Definitions

"Antibodies" (Abs) and "immunoglobulins" (Igs) are glycoproteins which exhibit binding specificity to a (target) antigen.

The camelid species are known to possess two different types of antibodies; the classical or "conventional" antibodies and also the heavy-chain antibodies.

As used herein, the term "Camelid antibody" refers to conventional Camelid antibodies of any isotype, including IgA, IgG, IgD, IgE or IgM. Native or naturally occurring "conventional" camelid antibodies are usually heterotetrameric glycoproteins, composed of two identical light (L) chains and two identical heavy (H) chains.

The term "antibody chain" is used interchangeably with the term "antibody domain", and refers to the heavy chain or the light chain of an antibody.

The term "antibody library" refers to a collection of antibodies and/or antibody fragments displayed for screening and/or combination into full antibodies. The antibodies and/or antibody fragments may be displayed on ribosomes; on phage; or on a cell surface, in particular yeast cell surface.

A human antibody chain is considered to belong to a specific "antibody chain family" if it has at least 80% sequence homology with other members of that family Based on this definition 23 human antibody chain families have been identified: 7 heavy chain ($V_H$) families; 6 Vκlight chain families; and 10 Vλ light chain families Thus, a human antibody chain is considered to belong to the human family Vλ6 if it has at least 80% sequence homology with other members of the Vλ6 family. It has been found that, in general, antibody chains have less than 70% sequence homology with members of other families.

A Camelid antibody chain is considered to belong to a specific human antibody chain family if it has at least 80% sequence homology with a human germline sequence of that family Preferably the sequence homology is at least 85%, more preferably 90%, still more preferably at least 95%.

Camelid antibodies can be obtained from peripheral blood or specific tissues, for example spleen, of a species in the family Camilidae. Antibodies can be obtained from a normal, healthy animal, or from a diseased animal. Preferably, however, the Camelid antibodies are obtained from the animal after active immunization of the animal with a target antigen, in order to elicit an immune response against the target antigen in which the animal raises Camelid conventional antibodies that are immunoreactive with the target antigen. Protocols for immunization of Camelids are described in US 2011/0300140, the disclosures of which are incorporated herein by reference.

The process will typically involve immunization of animals of a Camilidae species (including, but not limited to, llamas and alpacas). Preferably the animals belong to an outbred population, which contributes to the strength and the diversity of the immune response. Following active immunization, peripheral blood lymphocytes or biopsies such as lymph nodes or spleen biopsies can be isolated from the immunized animal. The harvested lymphocytes can be screened for production of conventional Camelid antibodies against the target antigen. For construction of a naïve antibody library no such screening is carried out.

Nucleic acid encoding Camelid VH and VL domains (whether obtained by active immunization or by other means) can be used to prepare a Camelid library, for example a Fab library, as described in US 2011/0300140.

It is also possible to construct a library of expression vectors encoding VH and/or VL domains of Camelid conventional antibodies to obtain amplified gene segments, each gene segment containing a sequence of nucleotides encoding a VH and/or VL domains of Camelid conventional antibodies. Constructing the expression vector library involves the following steps:
a) amplifying regions of nucleic acid molecules encoding VH and/or VL domains of Camelid conventional antibodies to obtain amplified gene segments, each gene segment containing a sequence of nucleotides encoding a VH domain or a sequence of nucleotides encoding a VL domain of a Camelid conventional antibody; and
b) cloning the gene segments obtained in a) into expression vectors, such that each expression vector contains at least a gene segment encoding a VH domain and/or gene segment encoding a VL domain, whereby a library of expression vectors is obtained.

Step a) may be carried out by any suitable amplification technique, for example PCR. In case PCR is used, the selection of appropriate primers is important. Use of suboptimal primers results in loss of valuable diversity because antibody chains belonging to important human families may escape isolation and detection. For example, in the past chains belonging to the human VH6, Vκ3 or Vλ6 families have escaped isolation and/or detection because of the use of primers that were not appropriate for sequences belonging to these families.

In a first embodiment the antibody library of the invention comprises antibody chains belonging to at least 7, preferably at least 10, more preferably at least 12, even more preferably at least 15 human antibody chain families. This embodiment makes use of the discovery that functional size of an antibody library is more important than absolute size. Consider two antibody libraries, A and B, of equal absolute size, say $10^{10}$ antibodies. Library A comprises antibody chains of only 5 different families, whereas library B comprises antibody chains of 10 different families. It can easily be seen that library B offers more possible permutations in an affinity maturation protocol, such as chain shuffling. Accordingly, library B offers a greater probability of generating a high-affinity antibody than does library A, even though both libraries are equal in absolute size.

Library diversity is also important better epitope coverage, with greater diversity increasing the likelihood of being able to target the epitope on the antigen that is functionally and/or therapeutically relevant. Library diversity is also important for increasing the probability of identifying antibody molecules having desirable secondary properties, such as binding specificity; cross-reactivity to orthologues of the target antigen; stability; ease of manufacture; etc.

Another important aspect of the library of this embodiment is that it represents a significant number of human chain families Murine antibody libraries can be highly diverse, owing to the large number of Vκfamilies in the murine germline. As such, murine antibody libraries meet the criterion of functional size, based on which one would expect such libraries to produce a significant number of high-affinity antibodies when screened against a specific target. Many of these "hits" are unusable, however, because of their dissimilarity to human antibodies. Other hits may require such extensive humanization engineering that they lose a significant part of their affinity. Libraries of the present invention, however, produce antibodies that require little humanization engineering.

It has been found that most or all antibody chain families are expressed by a plurality of unique genes. For example, there are at least five distinct genes for the Vλ1 chain family. This finding opens the door to even greater library diversity. An important aspect of the present invention is the development of primers that permit the extraction from an antibody pool of more than one gene for a given antibody chain family.

In a second embodiment the antibody library of the present invention comprises antibody chains of at least one of the following human chain families: VH6, Vκ3; and Vλ6. This embodiment is based on the insight that each of these families is sufficiently important to the diversity of human germline antibodies to warrant the effort of building Camelid antibody libraries that are large enough to contain harvestable amounts of chains of these families, and of developing the appropriate primers necessary to amplify and isolate them.

In a third embodiment the antibody library of the invention comprises at least members of the three human families VH3, Vκ1 and Vλ6; preferably members of the four human families VH1, VH3, Vκ1, and Vλ6; yet more preferably members of the five human families VH1, VH3, Vλ1, Vλ2, and Vλ6; even more preferably members of the six human families VH1, VH3, Vκ1, Vλ1, Vλ2, and Vλ6; most preferably members of the seven human families VH1, VH3, Vκ1, Vκ2, Vλ1, Vλ2, and Vλ6. This embodiment reflects the recognition that, in nature, these combinations of antibody chains, even though representing respectively 1.5%, 3.1%, 4.7%, 6.3%, and 7.8% of the possible permutations, they represent from about 50% to more than 80% of human antibodies. It follows that libraries comprising these combinations of chains of a high probability of producing useful therapeutic antibodies, even if the absolute size of such libraries is relatively small.

It will be understood that the criteria set forth for the above three embodiments are not mutually exclusive, and that a specific library may meet the criteria of two of the embodiments, and possibly of all three. For example, a library comprising chains of all 23 human families will certainly meet the criteria of all three embodiments.

DESCRIPTION OF ILLUSTRATIVE EMBODIMENTS/EXAMPLES

The following is a description of certain embodiments of the invention, given by way of example only.

Example 1

Description of Amplification Protocol Including the Primer Sequences.

Immunization, PBL isolation, RNA extraction and cDNA preparation were done as disclosed in U.S. Patent Application Publication 2011/0300140 to Dreier et al.

Figure 9B:
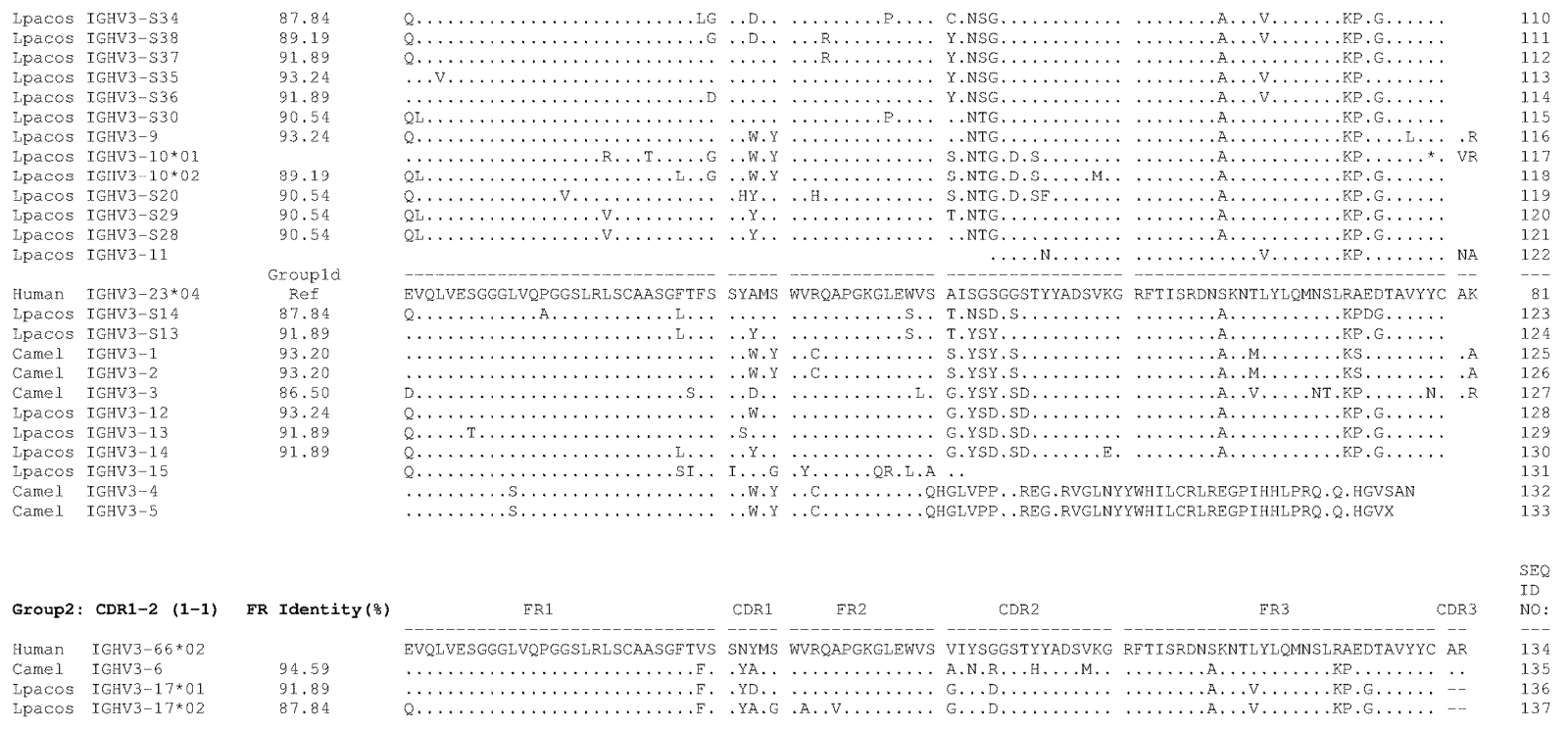
Figure 10C:
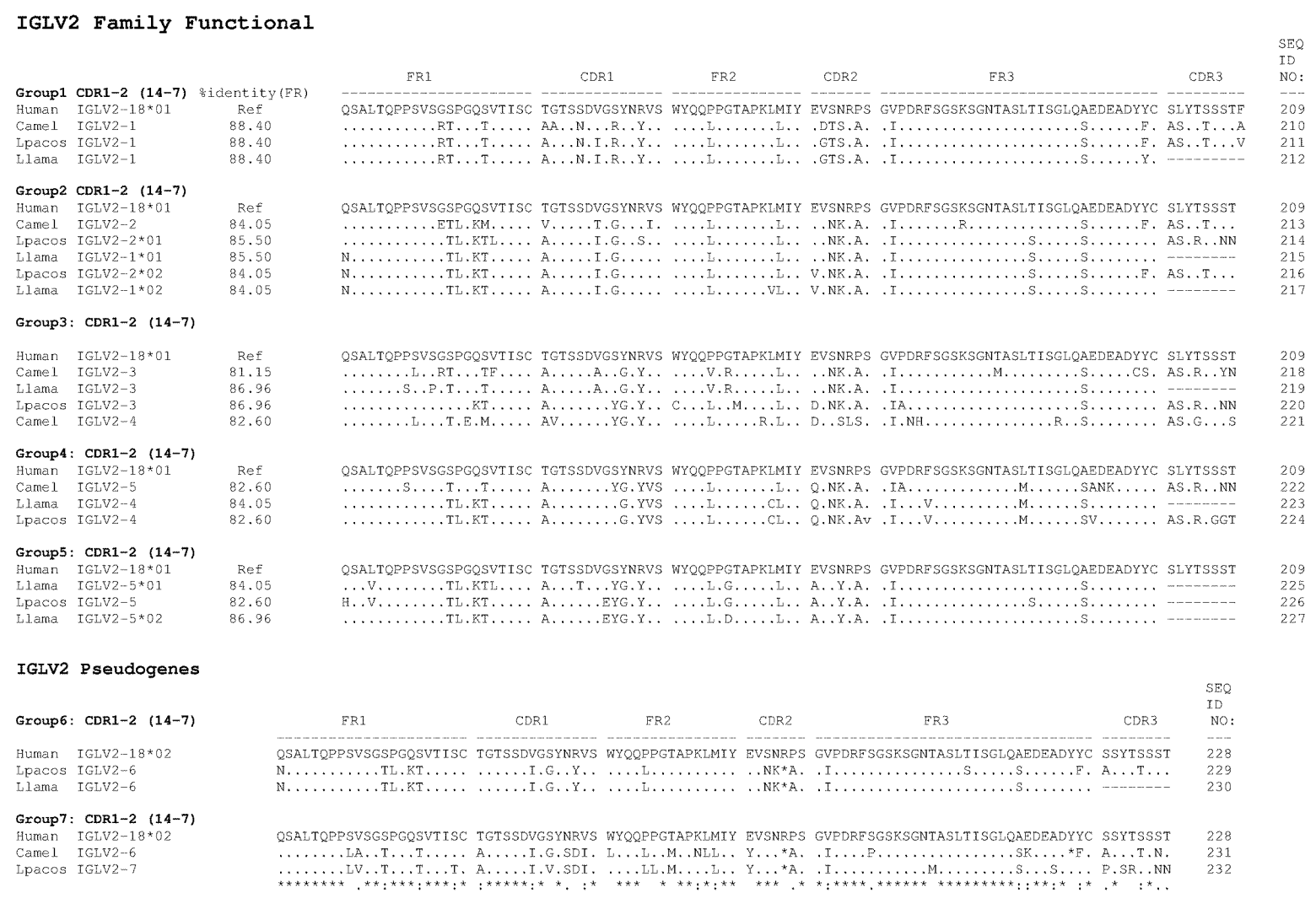

The Fab fragments were amplified by PCR with the cDNA as template and using primers annealing specifically to the frame work 1 (FR1) of the variable domains (BACK primers) and to the end of the constant domains (FOR primers) as described by de Haard et al. (JBC 1999). The sequences of the primers were designed on the basis of the germline sequences from camelids (*Lama pacos, Camelus ferus* and *Lama glama*) obtained from the Whole Genome Shotgun (WGS) database (www.ncbi.nlm.nih.gov/nuccore/ABRR00000000), High-throughput genome (HTG) database and sequenced amplicons. FIGS. 9A-11C show the alignment of the camelid VH, Vλ and Vκ families with the corresponding human germline. These sequences were used as templates for design of the FR1 primers described in Tables 1-3. An overview of the camelid germline sequences and the corresponding FR1 primers is shown in FIGS. 12A-14.

The amplification of the llama variable domain can be done either in one step PCR or in two steps PCR. For the one step PCR, the BACK and FOR primers used for the amplification contain restriction sites that allow the cloning of the PCR fragment into the pCB3 phagemide vector. For the two-step PCR, a primary PCR was done with the non-tagged primers (without restriction site). The amplicons were isolated and purified before a secondary PCR was done with the primers containing the restriction sites. The restriction sites are ApaLI for the BACK primers and AscI for the FOR primers. The restriction sites are SfiI and NotI for the BACK and FOR primers of VH-CH1, respectively. Alternatively, the DNA segments can be reamplified with primers tagged with restriction sites (FOR primers with AscI site and FR4 based BACK primers with BstEII site) and cloned as VL fragments thus creating chimeric Fab's containing llama derived V regions combined with human C regions. The antisense primers are shown in Table 4.

The PCRs were performed in a volume of 50 µl reactions using Phusion polymerase (ThermoFischer) and 500 pM of each primer for 28 cycles (1 min at 96° C., 1 min at 60° C., and 1 min at 72° C.

The construction of the Fab library was done as described in U.S. Patent Application Publication 2011/0300140 to Dreier et al.

TABLE 1

FR1 primers for amplification of camelid VH genes.

| | |
|---|---|
| >VH1-primer1 CAGGTCCAGCTGSTGCAGTCAGG | (SEQ ID NO: 1) |
| >VH1-primer2 GAGGTCCAGCTGGTGCAGCCAGG | (SEQ ID NO: 2) |
| >VH3-primer1 GAGGTGCAGSTGGTGGAGTCTGGG | (SEQ ID NO: 3) |
| >VH3-primer2 CAGGTGCAGCTGGTGGAGTCTGGG | (SEQ ID NO: 4) |
| >VH4-primer1 CAGGTGCAGCTGCAGGAGTCGGG | (SEQ ID NO: 5) |
| >VH5-primer1 CAGGTGMAGCTGGAGCAGCCTGTGG | (SEQ ID NO: 6) |
| >VH7-primer1 CAGGTGCAGCTGGTGCAGTCTGCG | (SEQ ID NO: 7) |
| >VH7-primer2 CAAGTGCAGCTGGTGCAGCCAGGG | (SEQ ID NO: 8) |

TABLE 2

FR1 primers for amplification of camelid Vλ genes.

| | |
|---|---|
| >Vλ1-Primer1 CAGTCTGTGCTGACTCAGCYGCCCTC | (SEQ ID NO: 9) |
| >Vλ1-Primer2 CAGTCTGTGCTGACTCAGCYGTCCTC | (SEQ ID NO: 10) |
| >Vλ1-primer3 CAGTCTGTGCTGACCCAGCKGGCCTC | (SEQ ID NO: 11) |
| >Vλ1-primer4 CAGTCTGGGCTGACACAGGAAGCCTC | (SEQ ID NO: 12) |
| >Vλ1-primer5 CAGTCTGTGCCGATTCAGCCGTCCTC | (SEQ ID NO: 13) |
| >Vλ1-primer6 AAGTCTGTGCCGACTCAGCTGCCCTT | (SEQ ID NO: 14) |
| >Vλ1-primer7 CAGACTGTGGTGACCCAGGAGCCGTC | (SEQ ID NO: 15) |
| >Vλ2-primer1 AACTCTGCCCTGACTCAGCCTCCATC | (SEQ ID NO: 16) |
| >Vλ2-primer2 CAGTCTGCCSTGACTCAGCCTYCCTC | (SEQ ID NO: 17) |
| >Vλ2-primer3 CAGTCTGCCYTGACTCAGCCTCCCTT | (SEQ ID NO: 18) |
| >Vλ2-primer4 CAGTCTGCCCTGATTCAGCCTCTCTC | (SEQ ID NO: 19) |
| >Vλ3-primer1 TCTTCTGCACTGACTCAGCCCTCCGC | (SEQ ID NO: 20) |
| >Vλ3-primer2 TCTTCTGCASTGACTCAGCCCTCCA | (SEQ ID NO: 21) |
| >Vλ3-primer3 TCCTACGAACTGACTCAGWCACCCTC | (SEQ ID NO: 22) |
| >Vλ3-primer4 GCCTCTTCAGTGACTCAGCCCTCCGC | (SEQ ID NO: 23) |
| >Vλ3-primer5 TCCTATGAGCTGACCCAGCAGGCTTC | (SEQ ID NO: 24) |

TABLE 2-continued

FR1 primers for amplification of camelid Vλ genes.

>Vλ4-primer1
CAGCCTGTGCTGTCGCAGCCACCCTC (SEQ ID NO: 25)

>Vλ4-primer2
CAGCCTGTGCTGATGCAGCTGCCCTC (SEQ ID NO: 26)

>Vλ4-primer3
CAGACTGTGCTGACGCAGCCGCCCTC (SEQ ID NO: 27)

>Vλ4-primer4
CAGCCTGAGCTGACACAGCCGCCCTC (SEQ ID NO: 28)

>Vλ4-primer5
GCGCCTGTGCTGACCCAGCCCCCGTC (SEQ ID NO: 29)

>Vλ4-primer6
GAGCCTGTGCTGACCCAGCCCYCGTC (SEQ ID NO: 30)

>Vλ5-primer1
CAGCATGTGGTGACTCAGCCGCCCTC (SEQ ID NO: 31)

>Vλ5-primer2
CAGCTTGTGSTGACTCAGCCGCCCTC (SEQ ID NO: 32)

>Vλ5-primer3
CAGCTTCTGCTGACTCAGCCGCCCTC (SEQ ID NO: 33)

>Vλ5-primer4
CAGCTTGTGCWGACTCAGCTGCCCTC (SEQ ID NO: 34)

>Vλ5-primer5
CAGCCTGTGCTGACTCAGCTGTCCTC (SEQ ID NO: 35)

>Vλ5-primer6
CAGCCTGTGCTGACTCAGCYGCCCTC (SEQ ID NO: 36)

>Vλ5-primer7
CAGCCTGTGGGGACTCAGCTGCCCTC (SEQ ID NO: 37)

>Vλ5-primer8
CAGCTTGTGGAGACTCAGCTGTCTTT (SEQ ID NO: 38)

>Vλ5-primer9
CAGACTGTGGGGACTCAGCCAGCCTC (SEQ ID NO: 39)

>Vλ6-primer1
GAGGTTGTGCTGACTCAGCCCAGCTC (SEQ ID NO: 40)

>Vλ7-primer1_(V · 1-primer7)
CAGACTGTGGTGACCCAGGAGCCGTC (SEQ ID NO: 41)

>Vλ8-primer1_(V · 1-primer7)
CAGACTGTGGTGACCCAGGAGCCGTC (SEQ ID NO: 42)

>Vλ8-primer2
CAGACTGTGRTGACCCAGGAGCCATC (SEQ ID NO: 43)

>Vλ8-primer3
CAGACTGTGGTGACCCAGRAGCCGTC (SEQ ID NO: 44)

>Vλ8-primer4
CAGACTGTGGTGACCCAGGTTTCATC (SEQ ID NO: 45)

TABLE 2-continued

FR1 primers for amplification of camelid Vλ genes.

>Vλ8-primer5
CAGACTGTGGTGACCCAACAGTCGTT (SEQ ID NO: 46)

>Vλ9-primer1
CAGCCTGTGCTGATGCAGCCGCCCTC (SEQ ID NO: 47)

>Vλ9-primer2
CAGCCTGTGCTGACACAGTCGCCCTC (SEQ ID NO: 48)

>Vλ9-primer3
CAGCCTATGCTGACACAGTCGTCCCC (SEQ ID NO: 49)

>Vλ9-primer4
CAGCCTGTGCTGACACAGACGCCCTC (SEQ ID NO: 50)

>Vλ9-primer5
CAGCCTGTGCCGACACAGTCACCATC (SEQ ID NO: 51)

>Vλ10-primer1
CAGGCAWGGCTGACTCAGCCCCRGTC (SEQ ID NO: 52)

TABLE 3

FR1 primers for amplification of camelid Vκ genes.

>Vκ1-Primer1
GCTACCCAGRTGACCCAGTCTYCCTCC (SEQ ID NO: 53)

>Vκ1-Primer2
GAAATTGTGCTGACCCAGTCTCCGGCC (SEQ ID NO: 54)

>Vκ2-Primer1
GATTTWGTGCTGACCCAGAYCCCAGGC (SEQ ID NO: 55)

>Vκ2-Primer2
GACGTTGTGCTGACCCAGACCCCAGGC (SEQ ID NO: 56)

>Vκ2-Primer3
AACATTGTACTGACCCGTTTTCTAGCC (SEQ ID NO: 57)

>Vκ3-Primer1
AGCGCTGAGCTGACCCAGACTCCAGCC (SEQ ID NO: 58)

>Vκ3-Primer2
CAGATCGCCCTGACTCAGTTTCCAGAA (SEQ ID NO: 59)

>Vκ3-Primer3
GGAGAGAATGTGGAGCAGAGTCCTCCC (SEQ ID NO: 60)

>Vκ4-Primer1
GACATCGTGATGACCCAGTCTCCCAGC (SEQ ID NO: 61)

>Vκ5-Primer1
GAAACAGTCCCCACCCAATCTCCAGCA (SEQ ID NO: 62)

>Vκ6-Primer1
GCGACCRTGCTGACCCAGTCCCCAGCC (SEQ ID NO: 63)

TABLE 4

Antisense primers (5'-3') used for amplification of the VH, Vλ and Vκ genes.

| | | |
|---|---|---|
| Clambda1-FOR | CTAACACTGGGAGGGGGACACCGTCTTCTC | SEQ ID NO: 64 |
| Clambda2-FOR (non-tagged) | CTAACACTGGGAGGGNCTCACNGTCTTCTC | SEQ ID NO: 65 |
| caClambda1-FOR-AscI (tagged) | GCCTCCACCGGGCGCGCCTTATTAACACTG GGAGGGGGACACCGTCTTCTC | SEQ ID NO: 66 |

TABLE 4-continued

Antisense primers (5'-3') used for amplification of the VH, Vλ and Vκ genes.

| | | |
|---|---|---|
| caCHkappa1-FOR (non-tagged) | TCAGCAGTGTCTCCGGTCGAAGCTCCT | SEQ ID NO: 67 |
| CH-FOR3(as) (non-tagged) | TCCTCCATGTGGTTCCACACGCTTGTCCACCTTGG | SEQ ID NO: 68 |
| CH1-FOR-NotI (tagged) | GCCTCCACCTGCGGCCGCGCATCCTCCATGTGGTTCCACACGCTT | SEQ ID NO: 69 |

In the primer sequences provided in Tables and herein the following notation has been used:
S—G or C
M—A or C
Y—T or C
K—G or T
W—A or T
R—G or A
N—A, C, T, G, unknown or other Thus, the invention has been described by reference to certain embodiments discussed above. It will be recognized that these embodiments are susceptible to various modifications and alternative forms well known to those of skill in the art. For example, the antibody library may be modified by modifying and/or fine tuning the PCR primers.

Many modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A camelid Fab library, said Fab library comprising camelid antibody heavy and light chain variable regions belonging to at least seven different human antibody chain families, wherein at least one of the human antibody chain families is selected from the group consisting of VH6 and Vκ3.

2. The camelid Fab library of claim 1, comprising antibody chains within one human antibody chain family that are expressed by at least two different genes.

3. The camelid Fab library of claim 1, wherein the camelid antibody heavy and light chain variable regions are llama antibody heavy and light chain variable regions.

4. A camelid Fab library, said Fab library comprising camelid antibody heavy and light chain variable regions belonging to at least seven different human antibody chain families, wherein at least one of the human antibody chain families is selected from the group consisting of VH6 and Vκ3, and wherein the library is displayed on a ribosome, on a phage particle, or on a cell surface.

* * * * *

SEQUENCE LISTING

<160> NUMBER OF SEQ ID NOS: 518

<210> SEQ ID NO 1
<211> LENGTH: 23
<212> TYPE: DNA
<213> ORGANISM: Artificial
<220> FEATURE:
<223> OTHER INFORMATION: Primer

<400> SEQUENCE: 1
caggtccagc tgstgcagtc agg                                          23

<210> SEQ ID NO 2
<211> LENGTH: 23
<212> TYPE: DNA
<213> ORGANISM: Artificial
<220> FEATURE:
<223> OTHER INFORMATION: Primer

<400> SEQUENCE: 2
gaggtccagc tggtgcagcc agg                                          23

<210> SEQ ID NO 3
<211> LENGTH: 24
<212> TYPE: DNA
<213> ORGANISM: Artificial
<220> FEATURE:
<223> OTHER INFORMATION: Primer

<400> SEQUENCE: 3
gaggtgcags tggtggagtc tggg                                         24

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4

```
caggtgcagc tggtggagtc tggg                                          24

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
caggtgcagc tgcaggagtc ggg                                           23

<210> SEQ ID NO 6
<211> LENGTH: 25
<212> TYPE: DNA
<213> ORGANISM: Artificial
<220> FEATURE:
<223> OTHER INFORMATION: Primer

<400> SEQUENCE: 6
caggtgmagc tggagcagcc tgtgg                                         25

<210> SEQ ID NO 7
<211> LENGTH: 24
<212> TYPE: DNA
<213> ORGANISM: Artificial
<220> FEATURE:
<223> OTHER INFORMATION: Primer

<400> SEQUENCE: 7
caggtgcagc tggtgcagtc tgcg                                          24

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
caagtgcagc tggtgcagcc aggg                                          24

<210> SEQ ID NO 9
<211> LENGTH: 26
<212> TYPE: DNA
<213> ORGANISM: Artificial
<220> FEATURE:
<223> OTHER INFORMATION: Primer

<400> SEQUENCE: 9
cagtctgtgc tgactcagcy gccctc                                        26

<210> SEQ ID NO 10
<211> LENGTH: 26
<212> TYPE: DNA
<213> ORGANISM: Artificial
<220> FEATURE:
<223> OTHER INFORMATION: Primer

<400> SEQUENCE: 10
cagtctgtgc tgactcagcy gtcctc                                        26

<210> SEQ ID NO 11
<211> LENGTH: 26
<212> TYPE: DNA
<213> ORGANISM: Artificial
```

```
<220> FEATURE:
<223> OTHER INFORMATION: Primer

<400> SEQUENCE: 11
cagtctgtgc tgacccagck ggcctc                                              26

<210> SEQ ID NO 12
<211> LENGTH: 26
<212> TYPE: DNA
<213> ORGANISM: Artificial
<220> FEATURE:
<223> OTHER INFORMATION: Primer

<400> SEQUENCE: 12
cagtctgggc tgacacagga agcctc                                              26

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
cagtctgtgc cgattcagcc gtcctc                                              26

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
aagtctgtgc cgactcagct gccctt                                              26

<210> SEQ ID NO 15
<211> LENGTH: 26
<212> TYPE: DNA
<213> ORGANISM: Artificial
<220> FEATURE:
<223> OTHER INFORMATION: Primer

<400> SEQUENCE: 15
cagactgtgg tgacccagga gccgtc                                              26

<210> SEQ ID NO 16
<211> LENGTH: 26
<212> TYPE: DNA
<213> ORGANISM: Artificial
<220> FEATURE:
<223> OTHER INFORMATION: Primer

<400> SEQUENCE: 16
aactctgccc tgactcagcc tccatc                                              26

<210> SEQ ID NO 17
<211> LENGTH: 26
<212> TYPE: DNA
<213> ORGANISM: Artificial
<220> FEATURE:
<223> OTHER INFORMATION: Primer

<400> SEQUENCE: 17
cagtctgccs tgactcagcc tycctc                                              26
```

```
<210> SEQ ID NO 18
<211> LENGTH: 26
<212> TYPE: DNA
<213> ORGANISM: Artificial
<220> FEATURE:
<223> OTHER INFORMATION: Primer

<400> SEQUENCE: 18
cagtctgccy tgactcagcc tccctt                                              26

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
cagtctgccc tgattcagcc tctctc                                              26

<210> SEQ ID NO 20
<211> LENGTH: 26
<212> TYPE: DNA
<213> ORGANISM: Artificial
<220> FEATURE:
<223> OTHER INFORMATION: Primer

<400> SEQUENCE: 20
tcttctgcac tgactcagcc ctccgc                                              26

<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
tcttctgcas tgactcagcc ctcca                                               25

<210> SEQ ID NO 22
<211> LENGTH: 26
<212> TYPE: DNA
<213> ORGANISM: Artificial
<220> FEATURE:
<223> OTHER INFORMATION: Primer

<400> SEQUENCE: 22
tcctacgaac tgactcagwc accctc                                              26

<210> SEQ ID NO 23
<211> LENGTH: 26
<212> TYPE: DNA
<213> ORGANISM: Artificial
<220> FEATURE:
<223> OTHER INFORMATION: Primer

<400> SEQUENCE: 23
gcctcttcag tgactcagcc ctccgc                                              26

<210> SEQ ID NO 24
<211> LENGTH: 26
<212> TYPE: DNA
<213> ORGANISM: Artificial
<220> FEATURE:
<223> OTHER INFORMATION: Primer
```

<400> SEQUENCE: 24
tcctatgagc tgacccagca ggcttc                                              26

<210> SEQ ID NO 25
<211> LENGTH: 26
<212> TYPE: DNA
<213> ORGANISM: Artificial
<220> FEATURE:
<223> OTHER INFORMATION: Primer

<400> SEQUENCE: 25
cagcctgtgc tgtcgcagcc accctc                                              26

<210> SEQ ID NO 26
<211> LENGTH: 26
<212> TYPE: DNA
<213> ORGANISM: Artificial
<220> FEATURE:
<223> OTHER INFORMATION: Primer

<400> SEQUENCE: 26
cagcctgtgc tgatgcagct gccctc                                              26

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
cagactgtgc tgacgcagcc gccctc                                              26

<210> SEQ ID NO 28
<211> LENGTH: 26
<212> TYPE: DNA
<213> ORGANISM: Artificial
<220> FEATURE:
<223> OTHER INFORMATION: Primer

<400> SEQUENCE: 28
cagcctgagc tgacacagcc gccctc                                              26

<210> SEQ ID NO 29
<211> LENGTH: 26
<212> TYPE: DNA
<213> ORGANISM: Artificial
<220> FEATURE:
<223> OTHER INFORMATION: Primer

<400> SEQUENCE: 29
gcgcctgtgc tgacccagcc cccgtc                                              26

<210> SEQ ID NO 30
<211> LENGTH: 26
<212> TYPE: DNA
<213> ORGANISM: Artificial
<220> FEATURE:
<223> OTHER INFORMATION: Primer

<400> SEQUENCE: 30
gagcctgtgc tgacccagcc cycgtc                                              26

<210> SEQ ID NO 31

```
<211> LENGTH: 26
<212> TYPE: DNA
<213> ORGANISM: Artificial
<220> FEATURE:
<223> OTHER INFORMATION: Primer

<400> SEQUENCE: 31
cagcatgtgg tgactcagcc gccctc                                              26

<210> SEQ ID NO 32
<211> LENGTH: 26
<212> TYPE: DNA
<213> ORGANISM: Artificial
<220> FEATURE:
<223> OTHER INFORMATION: Primer

<400> SEQUENCE: 32
cagcttgtgs tgactcagcc gccctc                                              26

<210> SEQ ID NO 33
<211> LENGTH: 26
<212> TYPE: DNA
<213> ORGANISM: Artificial
<220> FEATURE:
<223> OTHER INFORMATION: Primer

<400> SEQUENCE: 33
cagcttctgc tgactcagcc gccctc                                              26

<210> SEQ ID NO 34
<211> LENGTH: 26
<212> TYPE: DNA
<213> ORGANISM: Artificial
<220> FEATURE:
<223> OTHER INFORMATION: Primer

<400> SEQUENCE: 34
cagcttgtgc wgactcagct gccctc                                              26

<210> SEQ ID NO 35
<211> LENGTH: 26
<212> TYPE: DNA
<213> ORGANISM: Artificial
<220> FEATURE:
<223> OTHER INFORMATION: Primer

<400> SEQUENCE: 35
cagcctgtgc tgactcagct gtcctc                                              26

<210> SEQ ID NO 36
<211> LENGTH: 26
<212> TYPE: DNA
<213> ORGANISM: Artificial
<220> FEATURE:
<223> OTHER INFORMATION: Primer

<400> SEQUENCE: 36
cagcctgtgc tgactcagcy gccctc                                              26

<210> SEQ ID NO 37
<211> LENGTH: 26
<212> TYPE: DNA
<213> ORGANISM: Artificial
<220> FEATURE:
<223> OTHER INFORMATION: Primer

<400> SEQUENCE: 37
```

-continued cagcctgtgg ggactcagct gccctc    26

<210> SEQ ID NO 38
<211> LENGTH: 26
<212> TYPE: DNA
<213> ORGANISM: Artificial
<220> FEATURE:
<223> OTHER INFORMATION: Primer

<400> SEQUENCE: 38
cagcttgtgg agactcagct gtcttt    26

<210> SEQ ID NO 39
<211> LENGTH: 26
<212> TYPE: DNA
<213> ORGANISM: Artificial
<220> FEATURE:
<223> OTHER INFORMATION: Primer

<400> SEQUENCE: 39
cagactgtgg ggactcagcc agcctc    26

<210> SEQ ID NO 40
<211> LENGTH: 26
<212> TYPE: DNA
<213> ORGANISM: Artificial
<220> FEATURE:
<223> OTHER INFORMATION: Primer

<400> SEQUENCE: 40
gaggttgtgc tgactcagcc cagctc    26

<210> SEQ ID NO 41
<211> LENGTH: 26
<212> TYPE: DNA
<213> ORGANISM: Artificial
<220> FEATURE:
<223> OTHER INFORMATION: Primer

<400> SEQUENCE: 41
cagactgtgg tgacccagga gccgtc    26

<210> SEQ ID NO 42
<211> LENGTH: 26
<212> TYPE: DNA
<213> ORGANISM: Artificial
<220> FEATURE:
<223> OTHER INFORMATION: Primer

<400> SEQUENCE: 42
cagactgtgg tgacccagga gccgtc    26

<210> SEQ ID NO 43
<211> LENGTH: 26
<212> TYPE: DNA
<213> ORGANISM: Artificial
<220> FEATURE:
<223> OTHER INFORMATION: Primer

<400> SEQUENCE: 43
cagactgtgr tgacccagga gccatc    26

<210> SEQ ID NO 44
<211> LENGTH: 26
<212> TYPE: DNA

```
<213> ORGANISM: Artificial
<220> FEATURE:
<223> OTHER INFORMATION: Primer

<400> SEQUENCE: 44
cagactgtgg tgacccagra gccgtc                                          26

<210> SEQ ID NO 45
<211> LENGTH: 26
<212> TYPE: DNA
<213> ORGANISM: Artificial
<220> FEATURE:
<223> OTHER INFORMATION: Primer

<400> SEQUENCE: 45
cagactgtgg tgacccaggt ttcatc                                          26

<210> SEQ ID NO 46
<211> LENGTH: 26
<212> TYPE: DNA
<213> ORGANISM: Artificial
<220> FEATURE:
<223> OTHER INFORMATION: Primer

<400> SEQUENCE: 46
cagactgtgg tgacccaaca gtcgtt                                          26

<210> SEQ ID NO 47
<211> LENGTH: 26
<212> TYPE: DNA
<213> ORGANISM: Artificial
<220> FEATURE:
<223> OTHER INFORMATION: Primer

<400> SEQUENCE: 47
cagcctgtgc tgatgcagcc gccctc                                          26

<210> SEQ ID NO 48
<211> LENGTH: 26
<212> TYPE: DNA
<213> ORGANISM: Artificial
<220> FEATURE:
<223> OTHER INFORMATION: Primer

<400> SEQUENCE: 48
cagcctgtgc tgacacagtc gccctc                                          26

<210> SEQ ID NO 49
<211> LENGTH: 26
<212> TYPE: DNA
<213> ORGANISM: Artificial
<220> FEATURE:
<223> OTHER INFORMATION: Primer

<400> SEQUENCE: 49
cagcctatgc tgacacagtc gtcccc                                          26

<210> SEQ ID NO 50
<211> LENGTH: 26
<212> TYPE: DNA
<213> ORGANISM: Artificial
<220> FEATURE:
<223> OTHER INFORMATION: Primer

<400> SEQUENCE: 50
cagcctgtgc tgacacagac gccctc                                          26
```

<210> SEQ ID NO 51
<211> LENGTH: 26
<212> TYPE: DNA
<213> ORGANISM: Artificial
<220> FEATURE:
<223> OTHER INFORMATION: Primer

<400> SEQUENCE: 51
cagcctgtgc cgacacagtc accatc                                          26

<210> SEQ ID NO 52
<211> LENGTH: 26
<212> TYPE: DNA
<213> ORGANISM: Artificial
<220> FEATURE:
<223> OTHER INFORMATION: Primer

<400> SEQUENCE: 52
caggcawggc tgactcagcc ccrgtc                                          26

<210> SEQ ID NO 53
<211> LENGTH: 27
<212> TYPE: DNA
<213> ORGANISM: Artificial
<220> FEATURE:
<223> OTHER INFORMATION: Primer

<400> SEQUENCE: 53
gctacccagr tgacccagtc tycctcc                                         27

<210> SEQ ID NO 54
<211> LENGTH: 27
<212> TYPE: DNA
<213> ORGANISM: Artificial
<220> FEATURE:
<223> OTHER INFORMATION: Primer

<400> SEQUENCE: 54
gaaattgtgc tgacccagtc tccggcc                                         27

<210> SEQ ID NO 55
<211> LENGTH: 27
<212> TYPE: DNA
<213> ORGANISM: Artificial
<220> FEATURE:
<223> OTHER INFORMATION: Primer

<400> SEQUENCE: 55
gatttwgtgc tgacccagay cccaggc                                         27

<210> SEQ ID NO 56
<211> LENGTH: 27
<212> TYPE: DNA
<213> ORGANISM: Artificial
<220> FEATURE:
<223> OTHER INFORMATION: Primer

<400> SEQUENCE: 56
gacgttgtgc tgacccagac cccaggc                                         27

<210> SEQ ID NO 57
<211> LENGTH: 27
<212> TYPE: DNA
<213> ORGANISM: Artificial
<220> FEATURE:

<223> OTHER INFORMATION: Primer

<400> SEQUENCE: 57
aacattgtac tgacccgttt tctagcc                                27

<210> SEQ ID NO 58
<211> LENGTH: 27
<212> TYPE: DNA
<213> ORGANISM: Artificial
<220> FEATURE:
<223> OTHER INFORMATION: Primer

<400> SEQUENCE: 58
agcgctgagc tgacccagac tccagcc                                27

<210> SEQ ID NO 59
<211> LENGTH: 27
<212> TYPE: DNA
<213> ORGANISM: Artificial
<220> FEATURE:
<223> OTHER INFORMATION: Primer

<400> SEQUENCE: 59
cagatcgccc tgactcagtt tccagaa                                27

<210> SEQ ID NO 60
<211> LENGTH: 27
<212> TYPE: DNA
<213> ORGANISM: Artificial
<220> FEATURE:
<223> OTHER INFORMATION: Primer

<400> SEQUENCE: 60
ggagagaatg tggagcagag tcctccc                                27

<210> SEQ ID NO 61
<211> LENGTH: 27
<212> TYPE: DNA
<213> ORGANISM: Artificial
<220> FEATURE:
<223> OTHER INFORMATION: Primer

<400> SEQUENCE: 61
gacatcgtga tgacccagtc tcccagc                                27

<210> SEQ ID NO 62
<211> LENGTH: 27
<212> TYPE: DNA
<213> ORGANISM: Artificial
<220> FEATURE:
<223> OTHER INFORMATION: Primer

<400> SEQUENCE: 62
gaaacagtcc ccacccaatc tccagca                                27

<210> SEQ ID NO 63
<211> LENGTH: 27
<212> TYPE: DNA
<213> ORGANISM: Artificial
<220> FEATURE:
<223> OTHER INFORMATION: Primer

<400> SEQUENCE: 63
gcgaccrtgc tgacccagtc cccagcc                                27

```
<210> SEQ ID NO 64
<211> LENGTH: 30
<212> TYPE: DNA
<213> ORGANISM: Artificial
<220> FEATURE:
<223> OTHER INFORMATION: Primer

<400> SEQUENCE: 64
ctaacactgg gaggggggaca ccgtcttctc                                       30

<210> SEQ ID NO 65
<211> LENGTH: 30
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 65
ctaacactgg gagggnctca cngtcttctc                                        30

<210> SEQ ID NO 66
<211> LENGTH: 51
<212> TYPE: DNA
<213> ORGANISM: Artificial
<220> FEATURE:
<223> OTHER INFORMATION: Primer

<400> SEQUENCE: 66
gcctccaccg ggcgcgcctt attaacactg ggaggggggac accgtcttct c               51

<210> SEQ ID NO 67
<211> LENGTH: 27
<212> TYPE: DNA
<213> ORGANISM: Artificial
<220> FEATURE:
<223> OTHER INFORMATION: Primer

<400> SEQUENCE: 67
tcagcagtgt ctccggtcga agctcct                                           27

<210> SEQ ID NO 68
<211> LENGTH: 35
<212> TYPE: DNA
<213> ORGANISM: Artificial
<220> FEATURE:
<223> OTHER INFORMATION: Primer

<400> SEQUENCE: 68
tcctccatgt ggttccacac gcttgtccac cttgg                                  35

<210> SEQ ID NO 69
<211> LENGTH: 45
<212> TYPE: DNA
<213> ORGANISM: Artificial
<220> FEATURE:
<223> OTHER INFORMATION: Primer

<400> SEQUENCE: 69
gcctccacct gcggccgcgc atcctccatg tggttccaca cgctt                       45
```

-continued

<210> SEQ ID NO 70
<211> LENGTH: 98
<212> TYPE: PRT
<213> ORGANISM: Homo sapiens

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 71
<211> LENGTH: 98
<212> TYPE: PRT
<213> ORGANISM: Llama pacos

<400> SEQUENCE: 71

Gln Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg

<210> SEQ ID NO 72
<211> LENGTH: 96
<212> TYPE: PRT
<213> ORGANISM: Llama pacos

<400> SEQUENCE: 72

Gln Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
            20                  25                  30

Tyr Ile Asp Trp Val Arg Gln Ala Pro Gly Gln Gly Leu Glu Trp Met
        35                  40                  45

Gly Arg Ile Asp Pro Glu Asp Gly Gly Thr Asn Tyr Ala Gln Lys Phe
    50                  55                  60

Gln Gly Arg Val Thr Phe Thr Ala Asp Thr Ser Thr Ser Thr Ala Tyr
65                  70                  75                  80

```
Val Glu Leu Ser Ser Leu Arg Ser Glu Asp Thr Ala Val Cys Tyr Leu
                85                  90                  95
```

<210> SEQ ID NO 73
<211> LENGTH: 96
<212> TYPE: PRT
<213> ORGANISM: Llama pacos

<400> SEQUENCE: 73

```
Gln Val Gln Leu Val Gln Ser Gly Ala Glu Leu Arg Asn Pro Gly Ala
1               5                   10                  15

Ser Val Lys Val Ser Cys Lys Ala Ser Gly Tyr Thr Phe Thr Ser Tyr
                20                  25                  30

Tyr Ile Asp Trp Val Arg Gln Ala Pro Gly Gln Gly Leu Glu Trp Met
            35                  40                  45

Gly Arg Ile Asp Pro Glu Asp Gly Gly Thr Asn Tyr Ala Gln Lys Phe
        50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Asp Thr Ala Val Cys Tyr Cys
                85                  90                  95
```

<210> SEQ ID NO 74
<211> LENGTH: 96
<212> TYPE: PRT
<213> ORGANISM: Llama pacos

<400> SEQUENCE: 74

```
Glu Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Ser Tyr
                20                  25                  30

Tyr Ile Asp Trp Val Arg Gln Ala Pro Gly Gln Gly Leu Glu Trp Met
            35                  40                  45

Gly Arg Ile Asp Pro Glu Asp Gly Gly Thr Lys Tyr Ala Gln Lys Phe
        50                  55                  60

Gln Gly Arg Val Thr Phe Thr Ala Asp Thr Ser Thr Ser Thr Ala Tyr
65                  70                  75                  80

Val Glu Leu Ser Ser Leu Arg Ser Glu Gly Thr Ala Val Tyr Tyr Cys
                85                  90                  95
```

<210> SEQ ID NO 75
<211> LENGTH: 96
<212> TYPE: PRT
<213> ORGANISM: Llama pacos

<400> SEQUENCE: 75

```
Gln Val Gln Leu Val Gln Pro Gly Ala Glu Leu Arg Lys Pro Gly Ala
1               5                   10                  15

Leu Leu Lys Val Ser Cys Lys Ala Ser Gly Tyr Thr Phe Thr Ser Tyr
                20                  25                  30

Tyr Ile Asp Trp Val Arg Gln Ala Pro Gly Gln Gly Leu Gly Trp Val
            35                  40                  45

Gly Arg Ile Asp Pro Glu Asp Gly Gly Thr Asn Tyr Ala Gln Lys Phe
        50                  55                  60

Gln Gly Arg Val Thr Leu Thr Ala Asp Thr Ser Thr Ser Thr Ala Tyr
65                  70                  75                  80

Val Glu Leu Ser Ser Leu Arg Ser Glu Asp Thr Ala Val Val Cys Tyr
```

-continued

```
                    85                  90                  95

<210> SEQ ID NO 76
<211> LENGTH: 97
<212> TYPE: PRT
<213> ORGANISM: Llama pacos

<400> SEQUENCE: 76

Ala Gly Pro Ala Gly Ala Ala Arg Gly Ala Glu Glu Ala Trp Gly Phe
1               5                   10                  15

Ala Glu Gly Leu Leu Gln Gly Phe Trp Ile His Leu His Gln Leu Leu
                20                  25                  30

His Ala Trp Val Arg Gln Ala Pro Gly Gln Gly Leu Gly Trp Val Gly
            35                  40                  45

Arg Ile Asp Pro Glu Asp Gly Gly Thr Asn Tyr Ala Gln Lys Phe Gln
        50                  55                  60

Gly Arg Val Thr Leu Thr Ala Asp Thr Ser Ser Thr Ala Tyr Val
65                  70                  75                  80

Glu Leu Ser Ser Leu Arg Ser Glu Asp Thr Ala Val Cys Tyr Cys Val
                85                  90                  95

Arg

<210> SEQ ID NO 77
<211> LENGTH: 95
<212> TYPE: PRT
<213> ORGANISM: Camelus ferus

<400> SEQUENCE: 77

Val Gln Met Val Gln Pro Gly Leu Ser Gly Ser Leu Gly Leu Gln Arg
1               5                   10                  15

Ser Pro Ala Arg Leu Pro Asp Thr Pro Ser Pro Ala Thr Thr Thr Gly
                20                  25                  30

Cys Asp Arg Pro Leu Pro Gly Gln Gly Leu Gly Trp Val Gly Arg Thr
            35                  40                  45

Asp Pro Glu Asp Gly Glu Thr Lys Tyr Ala Gln Lys Phe Gln Gly Arg
        50                  55                  60

Val Thr Leu Thr Ala Asp Met Ser Ser Thr Ala Tyr Val Glu Leu
65                  70                  75                  80

Ser Ser Leu Arg Ser Glu Asp Thr Ala Val Cys Tyr Cys Ala Arg
                85                  90                  95

<210> SEQ ID NO 78
<211> LENGTH: 97
<212> TYPE: PRT
<213> ORGANISM: Camelus ferus

<400> SEQUENCE: 78

Ala Gly Pro Ala Gly Ala Ala Arg Ala Glu Leu Arg Lys Pro Gly Ala
1               5                   10                  15

Ser Val Lys Val Ser Cys Lys Ala Ser Gly Tyr Thr Phe Thr Arg Tyr
                20                  25                  30

Tyr Ile Asp Trp Val Arg Gln Ala Pro Gly Gln Gly Leu Trp Trp Val
            35                  40                  45

Gly Arg Thr Asp Pro Glu Asp Gly Glu Thr Lys Tyr Ala Gln Lys Phe
        50                  55                  60

Gln Gly Val Thr Leu Thr Ala Asp Thr Ser Thr Ser Thr Ala Tyr Met
65                  70                  75                  80
```

Glu Leu Ser Ser Leu Arg Ser Glu Asp Thr Ala Val Cys Tyr Cys Ala
                 85                  90                  95

Arg

<210> SEQ ID NO 79
<211> LENGTH: 96
<212> TYPE: PRT
<213> ORGANISM: Llama pacos

<400> SEQUENCE: 79

Gln Val Gln Leu Leu Gln Ser Gly Ala Glu Leu Arg Lys Pro Gly Ala
1               5                   10                  15

Ser Ala Lys Val Ser Tyr Lys Ala Ser Tyr Thr Phe Ala Ser Tyr Asn
            20                  25                  30

Val His Trp Val Glu Gln Ala Pro Gly Glu Glu Leu Glu Ser Met Gly
        35                  40                  45

Thr Asp Phe Lys Asp Gly Ala Thr Ser Cys Ala Glu Lys Phe Gln Gly
    50                  55                  60

Arg Val Thr Leu Thr Lys Asp Thr Ser Thr Thr Asp Met Lys
65                  70                  75                  80

Leu Ser Pro Leu Ile Ser Lys Asp Met Ala Met Tyr Ser Arg Val Arg
                85                  90                  95

<210> SEQ ID NO 80
<211> LENGTH: 96
<212> TYPE: PRT
<213> ORGANISM: Camelus ferus

<400> SEQUENCE: 80

Gln Val Gln Leu Leu Gln Ser Gly Ala Glu Leu Arg Lys Pro Gly Ala
1               5                   10                  15

Ser Ala Lys Val Ser Tyr Lys Ala Ser Tyr Thr Phe Ala Ser Tyr Asn
            20                  25                  30

Val His Trp Val Glu Gln Ala Pro Gly Glu Glu Leu Glu Ser Met Gly
        35                  40                  45

Thr Asp Phe Lys Asp Gly Ala Thr Ser Tyr Ala Glu Lys Phe Gln Gly
    50                  55                  60

Arg Val Thr Leu Thr Lys Asp Thr Ser Thr Ser Thr Ile Asp Met Lys
65                  70                  75                  80

Val Ser Pro Leu Ile Ser Lys Asp Met Ala Met Tyr Ser Cys Val Arg
                85                  90                  95

<210> SEQ ID NO 81
<211> LENGTH: 98
<212> TYPE: PRT
<213> ORGANISM: Homo sapiens

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys

<210> SEQ ID NO 82
<211> LENGTH: 98
<212> TYPE: PRT
<213> ORGANISM: Llama pacos

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Ala Met Ser Trp Val Arg Gln Ala Pro Gly Lys Gly Leu Glu Trp Val
            35                  40                  45

Ser Ala Ile Ser Trp Asn Gly Gly Ser Thr Tyr Tyr Ala Glu Ser Met
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys

<210> SEQ ID NO 83
<211> LENGTH: 96
<212> TYPE: PRT
<213> ORGANISM: Llama pacos

<400> SEQUENCE: 83

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
            35                  40                  45

Ser Ala Ile Ser Trp Asn Gly Gly Ser Thr Tyr Tyr Ala Glu Ser Met
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Gly Thr Ala Val Tyr Tyr Cys
                85                  90                  95

<210> SEQ ID NO 84
<211> LENGTH: 96
<212> TYPE: PRT
<213> ORGANISM: Llama pacos

<400> SEQUENCE: 84

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Gly Met Ser Trp Val Arg His Ser Pro Gly Lys Gly Leu Glu Trp Val
            35                  40                  45

Ser Ala Ile Ser Trp Asn Gly Gly Ser Thr Tyr Tyr Ala Glu Ser Met
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 85
<211> LENGTH: 98
<212> TYPE: PRT
<213> ORGANISM: Llama pacos

<400> SEQUENCE: 85

Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
                20                  25                  30

Tyr Met Ser Trp Val Arg Gln Ala Pro Gly Lys Gly Leu Glu Ser Val
            35                  40                  45

Ser Ser Ile Tyr Ser Tyr Ser Ser Asn Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Thr

<210> SEQ ID NO 86
<211> LENGTH: 98
<212> TYPE: PRT
<213> ORGANISM: Llama pacos

<400> SEQUENCE: 86

Gln Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
                20                  25                  30

Tyr Met Ser Trp Val Arg Gln Ala Pro Gly Lys Gly Leu Glu Ser Val
            35                  40                  45

Ser Ser Ile Tyr Ser Tyr Ser Ser Asn Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Thr

<210> SEQ ID NO 87
<211> LENGTH: 96
<212> TYPE: PRT
<213> ORGANISM: Llama pacos

<400> SEQUENCE: 87

Gln Val Gln Leu Val Glu Ser Val Gly Gly Leu Val Gln Asp Gly Gly
1               5                   10                  15

Ser Leu Arg Leu Ser Cys Ala Ala Ser Gly Arg Thr Phe Ser Ser Ser
                20                  25                  30

Ala Met Ser Trp Val Arg Gln Ala Pro Gly Lys Gly Leu Glu Trp Val
            35                  40                  45

Ser Ser Ile Tyr Ser Tyr Ser Ser Asn Thr Tyr Asn Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                85                  90                  95

<210> SEQ ID NO 88
<211> LENGTH: 96
<212> TYPE: PRT
<213> ORGANISM: Llama pacos

<400> SEQUENCE: 88

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Ser Val
            35                  40                  45

Ser Ser Ile Tyr Ser Tyr Ser Ser Asn Thr Tyr Tyr Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Asp Met Ala Val Tyr Tyr Cys
                85                  90                  95

<210> SEQ ID NO 89
<211> LENGTH: 96
<212> TYPE: PRT
<213> ORGANISM: Llama pacos

<400> SEQUENCE: 89

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Ser Val
            35                  40                  45

Ser Ser Ile Tyr Ser Tyr Ser Ser Asn Thr Tyr Tyr Ala Asp Ser Val
            50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Ser Glu Gly Thr Ala Val Tyr Tyr Cys
                85                  90                  95

<210> SEQ ID NO 90
<211> LENGTH: 68
<212> TYPE: PRT
<213> ORGANISM: Llama pacos

<400> SEQUENCE: 90

Ser Ser Ala Met Ser Trp Val Leu Gln Ala Pro Gly Lys Gly Leu Glu
 1               5                  10                  15

Trp Val Ser Ser Ile Tyr Ser Tyr Ser Ser Asn Thr Tyr Tyr Ala Asp
                20                  25                  30

Ser Val Lys Gly Arg Phe Thr Ile Ser Arg Asp Asn Ala Lys Asn Thr
            35                  40                  45

Leu Tyr Leu Gln Met Asn Ser Leu Lys Pro Glu Asp Thr Val Val Tyr
            50                  55                  60

Tyr Cys Ala Ala
65

<210> SEQ ID NO 91
<211> LENGTH: 96
<212> TYPE: PRT
<213> ORGANISM: Llama pacos

<400> SEQUENCE: 91

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Thr Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

<210> SEQ ID NO 92
<211> LENGTH: 96
<212> TYPE: PRT
<213> ORGANISM: Llama pacos

<400> SEQUENCE: 92

Glu Val Arg Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Ser
            20                  25                  30

Ala Met Ser Arg Val Arg Gln Val Pro Gly Lys Gly Leu Glu Trp Val
        35                  40                  45

Ser Ser Ile Tyr Ser Tyr Ser Ser Asn Thr Tyr Tyr Ala Asp Ser Val
    50                  55                  60

Lys Gly Arg Phe Thr Ile Ser Thr Asp Asn Ala Lys Asn Thr Leu Tyr
65                  70                  75                  80

Leu Gln Met Asn Ser Leu Lys Ser Glu Gly Thr Ala Val Tyr Tyr Cys
                85                  90                  95

<210> SEQ ID NO 93
<211> LENGTH: 98
<212> TYPE: PRT
<213> ORGANISM: Llama pacos

<400> SEQUENCE: 93

Gln Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Ser Ile Tyr Ser Tyr Ser Ser Asn Thr Tyr Tyr Ala Asp Ser Val
    50                  55                  60

Val Glu Leu Phe Thr Ile Ser Thr Glu Asn Ala Lys Asn Thr Leu Tyr

```
65                  70                  75                  80

Leu Gln Met Asn Ser Leu Lys Ser Glu Asp Thr Ala Val Tyr Tyr Cys
                85                  90                  95

Ala Lys

<210> SEQ ID NO 94
<211> LENGTH: 80
<212> TYPE: PRT
<213> ORGANISM: Llama pacos

<400> SEQUENCE: 94

Arg Leu Ser Cys Ala Ala Ser Gly Tyr Thr Phe Asp Asp Tyr Ala Met
1               5                   10                  15

Ser Trp Val Arg Gln Ala Pro Gly Lys Gly Leu Glu Trp Val Ser Ser
            20                  25                  30

Ile Tyr Ser Tyr Ser Ser Asn Thr Tyr Tyr Ala Asp Ser Val Lys Gly
        35                  40                  45

Arg Phe Thr Ile Ser Thr Glu Asn Ala Lys Asn Thr Leu Tyr Leu Gln
    50                  55                  60

Met Asn Ser Leu Lys Ser Glu Asp Thr Ala Val Tyr Tyr Cys Ala Lys
65                  70                  75                  80

<210> SEQ ID NO 95
<211> LENGTH: 98
<212> TYPE: PRT
<213> ORGANISM: Llama pacos

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Pro Glu Trp Val
        35                  40                  45

Ser Ala Ile Asn Ser Gly Gly Gly Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Ala Lys

<210> SEQ ID NO 96
<211> LENGTH: 96
<212> TYPE: PRT
<213> ORGANISM: Llama pacos

<400> SEQUENCE: 96

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Gly Gly Asp Gly Ser Thr Ser Tyr Ala Asp Ser Val
    50                  55                  60

Lys Gly Arg Ser Thr Ile Ser Arg Asp Asn Ala Lys Asn Thr Leu Tyr
```

```
                65                  70                  75                  80
Leu Gln Met Asn Ser Leu Lys Pro Glu Gly Thr Ala Val Tyr Tyr Cys
                    85                  90                  95

<210> SEQ ID NO 97
<211> LENGTH: 97
<212> TYPE: PRT
<213> ORGANISM: Llama pacos

<400> SEQUENCE: 97

Gln Val Gln Leu Val Glu Ser Gly Gly Gly Leu Val Gln Pro Gly Gly
1               5                   10                  15

Ser Leu Arg Leu Phe Cys Ala Ala Ser Gly Phe Thr Phe Ser Ser Tyr
                20                  25                  30

Tyr Met Ser Trp Val Arg His Ser Pro Gly Lys Gly Leu Glu Trp Val
            35                  40                  45

Ser Ala Ile Asn Ser Gly Gly Gly Ser Thr Ser Tyr Ala Asp Ser Met
        50                  55                  60

Lys Gly Gln Phe Thr Ile Ser Arg Asp Asn Thr Lys Asn Thr Leu Tyr
65                  70                  75                  80

Leu Gln Met Asn Ser Leu Lys Pro Glu Asp Thr Ala Val Tyr Tyr Cys Val
                    85                  90                  95

Arg

<210> SEQ ID NO 98
<211> LENGTH: 96
<212> TYPE: PRT
<213> ORGANISM: Llama pacos

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Asn Ser Gly Gly Gly Ser Thr Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                    85                  90                  95

<210> SEQ ID NO 99
<211> LENGTH: 96
<212> TYPE: PRT
<213> ORGANISM: Llama pacos

<400> SEQUENCE: 99

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
                20                  25                  30

Trp Met Tyr Trp Val Arg Gln Ala Pro Gly Lys Gly Leu Glu Trp Val
            35                  40                  45

Ser Ala Ile Asn Ser Gly Gly Gly Ser Thr Ser Tyr Ala Asp Ser Met
        50                  55                  60
```

```
Lys Gly Gln Phe Thr Ile Ser Ser Asp Asn Ala Arg Asn Thr Leu Tyr
 65                  70                  75                  80

Leu Gln Met Asn Ser Leu Lys Pro Glu Gly Thr Ala Val Tyr Tyr Cys
                 85                  90                  95
```

<210> SEQ ID NO 100
<211> LENGTH: 96
<212> TYPE: PRT
<213> ORGANISM: Llama pacos

<400> SEQUENCE: 100

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Met Asn Trp Val Arg Gln Ala Pro Gly Lys Gly Leu Glu Trp Val
                 35                  40                  45

Ser Ala Ile Asn Ser Gly Gly Gly Ser Thr Ser Tyr Ala Asp Ser Met
 50                  55                  60

Lys Gly Gln Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                 85                  90                  95
```

<210> SEQ ID NO 101
<211> LENGTH: 98
<212> TYPE: PRT
<213> ORGANISM: Llama pacos

<400> SEQUENCE: 101

```
Arg Cys Ser Trp Trp Ser Leu Gly Glu Ala Trp Cys Arg Leu Gly Gly
  1               5                  10                  15

Ser Leu Arg Leu Ser Cys Ala Ala Ser Gly Phe Thr Phe Gly Ser Tyr
                 20                  25                  30

Val Leu Ser Trp Val Cys His Ser Pro Gly Lys Gly Leu Glu Trp Val
                 35                  40                  45

Ser Ala Ile Asn Ser Gly Gly Gly Ser Thr Ser Tyr Ala Asp Ser Val
 50                  55                  60

Lys Gly Gln Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Val Arg
```

<210> SEQ ID NO 102
<211> LENGTH: 96
<212> TYPE: PRT
<213> ORGANISM: Llama pacos

<400> SEQUENCE: 102

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Gly Ser Tyr
                 20                  25                  30

Val Leu Ser Trp Val Cys His Ser Pro Gly Lys Gly Leu Glu Trp Val
                 35                  40                  45

Ser Ala Ile Asn Ser Cys Gly Ser Thr Ser Tyr Ala Asp Ser Val
 50                  55                  60
```

```
Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95
```

<210> SEQ ID NO 103
<211> LENGTH: 97
<212> TYPE: PRT
<213> ORGANISM: Llama pacos

<400> SEQUENCE: 103

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Asp Ile Asn Ser Gly Gly Gly Ser Thr Tyr Tyr Ala Asp Ser Val
        50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ala
                85                  90                  95

Thr
```

<210> SEQ ID NO 104
<211> LENGTH: 96
<212> TYPE: PRT
<213> ORGANISM: Llama pacos

<400> SEQUENCE: 104

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Asp Ile Asn Ser Gly Gly Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95
```

<210> SEQ ID NO 105
<211> LENGTH: 96
<212> TYPE: PRT
<213> ORGANISM: Llama pacos

<400> SEQUENCE: 105

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Gly Leu Glu Trp Val
            35                  40                  45

Ser Ala Ile Asn Ser Gly Gly Gly Ser Thr Tyr Tyr Ala Asp Ser Val
```

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

<210> SEQ ID NO 106
<211> LENGTH: 96
<212> TYPE: PRT
<213> ORGANISM: Llama pacos

<400> SEQUENCE: 106

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Asn Trp Val Arg Gln Ala Pro Gly Lys Gly Leu Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 107
<211> LENGTH: 96
<212> TYPE: PRT
<213> ORGANISM: Llama pacos

<400> SEQUENCE: 107

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Pro Glu Trp Val
        35                  40                  45

Ser Asp Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 108
<211> LENGTH: 96
<212> TYPE: PRT
<213> ORGANISM: Llama pacos

<400> SEQUENCE: 108

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Asp Met Ser Trp Val Arg Gln Ala Pro Gly Lys Gly Pro Glu Trp Val
        35                  40                  45

Ser Ala Ile Asn Ser Gly Gly Gly Ser Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 109
<211> LENGTH: 96
<212> TYPE: PRT
<213> ORGANISM: Llama pacos

<400> SEQUENCE: 109

Gln Val Gln Leu Val Glu Ser Gly Gly Leu Val Gln Ala Gly Gly
1               5                   10                  15

Ser Leu Lys His Ser Cys Ala Ala Ser Gly Leu Thr Phe Gly Ser Tyr
                20                  25                  30

Asp Met Ser Trp Val Arg Gln Ala Pro Gly Lys Gly Pro Glu Trp Val
                35                  40                  45

Ser Ala Ile Asn Ser Gly Gly Ser Thr Tyr Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 110
<211> LENGTH: 96
<212> TYPE: PRT
<213> ORGANISM: Llama pacos

<400> SEQUENCE: 110

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Gly Ser Tyr
                20                  25                  30

Asp Met Ser Trp Val Arg Gln Ala Pro Gly Lys Gly Pro Glu Trp Val
                35                  40                  45

Ser Cys Ile Asn Ser Gly Gly Ser Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 111
<211> LENGTH: 96
<212> TYPE: PRT
<213> ORGANISM: Llama pacos

<400> SEQUENCE: 111

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
                20                  25                  30

Asp Met Ser Trp Val Arg Arg Ala Pro Gly Lys Gly Leu Glu Trp Val
                35                  40                  45

Ser Tyr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Gly Thr Ala Val Tyr Tyr Cys
                85                  90                  95

<210> SEQ ID NO 112
<211> LENGTH: 96
<212> TYPE: PRT
<213> ORGANISM: Llama pacos

<400> SEQUENCE: 112

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Ala Pro Gly Lys Gly Leu Glu Trp Val
            35                  40                  45

Ser Tyr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 113
<211> LENGTH: 96
<212> TYPE: PRT
<213> ORGANISM: Llama pacos

<400> SEQUENCE: 113

Glu Val Gln Val Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Tyr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

<210> SEQ ID NO 114
<211> LENGTH: 96
<212> TYPE: PRT
<213> ORGANISM: Llama pacos

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asn Tyr
                20                  25                  30

Ala Met Ser Trp Val Arg Gln Ala Pro Gly Lys Gly Leu Glu Trp Val
            35                  40                  45

Ser Tyr Ile Asn Ser Gly Gly Gly Ser Thr Tyr Tyr Ala Asp Ser Val
            50                  55                  60

Lys Gly Arg Phe Thr Ile Ser Arg Asp Asn Ala Lys Asn Thr Val Tyr

```
                65                  70                  75                  80
Leu Gln Met Asn Ser Leu Lys Pro Glu Gly Thr Ala Val Tyr Tyr Cys
                    85                  90                  95

<210> SEQ ID NO 115
<211> LENGTH: 96
<212> TYPE: PRT
<213> ORGANISM: Llama pacos

<400> SEQUENCE: 115

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Pro Glu Trp Val
            35                  40                  45

Ser Ala Ile Asn Thr Gly Gly Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 116
<211> LENGTH: 98
<212> TYPE: PRT
<213> ORGANISM: Llama pacos

<400> SEQUENCE: 116

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Tyr Trp Val Arg Gln Ala Pro Gly Lys Gly Leu Glu Trp Val
            35                  40                  45

Ser Ala Ile Asn Thr Gly Gly Gly Ser Thr Tyr Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Asp Thr Ala Leu Tyr Tyr Cys
                85                  90                  95

Ala Arg

<210> SEQ ID NO 117
<211> LENGTH: 97
<212> TYPE: PRT
<213> ORGANISM: Llama pacos

<400> SEQUENCE: 117

Glu Val Gln Leu Val Glu Ser Gly Gly Gly Leu Val Gln Pro Gly Gly
1               5                   10                  15

Ser Leu Arg Arg Ser Cys Ala Thr Ser Gly Phe Thr Phe Gly Ser Tyr
                20                  25                  30

Trp Met Tyr Trp Val Arg Gln Ala Pro Gly Lys Gly Leu Glu Trp Val
            35                  40                  45

Ser Ser Ile Asn Thr Gly Gly Asp Ser Ser Tyr Tyr Ala Asp Ser Val
        50                  55                  60
```

-continued

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Cys Val
                 85                  90                  95

Arg

<210> SEQ ID NO 118
<211> LENGTH: 96
<212> TYPE: PRT
<213> ORGANISM: Llama pacos

<400> SEQUENCE: 118

Gln Leu Gln Leu Val Glu Ser Gly Gly Gly Leu Val Gln Pro Gly Gly
  1               5                  10                  15

Ser Leu Arg Leu Ser Cys Ala Ala Ser Gly Leu Thr Phe Gly Ser Tyr
             20                  25                  30

Trp Met Tyr Trp Val Arg Gln Ala Pro Gly Lys Gly Leu Glu Trp Val
         35                  40                  45

Ser Ser Ile Asn Thr Gly Gly Asp Ser Ser Tyr Tyr Ala Asp Ser Met
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                 85                  90                  95

<210> SEQ ID NO 119
<211> LENGTH: 96
<212> TYPE: PRT
<213> ORGANISM: Llama pacos

<400> SEQUENCE: 119

Gln Val Gln Leu Val Glu Ser Gly Gly Gly Leu Val Gln Pro Gly Val
  1               5                  10                  15

Ser Leu Arg Leu Ser Cys Ala Ala Ser Gly Phe Thr Phe Ser Ser His
             20                  25                  30

Tyr Met Ser Trp Val His Gln Ala Pro Gly Lys Gly Leu Glu Trp Val
         35                  40                  45

Ser Ser Ile Asn Thr Gly Gly Asp Ser Ser Phe Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                 85                  90                  95

<210> SEQ ID NO 120
<211> LENGTH: 96
<212> TYPE: PRT
<213> ORGANISM: Llama pacos

<400> SEQUENCE: 120

Gln Leu Gln Leu Val Glu Ser Gly Gly Gly Leu Val Gln Pro Gly Gly
  1               5                  10                  15

Ser Leu Arg Val Ser Cys Ala Ala Ser Gly Phe Thr Phe Ser Ser Tyr
             20                  25                  30

Tyr Met Ser Trp Val Arg Gln Ala Pro Gly Lys Gly Leu Glu Trp Val
         35                  40                  45

Ser Thr Ile Asn Thr Gly Gly Ser Thr Tyr Tyr Ala Asp Ser Val
     50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                 85                  90                  95
```

<210> SEQ ID NO 121
<211> LENGTH: 96
<212> TYPE: PRT
<213> ORGANISM: Llama pacos

<400> SEQUENCE: 121

```
Gln Leu Gln Leu Val Glu Ser Gly Gly Leu Val Gln Pro Gly Gly
 1               5                   10                  15

Ser Leu Arg Val Ser Cys Ala Ala Ser Gly Phe Thr Phe Ser Ser Tyr
                 20                  25                  30

Tyr Met Ser Trp Val Arg Gln Ala Pro Gly Lys Gly Leu Glu Trp Val
             35                  40                  45

Ser Ala Ile Asn Thr Gly Gly Ser Thr Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Gly Thr Ala Val Tyr Tyr Cys
                 85                  90                  95
```

<210> SEQ ID NO 122
<211> LENGTH: 45
<212> TYPE: PRT
<213> ORGANISM: Llama pacos

<400> SEQUENCE: 122

```
Gly Gly Gly Ser Thr Asn Tyr Ala Asp Ser Val Lys Gly Arg Phe Thr
 1               5                   10                  15

Ile Ser Arg Asp Asn Ser Lys Asn Thr Val Tyr Leu Gln Met Asn Ser
                 20                  25                  30

Leu Lys Pro Glu Gly Thr Ala Val Tyr Tyr Cys Asn Ala
             35                  40                  45
```

<210> SEQ ID NO 123
<211> LENGTH: 96
<212> TYPE: PRT
<213> ORGANISM: Llama pacos

<400> SEQUENCE: 123

```
Gln Val Gln Leu Val Glu Ser Gly Gly Gly Leu Val Gln Ala Gly Gly
 1               5                   10                  15

Ser Leu Arg Leu Ser Cys Ala Ala Ser Gly Leu Thr Phe Ser Ser Tyr
                 20                  25                  30

Ala Met Ser Trp Val Arg Gln Ala Pro Gly Lys Gly Leu Glu Ser Val
             35                  40                  45

Ser Thr Ile Asn Ser Asp Gly Ser Asn Thr Tyr Tyr Ala Asp Ser Val
         50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Asp Gly Thr Ala Val Tyr Tyr Cys
                 85                  90                  95
```

<210> SEQ ID NO 124
<211> LENGTH: 96

<212> TYPE: PRT
<213> ORGANISM: Llama pacos

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Tyr Met Ser Trp Val Arg Gln Ala Pro Gly Lys Gly Leu Glu Ser Val
        35                  40                  45

Ser Thr Ile Tyr Ser Tyr Gly Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 125
<211> LENGTH: 98
<212> TYPE: PRT
<213> ORGANISM: Camelus ferus

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Cys Gln Ala Pro Gly Lys Gly Leu Glu Trp Val
        35                  40                  45

Ser Ser Ile Tyr Ser Tyr Gly Ser Asn Thr Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Ser Glu Asp Thr Ala Val Tyr Tyr Cys
                85                  90                  95

Ala Ala

<210> SEQ ID NO 126
<211> LENGTH: 98
<212> TYPE: PRT
<213> ORGANISM: Camelus ferus

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Cys Gln Ala Pro Gly Lys Gly Leu Glu Trp Val
        35                  40                  45

Ser Ser Ile Tyr Ser Tyr Gly Ser Asn Thr Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Lys Ser Glu Asp Thr Ala Val Tyr Tyr Cys
                85                  90                  95

Ala Ala

<210> SEQ ID NO 127
<211> LENGTH: 98
<212> TYPE: PRT
<213> ORGANISM: Camelus ferus

<400> SEQUENCE: 127

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Tyr
            20                  25                  30

Asp Met Ser Trp Val Arg Gln Ala Pro Gly Lys Gly Leu Glu Trp Leu
        35                  40                  45

Ser Gly Ile Tyr Ser Tyr Gly Ser Asp Thr Tyr Tyr Ala Asp Ser Val
    50                  55                  60

Lys Gly Arg Phe Thr Ile Ser Arg Asp Asn Ala Lys Asn Val Leu Tyr
65                  70                  75                  80

Leu Gln Met Asn Thr Leu Lys Pro Glu Asp Thr Ala Val Tyr Asn Cys
                85                  90                  95

Ala Arg

<210> SEQ ID NO 128
<211> LENGTH: 96
<212> TYPE: PRT
<213> ORGANISM: Llama pacos

<400> SEQUENCE: 128

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Gly Ile Tyr Ser Asp Gly Ser Asp Thr Tyr Tyr Ala Asp Ser Val
    50                  55                  60

Lys Gly Arg Phe Thr Ile Ser Arg Asp Asn Ala Lys Asn Val Leu Tyr
65                  70                  75                  80

Leu Gln Met Asn Thr Leu Lys Pro Glu Gly Thr Ala Val Tyr Asn Cys
                85                  90                  95

<210> SEQ ID NO 129
<211> LENGTH: 96
<212> TYPE: PRT
<213> ORGANISM: Llama pacos

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Tyr Met Ser Trp Val Arg Gln Ala Pro Gly Lys Gly Leu Glu Ser Val
        35                  40                  45

Ser Gly Ile Tyr Ser Tyr Gly Asn Thr Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Pro Glu Gly Thr Ala Val Tyr Tyr Cys
                85                  90                  95

<210> SEQ ID NO 130
<211> LENGTH: 95
<212> TYPE: PRT
<213> ORGANISM: Llama pacos

<400> SEQUENCE: 130

Gln Val Gln Leu Val Glu Thr Gly Gly Gly Val Gln Pro Gly Gly Ser
1               5                   10                  15

Leu Arg Leu Ser Cys Ala Ala Ser Gly Phe Thr Phe Ser Ser Ser Ala
            20                  25                  30

Met Ser Trp Val Arg Gln Ala Pro Gly Lys Gly Leu Glu Trp Val Ser
        35                  40                  45

Gly Ile Tyr Ser Asp Gly Ser Asp Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Gly Thr Ala Val Tyr Tyr Cys
                85                  90                  95

<210> SEQ ID NO 131
<211> LENGTH: 51
<212> TYPE: PRT
<213> ORGANISM: Llama pacos

<400> SEQUENCE: 131

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Phe Ser Ile Tyr
            20                  25                  30

Ala Met Gly Trp Tyr Arg Gln Ala Pro Gly Lys Gln Arg Glu Leu Val
        35                  40                  45

Ala Ala Ile
    50

<210> SEQ ID NO 132
<211> LENGTH: 95
<212> TYPE: PRT
<213> ORGANISM: Camelus ferus

<400> SEQUENCE: 132

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Cys Gln Ala Pro Gly Lys Gly Leu Glu Trp Val
        35                  40                  45

Gln His Gly Leu Val Pro Pro Gly Ser Arg Glu Gly Ala Arg Val Gly
    50                  55                  60

Leu Asn Tyr Tyr Trp His Ile Leu Cys Arg Leu Arg Glu Gly Pro Ile
65                  70                  75                  80

His His Leu Pro Arg Gln Arg Gln Glu His Gly Val Ser Ala Asn
                85                  90                  95

<210> SEQ ID NO 133
<211> LENGTH: 93
<212> TYPE: PRT
<213> ORGANISM: Camelus ferus
<220> FEATURE:

```
<221> NAME/KEY: misc_feature
<222> LOCATION: (93)..(93)
<223> OTHER INFORMATION: Xaa can be any naturally occurring amino acid

<400> SEQUENCE: 133

Glu Val Gln Leu Val Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Cys Gln Ala Pro Gly Lys Gly Leu Glu Trp Val
        35                  40                  45

Gln His Gly Leu Val Pro Pro Gly Ser Arg Glu Gly Ala Arg Val Gly
    50                  55                  60

Leu Asn Tyr Tyr Trp His Ile Leu Cys Arg Leu Arg Glu Gly Pro Ile
65                  70                  75                  80

His His Leu Pro Arg Gln Arg Gln Glu His Gly Val Xaa
                85                  90

<210> SEQ ID NO 134
<211> LENGTH: 97
<212> TYPE: PRT
<213> ORGANISM: Homo sapiens

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 135
<211> LENGTH: 97
<212> TYPE: PRT
<213> ORGANISM: Camelus ferus

<400> SEQUENCE: 135

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ser Arg Gly Ser Thr His Tyr Ala Asp Ser Met Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ala
                85                  90                  95

Arg
```

<210> SEQ ID NO 136
<211> LENGTH: 95
<212> TYPE: PRT
<213> ORGANISM: Llama pacos

<400> SEQUENCE: 136

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Gly Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Gly Thr Ala Val Tyr Tyr Cys
                85                  90                  95
```

<210> SEQ ID NO 137
<211> LENGTH: 95
<212> TYPE: PRT
<213> ORGANISM: Llama pacos

<400> SEQUENCE: 137

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Ala Arg Gln Val Pro Gly Lys Gly Leu Glu Trp Val
        35                  40                  45

Ser Gly Ile Tyr Ser Asp Gly Ser Thr Tyr Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Ser Glu Gly Thr Ala Val Tyr Tyr Cys
                85                  90                  95
```

<210> SEQ ID NO 138
<211> LENGTH: 99
<212> TYPE: PRT
<213> ORGANISM: Homo sapiens

<400> SEQUENCE: 138

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg

<210> SEQ ID NO 139
<211> LENGTH: 99
<212> TYPE: PRT
<213> ORGANISM: Llama pacos

<400> SEQUENCE: 139

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg

<210> SEQ ID NO 140
<211> LENGTH: 97
<212> TYPE: PRT
<213> ORGANISM: Llama pacos

<400> SEQUENCE: 140

Gln Val Gln Leu Gln Glu Ser Gly Pro Asp Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 141
<211> LENGTH: 99
<212> TYPE: PRT
<213> ORGANISM: Llama pacos

<400> SEQUENCE: 141

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Tyr Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
    50                  55                  60

Leu Lys Ser Arg Thr Ser Ile Ser Arg Asp Thr Ser Lys Asn Gln Phe

```
                 65                  70                  75                  80
Ser Leu Gln Leu Ser Ser Val Thr Pro Glu Asp Thr Ala Val Tyr Tyr
                 85                  90                  95

Cys Ala Arg
```

<210> SEQ ID NO 142
<211> LENGTH: 64
<212> TYPE: PRT
<213> ORGANISM: Llama pacos

<400> SEQUENCE: 142

```
Trp Ser Trp Ile Arg Gln Pro Pro Gly Lys Gly Leu Glu Trp Met Gly
1               5                   10                  15

Val Ile Gly Tyr Glu Gly Ser Thr Tyr Tyr Ser Pro Ser Leu Lys Ser
                20                  25                  30

His Thr Ser Ile Ser Arg Asp Thr Ser Lys Asn Gln Phe Ser Leu Gln
                35                  40                  45

Leu Ser Ser Val Thr Pro Glu Asp Thr Ala Val Tyr Tyr Cys Ala Arg
            50                  55                  60
```

<210> SEQ ID NO 143
<211> LENGTH: 68
<212> TYPE: PRT
<213> ORGANISM: Llama pacos

<400> SEQUENCE: 143

```
Lys Pro Ser Gln Thr Leu Ser Leu Thr Cys Thr Val Ser Gly Gly Ser
1               5                   10                  15

Ile Thr Thr Asn Tyr Tyr Tyr Trp Ser Trp Ile Arg Gln Pro Pro Gly
                20                  25                  30

Lys Gly Leu Glu Trp Met Gly Ala Ile Ala Tyr Ser Gly Ser Thr Tyr
                35                  40                  45

Tyr Ser Pro Ser Leu Lys Ser Arg Thr Ser Ile Ser Arg Asp Thr Ser
            50                  55                  60

Lys Asn Gln Phe
65
```

<210> SEQ ID NO 144
<211> LENGTH: 97
<212> TYPE: PRT
<213> ORGANISM: Llama pacos

<400> SEQUENCE: 144

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
                20                  25                  30

Tyr Tyr Tyr Trp Ser Trp Ile Arg Gln Pro Pro Gly Lys Gly Leu Glu
                35                  40                  45

Trp Met Gly Ala Ile Ala Tyr Asp Gly Ser Thr Tyr Tyr Ser Pro Ser
            50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys
```

<210> SEQ ID NO 145
<211> LENGTH: 97
<212> TYPE: PRT
<213> ORGANISM: Llama pacos

<400> SEQUENCE: 145

Glu Val Gln Leu Gln Glu Ser Gly Pro Gly Leu Leu Lys Pro Ser Gln
1               5                   10                  15

Thr Leu Ser Leu Thr Cys Ala Val Tyr Gly Gly Ser Ile Thr Thr Ser
            20                  25                  30

Tyr Tyr Tyr Trp Ser Trp Ile Arg Gln Pro Pro Gly Lys Gly Leu Glu
        35                  40                  45

Trp Met Gly Ala Ile Ala Tyr Asp Gly Ser Thr Tyr Tyr Ser Pro Ser
    50                  55                  60

Leu Lys Ser His Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 146
<211> LENGTH: 97
<212> TYPE: PRT
<213> ORGANISM: Llama pacos

<400> SEQUENCE: 146

Gln Val Gln Arg Gln Glu Ser Gly Pro Gly Leu Val Lys Pro Ser Gln
1               5                   10                  15

Met Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Ala Tyr Asp Gly Ser Thr Tyr Tyr Ser Pro Ser
    50                  55                  60

Leu Lys Ser His Thr Ser Ile Ser Arg Asp Thr Ser Lys Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 147
<211> LENGTH: 97
<212> TYPE: PRT
<213> ORGANISM: Llama pacos

<400> SEQUENCE: 147

Glu Val Gln Val Gln Glu Ser Gly Pro Gly Leu Val Lys Pro Ser Gln
1               5                   10                  15

Ala Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Ser Leu Gln Leu Ser Ser Val Thr Pro Glu Gly Thr Ala Val Tyr Tyr

Cys

<210> SEQ ID NO 148
<211> LENGTH: 97
<212> TYPE: PRT
<213> ORGANISM: Llama pacos

<400> SEQUENCE: 148

Glu Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Asn Asn Gln Phe
65                  70                  75                  80

Ser Leu Gln Leu Ser Ser Val Thr Pro Glu Gly Thr Ala Val Tyr Tyr
                85                  90                  95

Cys

<210> SEQ ID NO 149
<211> LENGTH: 99
<212> TYPE: PRT
<213> ORGANISM: Camelus ferus

<400> SEQUENCE: 149

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Tyr Tyr Gly Trp Ser Trp Ile Cys Gln Pro Pro Gly Lys Gly Leu Glu
        35                  40                  45

Trp Met Gly Ala Ile Ala Tyr Ser Gly Ser Thr Tyr Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg

<210> SEQ ID NO 150
<211> LENGTH: 40
<212> TYPE: PRT
<213> ORGANISM: Llama pacos
<220> FEATURE:
<221> NAME/KEY: misc_feature
<222> LOCATION: (40)..(40)
<223> OTHER INFORMATION: Xaa can be any naturally occurring amino acid

<400> SEQUENCE: 150

Gln Val Gln Leu Gln Glu Ser Gly Pro Gly Leu Val Lys Pro Ser Gln
1               5                   10                  15

Met Leu Ser Leu Thr Cys Thr Val Ser Gly Gly Ser Ile Thr Thr Ser
            20                  25                  30

Cys Tyr Ala Trp Ser Trp Ile Xaa

```
              35                  40

<210> SEQ ID NO 151
<211> LENGTH: 94
<212> TYPE: PRT
<213> ORGANISM: Camelus ferus

<400> SEQUENCE: 151

Gln Val Gln Leu Gln Glu Ser Gly Pro Gly Leu Val Lys Pro Ser Gln
1               5                   10                  15

Thr Leu Pro Leu Thr Cys Thr Val Ser Gly Gly Ser Ile Thr Thr Ser
            20                  25                  30

Tyr Cys Ala Ser Trp Ile Arg Gln Pro Pro Gly Lys Gly Leu Glu Trp
        35                  40                  45

Met Gly Ala Ile Ala Leu Ser Gln Asn Leu Ile Leu Lys Val Lys His
    50                  55                  60

Leu Thr Asn Cys Leu Phe Tyr Ile Thr Lys Leu Asp Ser Lys Phe Ser
65                  70                  75                  80

Ile Asp Asp Asn Val Ser Lys His Ala Ile Cys Ile Thr Asp
                85                  90

<210> SEQ ID NO 152
<211> LENGTH: 39
<212> TYPE: PRT
<213> ORGANISM: Llama pacos

<400> SEQUENCE: 152

Gln Val Gln Leu Gln Glu Ser Gly Pro Gly Leu Val Lys Pro Ser Gln
1               5                   10                  15

Met Leu Ser Leu Thr Cys Thr Val Ser Gly Gly Ser Ile Thr Thr Ser
            20                  25                  30

Cys Tyr Ala Trp Ser Trp Ile
        35

<210> SEQ ID NO 153
<211> LENGTH: 96
<212> TYPE: PRT
<213> ORGANISM: Llama pacos

<400> SEQUENCE: 153

Gln Val Gln Leu Gln Glu Ser Gly Pro Gly Leu Val Lys Pro Ser Gln
1               5                   10                  15

Thr Leu Ser Leu Thr Cys Thr Ala Ser Gly Gly Ser Asn Thr Thr Ser
            20                  25                  30

Tyr Tyr Ala Trp Ser Trp Ile Arg Gln Pro Pro Gly Lys Gly Leu Glu
        35                  40                  45

Trp Met Gly Ala Ile Tyr Ser Gly Ser Thr Tyr Tyr Ser Pro Ser Leu
    50                  55                  60

Lys Ser Arg Thr Ser Ile Ser Arg Asp Thr Ser Asn Asn Gln Phe Ser
65                  70                  75                  80

Leu Gln Leu Ser Ser Val Thr Pro Glu Gly Thr Cys Val Tyr Tyr Cys
                85                  90                  95

<210> SEQ ID NO 154
<211> LENGTH: 96
<212> TYPE: PRT
<213> ORGANISM: Llama pacos

<400> SEQUENCE: 154
```

Glu Val Gln Leu Gln Glu Ser Gly Pro Gly Leu Val Lys Pro Ser Gln
1               5                   10                  15

Met Leu Ser Leu Thr Cys Thr Leu Ser Gly Asp Ser Ile Thr Thr Ser
            20                  25                  30

Cys Tyr Ala Trp Ser Trp Ile Arg Gln Pro Pro Gly Lys Gly Leu Glu
        35                  40                  45

Trp Met Gly Ala Ile Tyr Ser Gly Ser Thr Tyr Tyr Ser Pro Ser Leu
    50                  55                  60

Lys Ser Arg Thr Ser Ile Ser Arg Asp Thr Ser Lys Asn Gln Phe Ser
65                  70                  75                  80

Leu Gln Leu Ser Ser Val Thr Pro Glu Gly Thr Ala Val Tyr Tyr Cys
                85                  90                  95

<210> SEQ ID NO 155
<211> LENGTH: 96
<212> TYPE: PRT
<213> ORGANISM: Llama pacos

<400> SEQUENCE: 155

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Ile Thr Thr Ser
            20                  25                  30

Cys Tyr Ala Trp Ser Cys Ile Cys Gln Pro Pro Glu Lys Gly Leu Glu
        35                  40                  45

Trp Met Ala Ala Ile Tyr Ser Gly Ser Thr Tyr Tyr Ser Pro Ser Leu
    50                  55                  60

Lys Ser His Thr Ser Ile Ser Arg Asp Thr Ser Lys Asn Gln Phe Ser
65                  70                  75                  80

Leu Gln Leu Ser Ser Val Thr Pro Glu Gly Thr Ala Val Tyr Tyr Cys
                85                  90                  95

<210> SEQ ID NO 156
<211> LENGTH: 97
<212> TYPE: PRT
<213> ORGANISM: Llama pacos

<400> SEQUENCE: 156

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Ser
            20                  25                  30

Cys Tyr Ala Trp Ser Trp Ile His Gln Pro Pro Gly Lys Gly Leu Glu
        35                  40                  45

Met Gly Ala Ile Tyr Ser Gly Ser Thr Tyr Tyr Ser Pro Ser Leu Lys
    50                  55                  60

Ser His Thr Ser Ile Ser Arg Asp Thr Ser Lys Asn Gln Phe Ser Leu
65                  70                  75                  80

Gln Leu Ser Ser Val Thr Pro Glu Asp Thr Ala Val Tyr Tyr Cys Ala
                85                  90                  95

Arg

<210> SEQ ID NO 157
<211> LENGTH: 85
<212> TYPE: PRT
<213> ORGANISM: Llama pacos

<400> SEQUENCE: 157

Lys Pro Ser Gln Thr Leu Ser Leu Thr Cys Thr Val Ser Gly Gly Ser
1               5                   10                  15

Ile Thr Thr Ser Cys Tyr Ala Trp Ser Trp Ile His Gln Pro Pro Gly
                20                  25                  30

Lys Gly Leu Glu Met Gly Ala Ile Tyr Ser Gly Ser Thr Tyr Tyr Ser
            35                  40                  45

Pro Ser Leu Lys Ser His Thr Ser Ile Ser Arg Asp Thr Ser Lys Asn
50                      55                  60

Gln Phe Ser Leu Gln Leu Ser Ser Val Thr Pro Glu Asp Thr Ala Val
65                  70                  75                  80

Tyr Tyr Cys Ala Arg
                85

<210> SEQ ID NO 158
<211> LENGTH: 98
<212> TYPE: PRT
<213> ORGANISM: Homo sapiens

<400> SEQUENCE: 158

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Ala Ala Met Tyr Tyr Cys
                85                  90                  95

Val Arg

<210> SEQ ID NO 159
<211> LENGTH: 98
<212> TYPE: PRT
<213> ORGANISM: Camelus ferus

<400> SEQUENCE: 159

Gln Val Gln Leu Glu Gln Pro Val Ala Glu Leu Lys Met Pro Gly Glu
1               5                   10                  15

Ala Leu Arg Ile Ser Cys Lys Thr Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ala Ile Tyr Pro Gly Asp Ser Asp Thr Arg Tyr Ser Pro Ser Phe
50                  55                  60

Gln Gly His Ile Thr Ile Ser Ala Asp Lys Ser Thr Thr Ala Tyr
65                  70                  75                  80

Leu Gln Trp Ser Ser Leu Lys Ser Thr Asp Ser Ala Val Tyr Tyr Cys
                85                  90                  95

Ala Lys

<210> SEQ ID NO 160
<211> LENGTH: 97
<212> TYPE: PRT

<213> ORGANISM: Llama pacos

<400> SEQUENCE: 160

Gln Val Lys Leu Glu Gln Pro Ala Ala Glu Leu Lys Arg Pro Gly Glu
1               5                   10                  15

Thr Leu Arg Ile Ser Cys Lys Thr Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ala Ile Tyr Pro Gly Asp Ser Asp Thr Arg Tyr Ser Pro Ser Phe
    50                  55                  60

Gln Gly His Thr Thr Ile Ser Thr Asp Asn Pro Pro Ala Leu Pro Thr
65                  70                  75                  80

Cys Gly Gly Ala Ala Ser Pro Arg Thr Gln Pro Cys Ile Thr Val Gln
                85                  90                  95

Arg

<210> SEQ ID NO 161
<211> LENGTH: 98
<212> TYPE: PRT
<213> ORGANISM: Homo sapiens

<400> SEQUENCE: 161

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg

<210> SEQ ID NO 162
<211> LENGTH: 99
<212> TYPE: PRT
<213> ORGANISM: Camelus ferus
<220> FEATURE:
<221> NAME/KEY: misc_feature
<222> LOCATION: (99)..(99)
<223> OTHER INFORMATION: Xaa can be any naturally occurring amino acid

<400> SEQUENCE: 162

Gln Val Gln Leu Val Gln Ser Ala Ala Glu Leu Arg Ala Pro Gly Ala
1               5                   10                  15

Ser Val Lys Val Ser Cys Lys Ala Ser Gly Tyr Thr Phe Thr Ser Cys
            20                  25                  30

Ala Glu Leu Gly Thr Gly Pro Trp Lys Gly Thr Gly Val Tyr Gly Met
        35                  40                  45

Asp Gln His Arg His Trp Glu Ala Asn Ile Cys Pro Gly Leu Leu Gly
    50                  55                  60

Pro Met Cys Leu Leu His Gly Phe His Gln Tyr Ser Leu Ser Ala
65                  70                  75                  80

```
Asp Gln Gln Pro Glu Val Gly His Gly His Thr Leu Leu Cys Glu Arg
                85                  90                  95

Gln Cys Xaa

<210> SEQ ID NO 163
<211> LENGTH: 100
<212> TYPE: PRT
<213> ORGANISM: Llama pacos
<220> FEATURE:
<221> NAME/KEY: misc_feature
<222> LOCATION: (100)..(100)
<223> OTHER INFORMATION: Xaa can be any naturally occurring amino acid

<400> SEQUENCE: 163

Gln Val Gln Leu Val Gln Pro Ala Ala Glu Leu Arg Ala Pro Gly Ala
1               5                   10                  15

Ser Val Lys Val Ser Cys Lys Ala Ser Gly Tyr Thr Leu Thr Ser Cys
                20                  25                  30

Ala Glu Leu Gly Ala Thr Gly Pro Trp Lys Gly Thr Gly Val Tyr Gly
                35                  40                  45

Met Asp Gln His Arg His Trp Glu Ala Asn Ile Cys Pro Gly Leu Leu
            50                  55                  60

Gly Pro Met Cys Leu Leu His Gly His Phe His Gln His Ser Leu Ser
65              70                  75                      80

Ala Asp Gln Gln Pro Glu Val Gly His Gly Val Leu Leu Cys Glu
                85                  90                  95

Arg His Ser Xaa
            100

<210> SEQ ID NO 164
<211> LENGTH: 98
<212> TYPE: PRT
<213> ORGANISM: Homo sapiens

<400> SEQUENCE: 164

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
                35                  40                  45

Ile Tyr Ser Asn Asn Gln Arg Pro Ser Gly Val Pro Asp Arg Phe Ser
            50                  55                  60

Gly Ser Lys Ser Gly Thr Ser Ala Ser Leu Ala Ile Ser Gly Leu Arg
65              70                  75                      80

Ser Glu Asp Glu Ala Asp Tyr Tyr Cys Ala Ala Trp Asp Asp Ser Leu
                85                  90                  95

Ser Gly

<210> SEQ ID NO 165
<211> LENGTH: 98
<212> TYPE: PRT
<213> ORGANISM: Camelus ferus

<400> SEQUENCE: 165

Gln Ser Val Leu Thr Gln Pro Pro Ser Met Ser Gly Ser Leu Arg Gln
1               5                   10                  15

Ser Val Thr Ile Ser Cys Thr Gly Ser Ser Ser Asn Ile Trp Gly Asn
                20                  25                  30
```

Tyr Val Asn Trp His Gln Gln Leu Pro Gly Thr Ala Pro Lys Leu Leu
             35                  40                  45

Ile Tyr Asp Asn Ser Lys Arg Ala Ser Gly Val Pro Glu Arg Phe Ser
 50                  55                  60

Gly Ser Lys Ser Gly Ser Ser Ala Ser Leu Thr Ile Thr Gly Leu Gln
 65                  70                  75                  80

Ala Glu Asp Glu Gly Asp Tyr Tyr Cys Ala Ser Trp Asp Asp Ser Leu
                 85                  90                  95

Ser Gly

<210> SEQ ID NO 166
<211> LENGTH: 98
<212> TYPE: PRT
<213> ORGANISM: Llama pacos

<400> SEQUENCE: 166

Gln Ser Val Leu Thr Gln Pro Pro Ser Val Ser Gly Ser Pro Gly Gln
 1               5                  10                  15

Lys Phe Thr Ile Ser Cys Thr Gly Ser Ser Ser Asn Ile Gly Asp Asn
                 20                  25                  30

Tyr Val Asn Trp Tyr Gln His Leu Pro Gly Thr Ala Pro Lys Leu Leu
             35                  40                  45

Ile Tyr Ser Asn Ser Asn Arg Ala Ser Gly Val Pro Asp Arg Phe Ser
 50                  55                  60

Gly Ser Lys Ser Gly Ser Ser Ala Ser Leu Thr Ile Thr Gly Leu Gln
 65                  70                  75                  80

Ala Glu Asp Glu Ala Asp Tyr Tyr Cys Ser Ser Trp Asp Asp Ser Leu
                 85                  90                  95

Ser Gly

<210> SEQ ID NO 167
<211> LENGTH: 98
<212> TYPE: PRT
<213> ORGANISM: Llama pacos

<400> SEQUENCE: 167

Gln Ser Val Leu Thr Gln Pro Pro Ser Val Ser Gly Ser Pro Gly Gln
 1               5                  10                  15

Lys Phe Thr Ile Ser Cys Thr Gly Ser Ser Ser Asn Ile Gly Asp Asn
                 20                  25                  30

Tyr Val Asn Trp Tyr Gln His Leu Pro Gly Thr Ala Pro Lys Leu Leu
             35                  40                  45

Ile Tyr Ser Asn Ser Asn Arg Ala Ser Gly Val Pro Asp Arg Phe Ser
 50                  55                  60

Gly Ser Lys Ser Gly Ser Ser Ala Ser Leu Thr Ile Thr Gly Leu Gln
 65                  70                  75                  80

Ala Glu Asp Glu Ala Asp Tyr Tyr Cys Ser Ser Trp Asp Asp Ser Leu
                 85                  90                  95

Ser Gly

<210> SEQ ID NO 168
<211> LENGTH: 89
<212> TYPE: PRT
<213> ORGANISM: Llama glama

<400> SEQUENCE: 168

Gln Ser Val Leu Thr Gln Pro Pro Ser Val Ser Gly Ser Pro Gly Gln
1               5                   10                  15

Lys Phe Thr Ile Ser Cys Thr Gly Ser Ser Ser Asn Ile Gly Gly Asn
            20                  25                  30

Tyr Val Asn Trp Tyr Gln His Leu Pro Gly Thr Ala Pro Lys Leu Leu
            35                  40                  45

Ile Tyr Gly Asn Ser Asn Arg Ala Ser Gly Val Pro Glu Arg Phe Ser
        50                  55                  60

Gly Ser Lys Ser Gly Ser Ala Ser Leu Thr Ile Thr Gly Leu Gln
65                  70                  75                  80

Ala Glu Asp Glu Ala Asp Tyr Tyr Cys
                85

<210> SEQ ID NO 169
<211> LENGTH: 99
<212> TYPE: PRT
<213> ORGANISM: Homo sapiens

<400> SEQUENCE: 169

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 170
<211> LENGTH: 99
<212> TYPE: PRT
<213> ORGANISM: Camelus ferus

<400> SEQUENCE: 170

Gln Ser Val Leu Thr Gln Pro Pro Ser Val Ser Gly Ser Pro Gly Gln
1               5                   10                  15

Arg Val Ile Ile Ser Cys Thr Gly Ser Ser Ser Asn Ile Gly Gly Gly
            20                  25                  30

Tyr Ser Val Gln Trp Tyr Lys Gln Leu Pro Gly Thr Ala Pro Ile Leu
            35                  40                  45

Leu Ile Tyr Gly Asn Ser Asn Arg Ala Ser Gly Val Pro Asp Arg Phe
        50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Cys Tyr Cys Gly Ser Tyr Asp Ser Ser
                85                  90                  95

Leu Ser Gly

<210> SEQ ID NO 171
<211> LENGTH: 99
<212> TYPE: PRT
<213> ORGANISM: Llama pacos

<400> SEQUENCE: 171

Gln Ser Val Leu Thr Gln Leu Pro Ser Val Ser Gly Ser Pro Gly Gln
1               5                   10                  15

Lys Val Thr Ile Ser Cys Thr Gly Ser Ser Asn Ile Gly Gly Gly
            20                  25                  30

Tyr Ser Val Gln Trp Phe Gln Gln Leu Pro Gly Thr Pro Pro Lys Leu
        35                  40                  45

Leu Ile Tyr Gly Asn Ser Asn Arg Ala Ser Gly Val Pro Asp Arg Phe
    50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys Glu Cys Tyr Asp Asn Ser
                85                  90                  95

Leu Ser Gly

<210> SEQ ID NO 172
<211> LENGTH: 99
<212> TYPE: PRT
<213> ORGANISM: Llama pacos

<400> SEQUENCE: 172

Gln Ser Val Leu Thr Gln Leu Pro Ser Val Ser Gly Ser Pro Gly Gln
1               5                   10                  15

Lys Val Thr Ile Ser Cys Thr Gly Ser Ser Asn Ile Gly Gly Gly
            20                  25                  30

Tyr Ser Val Gln Trp Phe Gln Gln Leu Pro Gly Thr Pro Pro Lys Leu
        35                  40                  45

Leu Ile Tyr Gly Asn Ser Asn Arg Ala Ser Gly Val Pro Asp Arg Phe
    50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys Glu Cys Tyr Asp Asn Ser
                85                  90                  95

Leu Ser Gly

<210> SEQ ID NO 173
<211> LENGTH: 90
<212> TYPE: PRT
<213> ORGANISM: Llama glama

<400> SEQUENCE: 173

Gln Ser Val Leu Thr Gln Leu Pro Ser Val Ser Gly Ser Pro Gly Gln
1               5                   10                  15

Lys Val Thr Ile Ser Cys Thr Gly Ser Ser Asn Ile Gly Gly Gly
            20                  25                  30

Tyr Ser Val Gln Trp Phe Gln Gln Leu Pro Gly Thr Pro Pro Lys Leu
        35                  40                  45

Leu Ile Tyr Gly Asn Ser Asn Arg Ala Ser Gly Val Pro Asp Arg Phe
    50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys
                85                  90

<210> SEQ ID NO 174

```
<211> LENGTH: 99
<212> TYPE: PRT
<213> ORGANISM: Camelus ferus

<400> SEQUENCE: 174

Gln Ser Val Leu Thr Gln Pro Pro Ser Met Ser Gly Ser Leu Gly Gln
1               5                   10                  15

Arg Gly Thr Ile Ser Cys Thr Gly Ser Ser Asn Ile Gly Gly
            20                  25                  30

Tyr Gly Val Gln Trp Phe Gln Gln Leu Pro Gly Thr Ala Pro Lys Leu
        35                  40                  45

Leu Ile Tyr Gly Asn Ser Asn Arg Ala Ser Gly Val Pro Asp Arg Phe
    50                  55                  60

Ser Gly Ser Lys Ser Gly Ser Ser Ala Ser Leu Thr Ile Thr Gly Phe
65                  70                  75                  80

Gln Ala Asp Asp Glu Ala Asp Tyr Tyr Cys Gly Arg Tyr Asp Asn Ser
                85                  90                  95

Leu Ser Gly

<210> SEQ ID NO 175
<211> LENGTH: 99
<212> TYPE: PRT
<213> ORGANISM: Camelus ferus

<400> SEQUENCE: 175

Gln Ser Val Leu Thr Gln Leu Ser Ser Met Ser Gly Ser Pro Gly Gln
1               5                   10                  15

Thr Val Thr Ile Thr Cys Thr Gly Ser Ser Asn Ile Gly Gly Gly
            20                  25                  30

Tyr Tyr Leu Ser Trp Tyr Gln Gln Leu Pro Gly Thr Val Pro Lys Leu
        35                  40                  45

Leu Ile Tyr Asn Ala His Asn Arg Ala Ser Gly Val Pro Asn Arg Phe
    50                  55                  60

Ser Gly Ser Lys Ser Gly Ser Ser Ala Ser Leu Thr Ile Thr Gly Leu
65                  70                  75                  80

Gln Ala Glu Asp Glu Ala Asp Tyr Tyr Cys Gly Cys Tyr Asp Ser Ser
                85                  90                  95

Leu Ser Ala

<210> SEQ ID NO 176
<211> LENGTH: 99
<212> TYPE: PRT
<213> ORGANISM: Llama pacos

<400> SEQUENCE: 176

Gln Ser Val Leu Thr Gln Leu Ser Ser Met Ser Gly Ser Pro Gly Gln
1               5                   10                  15

Thr Val Thr Ile Thr Cys Thr Gly Ser Ser Asn Ile Gly Gly Gly
            20                  25                  30

Tyr Tyr Leu Ser Trp Tyr Gln Gln Leu Pro Gly Thr Ala Pro Lys Leu
        35                  40                  45

Leu Ile Tyr Asn Ala Asn Asn Arg Ala Ser Gly Val Pro Asn Arg Phe
    50                  55                  60

Ser Gly Ser Lys Thr Gly Ser Leu Ala Ser Leu Thr Ile Thr Gly Leu
65                  70                  75                  80

Gln Ala Glu Asp Glu Ala Asp Tyr Tyr Cys Gly Cys Tyr Asp Ser Ser
                85                  90                  95
```

Leu Ser Thr

<210> SEQ ID NO 177
<211> LENGTH: 90
<212> TYPE: PRT
<213> ORGANISM: Llama glama

<400> SEQUENCE: 177

Gln Ser Val Leu Thr Gln Leu Ser Ser Met Ser Gly Ser Pro Gly Gln
1               5                   10                  15

Thr Val Thr Ile Thr Cys Thr Gly Ser Ser Asn Ile Gly Gly Gly
            20                  25                  30

Tyr Tyr Leu Ser Trp Tyr Gln Gln Leu Pro Gly Thr Ala Pro Lys Leu
        35                  40                  45

Leu Ile Tyr Asn Ala Asn Asn Arg Ala Ser Gly Val Pro Asn Arg Phe
    50                  55                  60

Ser Gly Ser Lys Thr Gly Ser Leu Ala Ser Leu Thr Ile Thr Gly Leu
65                  70                  75                  80

Gln Ala Glu Asp Glu Ala Asp Tyr Tyr Cys
                85                  90

<210> SEQ ID NO 178
<211> LENGTH: 99
<212> TYPE: PRT
<213> ORGANISM: Camelus ferus

<400> SEQUENCE: 178

Gln Ser Val Leu Thr Gln Pro Pro Phe Val Ser Gly Ser Leu Gly Gln
1               5                   10                  15

Arg Ala Thr Ile Ser Cys Thr Gly Ser Ser Ser Asn Ile Gly His Gly
            20                  25                  30

Asn Tyr Val Asn Trp Tyr Gln Gln Leu Pro Gly Thr Cys Pro Arg Leu
        35                  40                  45

Leu Ile Tyr His Val Lys Asn Arg Ala Ser Gly Val Pro Asp Pro Phe
    50                  55                  60

Ser Gly Ser Lys Ser Gly Asn Ser Ala Ser Leu Ser Ile Thr Gly Leu
65                  70                  75                  80

Gln Ala Glu Asp Glu Ala Asp Tyr Tyr Cys Ala Asp Trp Asp Asn Ser
                85                  90                  95

Leu Ser Gly

<210> SEQ ID NO 179
<211> LENGTH: 99
<212> TYPE: PRT
<213> ORGANISM: Llama pacos

<400> SEQUENCE: 179

Gln Ser Val Leu Thr Gln Pro Pro Ser Val Ser Gly Ser Leu Gly His
1               5                   10                  15

Arg Val Thr Ile Ser Cys Thr Gly Ser Ser Lys Ile Arg Ser Gly
            20                  25                  30

Asn Tyr Val Asn Leu Tyr Gln His Leu Pro Gly Thr Cys Pro Arg Leu
        35                  40                  45

Leu Ile Tyr His Val Lys Asn Arg Ala Ser Gly Val Pro Asp Pro Phe
    50                  55                  60

Ser Gly Ser Lys Ser Ser Asn Ser Ala Ser Leu Ser Ile Thr Gly Leu
65                  70                  75                  80

Gln Ala Glu Asp Glu Ala Asp Tyr Tyr Cys Val Asp Trp Asp Asn Ser
                85                  90                  95

Leu Ser Ser

<210> SEQ ID NO 180
<211> LENGTH: 99
<212> TYPE: PRT
<213> ORGANISM: Llama pacos

<400> SEQUENCE: 180

Gln Ser Val Leu Thr Gln Pro Pro Ser Val Ser Gly Ser Leu Gly His
1               5                   10                  15

Arg Val Thr Ile Ser Cys Thr Gly Ser Ser Ser Lys Ile Arg Ser Gly
                20                  25                  30

Asn Tyr Val Asn Leu Tyr Gln His Leu Pro Gly Thr Cys Pro Arg Leu
            35                  40                  45

Leu Ile Tyr His Val Lys Asn Arg Ala Ser Gly Val Pro Asp Pro Phe
        50                  55                  60

Ser Gly Ser Lys Ser Ser Asn Ser Ala Ser Leu Ser Ile Thr Gly Leu
65                  70                  75                  80

Gln Ala Glu Asp Glu Ala Asp Tyr Tyr Cys Val Asp Trp Asp Asn Ser
                85                  90                  95

Leu Ser Ser

<210> SEQ ID NO 181
<211> LENGTH: 90
<212> TYPE: PRT
<213> ORGANISM: Llama glama

<400> SEQUENCE: 181

Gln Ser Val Leu Thr Gln Pro Pro Ser Val Ser Gly Ser Leu Gly His
1               5                   10                  15

Arg Val Thr Ile Ser Cys Thr Gly Ser Ser Ser Lys Ile Arg Ser Gly
                20                  25                  30

Asn Tyr Val Asn Leu Tyr Gln His Leu Pro Gly Thr Cys Pro Arg Leu
            35                  40                  45

Leu Ile Tyr His Val Lys Asn Arg Ala Ser Gly Val Pro Asp Pro Phe
        50                  55                  60

Ser Gly Ser Lys Ser Ser Asn Ser Ala Ser Leu Ser Ile Thr Gly Leu
65                  70                  75                  80

Gln Ala Glu Asp Glu Ala Asp Tyr Tyr Cys
                85                  90

<210> SEQ ID NO 182
<211> LENGTH: 99
<212> TYPE: PRT
<213> ORGANISM: Camelus ferus

<400> SEQUENCE: 182

Pro Ser Val Leu Thr Gln Pro Pro Ser Val Ser Gly Ser Pro Gly Gln
1               5                   10                  15

Arg Ala Thr Ile Ser Cys Thr Gly Ser Ser Ser Asn Ile Gly Arg Gly
                20                  25                  30

Asn Tyr Val Glu Trp Tyr Gln Gln Leu Pro Gly Lys Ala Pro Lys Leu
            35                  40                  45

Leu Ile Tyr Asp Val Asn Asn Arg Ala Ser Gly Val Pro Asn Arg Phe
        50                  55                  60

```
Ser Gly Ser Lys Ser Gly Asn Ser Val Ser Leu Thr Ile Thr Gly Leu
65                  70                  75                  80

Gln Ala Glu Asp Lys Ala Asp Tyr Tyr Cys Glu Asp Trp Gly Asn Ser
                85                  90                  95

Leu Asn Gly

<210> SEQ ID NO 183
<211> LENGTH: 98
<212> TYPE: PRT
<213> ORGANISM: Llama pacos

<400> SEQUENCE: 183

Ser Val Pro Ile Gln Pro Ser Val Ser Gly Ser Pro Gly Gln Arg
1               5                   10                  15

Val Thr Ile Ser Cys Thr Gly Ser Ser Asn Ile Gly Arg Gly Asn
                20                  25                  30

Tyr Val Ser Trp Tyr Gln Gln Leu Pro Gly Lys Ala Pro Lys Leu Leu
                35                  40                  45

Ile Tyr Asn Val Asn Asn Arg Ala Ser Gly Val Pro Asn Arg Phe Ser
            50                  55                  60

Gly Ser Lys Ser Gly Asn Ser Ala Ser Leu Thr Ile Thr Gly Leu Gln
65                  70                  75                  80

Ala Glu Asp Gln Ala Asp Tyr Tyr Cys Glu Asp Trp Glu Asn Ser Leu
                85                  90                  95

Asn Gly

<210> SEQ ID NO 184
<211> LENGTH: 98
<212> TYPE: PRT
<213> ORGANISM: Llama pacos

<400> SEQUENCE: 184

Ser Val Pro Ile Gln Pro Ser Val Ser Gly Ser Pro Gly Gln Arg
1               5                   10                  15

Val Thr Ile Ser Cys Thr Gly Ser Ser Asn Ile Gly Arg Gly Asn
                20                  25                  30

Tyr Val Ser Trp Tyr Gln Gln Leu Pro Gly Lys Ala Pro Lys Leu Leu
                35                  40                  45

Ile Tyr Asn Val Asn Asn Arg Ala Ser Gly Val Pro Asn Arg Phe Ser
            50                  55                  60

Gly Ser Lys Ser Gly Asn Ser Ala Ser Leu Thr Ile Thr Gly Leu Gln
65                  70                  75                  80

Ala Glu Asp Gln Ala Asp Tyr Tyr Cys Glu Asp Trp Glu Asn Ser Leu
                85                  90                  95

Asn Gly

<210> SEQ ID NO 185
<211> LENGTH: 90
<212> TYPE: PRT
<213> ORGANISM: Llama glama

<400> SEQUENCE: 185

Gln Ser Val Leu Thr Gln Leu Pro Ser Val Ser Gly Ser Pro Gly Gln
1               5                   10                  15

Arg Val Thr Ile Ser Cys Thr Gly Ser Ser Ser Asn Ile Gly His Gly
                20                  25                  30
```

```
Asn Tyr Val Ser Trp Tyr Gln Gln Leu Pro Gly Lys Ala Pro Lys Leu
            35                  40                  45

Leu Ile Tyr Asn Val Asn Asn Arg Ala Ser Gly Val Pro Asn Arg Phe
 50                  55                  60

Ser Gly Ser Lys Ser Gly Asn Ser Ala Ser Leu Thr Ile Thr Gly Leu
 65                  70                  75                  80

Gln Ala Glu Asp Glu Ala Asp Tyr Tyr Cys
                 85                  90
```

<210> SEQ ID NO 186
<211> LENGTH: 99
<212> TYPE: PRT
<213> ORGANISM: Llama pacos

<400> SEQUENCE: 186

```
Gln Ser Val Leu Thr Gln Pro Ser Ser Met Ser Gly Ser Pro Gly Gln
 1               5                  10                  15

Thr Val Thr Ile Ser Cys Thr Gly Ser Ser Ser Asn Ile Gly Arg Gly
             20                  25                  30

Tyr Ser Ile Gln Leu Phe Gln Gln Leu Pro Gly Thr Ala Pro Lys Leu
            35                  40                  45

Leu Ile Cys Gly Asn Ser Asn Arg Ala Ser Gly Val Pro Asp Arg Phe
 50                  55                  60

Ser Gly Ser Lys Ser Gly Ser Ser Ala Ser Leu Thr Ile Thr Gly Leu
 65                  70                  75                  80

Gln Ala Glu Asp Glu Ala Asp Tyr Tyr Cys Gly Cys Tyr Asp Ser Ser
                 85                  90                  95

Leu Ser Gly
```

<210> SEQ ID NO 187
<211> LENGTH: 90
<212> TYPE: PRT
<213> ORGANISM: Llama glama

<400> SEQUENCE: 187

```
Gln Ser Val Leu Thr Gln Pro Ser Ser Met Ser Gly Ser Pro Gly Gln
 1               5                  10                  15

Arg Val Thr Ile Ser Cys Thr Gly Ser Ser Ser Asn Ile Gly Arg Gly
             20                  25                  30

Tyr Ser Ile Gln Leu Phe Gln Gln Leu Pro Gly Thr Ala Pro Lys Leu
            35                  40                  45

Leu Ile Cys Gly Asn Ser Asn Arg Ala Ser Gly Val Pro Asp Arg Phe
 50                  55                  60

Ser Gly Ser Lys Ser Gly Ser Ser Ala Ser Leu Thr Ile Thr Gly Leu
 65                  70                  75                  80

Gln Ala Glu Asp Glu Ala Asp Tyr Tyr Cys
                 85                  90
```

<210> SEQ ID NO 188
<211> LENGTH: 99
<212> TYPE: PRT
<213> ORGANISM: Homo sapiens

<400> SEQUENCE: 188

```
Gln Ser Val Val Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
             20                  25                  30
```

Tyr Asp Val His Trp Tyr Gln Gln Leu Pro Gly Thr Ala Pro Lys Leu
                35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly

<210> SEQ ID NO 189
<211> LENGTH: 99
<212> TYPE: PRT
<213> ORGANISM: Camelus ferus

<400> SEQUENCE: 189

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Ser Ser Ser
                20                  25                  30

Asn Tyr Pro Gly Trp Ile Gln Gln Thr Pro Gly Gln Val Pro Arg Thr
                35                  40                  45

Leu Ile Tyr Ser Thr Ser Ser Arg Pro Ser Gly Ile Pro Ser Arg Phe
        50                  55                  60

Ala Gly Thr Ile Ser Gly Asn Lys Ala Thr Leu Thr Ile Thr Gly Ala
65                  70                  75                  80

Gln Pro Glu Asp Glu Ala Asp Tyr Tyr Cys Ala Leu Tyr Pro Gly Ser
                85                  90                  95

Tyr Leu Asp

<210> SEQ ID NO 190
<211> LENGTH: 87
<212> TYPE: PRT
<213> ORGANISM: Llama glama

<400> SEQUENCE: 190

Gln Ser Val Pro Thr Gln Pro Pro Phe Val Ser Gly Ser Pro Gly Gln
1               5                   10                  15

Arg Val Thr Leu Ser Cys Thr Gly Ser Ser Ser Asn Ile Gly Arg Gly
                20                  25                  30

Cys Tyr Val Arg Trp Phe Gln Gln Leu Pro Gly Thr Ala Pro Arg Leu
                35                  40                  45

Leu Ile Tyr Asp Val Asn Tyr Ala Ser Gly Pro Asp Val Phe Gly
        50                  55                  60

Ser Lys Ser Ala Thr Trp Ser Pro Thr Ser Leu Gly Ser Ser Gln Arg
65                  70                  75                  80

Met Arg Leu Ile Ile Thr Val
                85

<210> SEQ ID NO 191
<211> LENGTH: 87
<212> TYPE: PRT
<213> ORGANISM: Llama pacos

<400> SEQUENCE: 191

Lys Ser Val Pro Thr Gln Leu Pro Phe Val Tyr Gly Ser Pro Gly Gln
1               5                   10                  15

```
Arg Val Thr Leu Ser Cys Thr Gly Ser Ser Asn Ile Gly Arg Gly
             20                  25                  30

Cys Tyr Val Arg Trp Phe Gln Gln Leu Pro Gly Thr Ala Pro Arg Leu
         35                  40                  45

Leu Ile Tyr Asp Val Asn Tyr Ala Ser Gly Pro Asp Val Phe Gly
     50                  55                  60

Ser Lys Ser Ala Thr Trp Ser Pro Thr Ser Leu Gly Ser Ser Gln Arg
 65                  70                  75                  80

Met Arg Leu Thr Ile Thr Val
                 85

<210> SEQ ID NO 192
<211> LENGTH: 89
<212> TYPE: PRT
<213> ORGANISM: Camelus ferus

<400> SEQUENCE: 192

Pro Ser Val Ser Thr Pro Pro Ser Val Ser Gly Ser Gly Gln Arg
 1               5                  10                  15

Val Thr Met Ser Cys Thr Gly Ser Ser Ser Asn Ile Gly Cys Gly Asn
             20                  25                  30

Tyr Val His Trp Phe Gln Gln Leu Pro Gly Thr Ala Pro Arg Leu Leu
         35                  40                  45

Ile Tyr Asp Val Asn Cys Arg Ala Ser Gly Val Pro Asp Arg Phe Phe
     50                  55                  60

Gly Ser Glu Ser Ser Asn Thr Val Ser Leu Asn Ile Ser Gly Leu Gln
 65                  70                  75                  80

Pro Glu Asp Glu Val Asp Tyr Tyr Cys
                 85

<210> SEQ ID NO 193
<211> LENGTH: 88
<212> TYPE: PRT
<213> ORGANISM: Llama glama

<400> SEQUENCE: 193

Gln Ser Val Leu Ser Gln Pro Pro Ser Met Ser Gly Ser Pro Gly Gln
 1               5                  10                  15

Lys Val Thr Val Ser Cys Thr Gly Ser Ala Thr Ile Leu Gly Val Val
             20                  25                  30

Ile Met Cys Asn Gly Thr Asn Ser Ser Gln Glu Trp Pro Pro Asn Phe
         35                  40                  45

Ser Thr Met Leu Thr Ile Glu Pro Trp Gly Ser Pro Thr Asp Ser Leu
     50                  55                  60

Ala Pro Ser Leu Ala Ala Leu Pro Pro Pro Ser Leu Gly Ser Arg Leu
 65                  70                  75                  80

Arg Thr Arg Leu Thr Ile Thr Val
                 85

<210> SEQ ID NO 194
<211> LENGTH: 88
<212> TYPE: PRT
<213> ORGANISM: Llama glama

<400> SEQUENCE: 194

Gln Ser Val Leu Thr Gln Ser Pro Ser Met Ser Gly Ser Pro Gly Gln
 1               5                  10                  15
```

Arg Val Thr Ile Ser Cys Thr Gly Ser Ala Thr Ile Leu Gly Val Val
            20                  25                  30

Ile Met Cys Ser Gly Thr Asn Ser Ser His Glu Trp Pro Pro Asn Phe
            35                  40                  45

Ser Thr Met Leu Thr Val Met Pro Gln Ala Ser Pro Thr Asp Ser Leu
50                  55                  60

Ala Pro Ser Leu Gly Thr Arg Pro Pro Ser Leu Gly Ser Arg Leu
65                  70                  75                  80

Arg Thr Arg Leu Thr Ile Thr Val
            85

<210> SEQ ID NO 195
<211> LENGTH: 88
<212> TYPE: PRT
<213> ORGANISM: Llama glama

<400> SEQUENCE: 195

Gln Ser Val Leu Thr Gln Pro Pro Ser Met Ser Gly Ser Pro Gly Gln
1               5                   10                  15

Lys Val Thr Val Ser Cys Thr Gly Ser Ala Lys Ile Leu Gly Val Val
            20                  25                  30

Ile Met Cys Asn Gly Thr Asn Ser Ser Gln Glu Trp Pro Pro Asn Phe
            35                  40                  45

Ser Thr Met Leu Thr Ile Glu Pro Trp Gly Ser Arg Thr Val Ser Leu
50                  55                  60

Ala Pro Ser Leu Ala Ala Leu Pro Pro Ser Leu Gly Ser Arg Leu
65                  70                  75                  80

Arg Thr Arg Leu Thr Ile Thr Val
            85

<210> SEQ ID NO 196
<211> LENGTH: 88
<212> TYPE: PRT
<213> ORGANISM: Llama glama

<400> SEQUENCE: 196

Gln Pro Val Leu Thr Gln Glu Leu Ala Val Trp Glu Ser Leu Gly Asp
1               5                   10                  15

Gly His Thr Ile Ser Tyr Ser Gly Asn Ala Asn Lys Ile Lys Ser Cys
            20                  25                  30

Glu Cys Leu Asp Val Pro Gln Leu Pro Glu Met Cys Pro Pro Leu Gly
            35                  40                  45

Ile Ser Arg Val Lys Asn Gly Ala Ser Gly Val Pro His Leu Phe Trp
50                  55                  60

Gly Ser Lys Tyr Ser Thr Pro Pro Gly Ser Val Arg Ser Thr Leu
65                  70                  75                  80

Lys Lys Thr Leu Ser Ile Thr Val
            85

<210> SEQ ID NO 197
<211> LENGTH: 95
<212> TYPE: PRT
<213> ORGANISM: Camelus ferus

<400> SEQUENCE: 197

Gln Ser Gly Leu Thr Gln Glu Ala Ser Glu Ser Gly Ala Val Gly Gln
1               5                   10                  15

Lys Ile Thr Leu Ser Cys Thr Asn Ser Asn Ser Val Gly Ala Asn Pro

```
            20                  25                  30
Met Gly Trp Tyr Gln His Ser Ser Arg His Thr Pro Lys Leu Met Leu
            35                  40                  45

Arg Ser Ser Trp Pro Ser Gly Ile Pro Asp Arg Phe Leu Gly Ser Lys
            50                  55                  60

Ser Gly Asn Met Ala Ser Leu Ala Ile Ser Asp Leu Gln Pro Glu Asp
65                  70                  75                  80

Glu Ala Glu His Tyr Gly Ser Thr Leu Asp Ser Ser Thr Ser Gly
                    85                  90                  95

<210> SEQ ID NO 198
<211> LENGTH: 95
<212> TYPE: PRT
<213> ORGANISM: Llama pacos

<400> SEQUENCE: 198

Gln Ser Gly Leu Thr Gln Glu Ala Ser Val Ser Gly Ala Val Gly Gln
1               5                   10                  15

Lys Ile Thr Leu Ser Cys Thr Asn Ser Asn Asn Val Gly Ala Asn Pro
            20                  25                  30

Met Gly Trp Tyr Gln His Ser Ser Arg His Thr Pro Lys Leu Met Leu
            35                  40                  45

Arg Ser Ser Trp Pro Ser Gly Ile Pro Asp Arg Phe Ser Gly Ser Lys
            50                  55                  60

Ser Gly Asn Met Ala Ser Leu Ala Ile Ser Asp Phe Gln Pro Glu Asp
65                  70                  75                  80

Glu Ala Glu His Tyr Gly Ser Thr Leu Asp Ser Ser Thr Ser Gly
                    85                  90                  95

<210> SEQ ID NO 199
<211> LENGTH: 99
<212> TYPE: PRT
<213> ORGANISM: Camelus ferus

<400> SEQUENCE: 199

Pro Ala Leu Thr Gln Pro Glu Ala Leu Leu Val Phe Pro Gly Gln Val
1               5                   10                  15

Ala Gln Leu Ser Cys Met Leu Ser Pro Arg Tyr Ala Thr Val Gly Asp
            20                  25                  30

Tyr Gly Val Ser Trp Tyr Gln Arg Ala Gly Ser Ala Pro Arg Tyr
            35                  40                  45

Leu Ile Tyr Tyr Arg Ser Glu Glu Asp Tyr His Arg Pro Pro Asp Ile
            50                  55                  60

Pro Asp Arg Phe Ser Ala Ala Thr Asp Lys Ala His Asn Ala Cys Ile
65                  70                  75                  80

Leu Thr Ile Ser Pro Val Gln Pro Glu Asp Glu Ala Asp Tyr Tyr Cys
                    85                  90                  95

Ser Val Gly

<210> SEQ ID NO 200
<211> LENGTH: 99
<212> TYPE: PRT
<213> ORGANISM: Llama pacos

<400> SEQUENCE: 200

Pro Ala Leu Thr Gln Pro Glu Ala Leu Leu Val Phe Pro Gly Gln Val
1               5                   10                  15
```

```
Ala Gln Leu Ser Cys Met Leu Ser Pro Arg Tyr Ala Thr Val Gly Asp
            20                  25                  30

Tyr Gly Val Ser Trp Tyr Gln Gln Arg Ala Gly Ser Ala Pro Arg Tyr
        35                  40                  45

Leu Ile Tyr Tyr Arg Ser Glu Glu Asp Tyr His Arg Pro Pro Asp Ile
    50                  55                  60

Pro Asp Arg Phe Ser Ala Ala Thr Asp Lys Ala His Asn Ala Cys Ile
65                  70                  75                  80

Leu Thr Ile Ser Pro Val Gln Pro Glu Asp Glu Ala Asp Tyr Tyr Cys
                85                  90                  95

Ser Val Gly

<210> SEQ ID NO 201
<211> LENGTH: 96
<212> TYPE: PRT
<213> ORGANISM: Camelus ferus

<400> SEQUENCE: 201

Gln Ser Val Leu Thr Gln Arg Ala Ser Val Pro Glu Cys Leu Gly Cys
1               5                   10                  15

Thr Val Thr Arg Phe Arg Thr Arg Ser Ser Ser Asn Phe Trp Gly Met
            20                  25                  30

Ser Gln Thr Gly Ser Ser Val Cys Gln Val Pro Arg Val Leu Thr Tyr
        35                  40                  45

Lys Arg Asn Ser Gln Pro Leu Gly Val Pro Ala Val Phe Ser Gly Ser
    50                  55                  60

Thr Leu Gly Asn Pro Ala Phe Leu Ala Ile Ala Gly Leu Arg Ala Glu
65                  70                  75                  80

Asp Lys Thr Ser Arg Tyr Cys Pro Leu Tyr Asp Thr Thr Val Glu Pro
                85                  90                  95

<210> SEQ ID NO 202
<211> LENGTH: 96
<212> TYPE: PRT
<213> ORGANISM: Llama pacos

<400> SEQUENCE: 202

Gln Ser Val Leu Thr Gln Leu Ala Ser Val Pro Gly Ser Leu Gly Tyr
1               5                   10                  15

Thr Val Thr Arg Phe Cys Thr Arg Ser Ser Ser Asn Phe Arg Gly Met
            20                  25                  30

Pro Gln Thr Gly Ser Ser Val Cys Gln Val Pro Ser Val Leu Thr Tyr
        35                  40                  45

Glu Lys Asn Ser Arg Pro Leu Gly Val Pro Ala Gly Phe Ser Gly Ser
    50                  55                  60

Thr Leu Gly Asn Pro Ala Ser Leu Thr Thr Ala Gly Leu Arg Ala Glu
65                  70                  75                  80

Asp Lys Thr Ser Arg Tyr Cys Asp Thr Thr Val Arg Pro Thr Pro Pro
                85                  90                  95

<210> SEQ ID NO 203
<211> LENGTH: 97
<212> TYPE: PRT
<213> ORGANISM: Camelus ferus

<400> SEQUENCE: 203

Pro Ser Leu Cys Leu Ser Arg Pro Leu Cys Leu Asp Pro Arg Ala Arg
1               5                   10                  15
```

Gly Ser Pro Thr Pro Ala Lys Asp Gln Gln His Ile Gly Ser Gly Tyr
            20                  25                  30

Tyr Val Gln Trp Tyr Gln Gln Leu Pro Gly Met Ala Pro Lys Leu Leu
        35                  40                  45

Ile Tyr Asn Ala Asn Ser Arg Ala Leu Gly Val Pro Glu Cys Phe Ser
50                  55                  60

Gly Ser Lys Ser Gly Ser Ser Ala Ser Leu Thr Ile Thr Gly Leu Gln
65                  70                  75                  80

Ala Glu Asp Glu Ala Asp Cys Tyr Cys Gly Ser Tyr Asp Ser Ser Leu
                85                  90                  95

Ser

<210> SEQ ID NO 204
<211> LENGTH: 96
<212> TYPE: PRT
<213> ORGANISM: Camelus ferus

<400> SEQUENCE: 204

Ser Leu Cys Leu Ser Arg Pro Leu Cys Leu Asp Pro Arg Ala Arg Gly
1               5                   10                  15

Ser Pro Thr Pro Ala Lys Asp Gln Gln His Ile Gly Ser Gly Tyr Tyr
            20                  25                  30

Val Gln Trp Tyr Gln Gln Leu Pro Gly Met Ala Pro Lys Leu Leu Ile
        35                  40                  45

Tyr Asn Ala Asn Ser Arg Ala Leu Gly Val Pro Glu Cys Phe Ser Gly
    50                  55                  60

Ser Lys Ser Gly Ser Ser Ala Ser Leu Thr Ile Thr Gly Leu Gln Ala
65                  70                  75                  80

Glu Asp Glu Ala Asp Cys Tyr Cys Gly Ser Tyr Asp Ser Ser Leu Ser
                85                  90                  95

<210> SEQ ID NO 205
<211> LENGTH: 90
<212> TYPE: PRT
<213> ORGANISM: Llama pacos

<400> SEQUENCE: 205

Ser Val Leu Thr Pro Pro Ser Val Leu Asp Pro Arg Ala Arg Gly Ser
1               5                   10                  15

Pro Ser Pro Ala Leu Glu Ala Ala Thr Leu Gly Leu Ser Glu Leu
            20                  25                  30

Val Pro Thr Ala Pro Arg Ile Gly Pro Gln Thr Pro Asp Leu Trp Gln
        35                  40                  45

Gln Arg Leu Arg Gly Pro Glu His Phe Ser Gly Phe Lys Ser Gly Ser
    50                  55                  60

Ser Ala Ser Leu Thr Ile Thr Gly Leu Gln Ala Glu Asp Glu Ala Asp
65                  70                  75                  80

Tyr Tyr Cys Ser Ser Trp Asp Asp Arg Leu
                85                  90

<210> SEQ ID NO 206
<211> LENGTH: 85
<212> TYPE: PRT
<213> ORGANISM: Llama glama
<220> FEATURE:
<221> NAME/KEY: misc_feature
<222> LOCATION: (5)..(5)
<223> OTHER INFORMATION: Xaa can be any naturally occurring amino acid

```
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid

<400> SEQUENCE: 206

Ser Leu Leu Thr Xaa Pro Pro Ser Val Leu Asp Pro Arg Ala Arg Gly
1               5                   10                  15

Ser Pro Ser Pro Ala Leu Glu Ala Ala Ala Thr Leu Gly Xaa Leu Ser
            20                  25                  30

Glu Leu Val Pro Thr Ala Pro Arg Ile Gly Pro Gln Thr Pro Asp Leu
        35                  40                  45

Trp Xaa Gln Gln Xaa Arg Leu Arg Gly Pro Xaa Ala Leu Leu Trp Leu
    50                  55                  60

Gln Val Trp Gln Leu Gly Leu Pro Asp His His Trp Ala Pro Gly Xaa
65                  70                  75                  80

Gly Xaa Gly Xaa Leu
            85

<210> SEQ ID NO 207
<211> LENGTH: 97
<212> TYPE: PRT
<213> ORGANISM: Camelus ferus

<400> SEQUENCE: 207

Ile Ser Leu Cys Arg Leu Ser Arg Pro Leu Cys Leu Asp Pro Arg Ala
1               5                   10                  15

Arg Arg Ser Pro Ser Pro Ala Leu Glu Ala Ala Ala Thr Leu Gly Val
            20                  25                  30

Val Val Met Cys Ala Gly Ser Asn Ser Ser Gln Glu Leu Leu Ile Tyr
        35                  40                  45

Asp Val Asn Tyr Arg Ala Ser Gly Gly Pro Asp Phe Phe Asp Ser Lys
    50                  55                  60

Ser Gly Asn Thr Val Ser Leu Thr Ile Thr Gly Leu Gln Pro Glu Asp
65                  70                  75                  80

Glu Ala Asp Asn Tyr Cys Ala Val Glu Met Ser Ser His Leu Tyr Ala
                85                  90                  95

Val

<210> SEQ ID NO 208
```

```
<211> LENGTH: 94
<212> TYPE: PRT
<213> ORGANISM: Camelus ferus

<400> SEQUENCE: 208

Pro Gly Leu Cys Leu Ser Arg Pro Leu Cys Trp Ile Pro Glu Pro Glu
1               5                   10                  15

Gly His His Leu Leu His Trp Lys Gln Gln Gln His Cys Gly Leu Ser
            20                  25                  30

Glu Leu Val Pro Thr Ala Pro Arg Ile Ala Pro Lys Leu Leu Ile Tyr
        35                  40                  45

Gly Asn Ser Asn Arg Asp Ser Gly Val Pro His Phe Ser Gly Phe
    50                  55                  60

Lys Ser Gly Ser Ser Ala Ser Leu Thr Ile Thr Gly Leu Gln Ala Glu
65                  70                  75                  80

Asp Glu Gly Asp Tyr Tyr Cys Ala Ser Trp Asp Asp Ser Leu
                85                  90

<210> SEQ ID NO 209
<211> LENGTH: 99
<212> TYPE: PRT
<213> ORGANISM: Homo sapiens

<400> SEQUENCE: 209

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ser Tyr
            20                  25                  30

Asn Arg Val Ser Trp Tyr Gln Gln Pro Pro Gly Thr Ala Pro Lys Leu
        35                  40                  45

Met Ile Tyr Glu Val Ser Asn Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Leu Tyr Thr Ser Ser
                85                  90                  95

Ser Thr Phe

<210> SEQ ID NO 210
<211> LENGTH: 99
<212> TYPE: PRT
<213> ORGANISM: Camelus ferus

<400> SEQUENCE: 210

Gln Ser Ala Leu Thr Gln Pro Pro Ser Val Ser Arg Thr Pro Gly Gln
1               5                   10                  15

Thr Val Thr Ile Ser Cys Ala Ala Thr Ser Asn Asp Val Gly Arg Tyr
            20                  25                  30

Asn Tyr Val Ser Trp Tyr Gln Gln Leu Pro Gly Thr Ala Pro Lys Leu
        35                  40                  45

Leu Ile Tyr Glu Asp Thr Ser Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Phe Cys Ala Ser Tyr Thr Thr Ser
                85                  90                  95

Ser Thr Ala
```

<210> SEQ ID NO 211
<211> LENGTH: 99
<212> TYPE: PRT
<213> ORGANISM: Llama pacos

<400> SEQUENCE: 211

Gln Ser Ala Leu Thr Gln Pro Pro Ser Val Ser Arg Thr Pro Gly Gln
1               5                   10                  15

Thr Val Thr Ile Ser Cys Ala Gly Thr Ser Asn Asp Ile Gly Arg Tyr
            20                  25                  30

Asn Tyr Val Ser Trp Tyr Gln Gln Leu Pro Gly Thr Ala Pro Lys Leu
        35                  40                  45

Leu Ile Tyr Glu Gly Thr Ser Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Phe Cys Ala Ser Tyr Thr Thr Ser
                85                  90                  95

Ser Thr Val

<210> SEQ ID NO 212
<211> LENGTH: 90
<212> TYPE: PRT
<213> ORGANISM: Llama glama

<400> SEQUENCE: 212

Gln Ser Ala Leu Thr Gln Pro Pro Ser Val Ser Arg Thr Pro Gly Gln
1               5                   10                  15

Thr Val Thr Ile Ser Cys Ala Gly Thr Ser Asn Asp Ile Gly Arg Tyr
            20                  25                  30

Asn Tyr Val Ser Trp Tyr Gln Gln Leu Pro Gly Thr Ala Pro Lys Leu
        35                  40                  45

Leu Ile Tyr Glu Gly Thr Ser Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys
                85                  90

<210> SEQ ID NO 213
<211> LENGTH: 98
<212> TYPE: PRT
<213> ORGANISM: Camelus ferus

<400> SEQUENCE: 213

Gln Ser Ala Leu Thr Gln Pro Pro Ser Val Ser Glu Thr Leu Gly Lys
1               5                   10                  15

Met Val Thr Ile Ser Cys Val Gly Thr Ser Ser Asp Thr Gly Gly Tyr
            20                  25                  30

Asn Tyr Ile Ser Trp Tyr Gln Gln Leu Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Arg Ser Gly Asn Thr Ala Ser Leu Thr Ile Ser Gly Leu
65                  70                  75                  80

Gln Ser Glu Asp Glu Ala Asp Tyr Phe Cys Ala Ser Tyr Thr Thr Ser

Ser Thr

<210> SEQ ID NO 214
<211> LENGTH: 98
<212> TYPE: PRT
<213> ORGANISM: Llama pacos

<400> SEQUENCE: 214

Gln Ser Ala Leu Thr Gln Pro Pro Ser Val Ser Gly Thr Leu Gly Lys
1               5                   10                  15

Thr Leu Thr Ile Ser Cys Ala Gly Thr Ser Ser Asp Ile Gly Gly Tyr
            20                  25                  30

Asn Ser Val Ser Trp Tyr Gln Gln Leu Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn

<210> SEQ ID NO 215
<211> LENGTH: 90
<212> TYPE: PRT
<213> ORGANISM: Llama glama

<400> SEQUENCE: 215

Asn Ser Ala Leu Thr Gln Pro Pro Ser Val Ser Gly Thr Leu Gly Lys
1               5                   10                  15

Thr Val Thr Ile Ser Cys Ala Gly Thr Ser Ser Asp Ile Gly Gly Tyr
            20                  25                  30

Asn Tyr Val Ser Trp Tyr Gln Gln Leu Pro Gly Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys
                85                  90

<210> SEQ ID NO 216
<211> LENGTH: 98
<212> TYPE: PRT
<213> ORGANISM: Llama pacos

<400> SEQUENCE: 216

Asn Ser Ala Leu Thr Gln Pro Pro Ser Val Ser Gly Thr Leu Gly Lys
1               5                   10                  15

Thr Val Thr Ile Ser Cys Ala Gly Thr Ser Ser Asp Ile Gly Gly Tyr
            20                  25                  30

Asn Tyr Val Ser Trp Tyr Gln Gln Leu Pro Gly Thr Ala Pro Lys Leu
        35                  40                  45

Leu Ile Tyr Val Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu

```
                          65                  70                  75                  80
Gln Ser Glu Asp Glu Ala Asp Tyr Phe Cys Ala Ser Tyr Thr Thr Ser
                     85                  90                  95

Ser Thr

<210> SEQ ID NO 217
<211> LENGTH: 90
<212> TYPE: PRT
<213> ORGANISM: Llama glama

<400> SEQUENCE: 217

Asn Ser Ala Leu Thr Gln Pro Pro Ser Val Ser Gly Thr Leu Gly Lys
1               5                   10                  15

Thr Val Thr Ile Ser Cys Ala Gly Thr Ser Ser Asp Ile Gly Gly Tyr
            20                  25                  30

Asn Tyr Val Ser Trp Tyr Gln Gln Leu Pro Gly Thr Ala Pro Lys Val
        35                  40                  45

Leu Ile Tyr Val Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys
                85                  90

<210> SEQ ID NO 218
<211> LENGTH: 98
<212> TYPE: PRT
<213> ORGANISM: Camelus ferus

<400> SEQUENCE: 218

Gln Ser Ala Leu Thr Gln Pro Pro Leu Val Ser Arg Thr Pro Gly Gln
1               5                   10                  15

Thr Phe Thr Ile Ser Cys Ala Gly Thr Ser Ser Asp Ala Gly Ser Gly
            20                  25                  30

Asn Tyr Val Ser Trp Tyr Gln Gln Val Pro Arg Thr Ala Pro Lys Leu
        35                  40                  45

Leu Ile Tyr Glu Val Asn Lys Arg Ala Ser Gly Ile Pro Asp Arg Phe
    50                  55                  60

Ser Gly Ser Lys Ser Gly Asn Met Ala Ser Leu Thr Ile Ser Gly Leu
65                  70                  75                  80

Gln Ser Glu Asp Glu Ala Asp Cys Ser Cys Ala Ser Tyr Arg Ser Ser
                85                  90                  95

Tyr Asn

<210> SEQ ID NO 219
<211> LENGTH: 90
<212> TYPE: PRT
<213> ORGANISM: Llama glama

<400> SEQUENCE: 219

Gln Ser Ala Leu Thr Gln Pro Ser Ser Val Pro Gly Thr Pro Gly Gln
1               5                   10                  15

Thr Val Thr Ile Ser Cys Ala Gly Thr Ser Ser Asp Ala Gly Ser Gly
            20                  25                  30

Asn Tyr Val Ser Trp Tyr Gln Gln Val Pro Arg Thr Ala Pro Lys Leu
        35                  40                  45

Leu Ile Tyr Glu Val Asn Lys Arg Ala Ser Gly Ile Pro Asp Arg Phe
```

```
                 50                  55                  60
Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys
                 85                  90

<210> SEQ ID NO 220
<211> LENGTH: 98
<212> TYPE: PRT
<213> ORGANISM: Llama pacos

<400> SEQUENCE: 220

Gln Ser Ala Leu Thr Gln Pro Pro Ser Val Ser Gly Ser Pro Gly Lys
  1               5                  10                  15

Thr Val Thr Ile Ser Cys Ala Gly Thr Ser Ser Asp Val Gly Tyr Gly
                 20                  25                  30

Asn Tyr Val Ser Cys Tyr Gln Gln Leu Pro Gly Met Ala Pro Lys Leu
                 35                  40                  45

Leu Ile Tyr Asp Val Asn Lys Arg Ala Ser Gly Ile Ala Asp Arg Phe
             50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys Ala Ser Tyr Arg Ser Ser
                 85                  90                  95

Asn Asn

<210> SEQ ID NO 221
<211> LENGTH: 98
<212> TYPE: PRT
<213> ORGANISM: Camelus ferus

<400> SEQUENCE: 221

Gln Ser Ala Leu Thr Gln Pro Pro Leu Val Ser Gly Thr Pro Glu Gln
  1               5                  10                  15

Met Val Thr Ile Ser Cys Ala Val Thr Ser Ser Asp Val Gly Tyr Gly
                 20                  25                  30

Asn Tyr Val Ser Trp Tyr Gln Gln Leu Pro Gly Thr Ala Pro Arg Leu
                 35                  40                  45

Leu Ile Tyr Asp Val Ser Leu Ser Ser Gly Ile Pro Asn His Phe
             50                  55                  60

Ser Gly Ser Lys Ser Gly Asn Thr Ala Ser Leu Thr Ile Ser Arg Leu
 65                  70                  75                  80

Gln Ser Glu Asp Glu Ala Asp Tyr Tyr Cys Ala Ser Tyr Gly Ser Ser
                 85                  90                  95

Tyr Ser

<210> SEQ ID NO 222
<211> LENGTH: 98
<212> TYPE: PRT
<213> ORGANISM: Camelus ferus

<400> SEQUENCE: 222

Gln Ser Ala Leu Thr Gln Pro Ser Ser Val Ser Gly Thr Pro Gly Gln
  1               5                  10                  15

Thr Val Thr Ile Ser Cys Ala Gly Thr Ser Ser Asp Val Gly Tyr Gly
                 20                  25                  30

Asn Tyr Val Ser Trp Tyr Gln Gln Leu Pro Gly Thr Ala Pro Lys Leu
```

```
            35                  40                  45
Leu Ile Tyr Gln Val Asn Lys Arg Ala Ser Gly Ile Ala Asp Arg Phe
 50                  55                  60
Ser Gly Ser Lys Ser Gly Asn Thr Ala Ser Met Thr Ile Ser Gly Leu
65                  70                  75                  80
Gln Ser Ala Asn Lys Ala Asp Tyr Tyr Cys Ala Ser Tyr Arg Ser Ser
                85                  90                  95
Asn Asn

<210> SEQ ID NO 223
<211> LENGTH: 90
<212> TYPE: PRT
<213> ORGANISM: Llama glama

<400> SEQUENCE: 223

Gln Ser Ala Leu Thr Gln Pro Pro Ser Val Ser Gly Thr Leu Gly Lys
1               5                   10                  15
Thr Val Thr Ile Ser Cys Ala Gly Thr Ser Ser Asp Val Gly Ser Gly
                20                  25                  30
Asn Tyr Val Ser Trp Tyr Gln Gln Leu Pro Gly Thr Ala Pro Lys Cys
            35                  40                  45
Leu Ile Tyr Gln Val Asn Lys Arg Ala Ser Gly Ile Pro Asp Arg Val
 50                  55                  60
Ser Gly Ser Lys Ser Gly Asn Thr Ala Ser Met Thr Ile Ser Gly Leu
65                  70                  75                  80
Gln Ser Glu Asp Glu Ala Asp Tyr Tyr Cys
                85                  90

<210> SEQ ID NO 224
<211> LENGTH: 98
<212> TYPE: PRT
<213> ORGANISM: Llama pacos

<400> SEQUENCE: 224

Gln Ser Ala Leu Thr Gln Pro Pro Ser Val Ser Gly Thr Leu Gly Lys
1               5                   10                  15
Thr Val Thr Ile Ser Cys Ala Gly Thr Ser Ser Asp Val Gly Ser Gly
                20                  25                  30
Asn Tyr Val Ser Trp Tyr Gln Gln Leu Pro Gly Thr Ala Pro Lys Cys
            35                  40                  45
Leu Ile Tyr Gln Val Asn Lys Arg Ala Ser Gly Ile Pro Asp Arg Val
 50                  55                  60
Ser Gly Ser Lys Ser Gly Asn Thr Ala Ser Met Thr Ile Ser Gly Leu
65                  70                  75                  80
Gln Ser Val Asp Glu Ala Asp Tyr Tyr Cys Ala Ser Tyr Arg Ser Gly
                85                  90                  95
Gly Thr

<210> SEQ ID NO 225
<211> LENGTH: 90
<212> TYPE: PRT
<213> ORGANISM: Llama glama

<400> SEQUENCE: 225

Gln Ser Ala Val Thr Gln Pro Pro Ser Val Ser Gly Thr Leu Gly Lys
1               5                   10                  15
Thr Leu Thr Ile Ser Cys Ala Gly Thr Ser Thr Asp Val Gly Tyr Gly
```

-continued

```
                20                  25                  30

Asn Tyr Val Ser Trp Tyr Gln Gln Leu Pro Gly Thr Ala Pro Lys Leu
            35                  40                  45

Leu Ile Tyr Ala Val Ser Tyr Arg Ala Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys
                85                  90

<210> SEQ ID NO 226
<211> LENGTH: 90
<212> TYPE: PRT
<213> ORGANISM: Llama pacos

<400> SEQUENCE: 226

His Ser Ala Val Thr Gln Pro Pro Ser Val Gly Thr Leu Gly Lys
 1               5                  10                  15

Thr Val Thr Ile Ser Cys Ala Gly Thr Ser Ser Asp Val Glu Tyr Gly
                20                  25                  30

Asn Tyr Val Ser Trp Tyr Gln Gln Leu Pro Gly Thr Ala Pro Lys Leu
            35                  40                  45

Leu Ile Tyr Ala Val Ser Tyr Arg Ala Ser Gly Ile Pro Asp Arg Phe
 50                  55                  60

Ser Gly Ser Lys Ser Gly Asn Thr Ala Ser Leu Ser Ile Ser Gly Leu
 65                  70                  75                  80

Gln Ser Glu Asp Glu Ala Asp Tyr Tyr Cys
                85                  90

<210> SEQ ID NO 227
<211> LENGTH: 90
<212> TYPE: PRT
<213> ORGANISM: Llama glama

<400> SEQUENCE: 227

Gln Ser Ala Leu Thr Gln Pro Pro Ser Val Gly Thr Leu Gly Lys
 1               5                  10                  15

Thr Val Thr Ile Ser Cys Ala Gly Thr Ser Ser Asp Val Glu Tyr Gly
                20                  25                  30

Asn Tyr Val Ser Trp Tyr Gln Gln Leu Pro Asp Thr Ala Pro Lys Leu
            35                  40                  45

Leu Ile Tyr Ala Val Ser Tyr Arg Ala Ser Gly Ile Pro Asp Arg Phe
 50                  55                  60

Ser Gly Ser Lys Ser Gly Asn Thr Ala Ser Leu Thr Ile Ser Gly Leu
 65                  70                  75                  80

Gln Ser Glu Asp Glu Ala Asp Tyr Tyr Cys
                85                  90

<210> SEQ ID NO 228
<211> LENGTH: 98
<212> TYPE: PRT
<213> ORGANISM: Homo sapiens

<400> SEQUENCE: 228

Gln Ser Ala Leu Thr Gln Pro Pro Ser Val Ser Gly Ser Pro Gly Gln
 1               5                  10                  15

Ser Val Thr Ile Ser Cys Thr Gly Thr Ser Ser Asp Val Gly Ser Tyr
                20                  25                  30
```

Asn Arg Val Ser Trp Tyr Gln Gln Pro Pro Gly Thr Ala Pro Lys Leu
            35                  40                  45

Met Ile Tyr Glu Val Ser Asn Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Ser
                 85                  90                  95

Ser Thr

<210> SEQ ID NO 229
<211> LENGTH: 97
<212> TYPE: PRT
<213> ORGANISM: Llama pacos

<400> SEQUENCE: 229

Asn Ser Ala Leu Thr Gln Pro Pro Ser Val Ser Gly Thr Leu Gly Lys
 1               5                  10                  15

Thr Val Thr Ile Ser Cys Thr Gly Thr Ser Ser Asp Ile Gly Gly Tyr
            20                  25                  30

Asn Tyr Val Ser Trp Tyr Gln Gln Leu Pro Gly Thr Ala Pro Lys Leu
            35                  40                  45

Leu Ile Tyr Glu Val Asn Lys Ala Ser Gly Ile Pro Asp Arg Phe Ser
 50                  55                  60

Gly Ser Lys Ser Gly Asn Thr Ala Ser Leu Ser Ile Ser Gly Leu Gln
 65                  70                  75                  80

Ser Glu Asp Glu Ala Asp Tyr Phe Cys Ala Ser Tyr Thr Thr Ser Ser
                 85                  90                  95

Thr

<210> SEQ ID NO 230
<211> LENGTH: 89
<212> TYPE: PRT
<213> ORGANISM: Llama glama

<400> SEQUENCE: 230

Asn Ser Ala Leu Thr Gln Pro Pro Ser Val Ser Gly Thr Leu Gly Lys
 1               5                  10                  15

Thr Val Thr Ile Ser Cys Thr Gly Thr Ser Ser Asp Ile Gly Gly Tyr
            20                  25                  30

Asn Tyr Val Ser Trp Tyr Gln Gln Leu Pro Gly Thr Ala Pro Lys Leu
            35                  40                  45

Leu Ile Tyr Glu Val Asn Lys Ala Ser Gly Ile Pro Asp Arg Phe Ser
 50                  55                  60

Gly Ser Lys Ser Gly Asn Thr Ala Ser Leu Thr Ile Ser Gly Leu Gln
 65                  70                  75                  80

Ser Glu Asp Glu Ala Asp Tyr Tyr Cys
                 85

<210> SEQ ID NO 231
<211> LENGTH: 96
<212> TYPE: PRT
<213> ORGANISM: Camelus ferus

<400> SEQUENCE: 231

Gln Ser Ala Leu Thr Gln Pro Pro Leu Ala Ser Gly Thr Pro Gly Gln
 1               5                  10                  15

-continued

Thr Val Thr Ile Ser Cys Ala Gly Thr Ser Ser Asp Ile Gly Gly Tyr
            20                  25                  30

Ser Asp Ile Ser Leu Tyr Gln Gln Leu Pro Gly Met Ala Pro Asn Leu
        35                  40                  45

Leu Ile Tyr Tyr Val Ser Asn Ala Ser Gly Ile Pro Asp Arg Phe Pro
    50                  55                  60

Gly Ser Lys Ser Gly Asn Thr Ala Ser Leu Thr Ile Ser Gly Leu Gln
65                  70                  75                  80

Ser Lys Asp Glu Ala Asp Phe Cys Ala Ser Tyr Thr Thr Ser Asn Thr
                85                  90                  95

<210> SEQ ID NO 232
<211> LENGTH: 97
<212> TYPE: PRT
<213> ORGANISM: Llama pacos

<400> SEQUENCE: 232

Gln Ser Ala Leu Thr Gln Pro Pro Leu Val Ser Gly Thr Pro Gly Gln
1               5                   10                  15

Thr Val Thr Ile Thr Cys Ala Gly Thr Ser Ser Asp Ile Gly Val Tyr
            20                  25                  30

Ser Asp Ile Ser Trp Tyr Gln Gln Leu Leu Gly Met Ala Pro Lys Leu
        35                  40                  45

Leu Ile Tyr Tyr Val Ser Asn Ala Ser Gly Ile Pro Asp Arg Phe Ser
    50                  55                  60

Gly Ser Lys Ser Gly Asn Met Ala Ser Leu Thr Ile Ser Gly Leu Gln
65                  70                  75                  80

Ser Glu Asp Glu Ser Asp Tyr Tyr Cys Pro Ser Ser Arg Ser Ser Asn
                85                  90                  95

Asn

<210> SEQ ID NO 233
<211> LENGTH: 97
<212> TYPE: PRT
<213> ORGANISM: Llama pacos

<400> SEQUENCE: 233

Gln Ser Ala Leu Thr Gln Pro Pro Leu Val Ser Gly Thr Pro Gln Thr
1               5                   10                  15

Val Thr Ile Ser Cys Ala Gly Thr Ser Ser Asp Ala Gly Ser Gly Asn
            20                  25                  30

Tyr Val Ser Trp Tyr Gln Gln Leu Pro Gly Thr Ala Pro Lys Leu Leu
        35                  40                  45

Ile Tyr Asp Val Ser Ser Arg Ser Ser Gly Ile Thr Asp Arg Phe Ser
    50                  55                  60

Gly Ser Lys Ser Gly Asn Thr Ala Ser Leu Thr Thr Ser Gly Leu Gln
65                  70                  75                  80

Ser Glu Asp Glu Ala Asp Tyr Tyr Cys Ala Ser Tyr Arg Ser Ser Asn
                85                  90                  95

Asn

<210> SEQ ID NO 234
<211> LENGTH: 97
<212> TYPE: PRT
<213> ORGANISM: Llama pacos

<400> SEQUENCE: 234

Gln Ser Ala Leu Thr Gln Pro Pro Leu Val Ser Gly Thr Pro Gln Thr
1               5                   10                  15

Val Thr Ile Ser Cys Ala Gly Thr Ser Ser Asp Ala Gly Ser Gly Asn
            20                  25                  30

Tyr Val Ser Trp Tyr Gln Gln Val Pro Arg Thr Ala Pro Lys Leu Leu
            35                  40                  45

Ile Tyr Glu Val Asn Lys Arg Ala Ser Gly Ile Pro Asp Arg Phe Ser
    50                  55                  60

Gly Ser Lys Ser Gly Asn Val Ala Ser Leu Ser Ile Ser Gly Leu Gln
65                  70                  75                  80

Ser Glu Asp Lys Ala Asp Cys Ser Cys Ala Ser Tyr Thr Thr Ser Ser
                85                  90                  95

Thr

<210> SEQ ID NO 235
<211> LENGTH: 75
<212> TYPE: PRT
<213> ORGANISM: Camelus ferus

<400> SEQUENCE: 235

Gly Thr Ser Ser Asp Val Gly Ser Gly Asn Tyr Val Ser Trp His Gln
1               5                   10                  15

Gln Leu Pro Gly Thr Ala Pro Lys Phe Leu Ile Tyr Gln Val Asn Lys
            20                  25                  30

Arg Ala Ser Gly Ile Ser Asp Arg Phe Ser Gly Ser Lys Ser Gly Asn
            35                  40                  45

Thr Ala Ser Leu Thr Ile Ser Gly Leu Gln Ser Ala Asp Glu Ala Asp
    50                  55                  60

Tyr Tyr Cys Ala Ser Tyr Gly Ser Ser Tyr Asn
65                  70                  75

<210> SEQ ID NO 236
<211> LENGTH: 90
<212> TYPE: PRT
<213> ORGANISM: Llama glama

<400> SEQUENCE: 236

His Ser Ala Val Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
            35                  40                  45

Leu Ile Tyr Ala Val Ser Tyr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys
                85                  90

<210> SEQ ID NO 237
<211> LENGTH: 65
<212> TYPE: PRT
<213> ORGANISM: Camelus ferus

<400> SEQUENCE: 237

Ser Val Ser Trp Tyr Gln Gln Leu Pro Gly Met Ala Pro Lys Leu Leu

```
                1               5                   10                  15
            Ile Tyr Ala Val Ser Tyr Arg Ala Ser Val Ile Ala Asp His Phe Ser
                                20                  25                  30

Gly Ser Lys Ser Glu Asn Thr Ala Ser Leu Thr Ile Ser Gly Leu Gln
                        35                  40                  45

Ser Ala Asn Lys Ala Asp Tyr Tyr Cys Ala Ser Tyr Arg Ser Ser Asn
                    50                  55                  60

Asn
            65

<210> SEQ ID NO 238
<211> LENGTH: 35
<212> TYPE: PRT
<213> ORGANISM: Camelus ferus

<400> SEQUENCE: 238

Phe Ser Gly Ser Arg Ser Gly Ser Thr Ala Ser Gln Thr Ile Ser Gly
            1               5                   10                  15

Leu Gln Pro Glu Asp Glu Ala Asp Tyr Tyr Cys Ser Val Trp Asp Gly
                        20                  25                  30

Ser Leu Ser
                    35

<210> SEQ ID NO 239
<211> LENGTH: 34
<212> TYPE: PRT
<213> ORGANISM: Llama pacos

<400> SEQUENCE: 239

Ser Gly Ser Lys Ser Gly Asn Thr Ala Ser Leu Thr Val Ser Gly Leu
            1               5                   10                  15

Trp Ser Glu Asp Glu Ala Asp Tyr Tyr Cys Ala Ser Tyr Arg Ser Gly
                        20                  25                  30

Gly Pro

<210> SEQ ID NO 240
<211> LENGTH: 37
<212> TYPE: PRT
<213> ORGANISM: Llama pacos

<400> SEQUENCE: 240

Asp Thr Ser Ser Asp Ser Lys Ser Ser Asn Lys Ala Thr Leu Thr Val
            1               5                   10                  15

Pro Gly Leu Arg Ser Glu Asp Glu Ala Asp Tyr Tyr Cys Ala Ser Tyr
                        20                  25                  30

Arg Ser Ser Gly Pro
                    35

<210> SEQ ID NO 241
<211> LENGTH: 95
<212> TYPE: PRT
<213> ORGANISM: Homo sapiens

<400> SEQUENCE: 241

Ser Tyr Glu Leu Thr Gln Pro Leu Ser Val Ser Val Ala Leu Gly Gln
            1               5                   10                  15

Thr Ala Arg Ile Thr Cys Gly Gly Asn Asn Ile Gly Ser Lys Asn Val
                        20                  25                  30

His Trp Tyr Gln Gln Lys Pro Gly Gln Ala Pro Val Leu Val Ile Tyr
```

```
                35                  40                  45

Arg Asp Ser Asn Arg Pro Ser Gly Ile Pro Glu Arg Phe Ser Gly Ser
         50                  55                  60

Asn Ser Gly Asn Thr Ala Thr Leu Thr Ile Ser Arg Ala Gln Ala Gly
 65                  70                  75                  80

Asp Glu Ala Asp Tyr Tyr Cys Gln Val Trp Asp Ser Thr Ala
                 85                  90                  95

<210> SEQ ID NO 242
<211> LENGTH: 95
<212> TYPE: PRT
<213> ORGANISM: Camelus ferus

<400> SEQUENCE: 242

Ser Tyr Glu Leu Thr Gln Ser Pro Ser Val Ser Val Ala Leu Arg Gln
 1               5                  10                  15

Thr Ala Lys Ile Thr Cys Gly Gly Asp Asn Ile Gly Ser Lys Ser Val
             20                  25                  30

His Trp Tyr Gln Gln Lys Pro Gly Gln Ala Pro Val Leu Val Ile Tyr
                35                  40                  45

Ala Asp Asn Ser Arg Pro Ser Gly Ile Pro Glu Arg Phe Ser Gly Ser
         50                  55                  60

Asn Ser Gly Asn Thr Ala Thr Leu Thr Ile Ser Gly Ala Gln Ala Glu
 65                  70                  75                  80

Asp Glu Ala Asp Tyr Tyr Cys Gln Val Trp Asp Ser Ser Ala
                 85                  90                  95

<210> SEQ ID NO 243
<211> LENGTH: 95
<212> TYPE: PRT
<213> ORGANISM: Llama pacos

<400> SEQUENCE: 243

Ser Tyr Glu Leu Thr Gln Thr Pro Ser Val Ser Val Ala Leu Arg Gln
 1               5                  10                  15

Thr Ala Lys Ile Thr Cys Gly Gly Asp Asn Ile Gly Ser Lys Ser Ala
             20                  25                  30

Gln Trp Tyr Gln Gln Lys Pro Gly Gln Ala Pro Val Leu Val Ile Tyr
                35                  40                  45

Ala Asp Ser Arg Arg Pro Ser Gly Ile Pro Glu Arg Phe Ser Gly Ser
         50                  55                  60

Asn Ser Gly Asn Thr Ala Thr Leu Thr Ile Ser Gly Ala Gln Ala Glu
 65                  70                  75                  80

Asp Glu Ala Asp Tyr Tyr Cys His Val Trp Asp Ser Ser Ala Asn
                 85                  90                  95

<210> SEQ ID NO 244
<211> LENGTH: 87
<212> TYPE: PRT
<213> ORGANISM: Llama glama

<400> SEQUENCE: 244

Ser Tyr Glu Leu Thr Gln Ser Pro Ser Val Ser Val Ala Leu Arg Gln
 1               5                  10                  15

Ala Ala Lys Ile Thr Cys Gly Gly Asp Asn Ile Ala Ser Lys Tyr Ala
             20                  25                  30

Asn Trp Tyr Gln Gln Lys Pro Gly Gln Ala Pro Val Leu Val Ile Tyr
                35                  40                  45
```

```
Lys Asp Ser Asn Arg Pro Ser Gly Ile Pro Glu Arg Phe Ser Gly Ser
        50                  55                  60

Asn Ser Gly Asn Thr Ala Thr Leu Thr Val Ser Gly Ala Gln Ala Glu
 65                  70                  75                  80

Asp Glu Ala Asp Tyr Tyr Cys
                85

<210> SEQ ID NO 245
<211> LENGTH: 95
<212> TYPE: PRT
<213> ORGANISM: Llama pacos

<400> SEQUENCE: 245

Ser Tyr Glu Leu Thr Gln Ser Pro Ser Val Ser Val Ala Leu Arg Gln
 1               5                  10                  15

Ala Ala Lys Ile Thr Cys Gly Gly Asp Asn Ile Ala Ser Lys Tyr Ala
                20                  25                  30

His Trp Tyr Gln Gln Lys Pro Gly Gln Ser Pro Val Leu Val Ile Tyr
            35                  40                  45

Lys Asp Ser Asn Arg Pro Ser Gly Ile Pro Glu Arg Phe Ser Gly Ser
        50                  55                  60

Asn Ser Gly Asn Thr Ala Thr Leu Thr Val Ser Gly Ala Gln Ala Glu
 65                  70                  75                  80

Asp Glu Ala Asp Tyr Tyr Cys Gln Val Trp Asp Ser Ser Ala Asn
                85                  90                  95

<210> SEQ ID NO 246
<211> LENGTH: 87
<212> TYPE: PRT
<213> ORGANISM: Llama glama

<400> SEQUENCE: 246

Ser Tyr Glu Leu Thr Gln Ser Pro Ser Val Ser Val Ala Leu Arg Gln
 1               5                  10                  15

Ala Ala Lys Ile Thr Cys Gly Gly Asp Asn Ile Ala Ser Lys Tyr Ala
                20                  25                  30

Asn Trp Tyr Gln Gln Lys Pro Gly Gln Ala Pro Val Leu Val Ile Tyr
            35                  40                  45

Lys Asp Ser Asn Arg Pro Ser Gly Ile Pro Glu Arg Phe Ser Gly Ser
        50                  55                  60

Asn Ser Gly Asn Thr Ala Thr Leu Thr Val Ser Gly Ala Gln Ala Glu
 65                  70                  75                  80

Asp Glu Ala Asp Tyr Tyr Cys
                85

<210> SEQ ID NO 247
<211> LENGTH: 87
<212> TYPE: PRT
<213> ORGANISM: Llama glama

<400> SEQUENCE: 247

Ser Tyr Glu Leu Thr Gln Thr Pro Ser Val Ser Val Ala Leu Arg Gln
 1               5                  10                  15

Thr Ala Lys Ile Thr Cys Gly Gly Asp Asn Ile Gly Ser Lys Tyr Ala
                20                  25                  30

His Trp Tyr Gln Gln Lys Pro Gly Gln Ser Pro Val Leu Val Ile Tyr
            35                  40                  45
```

Lys Asp Ser Asn Arg Pro Ser Gly Ile Pro Glu Arg Phe Ser Gly Ser
    50                  55                  60

Asn Ser Gly Asn Thr Ala Thr Leu Thr Val Ser Gly Ala Arg Ala Glu
65                  70                  75                  80

Asp Glu Ala Asp Tyr Tyr Cys
                85

<210> SEQ ID NO 248
<211> LENGTH: 87
<212> TYPE: PRT
<213> ORGANISM: Llama glama

<400> SEQUENCE: 248

Ser Tyr Gly Leu Thr Gln Ser Pro Ser Val Ser Val Ala Leu Arg Gln
1               5                   10                  15

Thr Ala Lys Ile Thr Cys Gly Gly Asp Asn Ile Gly Ser Lys Asn Ala
                20                  25                  30

His Trp Tyr Gln Gln Lys Pro Gly Gln Ala Pro Val Leu Val Ile Tyr
            35                  40                  45

Arg Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Ala Gln Val Glu
65                  70                  75                  80

Asp Glu Ala Asp Tyr Tyr Cys
                85

<210> SEQ ID NO 249
<211> LENGTH: 87
<212> TYPE: PRT
<213> ORGANISM: Llama glama

<400> SEQUENCE: 249

Ser Tyr Glu Leu Thr Gln Thr Pro Ser Val Ser Val Ala Leu Arg Gln
1               5                   10                  15

Thr Ala Lys Ile Thr Cys Gly Gly Asp Asn Ile Gly Asn Lys Tyr Ala
                20                  25                  30

Tyr Trp Tyr Gln Gln Lys Pro Gly Gln Ala Pro Val Leu Val Ile Tyr
            35                  40                  45

Arg Asp Ser Glu Arg Pro Ser Gly Ile Pro Gly Arg Phe Ser Gly Ser
    50                  55                  60

Asn Ser Gly Asn Thr Ala Ile Leu Thr Val Ser Gly Ala Leu Ala Glu
65                  70                  75                  80

Asp Glu Ala Asp Tyr Tyr Cys
                85

<210> SEQ ID NO 250
<211> LENGTH: 95
<212> TYPE: PRT
<213> ORGANISM: Llama pacos

<400> SEQUENCE: 250

Ser Tyr Glu Leu Thr Gln Gln Ala Ser Val Ser Val Asp Leu Gln Gln
1               5                   10                  15

Thr Ala Ser Ile Thr Cys Ser Gly Asp Leu Leu Asp Lys Lys Tyr Thr
                20                  25                  30

Gln Trp Tyr Gln Gln Lys Pro Gly Gln Ala Pro Val Leu Val Ile Tyr
            35                  40                  45

Lys Asp Ser Glu Arg Pro Ser Gly Ile Pro Glu Arg Phe Ser Gly Ser

```
                 50                  55                  60

Ser Ser Gly Lys Thr Ala Thr Leu Thr Ile Ser Gly Ala Gln Ala Glu
 65                  70                  75                  80

Asp Glu Ala Asp Tyr Tyr Cys His Ser Ala Asp Ser Ser Asp Asn
                 85                  90                  95

<210> SEQ ID NO 251
<211> LENGTH: 94
<212> TYPE: PRT
<213> ORGANISM: Homo sapiens

<400> SEQUENCE: 251

Ser Tyr Glu Leu Thr Gln Pro Pro Ser Val Ser Val Ser Pro Gly Gln
  1               5                  10                  15

Thr Ala Arg Ile Thr Cys Ser Gly Asp Ala Leu Pro Lys Gln Tyr Ala
                 20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
         50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser Gly
                 85                  90

<210> SEQ ID NO 252
<211> LENGTH: 94
<212> TYPE: PRT
<213> ORGANISM: Camelus ferus

<400> SEQUENCE: 252

Ser Ser Ala Leu Thr Gln Pro Ser Ala Val Ser Val Ser Leu Gly Gln
  1               5                  10                  15

Thr Ala Arg Ile Thr Cys Gln Gly Gly Asn Leu Gly Ser Ser Tyr Val
                 20                  25                  30

His Trp Tyr Gln Gln Lys Pro Gly Gln Ala Pro Val Leu Val Ile Tyr
             35                  40                  45

Gly Asp Asp Ser Arg Pro Ser Gly Ile Pro Glu Arg Phe Ser Gly Ser
         50                  55                  60

Ser Ser Gly Gly Thr Ala Thr Leu Thr Ile Ser Gly Ala Gln Ala Glu
 65                  70                  75                  80

Asp Glu Ala Asp Tyr Tyr Cys Gln Ser Tyr Asp Ser Ser Ser
                 85                  90

<210> SEQ ID NO 253
<211> LENGTH: 94
<212> TYPE: PRT
<213> ORGANISM: Llama pacos

<400> SEQUENCE: 253

Ser Ser Ala Leu Thr Gln Pro Ser Ala Leu Ser Val Ser Leu Gly Gln
  1               5                  10                  15

Thr Ala Arg Ile Thr Cys Gln Gly Gly Asn Phe Gly Ser Ser Tyr Ala
                 20                  25                  30

Phe Trp Tyr Gln Gln Lys Pro Gly Gln Ala Pro Val Leu Ile Ile Tyr
             35                  40                  45

Gly Asp Asp Ser Arg Pro Ser Gly Ile Pro Glu Arg Phe Ser Gly Ser
         50                  55                  60
```

```
Ser Ser Gly Gly Thr Ala Thr Leu Thr Ile Ser Gly Ala Gln Ala Gln
65                  70                  75                  80

Asp Glu Ala Asp Tyr Tyr Cys Gln Ser Gly Ser Ser Ala
                85                  90
```

<210> SEQ ID NO 254
<211> LENGTH: 94
<212> TYPE: PRT
<213> ORGANISM: Camelus ferus

<400> SEQUENCE: 254

```
Ser Ser Ala Leu Thr Gln Pro Ser Thr Val Ser Val Ser Leu Gly Gln
1               5                   10                  15

Thr Ala Arg Ile Thr Cys Gln Gly Gly Asn Phe Gly Ser Ser Tyr Ala
                20                  25                  30

Phe Trp Tyr Gln Gln Lys Pro Gly Gln Ala Pro Val Met Val Ile Tyr
            35                  40                  45

Arg Asp Ser Asn Arg Pro Ser Gly Ile Pro Glu Arg Phe Ser Gly Ser
        50                  55                  60

Ser Ser Gly Asp Thr Ala Thr Leu Asn Ile Ser Gly Ala Gln Ala Glu
65                  70                  75                  80

Asp Glu Ala Asn Tyr Tyr Cys His Ser Ala Asp Ser Ser Gly
                85                  90
```

<210> SEQ ID NO 255
<211> LENGTH: 94
<212> TYPE: PRT
<213> ORGANISM: Llama pacos

<400> SEQUENCE: 255

```
Ser Ser Ala Leu Thr Gln Pro Ser Ala Val Ser Val Ser Leu Gly Gln
1               5                   10                  15

Thr Ala Arg Ile Thr Cys Gln Gly Gly Asn Phe Gly Ser Tyr Tyr Gly
                20                  25                  30

Ser Trp Tyr Gln Gln Lys Pro Ser Gln Ala Pro Val Leu Val Ile Phe
            35                  40                  45

Lys Asp Ser Glu Arg Pro Ser Gly Ile Pro Glu Arg Phe Ser Gly Ser
        50                  55                  60

Ser Ser Gly Asp Thr Ala Thr Leu Thr Ile Ser Gly Ala Gln Ala Glu
65                  70                  75                  80

Asp Glu Ala Asp Tyr Tyr Cys Leu Ser Tyr Glu Ser Ser Gly
                85                  90
```

<210> SEQ ID NO 256
<211> LENGTH: 94
<212> TYPE: PRT
<213> ORGANISM: Llama pacos

<400> SEQUENCE: 256

```
Ser Ser Ala Leu Thr Gln Pro Ser Ala Val Ser Val Ser Leu Gly Gln
1               5                   10                  15

Thr Ala Arg Ile Thr Cys Gln Gly Gly Asn Leu Gly Ser Tyr Tyr Gly
                20                  25                  30

Ser Trp Tyr Gln Gln Lys Pro Gly Gln Ala Pro Val Gln Val Ile Tyr
            35                  40                  45

Gly Asn Ser Asn Arg Pro Ser Gly Ile Pro Glu Arg Phe Ser Gly Ser
        50                  55                  60
```

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Tyr Glu Ser Ser Gly
            85                  90

<210> SEQ ID NO 257
<211> LENGTH: 87
<212> TYPE: PRT
<213> ORGANISM: Llama glama

<400> SEQUENCE: 257

Ser Ser Ala Leu Thr Gln Pro Ser Thr Val Ser Val Ser Leu Gly Gln
1               5                   10                  15

Thr Ala Gly Ile Thr Cys Gln Gly Gly Asn Ile Gly Ser Tyr Tyr Ala
            20                  25                  30

His Trp Tyr Gln Gln Lys Pro Gly Gln Ala Pro Val Leu Val Ile Tyr
        35                  40                  45

Gly Asn Ser Asn Arg Pro Ser Gly Ile Pro Glu Trp Phe Ser Gly Ser
    50                  55                  60

Ser Ala Gly Ser Thr Ala Thr Leu Thr Ile Ser Gly Ala Pro Ala Glu
65                  70                  75                  80

Asp Glu Ala Asp Tyr Tyr Cys
            85

<210> SEQ ID NO 258
<211> LENGTH: 94
<212> TYPE: PRT
<213> ORGANISM: Camelus ferus

<400> SEQUENCE: 258

Ser Ser Ala Leu Thr Gln Pro Ser Ala Val Ser Val Ser Leu Gly Glu
1               5                   10                  15

Thr Ala Arg Ile Thr Cys Gln Gly Gly Asn Val Gly Ser Asn Tyr Ala
            20                  25                  30

Ser Trp Tyr Gln Gln Lys Pro Gly Gln Ala Pro Val Leu Val Ile Tyr
        35                  40                  45

Gly Asp Asp Ser Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Tyr Asp Ser Ser Gly
            85                  90

<210> SEQ ID NO 259
<211> LENGTH: 87
<212> TYPE: PRT
<213> ORGANISM: Llama glama

<400> SEQUENCE: 259

Ser Ser Ala Leu Thr Gln Pro Ser Ala Val Ser Val Ser Leu Gly Gln
1               5                   10                  15

Thr Ala Arg Ile Thr Cys Gln Gly Gly Asn Phe Gly Ser Tyr Tyr Pro
            20                  25                  30

His Trp Tyr Gln Gln Lys Pro Gly Gln Ala Pro Val Leu Val Ile Tyr
        35                  40                  45

Arg Asp Ser Glu Arg Pro Ser Gly Ile Pro Glu Arg Phe Ser Gly Ser
    50                  55                  60

Arg Leu Gly Gly Thr Ala Thr Leu Thr Ile Ser Gly Ala Gln Thr Glu

```
65                  70                  75                  80

Asp Glu Ala Asp Tyr Tyr Cys
                85

<210> SEQ ID NO 260
<211> LENGTH: 87
<212> TYPE: PRT
<213> ORGANISM: Llama glama

<400> SEQUENCE: 260

Ser Ser Ala Leu Thr Gln Pro Ser Ala Val Ser Val Ser Leu Gly Gln
1               5                   10                  15

Thr Ala Arg Ile Thr Cys Gln Gly Gly Asn Phe Gly Gly Tyr Tyr Pro
            20                  25                  30

His Trp Tyr Gln Gln Lys Pro Gly Gln Ala Pro Val Leu Val Ile Tyr
        35                  40                  45

Gln Cys Asn Asn Arg Pro Ser Gly Ile Ser Glu Arg Phe Ser Gly Thr
    50                  55                  60

Lys Ser Gly Asp Thr Ala Thr Leu Thr Ile Ser Gly Ala Gln Ala Glu
65                  70                  75                  80

Asp Glu Ala Asp Tyr Tyr Cys
                85

<210> SEQ ID NO 261
<211> LENGTH: 97
<212> TYPE: PRT
<213> ORGANISM: Homo sapiens

<400> SEQUENCE: 261

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ala Asp Ser Ser Gly Thr Tyr
                85                  90                  95

Pro

<210> SEQ ID NO 262
<211> LENGTH: 96
<212> TYPE: PRT
<213> ORGANISM: Llama pacos

<400> SEQUENCE: 262

Ser Ser Ala Leu Thr Gln Pro Ser Ala Val Ser Val Ser Leu Gly Gln
1               5                   10                  15

Thr Ala Arg Ile Thr Cys Gln Gly Gly Ser Leu Gly Ser Tyr Tyr Gly
            20                  25                  30

Ser Trp Tyr Arg Gln Lys Pro Gly Gln Ala Pro Val Leu Val Ile Tyr
        35                  40                  45

Gly Asn Asn Asn Arg Pro Ser Gly Ile Pro Glu Arg Phe Ser Gly Ser
    50                  55                  60
```

-continued

Ser Ser Gly Asp Thr Ala Thr Leu Thr Ile Ser Gly Ala Gln Ala Glu
65                  70                  75                  80

Asp Glu Ala Asp Tyr Tyr Cys Gln Ser Gly Ser Ser Asp Asn Ala
                85                  90                  95

<210> SEQ ID NO 263
<211> LENGTH: 97
<212> TYPE: PRT
<213> ORGANISM: Llama pacos

<400> SEQUENCE: 263

Ala Ser Ser Val Thr Gln Pro Ser Ala Val Ser Val Ser Leu Gly Gln
1               5                   10                  15

Thr Ala Ser Ile Thr Cys Gln Phe Gly Ser Leu Gly Ser Tyr Tyr Ala
            20                  25                  30

His Trp Leu Gln Gln Lys Pro Gly Gln Ser Pro Val Leu Val Ile Tyr
        35                  40                  45

Asn Asp Asn Ser Arg Pro Ser Gly Ile Pro Glu Arg Phe Ser Gly Ser
    50                  55                  60

Arg Ser Gly Asp Thr Ala Thr Leu Thr Val Ser Gly Ser Gln Ala Glu
65                  70                  75                  80

Asp Glu Ala Asp Tyr Tyr Cys Gln Val Trp Asp Ser Gly Tyr Asn
                85                  90                  95

Ala

<210> SEQ ID NO 264
<211> LENGTH: 97
<212> TYPE: PRT
<213> ORGANISM: Camelus ferus

<400> SEQUENCE: 264

Ser Ser Ala Val Thr Gln Pro Ser Thr Val Ser Val Ser Leu Gly Gln
1               5                   10                  15

Thr Ala Ser Ile Thr Cys Gln Phe Gly Ser Leu Gly Ser Tyr Tyr Ser
            20                  25                  30

His Trp Leu Gln Gln Lys Pro Gly Gln Ala Pro Val Leu Val Ile Tyr
        35                  40                  45

Asn Asp Asn Ser Arg Pro Ser Gly Ile Pro Glu Arg Phe Ser Gly Ser
    50                  55                  60

Arg Ser Gly Asp Thr Ala Thr Leu Thr Ile Ser Gly Ala Gln Ala Glu
65                  70                  75                  80

Asp Glu Ala Asp Tyr Tyr Cys Gln Val Trp Asp Ser Ser Gly Tyr Asn
                85                  90                  95

Ala

<210> SEQ ID NO 265
<211> LENGTH: 97
<212> TYPE: PRT
<213> ORGANISM: Camelus ferus

<400> SEQUENCE: 265

Pro Ser Ala Leu Thr Gln Pro Ser Thr Val Ser Val Ser Leu Gly Gln
1               5                   10                  15

Thr Ala Lys Ile Thr Cys Gln Gly Gly Ser Leu Arg Ser Tyr Tyr Ala
            20                  25                  30

His Trp Tyr Gln Gln Lys Pro Gly Leu Ala Pro Val Leu Val Ile Tyr
        35                  40                  45

```
Lys Asp Ser Asn Arg Pro Ser Gly Ile Pro Glu Arg Phe Ser Gly Ser
        50                  55                  60

Arg Ser Gly Gly Thr Ala Thr Leu Thr Ile Ser Arg Thr Gln Ala Glu
 65                  70                  75                  80

Asp Glu Ala Asp Tyr Tyr Cys Leu Ser Ala Asp Ser Ser Asp Tyr Asn
                85                  90                  95

Ala
```

<210> SEQ ID NO 266
<211> LENGTH: 97
<212> TYPE: PRT
<213> ORGANISM: Llama pacos

<400> SEQUENCE: 266

```
Ser Ser Ala Leu Thr Gln Pro Ser Thr Val Ser Val Ser Leu Gly Gln
 1               5                  10                  15

Thr Ala Lys Ile Thr Cys Gln Gly Gly Ser Leu Glu Ser Tyr Tyr Ala
                20                  25                  30

His Trp Tyr Gln Gln Lys Pro Asp Gln Ala Pro Val Leu Val Ile Tyr
                35                  40                  45

Arg Asp Ser Asn Arg Pro Ser Gly Ile Pro Glu Arg Phe Ser Gly Ser
        50                  55                  60

Arg Ser Gly Gly Thr Ala Thr Leu Thr Ile Ser Gly Ile Gln Ala Glu
 65                  70                  75                  80

Asp Glu Ala Asp Tyr Tyr Cys Leu Ser Ala Asp Ser Ser Asp Tyr Asn
                85                  90                  95

Ala
```

<210> SEQ ID NO 267
<211> LENGTH: 96
<212> TYPE: PRT
<213> ORGANISM: Llama pacos

<400> SEQUENCE: 267

```
Ser Ser Ala Leu Thr Gln Pro Ser Thr Val Ser Val Ser Leu Gly Gln
 1               5                  10                  15

Met Ala Arg Ile Thr Cys Gln Gly Gly Ser Leu Gly Ser Tyr Asp Ala
                20                  25                  30

His Trp Tyr Gln Gln Lys Pro Gly Gln Ala Pro Val Leu Val Ile His
                35                  40                  45

Asp Asp Asn Ser Arg Pro Ser Gly Ile Pro Glu Arg Phe Ser Gly Ser
        50                  55                  60

Arg Ser Gly Gly Thr Ala Thr Leu Thr Ile Ser Gly Ala Gln Ala Glu
 65                  70                  75                  80

Asp Glu Ala Asp Tyr Tyr Cys Gln Ser Tyr Asp Ser Ser Ala Asn Ala
                85                  90                  95
```

<210> SEQ ID NO 268
<211> LENGTH: 97
<212> TYPE: PRT
<213> ORGANISM: Llama pacos

<400> SEQUENCE: 268

```
Ser Ser Ala Leu Thr Gln Pro Ser Met Val Ser Val Ser Leu Gly Gln
 1               5                  10                  15

Thr Ala Arg Thr Thr Cys Gln Gly Gly Ser Leu Gly Ser Tyr Gly Ala
                20                  25                  30
```

Asn Trp Tyr Gln Gln Lys Pro Gly Arg Ala Pro Val Leu Val Ile Tyr
                35                  40                  45

Glu Asp Ser Lys Arg Pro Ser Gly Ile Pro Glu Trp Phe Ser Gly Ser
 50                  55                  60

Lys Ser Gly Gly Pro Ala Thr Leu Thr Ile Ser Gly Ala Gln Ala Glu
65                  70                  75                  80

Asp Glu Ala Asp Tyr Tyr Cys Gln Val Trp Asp Ser Gly Tyr Asn
                85                  90                  95

Ala

<210> SEQ ID NO 269
<211> LENGTH: 87
<212> TYPE: PRT
<213> ORGANISM: Llama glama

<400> SEQUENCE: 269

Ser Ser Ala Leu Thr Gln Pro Ser Ala Val Ser Val Ser Leu Gly Gln
1               5                   10                  15

Thr Ala Lys Ile Thr Cys Gln Gly Gly Ser Leu Gly Ser Ser Tyr Ala
                20                  25                  30

His Trp Tyr Gln Gln Lys Pro Gly Gln Ala Pro Val Leu Val Ile Tyr
                35                  40                  45

Asp Asp Asp Ser Arg Pro Ser Gly Ile Pro Glu Arg Phe Ser Gly Ser
 50                  55                  60

Ser Ser Gly Gly Arg Ala Thr Leu Thr Ile Ser Gly Ala Gln Ala Glu
65                  70                  75                  80

Asp Glu Ala Asp Tyr Tyr Cys
                85

<210> SEQ ID NO 270
<211> LENGTH: 96
<212> TYPE: PRT
<213> ORGANISM: Llama pacos

<400> SEQUENCE: 270

Ser Ser Ala Leu Thr Gln Pro Ser Ala Leu Ser Val Thr Leu Gly Gln
1               5                   10                  15

Thr Ala Lys Ile Thr Cys Gln Gly Gly Ser Leu Gly Ser Ser Tyr Ala
                20                  25                  30

His Trp Tyr Gln Gln Lys Pro Gly Gln Ala Pro Val Leu Val Ile Tyr
                35                  40                  45

Asp Asp Asp Ser Arg Pro Ser Gly Ile Pro Glu Arg Phe Ser Gly Ser
 50                  55                  60

Ser Ser Gly Gly Arg Ala Thr Leu Thr Ile Ser Gly Ala Gln Ala Glu
65                  70                  75                  80

Asp Glu Gly Asp Tyr Tyr Cys Gln Ser Ala Asp Ser Ser Gly Asn Ala
                85                  90                  95

<210> SEQ ID NO 271
<211> LENGTH: 96
<212> TYPE: PRT
<213> ORGANISM: Llama pacos

<400> SEQUENCE: 271

Ser Ser Ala Leu Thr Gln Pro Ser Ala Val Ser Val Ser Leu Gly Gln
1               5                   10                  15

Thr Ala Arg Ile Thr Cys Gln Gly Ser Ser Leu Gly Ser Ser Tyr Ala
                20                  25                  30

His Trp Tyr Gln Gln Met Pro Gly Gln Ala Pro Val Leu Val Ile Tyr
            35                  40                  45

Arg Asp Ser Glu Arg Pro Ser Gly Ile Pro Glu Arg Phe Ser Gly Ser
        50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys Gln Ser Ala Asp Ser Ser Asp Asn Ala
                85                  90                  95

<210> SEQ ID NO 272
<211> LENGTH: 87
<212> TYPE: PRT
<213> ORGANISM: Llama glama

<400> SEQUENCE: 272

Ser Ser Ala Leu Thr Gln Pro Ser Ala Val Ser Val Ser Leu Gly Gln
1               5                   10                  15

Thr Ala Arg Ile Thr Cys Gln Gly Ser Ser Leu Gly Ser Ser Tyr Ala
            20                  25                  30

His Trp Tyr Gln Gln Met Pro Gly Gln Ala Pro Val Leu Val Ile Tyr
        35                  40                  45

Arg Asp Ser Glu Arg Pro Ser Gly Ile Pro Glu Arg Phe Ser Gly Ser
    50                  55                  60

Ser Ser Gly Gly Thr Ala Thr Leu Thr Ile Ser Gly Ala Gln Ala Glu
65                  70                  75                  80

Asp Glu Ala Asp Tyr Tyr Cys
                85

<210> SEQ ID NO 273
<211> LENGTH: 87
<212> TYPE: PRT
<213> ORGANISM: Llama glama

<400> SEQUENCE: 273

Ser Ser Ala Leu Thr Gln Pro Ser Ala Val Ser Val Ser Leu Gly Gln
1               5                   10                  15

Thr Ala Arg Ile Thr Cys Arg Gly Asp Ser Leu Glu Arg Tyr Gly Ala
            20                  25                  30

Asn Trp Tyr Gln Gln Lys Pro Gly Gln Ala Arg Val Gln Val Ile Tyr
        35                  40                  45

Gly Asp Asp Ile Arg Pro Ser Gly Ile Pro Glu Arg Phe Ser Gly Ser
    50                  55                  60

Arg Leu Gly Gly Thr Ala Thr Leu Thr Ile Ser Gly Ala Gln Ala Glu
65                  70                  75                  80

Asp Glu Ala Asp Tyr Tyr Cys
                85

<210> SEQ ID NO 274
<211> LENGTH: 94
<212> TYPE: PRT
<213> ORGANISM: Llama pacos

<400> SEQUENCE: 274

Ser Ser Ala Leu Thr Gln Pro Ser Ala Val Ser Val Ser Leu Gly Gln
1               5                   10                  15

Thr Ala Arg Ile Thr Cys Arg Gly Asp Ser Leu Glu Arg Tyr Gly Ala
            20                  25                  30

Asn Trp Tyr Gln Gln Lys Pro Gly Gln Ala Arg Val Gln Val Ile Tyr
            35                  40                  45

Gly Asp Asp Ile Arg Pro Ser Gly Ile Pro Glu Arg Phe Ser Gly Ser
 50                  55                  60

Arg Leu Gly Gly Thr Ala Thr Leu Thr Ile Ser Gly Ala Gln Ala Glu
 65                  70                  75                  80

Asp Glu Ala Asp Tyr Tyr Cys Gln Ser Ser Asp Ser Gly
                 85                  90

<210> SEQ ID NO 275
<211> LENGTH: 87
<212> TYPE: PRT
<213> ORGANISM: Llama glama

<400> SEQUENCE: 275

Ser Ser Ala Leu Thr Gln Pro Ser Ala Val Ser Val Ser Leu Gly Gln
 1               5                  10                  15

Met Ala Arg Ile Thr Cys Gln Gly Asp Ser Leu Glu Ser Tyr Gly Ala
                 20                  25                  30

Asn Trp Tyr Gln Gln Lys Pro Gly Gln Ala Pro Val Leu Val Ile His
            35                  40                  45

Gly Asp Asp Ser Arg Pro Ser Gly Ile Pro Glu Arg Phe Ser Gly Ser
 50                  55                  60

Ser Ser Gly Gly Thr Ala Thr Leu Thr Ile Ser Gly Ala Gln Ala Glu
 65                  70                  75                  80

Asp Glu Ala Asp Tyr Tyr Cys
                 85

<210> SEQ ID NO 276
<211> LENGTH: 94
<212> TYPE: PRT
<213> ORGANISM: Llama pacos

<400> SEQUENCE: 276

Ser Ser Ala Leu Thr Gln Pro Ser Ala Val Ser Val Ser Leu Gly Gln
 1               5                  10                  15

Thr Ala Arg Ile Thr Cys Gln Gly Asp Ser Leu Glu Ser Tyr Gly Ala
                 20                  25                  30

Asn Trp Tyr Gln Gln Lys Pro Gly Gln Ala Pro Val Leu Val Ile Tyr
            35                  40                  45

Gly Asp Asp Ser Arg Pro Ser Gly Ile Pro Glu Arg Phe Ser Gly Ser
 50                  55                  60

Ser Ser Gly Gly Thr Ala Thr Leu Thr Ile Ser Gly Ala Gln Ala Glu
 65                  70                  75                  80

Asp Glu Gly Asp Tyr Tyr Cys Gln Ser Glu Asp Ser Ser Val
                 85                  90

<210> SEQ ID NO 277
<211> LENGTH: 87
<212> TYPE: PRT
<213> ORGANISM: Llama glama

<400> SEQUENCE: 277

Ser Ser Ala Leu Thr Gln Pro Ser Ala Val Ser Val Ser Leu Gly Gln
 1               5                  10                  15

Met Ala Arg Ile Thr Cys Gln Gly Asp Ser Leu Gly Ser Tyr Gly Ala
                 20                  25                  30

Asn Trp His Gln Gln Lys Pro Gly Gln Ala Pro Val Leu Leu Ile Tyr

```
                35                  40                  45

Gly Asp Asn Ser Arg Pro Ser Gly Ile Pro Glu Arg Phe Ser Gly Ser
         50                  55                  60

Lys Ser Gly Gly Thr Ala Thr Leu Thr Ile Ser Gly Ala Gln Ala Glu
 65                  70                  75                  80

Asp Glu Ala Asp Tyr Tyr Cys
                 85

<210> SEQ ID NO 278
<211> LENGTH: 93
<212> TYPE: PRT
<213> ORGANISM: Homo sapiens

<400> SEQUENCE: 278

Ser Tyr Glu Leu Met Gln Pro Pro Ser Val Ser Val Ser Pro Gly Gln
  1               5                  10                  15

Thr Ala Arg Ile Thr Cys Ser Gly Asp Ala Leu Pro Lys Gln Tyr Ala
                 20                  25                  30

Tyr Trp Tyr Gln Gln Lys Pro Gly Gln Ala Pro Val Leu Val Ile Tyr
             35                  40                  45

Lys Asp Ser Glu Arg Pro Ser Gly Ile Pro Glu Arg Phe Ser Gly Ser
         50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gln Ser Ala Asp Ser Ser
                 85                  90

<210> SEQ ID NO 279
<211> LENGTH: 93
<212> TYPE: PRT
<213> ORGANISM: Homo sapiens

<400> SEQUENCE: 279

Ser Ser Glu Leu Thr Gln Asp Pro Ala Val Ser Val Ala Leu Gly Gln
  1               5                  10                  15

Thr Val Arg Ile Thr Cys Gln Gly Asp Ser Leu Arg Ser Tyr Tyr Ala
                 20                  25                  30

Ser Trp Tyr Gln Gln Lys Pro Gly Gln Ala Pro Val Leu Val Ile Tyr
             35                  40                  45

Gly Lys Asn Asn Arg Pro Ser Gly Ile Pro Asp Arg Phe Ser Gly Ser
         50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser
                 85                  90

<210> SEQ ID NO 280
<211> LENGTH: 92
<212> TYPE: PRT
<213> ORGANISM: Homo sapiens

<400> SEQUENCE: 280

Ser Ser Gly Pro Thr Gln Val Pro Ala Val Ser Val Ala Leu Gly Gln
  1               5                  10                  15

Met Ala Arg Ile Thr Cys Gln Gly Asp Ser Met Glu Gly Ser Tyr Glu
                 20                  25                  30

His Trp Tyr Gln Gln Lys Pro Gly Gln Ala Pro Val Leu Val Ile Tyr
             35                  40                  45
```

```
Asp Ser Ser Asp Arg Pro Ser Arg Ile Pro Glu Arg Phe Ser Gly Ser
        50                  55                  60

Lys Ser Gly Asn Thr Thr Leu Thr Ile Thr Gly Ala Gln Ala Glu
 65                  70                  75                  80

Asp Glu Ala Asp Tyr Tyr Tyr Gln Leu Ile Asp Asn
                85                  90
```

<210> SEQ ID NO 281
<211> LENGTH: 92
<212> TYPE: PRT
<213> ORGANISM: Llama pacos

<400> SEQUENCE: 281

```
Ser Ser Ala Leu Thr Gln Pro Ser Ala Val Ser Val Ser Leu Gly Gln
 1               5                  10                  15

Thr Ala Arg Ile Thr Cys Gln Gly Gly Ser Ile Glu Ser Tyr Ala Ala
                20                  25                  30

His Trp Tyr Gln Gln Lys Pro Gly Gln Phe Pro Val Leu Val Ile Tyr
                35                  40                  45

Gly Asp Asp Arg Arg Pro Ser Gly Ile Pro Glu Arg Phe Ser Gly Ser
        50                  55                  60

Ser Ser Gly Gly Thr Ala Thr Leu Thr Ile Ser Gly Pro Arg Pro Arg
 65                  70                  75                  80

Thr Arg Pro Thr Ile Thr Val Thr Gln Gln Thr Ala
                85                  90
```

<210> SEQ ID NO 282
<211> LENGTH: 89
<212> TYPE: PRT
<213> ORGANISM: Llama pacos

<400> SEQUENCE: 282

```
Ser Tyr Glu Leu Thr Gln Ser Pro Val Ser Ala Asn Pro Arg Met Ala
 1               5                  10                  15

Lys Phe Thr Cys Gly Arg Asp Ser Ile Gly Asn Lys Tyr Ala Tyr Trp
                20                  25                  30

Tyr Gln Gln Lys Pro Gly Gln Ala Pro Val Leu Val Ile Tyr Arg Asp
                35                  40                  45

Ser Glu Arg Ser Leu Gly Ser Gln Thr Ser Ile His Ala Pro Thr Arg
        50                  55                  60

Gly Thr Trp Pro Pro Pro Ser Ala Gly Pro Arg Pro Arg Thr Arg Leu
 65                  70                  75                  80

Thr Ile Thr Val Ser His Asp Ser Ser
                85
```

<210> SEQ ID NO 283
<211> LENGTH: 90
<212> TYPE: PRT
<213> ORGANISM: Llama pacos

<400> SEQUENCE: 283

```
Ser Phe Glu Leu Thr Gln Ser Pro Val Ser Val Asn Pro Gly Met Ala
 1               5                  10                  15

Lys Leu Thr Cys Gly Arg Asn Ser Ile Gly Asn Lys Tyr Ala Tyr Trp
                20                  25                  30

Tyr Gln Gln Lys Pro Gly Gln Ala Pro Val Leu Val Ile Tyr Arg Asp
                35                  40                  45
```

-continued

Ser Glu Arg Ser Leu Gly Ser Gln Thr Ser Thr His Ala Pro Thr Arg
 50                  55                  60

Gly Thr Trp Pro Pro Ser Ala Gly Pro Arg Pro Arg Thr Ser Leu
 65              70                  75                  80

Thr Ile Thr Val Ser His Met Thr Ala Val
             85                  90

<210> SEQ ID NO 284
<211> LENGTH: 90
<212> TYPE: PRT
<213> ORGANISM: Llama pacos

<400> SEQUENCE: 284

Ser Tyr Gly Leu Thr Gln Ser Pro Ser Val Ser Val Asn Pro Gly Pro
1               5                   10                  15

Ala Lys Leu Thr Cys Gly Arg Asp Ser Ile Gly Asn Lys Tyr Ala Tyr
             20                  25                  30

Trp Tyr Gln Gln Lys Pro Gly Gln Ala Pro Val Leu Val Ile Tyr Arg
         35                  40                  45

Asp Ser Lys Arg Pro Leu Gly Ser Gln Thr Ser Thr His Ala Pro Thr
 50                  55                  60

Arg Gly Thr Arg Pro Pro Ser Ala Gly Pro Trp Pro Arg Thr Arg
 65                  70                  75                  80

Leu Thr Ile Thr Val Ser His Met Thr Ala
             85                  90

<210> SEQ ID NO 285
<211> LENGTH: 92
<212> TYPE: PRT
<213> ORGANISM: Camelus ferus

<400> SEQUENCE: 285

Ser Tyr Glu Leu Thr Ser Pro Ser Val Ser Val Asn Leu Gly Gln Met
1               5                   10                  15

Ala Lys Ile Thr Cys Gly Gly Asp Asn Ile Gly Ser Lys Ser Ala Pro
             20                  25                  30

Trp Cys Gln Gln Lys Pro Gly Gln Ala Pro Val Leu Val Ile Cys Gly
         35                  40                  45

Asp Asn Ser Arg Pro Ser Gly Ile Pro Glu Trp Phe Ser Gly Ser Asn
 50                  55                  60

Ser Lys Asn Thr Ala Thr Leu Thr Ile Ser Gly Ala Gln Ala Lys Asp
 65                  70                  75                  80

Lys Ala Asn Tyr Tyr Cys Gln Val Trp Asp Arg Ser
             85                  90

<210> SEQ ID NO 286
<211> LENGTH: 90
<212> TYPE: PRT
<213> ORGANISM: Camelus ferus

<400> SEQUENCE: 286

Lys Asn Leu Ser His Pro Arg Cys Gln Ile Arg Asp Arg Trp Thr Ala
1               5                   10                  15

Lys Ile Ile Cys Val Gly Asp Asn Ile Gly Ser Lys Ser Ala Tyr Trp
             20                  25                  30

Tyr Gln Lys Lys Thr Gly Gln Ala Thr Val Leu Val Ile Tyr Gly Asp
         35                  40                  45

Asn Asn Gln Ala Leu Gly Ile Pro Asp Phe Ser Gly Ser Asn Ser Gly

-continued

```
                50                  55                  60
Asn Thr Ala Thr Leu Thr Ile Ser Arg Ala Gln Ala Lys Gly Glu Ala
 65                  70                  75                  80

Asp His Tyr Cys Gln Val Trp Asp Ser Ser
                 85                  90

<210> SEQ ID NO 287
<211> LENGTH: 54
<212> TYPE: PRT
<213> ORGANISM: Llama pacos

<400> SEQUENCE: 287

Lys Pro Gly Gln Ala Pro Val Leu Val Met Tyr Asp Asp Asp Ser Gly
  1               5                  10                  15

His Ser Gly Ile Pro Glu Trp Phe Ser Gly Ser His Ser Gly Asn Thr
             20                  25                  30

Val Thr Leu Thr Ile Ser Gly Ala Gln Val Glu Asp Glu Ala Asp Tyr
         35                  40                  45

Tyr Cys Gln Ser Tyr Asp
     50

<210> SEQ ID NO 288
<211> LENGTH: 56
<212> TYPE: PRT
<213> ORGANISM: Llama pacos

<400> SEQUENCE: 288

Ser Pro Ala Gln Ala Pro Val Leu Val Ile Tyr Asp Asp Asn Ser Gly
  1               5                  10                  15

His Ser Gly Ile Pro Glu Trp Phe Ser Gly Ser His Ser Gly Asn Thr
             20                  25                  30

Val Thr Leu Asn Ile Ser Arg Ala Gln Val Glu Asp Glu Ala Gly Tyr
         35                  40                  45

Tyr Ser Gln Ser Tyr Asp Ser Asn
     50                  55

<210> SEQ ID NO 289
<211> LENGTH: 49
<212> TYPE: PRT
<213> ORGANISM: Llama pacos

<400> SEQUENCE: 289

Lys Pro Gly Gln Ala Pro Val Leu Val Ile Tyr Asp Asp Asn Thr Gly
  1               5                  10                  15

His Ser Gly Ile Pro Glu Trp Phe Ser Gly Ser His Ser Gly Asn Thr
             20                  25                  30

Val Thr Leu Asn Ile Ser Arg Ala Gln Val Glu Asp Glu Ala Asp Tyr
         35                  40                  45

Tyr

<210> SEQ ID NO 290
<211> LENGTH: 56
<212> TYPE: PRT
<213> ORGANISM: Camelus ferus

<400> SEQUENCE: 290

Lys Pro Gly Gln Ala Pro Val Leu Val Ile Tyr Asp Asp Asn Ser Gly
  1               5                  10                  15

His Ser Gly Ile Pro Glu Trp Phe Ser Gly Ser Asp Ser Gly Tyr Thr
```

```
                    20                  25                  30
Val Thr Leu Thr Ile Ser Arg Thr Gln Val Glu Asp Glu Ala Asp Tyr
            35                  40                  45
Tyr Cys Gln Ser Tyr Asp Ser Ser
        50                  55

<210> SEQ ID NO 291
<211> LENGTH: 92
<212> TYPE: PRT
<213> ORGANISM: Llama pacos

<400> SEQUENCE: 291

Ser Tyr Glu Leu Thr Gln Ser Pro Ser Val Ser Val Lys Leu Gly Gln
1               5                   10                  15

Thr Ala Lys Ile Thr Tyr Gly Arg Lys Glu Leu Glu Ile His Met Leu
            20                  25                  30

Thr Gly Thr Ser Arg Ser Arg Ala Arg Pro Leu Cys Trp Ser Ser Thr
        35                  40                  45

Glu Ile Ala Asn Gly Pro Gln Gly Ser Arg Ala Gly Ser Gln Ala Pro
    50                  55                  60

Thr Pro Gly Thr Arg Pro Pro Ser Ala Gly Pro Arg Pro Arg Thr
65                  70                  75                  80

Arg Pro Thr Thr Thr Val Lys Cys Gly Thr Ala Ala
                85                  90

<210> SEQ ID NO 292
<211> LENGTH: 67
<212> TYPE: PRT
<213> ORGANISM: Camelus ferus

<400> SEQUENCE: 292

Ser Ser Ala Leu Thr Gln Pro Ser Ala Val Ser Val Ser Leu Gly Gln
1               5                   10                  15

Met Ala Arg Ile Thr Cys Gln Gly Gly Ser Leu Gly Ser Ser Tyr Ala
            20                  25                  30

Tyr Trp Tyr Gln Gln Lys Thr Gly Ile Ser Lys Leu Asn Arg Thr Arg
        35                  40                  45

Leu Tyr Cys Ile Ala Gln Gly Asn Ile His Lys Met Phe Leu Thr Glu
    50                  55                  60

Lys Lys Ile
65

<210> SEQ ID NO 293
<211> LENGTH: 75
<212> TYPE: PRT
<213> ORGANISM: Llama pacos

<400> SEQUENCE: 293

Ser Asp Ser Val Thr Leu Gly Val Gly Glu Pro Gly Ile Glu Ser Gln
1               5                   10                  15

Asp His Leu Trp Gln Gly Gln His Trp Lys Ile Cys Leu Leu Val Pro
            20                  25                  30

Ala Gln Ala Arg Ser Gly Pro Cys Ser Gly His Leu Gln Arg Arg Thr
        35                  40                  45

Ala Leu Gly Ile Pro Asp Gln Tyr Ser Gly Ser Asn Ser Gly Asn Met
    50                  55                  60

Ala Thr Leu Thr Ile Ser Gly Ala Glu Ala Glu
65                  70                  75
```

<210> SEQ ID NO 294
<211> LENGTH: 35
<212> TYPE: PRT
<213> ORGANISM: Llama pacos

<400> SEQUENCE: 294

Ser Ser Ala Leu Thr Gln Pro Ser Met Val Ser Val Ser Leu Gly Gln
1               5                   10                  15

Thr Ala Arg Thr Thr Cys Gln Gly Gly Ser Leu Gly Ser Tyr Gly Ala
            20                  25                  30

Asn Trp Tyr
        35

<210> SEQ ID NO 295
<211> LENGTH: 98
<212> TYPE: PRT
<213> ORGANISM: Homo sapiens

<400> SEQUENCE: 295

Gln Pro Val Leu Thr Gln Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp His Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
        50                  55                  60

Arg Phe Ser Gly Ser Ser Ser Gly Ala Asp Arg Tyr Leu Thr Ile Ser
65                  70                  75                  80

Asn Leu Gln Ser Glu Asp Glu Ala Asp Tyr Tyr Cys Glu Thr Trp Asp
                85                  90                  95

Ser Asn

<210> SEQ ID NO 296
<211> LENGTH: 98
<212> TYPE: PRT
<213> ORGANISM: Camelus ferus

<400> SEQUENCE: 296

Gln Pro Val Leu Ser Gln Pro Ser Ala Ser Ala Ser Leu Gly Thr
1               5                   10                  15

Ser Ala Lys Leu Thr Cys Thr Leu Ser Ser Gly Tyr Ser Ser Tyr Ser
            20                  25                  30

Val Asp Trp Tyr Gln Gln Val Pro Gly Lys Ser Pro Arg Phe Leu Met
            35                  40                  45

Arg Val Gly Thr Ser Gly Val Gly Ser Lys Gly Asp Gly Ile Pro Asp
        50                  55                  60

Arg Phe Ser Val Leu Gly Ser Gly Leu Asn Arg Tyr Leu Thr Ile Lys
65                  70                  75                  80

Asn Ile Gln Glu Glu Asp Glu Ser Asp Tyr His Cys Gly Ala Asp His
                85                  90                  95

Gly Ser

<210> SEQ ID NO 297
<211> LENGTH: 98
<212> TYPE: PRT
<213> ORGANISM: Llama pacos

<400> SEQUENCE: 297

Gln Pro Val Leu Ser Gln Pro Pro Ser Ala Ser Ala Ser Leu Gly Ala
1               5                   10                  15

Ser Ala Lys Leu Thr Cys Thr Leu Ser Ser Gly Tyr Ser Ser Tyr Ser
            20                  25                  30

Val Asp Trp Tyr Gln Gln Val Pro Gly Lys Ser Pro Trp Phe Leu Met
        35                  40                  45

Arg Val Gly Ser Ser Gly Val Gly Ser Lys Gly Asp Gly Ile Pro Asp
    50                  55                  60

Arg Phe Ser Val Leu Gly Ser Gly Leu Asn Arg Tyr Leu Thr Ile Lys
65                  70                  75                  80

Asn Ile Gln Glu Glu Asp Glu Ser Asp Tyr His Cys Gly Ala Asp His
                85                  90                  95

Gly Ser

<210> SEQ ID NO 298
<211> LENGTH: 92
<212> TYPE: PRT
<213> ORGANISM: Llama glama

<400> SEQUENCE: 298

Gln Pro Val Leu Ser Gln Pro Pro Ser Ala Ser Ala Ser Leu Gly Ala
1               5                   10                  15

Ser Ala Lys Leu Thr Cys Thr Leu Ser Ser Gly Tyr Ser Ser Tyr Ser
            20                  25                  30

Val Asp Trp Tyr Gln Gln Val Pro Gly Lys Ser Pro Trp Phe Leu Met
        35                  40                  45

Arg Val Gly Ser Ser Gly Val Gly Ser Lys Gly Ser Gly Val Ser Asp
    50                  55                  60

Arg Phe Ser Gly Ser Ser Ser Gly Leu Glu Arg Tyr Leu Thr Ile Gln
65                  70                  75                  80

Asn Val Gln Glu Glu Asp Glu Ala Asp Tyr Tyr Cys
                85                  90

<210> SEQ ID NO 299
<211> LENGTH: 92
<212> TYPE: PRT
<213> ORGANISM: Llama glama

<400> SEQUENCE: 299

Gln Pro Val Leu Ser Gln Pro Pro Ser Ala Ser Ala Ser Leu Gly Ala
1               5                   10                  15

Ser Ala Lys Leu Thr Cys Thr Leu Ser Ser Gly Tyr Ser Ser Tyr Ser
            20                  25                  30

Val Asp Trp Tyr Gln Gln Val Pro Gly Lys Ser Pro Trp Phe Leu Met
        35                  40                  45

Arg Val Gly Ser Ser Gly Val Gly Ser Lys Gly Ser Gly Val Ser Asp
    50                  55                  60

Arg Phe Ser Gly Ser Ser Ser Gly Leu Glu Arg Tyr Leu Thr Ile Gln
65                  70                  75                  80

Asn Val Gln Glu Asp Glu Glu Ala Glu Tyr Val Cys
                85                  90

<210> SEQ ID NO 300
<211> LENGTH: 99
<212> TYPE: PRT

<213> ORGANISM: Camelus ferus

<400> SEQUENCE: 300

Ala Pro Val Leu Thr Gln Pro Pro Ser Ala Ser Ala Ser Leu Gly Thr
1               5                   10                  15

Ala Val Arg Leu Pro Cys Thr Leu Gly Ser Glu His Ser Thr His Tyr
            20                  25                  30

Ile Gln Trp Phe Arg Gln Arg Ser Gly Gln Thr Pro Ser Phe Leu Met
        35                  40                  45

Lys Val Thr Ser Asp Gly Thr Val Thr Lys Gly Asp Gly Leu Pro Gly
50                  55                  60

Arg Phe Ser Gly Ser Ser Gly Ala Asp Arg Tyr Leu Thr Val Ser
65                  70                  75                  80

Asn Ile Gln Ser Lys Asp Lys Ala Glu Tyr Tyr Cys Gly Val Asn Tyr
                85                  90                  95

Lys Ser Asp

<210> SEQ ID NO 301
<211> LENGTH: 99
<212> TYPE: PRT
<213> ORGANISM: Llama pacos
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid

<400> SEQUENCE: 301

Ala Pro Val Leu Thr Gln Pro Pro Ser Ala Ser Ala Ser Leu Gly Thr
1               5                   10                  15

Ala Val Lys Leu Pro Cys Thr Leu Ser Ser Glu His Ser Thr His Tyr
            20                  25                  30

Ile Gln Trp Phe Arg Gln Arg Ser Gly Gln Thr Pro Xaa Cys Leu Met
        35                  40                  45

Lys Val Thr Ser Asn Gly Thr Val Thr Lys Gly Asp Gly Leu Pro Gly
50                  55                  60

Arg Phe Ser Gly Ser Ser Gly Ala Asp Arg Tyr Leu Thr Val Ser
65                  70                  75                  80

Ser Ile Gln Ser Glu Asp Glu Ala Asp Xaa Tyr Cys Gly Val Asn Tyr
                85                  90                  95

Lys Ser Asp

<210> SEQ ID NO 302
<211> LENGTH: 91
<212> TYPE: PRT
<213> ORGANISM: Llama glama

<400> SEQUENCE: 302

Ala Pro Val Leu Thr Gln Pro Pro Ser Ala Ser Ala Ser Leu Gly Thr
1               5                   10                  15

Ala Val Lys Leu Pro Cys Thr Leu Ser Ser Glu His Ser Thr His Tyr
            20                  25                  30

Ile Gln Trp Phe Arg Gln Arg Ser Gly Gln Thr Pro Cys Leu Met Lys
        35                  40                  45

Gly Thr Ser Asn Gly Thr Val Thr Lys Gly Asp Gly Leu Pro Gly Arg
50                  55                  60

```
Phe Ser Gly Ser Ser Gly Ala Asp Arg Tyr Leu Thr Val Ser Ser
65                  70                  75                  80

Ile Gln Ser Glu Asp Glu Ala Asp Tyr Tyr Cys
                85                  90

<210> SEQ ID NO 303
<211> LENGTH: 91
<212> TYPE: PRT
<213> ORGANISM: Llama glama

<400> SEQUENCE: 303

Glu Pro Val Leu Thr Gln Pro Ser Gly Ser Ala Ser Leu Gly Met
1               5                   10                  15

Ala Val Lys Leu Pro Cys Thr Leu Ser Ser Glu His Ser Thr Tyr Tyr
                20                  25                  30

Leu Gln Trp Phe Arg Gln Arg Ser Gly Gln Thr Pro Cys Leu Met Glu
            35                  40                  45

Val Thr Ser Asn Gly Thr Val Thr Lys Gly Asp Gly Leu Pro Gly Arg
        50                  55                  60

Phe Ser Gly Ser Ser Gly Ala Asp Arg Tyr Leu Thr Val Ser Ser
65                  70                  75                  80

Ile Gln Ser Glu Asp Glu Ala Asp Tyr Tyr Cys
                85                  90

<210> SEQ ID NO 304
<211> LENGTH: 91
<212> TYPE: PRT
<213> ORGANISM: Llama glama

<400> SEQUENCE: 304

Glu Pro Val Leu Thr Gln Pro Ser Ser Gly Ser Ala Ser Leu Gly Met
1               5                   10                  15

Ala Val Lys Leu Pro Cys Thr Leu Ser Ser Glu His Ser Thr Tyr Tyr
                20                  25                  30

Leu Gln Trp Phe Arg Gln Arg Ser Gly Lys Thr Pro Cys Leu Met Lys
            35                  40                  45

Val Thr Ser Asp Gly Thr Val Thr Lys Gly Asp Gly Leu Pro Gly His
        50                  55                  60

Phe Ser Ala Ser Ser Arg Ala Gly Cys Tyr Leu Thr Val Ser Asn
65                  70                  75                  80

Ile Gln Ser Glu Asp Glu Ala Asp Tyr Tyr Cys
                85                  90

<210> SEQ ID NO 305
<211> LENGTH: 97
<212> TYPE: PRT
<213> ORGANISM: Llama pacos

<400> SEQUENCE: 305

Ala Pro Val Leu Thr Gln Pro Pro Ser Ala Ser Ser Ser Leu Gly Thr
1               5                   10                  15

Gly Val Lys Leu Arg Cys Thr Leu Ser Ser Glu His Ser Thr His Tyr
                20                  25                  30

Ile Gln Trp Phe Gln Gln Arg Ser Gly Gln Thr Pro Cys Leu Met Lys
            35                  40                  45

Val Thr Ser Asp Gly Thr Val Thr Lys Gly Asp Gly Leu Pro Ser Cys
        50                  55                  60
```

```
Phe Ser Gly Ser Ser Gly Ala Asp Arg Tyr Leu Thr Val Ser Asn
 65                  70                  75                  80

Ile Gln Ser Glu Asp Glu Ala Asp Tyr Cys Gly Val Asn Tyr Lys Thr
                 85                  90                  95

Asp
```

```
<210> SEQ ID NO 306
<211> LENGTH: 91
<212> TYPE: PRT
<213> ORGANISM: Llama glama

<400> SEQUENCE: 306

Ala Pro Val Leu Thr Gln Pro Pro Ser Ala Ser Ser Leu Gly Thr
 1               5                  10                  15

Gly Val Lys Leu Arg Cys Thr Leu Ser Ser Glu His Ser Thr His Tyr
                 20                  25                  30

Ile Gln Trp Phe Gln Gln Arg Ser Gly Gln Thr Pro Cys Leu Met Lys
                 35                  40                  45

Val Thr Ser Asp Gly Thr Val Thr Lys Gly Asp Gly Leu Pro Ser Cys
                 50                  55                  60

Phe Ser Gly Ser Ser Gly Ala Asp Arg Tyr Leu Thr Val Ser Asn
 65                  70                  75                  80

Ile Gln Ser Glu Asp Glu Ala Asp Tyr Tyr Cys
                 85                  90
```

```
<210> SEQ ID NO 307
<211> LENGTH: 98
<212> TYPE: PRT
<213> ORGANISM: Llama pacos

<400> SEQUENCE: 307

Ala Pro Val Leu Thr Gln Pro Pro Ser Ala Ser Ala Ser Leu Gly Thr
 1               5                  10                  15

Val Val Lys Leu Pro Cys Thr Leu Ser Ser Glu His Ser Thr His Tyr
                 20                  25                  30

Ile Gln Leu Phe Arg Gln Arg Ser Gly Gln Thr Ser Tyr Cys Leu Met
                 35                  40                  45

Lys Val Thr Ser Asp Gly Arg Val Thr Lys Gly Asn Gly Leu Pro Val
                 50                  55                  60

Thr Ser Gln Ala Pro Ala Pro Gly Leu Val Ala Thr Pro Ser Pro Thr
 65                  70                  75                  80

Ser Ser Pro Arg Thr Arg Leu Thr Asn Thr Val Glu Ser Thr Ile Lys
                 85                  90                  95

Val Met
```

```
<210> SEQ ID NO 308
<211> LENGTH: 96
<212> TYPE: PRT
<213> ORGANISM: Llama pacos

<400> SEQUENCE: 308

Val Pro Val Leu Thr Gln Pro Pro Ser Ala Ser Ala Ser Leu Gly Thr
 1               5                  10                  15

Ala Val Lys Leu Pro Cys Thr Leu Ser Ser Glu His Ser Thr His Tyr
                 20                  25                  30

Ile Gln Trp Phe Arg Gln Arg Ser Gly Gln Thr Pro Cys Leu Met Lys
                 35                  40                  45
```

Val Thr Asn Asn Gly Thr Val Asn Lys Gly Asp Gly Ser Pro Val Ala
    50                  55                  60

Ser Ala Pro Ala Pro Gly Leu Thr Ala Thr Pro Ser Pro Thr Ser Ser
65                  70                  75                  80

Pro Arg Met Arg Leu Thr Asn Thr Val Glu Ser Thr Ile Lys Val Met
                85                  90                  95

<210> SEQ ID NO 309
<211> LENGTH: 97
<212> TYPE: PRT
<213> ORGANISM: Llama pacos

<400> SEQUENCE: 309

Gln Thr Val Leu Thr Gln Pro Pro Ser Ala Ser Ala Thr Gln Arg Pro
1               5                   10                  15

Trp Ala Lys Val Thr Cys Thr Leu Ser Ser Gly Tyr Ser Val Tyr Ser
                20                  25                  30

Val Asp Trp Gln Gln Val Ser Gly Lys Gly Pro Arg Phe Leu Met Val
            35                  40                  45

Gly Thr Ser Gly Gly Asp Thr Lys Glu Asp Gly Leu Ser Asn Ser Phe
        50                  55                  60

Ser Gly Ser Gly Ser Gly Leu Glu Arg Tyr Leu Thr Ile Gln Asn Phe
65                  70                  75                  80

Gln Glu Asp Glu Glu Ala Glu Tyr Val Cys Gly Ala Asn His Gly Ser
                85                  90                  95

Gly

<210> SEQ ID NO 310
<211> LENGTH: 97
<212> TYPE: PRT
<213> ORGANISM: Llama pacos

<400> SEQUENCE: 310

Gln Thr Val Leu Thr Gln Pro Pro Ser Ala Ser Ala Thr Gln Arg Pro
1               5                   10                  15

Trp Ala Lys Val Thr Cys Thr Leu Ser Ser Gly Tyr Ser Val Tyr Ser
                20                  25                  30

Val Asp Trp Gln Gln Val Ser Gly Lys Gly Pro Arg Phe Leu Met Val
            35                  40                  45

Gly Thr Ser Gly Gly Asp Thr Lys Glu Asp Gly Leu Ser Asn Ser Phe
        50                  55                  60

Ser Gly Ser Gly Ser Gly Leu Glu Arg Tyr Leu Thr Ile Gln Asn Phe
65                  70                  75                  80

Gln Glu Asp Glu Glu Ala Glu Tyr Val Cys Gly Ala Asn His Gly Ser
                85                  90                  95

Gly

<210> SEQ ID NO 311
<211> LENGTH: 90
<212> TYPE: PRT
<213> ORGANISM: Llama glama

<400> SEQUENCE: 311

Gln Thr Val Leu Thr Gln Pro Pro Ser Ala Ser Ala Thr Gln Arg Pro
1               5                   10                  15

Trp Ala Lys Val Thr Cys Thr Leu Ser Ser Gly Tyr Ser Val Tyr Ser
                20                  25                  30

-continued

Val Asp Trp Gln Gln Val Ser Gly Lys Gly Pro Arg Phe Leu Met Val
         35                  40                  45

Gly Thr Ser Gly Gly Asp Thr Lys Glu Asp Gly Leu Ser Asn Ser Phe
 50                  55                  60

Ser Gly Ser Gly Ser Gly Leu Glu Arg Tyr Leu Thr Ile Gln Asn Phe
 65                  70                  75                  80

Gln Glu Asp Glu Glu Ala Glu Tyr Val Cys
                 85                  90

<210> SEQ ID NO 312
<211> LENGTH: 98
<212> TYPE: PRT
<213> ORGANISM: Camelus ferus

<400> SEQUENCE: 312

Ser Arg Pro Cys Ile Cys Leu Pro Gly Ser Leu Ser Gln Ala Glu Leu
 1               5                  10                  15

Tyr Pro Glu Gln Trp Leu Gln Trp Leu Ser Gly Tyr Ser Ser Tyr Ser
                 20                  25                  30

Val Asp Trp Tyr Gln Gln Val Pro Gly Lys Cys Pro Arg Phe Leu Met
         35                  40                  45

Arg Val Ser Ile Ser Gly Val Gly Ser Lys Val Asp Gly Val Ser Asp
 50                  55                  60

His Phe Ser Gly Ser Gly Ser Gly Leu Glu His Tyr Leu Thr Ile Gln
 65                  70                  75                  80

Asn Phe Arg Glu Glu Asp Glu Ala Glu Tyr Ile Ile His Gly Ala Asp
                 85                  90                  95

His Gly

<210> SEQ ID NO 313
<211> LENGTH: 97
<212> TYPE: PRT
<213> ORGANISM: Camelus ferus

<400> SEQUENCE: 313

Gln Pro Glu Leu Thr Gln Pro Pro Ser Ala Ser Ala Thr Leu Ala Ser
 1               5                  10                  15

Ala Lys Leu Thr Cys Thr Leu Ser Ser Gly Tyr Ser Gly Tyr Ser Val
                 20                  25                  30

Asp Trp Tyr Gln Gln Val Pro Gly Asn Gly Pro Gln Phe Leu Met Arg
         35                  40                  45

Val Gly Thr Ser Gly Asp Glu Ser Lys Trp Val Gly Ser Leu Ile Val
 50                  55                  60

Ser Gln Ala Gln Val Leu Val Trp Thr Asp Thr Pro Ser Arg Thr Ser
 65                  70                  75                  80

Arg Arg Lys Thr Arg Leu Asn Thr Ser Val Gly Gln Thr Met Ala Val
                 85                  90                  95

Gly

<210> SEQ ID NO 314
<211> LENGTH: 97
<212> TYPE: PRT
<213> ORGANISM: Camelus ferus

<400> SEQUENCE: 314

Gln Pro Glu Leu Thr Gln Pro Pro Ser Ala Ser Ala Thr Leu Ala Ser
 1               5                  10                  15

Ala Lys Leu Thr Cys Thr Leu Ser Ser Gly Tyr Ser Gly Tyr Ser Val
            20                  25                  30

Asp Trp Tyr Gln Gln Val Pro Gly Asn Gly Pro Gln Phe Leu Met Arg
        35                  40                  45

Val Gly Thr Ser Gly Asp Glu Ser Lys Trp Val Gly Ser Leu Ile Val
    50                  55                  60

Ser Gln Ala Gln Val Leu Val Trp Thr Asp Thr Pro Ser Arg Thr Ser
65                  70                  75                  80

Arg Arg Lys Thr Arg Leu Asn Thr Ser Val Gly Gln Thr Met Ala Val
                85                  90                  95

Gly

<210> SEQ ID NO 315
<211> LENGTH: 99
<212> TYPE: PRT
<213> ORGANISM: Camelus ferus
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid

<400> SEQUENCE: 315

Gln Pro Val Leu Arg Gln Pro Ser Ala Ser Thr Ser Leu Gly Ala
1               5                   10                  15

Leu Ala Lys Leu Thr Cys Thr Leu Ser Ser Asp Tyr Ser Tyr Ser
            20                  25                  30

Val Asp Trp Tyr Gln Gln Val Pro Gly Lys Gly Pro Trp Phe Leu Ser
        35                  40                  45

Gln Xaa Val Pro Val Val Leu Ala Pro Arg Gln Val Arg Ser Leu Ile
    50                  55                  60

Pro Ser Gln Ala Arg Ala Leu Ala Trp Ser Thr Leu Xaa Pro Ser Arg
65                  70                  75                  80

Thr Ser Gly Arg Arg Ser Arg Leu Thr Thr Ser Val Gly Gln Thr Met
                85                  90                  95

Ala Ala Thr

<210> SEQ ID NO 316
<211> LENGTH: 103
<212> TYPE: PRT
<213> ORGANISM: Homo sapiens

<400> SEQUENCE: 316

Gln Pro Val Leu Thr Gln Pro Thr Ser Leu Ser Ala Ser Pro Gly Ala
1               5                   10                  15

Ser Ala Arg Phe Thr Cys Thr Leu Arg Ser Gly Ile Asn Val Gly Thr
            20                  25                  30

Tyr Arg Ile Tyr Trp Tyr Gln Gln Lys Pro Gly Ser Leu Pro Arg Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Thr Asn Ala Gly Leu
65                  70                  75                  80

Leu Leu Ile Ser Gly Leu Gln Ser Glu Asp Glu Ala Asp Tyr Tyr Cys
                85                  90                  95

```
Ala Ile Trp Tyr Ser Ser Thr
            100

<210> SEQ ID NO 317
<211> LENGTH: 103
<212> TYPE: PRT
<213> ORGANISM: Camelus ferus

<400> SEQUENCE: 317

Gln Pro Val Leu Thr Gln Pro Pro Ser Leu Ser Ala Ser Leu Gly Ala
1               5                   10                  15

Ser Ala Arg Leu Asn Cys Thr Leu Ser Ser Gly Thr Val Val Gly Gly
            20                  25                  30

Tyr His Ile Asn Trp Phe Gln Lys Lys Ala Gly Ser Pro Pro Arg Tyr
        35                  40                  45

Leu Leu Arg Phe Tyr Ser Asp Ser Asn Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Gly Thr Tyr His Gly Asn Thr
            100

<210> SEQ ID NO 318
<211> LENGTH: 103
<212> TYPE: PRT
<213> ORGANISM: Camelus ferus

<400> SEQUENCE: 318

Gln Pro Val Leu Thr Gln Pro Pro Ser Leu Ser Ala Ser Leu Gly Ala
1               5                   10                  15

Ser Ala Arg Leu Asn Cys Thr Leu Ser Ser Gly Thr Val Val Gly Gly
            20                  25                  30

Tyr His Ile Asn Trp Phe Gln Lys Lys Ala Gly Ser Pro Pro Arg Tyr
        35                  40                  45

Leu Leu Arg Phe Tyr Ser Asp Ser Asn Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Gly Thr Tyr His Gly Asn Thr
            100

<210> SEQ ID NO 319
<211> LENGTH: 103
<212> TYPE: PRT
<213> ORGANISM: Llama pacos

<400> SEQUENCE: 319

Gln Pro Val Leu Thr Gln Pro Pro Ser Leu Ser Ala Ser Pro Gly Ala
1               5                   10                  15

Ser Ala Arg Leu Thr Cys Ser Leu Ser Ser Gly Thr Ile Val Gly Gly
            20                  25                  30

Tyr His Ile Asn Trp Tyr Gln Gln Lys Ala Gly Ser Pro Pro Arg Tyr
        35                  40                  45

Leu Leu Arg Phe Tyr Ser Asp Ser Asn Lys His Gln Gly Ser Gly Val
```

```
                    50                  55                  60
Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                    85                  90                  95

Gly Thr Tyr His Ser Asn Thr
                100

<210> SEQ ID NO 320
<211> LENGTH: 103
<212> TYPE: PRT
<213> ORGANISM: Llama pacos

<400> SEQUENCE: 320

Gln Pro Val Leu Thr Gln Pro Pro Ser Leu Ser Ala Ser Pro Gly Ala
 1               5                  10                  15

Ser Ala Arg Leu Thr Cys Ser Leu Ser Ser Gly Thr Ile Val Gly Gly
                20                  25                  30

Tyr His Ile Asn Trp Tyr Gln Gln Lys Ala Gly Ser Pro Arg Tyr
                35                  40                  45

Leu Leu Arg Phe Tyr Ser Asp Ser Asn Lys His Gln Gly Ser Gly Val
                50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                    85                  90                  95

Gly Thr Tyr His Ser Asn Thr
                100

<210> SEQ ID NO 321
<211> LENGTH: 96
<212> TYPE: PRT
<213> ORGANISM: Llama glama

<400> SEQUENCE: 321

Gln Pro Val Leu Thr Gln Leu Pro Ser Leu Ser Ala Ser Pro Gly Ala
 1               5                  10                  15

Ser Ala Arg Leu Thr Cys Ser Leu Ser Ser Gly Thr Ile Val Gly Gly
                20                  25                  30

Tyr His Ile Asn Trp Tyr Gln Gln Lys Ala Gly Ser Pro Arg Tyr
                35                  40                  45

Leu Leu Arg Phe Tyr Ser Asp Ser Asn Lys His Gln Gly Ser Gly Val
                50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                    85                  90                  95

<210> SEQ ID NO 322
<211> LENGTH: 104
<212> TYPE: PRT
<213> ORGANISM: Homo sapiens

<400> SEQUENCE: 322

Gln Pro Val Leu Thr Gln Pro Ser Ser His Ser Ala Ser Ser Gly Ala
 1               5                  10                  15

Ser Val Arg Leu Thr Cys Met Leu Ser Ser Gly Phe Ser Val Gly Asp
                20                  25                  30
```

Phe Trp Ile Arg Trp Tyr Gln Gln Lys Pro Gly Asn Pro Pro Arg Tyr
            35                  40                  45

Leu Leu Tyr Tyr His Ser Asp Ser Asn Lys Gly Gln Gly Ser Gly Val
 50                  55                  60

Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys
                100

<210> SEQ ID NO 323
<211> LENGTH: 104
<212> TYPE: PRT
<213> ORGANISM: Camelus ferus

<400> SEQUENCE: 323

Gln Pro Val Leu Thr Gln Pro Ser Ser Leu Ser Val Ser Leu Gly Ala
 1               5                  10                  15

Ser Ala Arg Leu Thr Cys Thr Leu Ser Ser Gly Phe Lys Val Gly Asp
                 20                  25                  30

Phe Trp Ile Arg Trp His Gln Gln Lys Pro Gly Asn Pro Pro Arg Tyr
            35                  40                  45

Leu Leu Thr Phe His Ser Asp Ser Asp Lys His Gln Gly Ser Gly Val
 50                  55                  60

Pro Ser Arg Phe Ser Gly Ser Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95

Ala Thr Tyr His Gly Asn Ser Lys
                100

<210> SEQ ID NO 324
<211> LENGTH: 104
<212> TYPE: PRT
<213> ORGANISM: Llama pacos

<400> SEQUENCE: 324

Gln Pro Val Leu Thr Gln Leu Ser Ser Leu Ser Ala Ser Leu Gly Ala
 1               5                  10                  15

Ser Ala Arg Leu Thr Cys Thr Leu Ser Ser Gly Phe Lys Val Gly Asp
                 20                  25                  30

Phe Trp Ile Arg Trp Tyr Gln Gln Lys Pro Gly Asn Pro Pro Arg Tyr
            35                  40                  45

Leu Leu Thr Phe His Ser Asp Ser Asp Lys His Gln Gly Ser Gly Val
 50                  55                  60

Pro Ser Arg Phe Ser Gly Ser Asp Ala Ser Ala Asn Ala Gly Leu
 65                  70                  75                  80

Leu Leu Ile Ser Gly Leu Gln His Glu Asp Glu Ala Asp Tyr Tyr Cys
                 85                  90                  95

Ala Thr Tyr His Gly Asn Ser Lys
                100

<210> SEQ ID NO 325
<211> LENGTH: 104
<212> TYPE: PRT
<213> ORGANISM: Llama pacos

<400> SEQUENCE: 325

Gln Pro Val Leu Thr Gln Leu Ser Ser Leu Ser Ala Ser Leu Gly Ala
1               5                   10                  15

Ser Ala Arg Leu Thr Cys Thr Leu Ser Ser Gly Phe Lys Val Gly Asp
                20                  25                  30

Phe Trp Ile Arg Trp Tyr Gln Gln Lys Pro Gly Asn Pro Pro Arg Tyr
            35                  40                  45

Leu Leu Thr Phe His Ser Asp Ser Asp Lys His Gln Gly Ser Gly Val
        50                  55                  60

Pro Ser Arg Phe Ser Gly Ser Ser Asp Ala Ser Ala Asn Ala Gly Leu
65                  70                  75                  80

Leu Leu Ile Ser Gly Leu Gln His Glu Asp Glu Ala Asp Tyr Tyr Cys
                85                  90                  95

Ala Thr Tyr His Gly Asn Ser Lys
            100

<210> SEQ ID NO 326
<211> LENGTH: 96
<212> TYPE: PRT
<213> ORGANISM: Llama glama

<400> SEQUENCE: 326

Gln Pro Val Leu Thr Gln Leu Ser Ser Leu Ser Ala Ser Leu Gly Ala
1               5                   10                  15

Ser Ala Arg Leu Thr Cys Thr Leu Ser Ser Gly Phe Lys Val Gly Asp
                20                  25                  30

Phe Trp Ile Arg Trp Tyr Gln Gln Lys Pro Gly Asn Pro Pro Arg Tyr
            35                  40                  45

Leu Leu Thr Phe His Ser Asp Ser Asp Lys His Gln Gly Ser Gly Val
        50                  55                  60

Pro Ser Arg Phe Ser Gly Ser Ser Asp Ala Ser Ala Asn Ala Gly Leu
65                  70                  75                  80

Leu Leu Ile Ser Gly Leu Gln His Glu Asp Glu Ala Asp Tyr Tyr Cys
                85                  90                  95

<210> SEQ ID NO 327
<211> LENGTH: 104
<212> TYPE: PRT
<213> ORGANISM: Homo sapiens

<400> SEQUENCE: 327

Gln Pro Val Leu Thr Gln Pro Pro Ser Ser Ala Ser Pro Gly Glu
1               5                   10                  15

Ser Ala Arg Leu Thr Cys Thr Leu Pro Ser Asp Ile Asn Val Gly Ser
                20                  25                  30

Tyr Asn Ile Tyr Trp Tyr Gln Gln Lys Pro Gly Ser Pro Pro Arg Tyr
            35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala Ser
            100

<210> SEQ ID NO 328
<211> LENGTH: 104
<212> TYPE: PRT
<213> ORGANISM: Camelus ferus

<400> SEQUENCE: 328

Gln Thr Val Gly Thr Gln Pro Ala Ser Phe Ser Ala Ser Leu Gly Ala
1               5                   10                  15

Ser Ala Arg Leu Thr Cys Thr Leu Ser Ser Gly Asn Ser Val Gly Ser
            20                  25                  30

Tyr Asp Ile Ser Ser Tyr Gln Gln Lys Ala Gly Ser Pro Pro Arg Tyr
        35                  40                  45

Leu Leu Tyr Tyr Tyr Ser Asp Ser Tyr Lys His Gln Gly Ser Gly Val
    50                  55                  60

Leu Ser Arg Phe Ser Gly Ser Arg Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

Ala Ala Trp Asp Gly Ser Ser Glu
            100

<210> SEQ ID NO 329
<211> LENGTH: 104
<212> TYPE: PRT
<213> ORGANISM: Llama pacos

<400> SEQUENCE: 329

Gln Pro Val Gly Thr Gln Leu Pro Ser Phe Ser Ala Pro Leu Gly Ala
1               5                   10                  15

Ser Ala Arg Leu Thr Cys Thr Leu Ser Ser Gly Asn Ser Val Gly Ser
            20                  25                  30

Tyr Asp Ile Ser Trp Tyr Gln His Lys Ala Gly Ser Pro Pro Arg Tyr
        35                  40                  45

Leu Leu Tyr Tyr Tyr Thr Asp Ser Asp Lys Gln Gln Gly Ser Gly Val
    50                  55                  60

Pro Ser Arg Phe Ser Gly Ser Lys Asp Ala Ser Ala Asn Ser Gly Leu
65                  70                  75                  80

Leu Leu Ile Ser Gly Leu Gln Pro Asp Glu Ala Asp Tyr Tyr Cys
                85                  90                  95

Val Ala Trp Asp Ser Ser Ser Glu
            100

<210> SEQ ID NO 330
<211> LENGTH: 104
<212> TYPE: PRT
<213> ORGANISM: Llama pacos

<400> SEQUENCE: 330

Gln Pro Val Gly Thr Gln Leu Pro Ser Phe Ser Ala Pro Leu Gly Ala
1               5                   10                  15

Ser Ala Arg Leu Thr Cys Thr Leu Ser Ser Gly Asn Ser Val Gly Ser
            20                  25                  30

Tyr Asp Ile Ser Trp Tyr Gln His Lys Ala Gly Ser Pro Pro Arg Tyr
        35                  40                  45

Leu Leu Tyr Tyr Tyr Thr Asp Ser Asp Lys Gln Gln Gly Ser Gly Val
    50                  55                  60

Pro Ser Arg Phe Ser Gly Ser Lys Asp Ala Ser Ala Asn Ser Gly Leu

-continued

Leu Leu Ile Ser Gly Leu Gln Pro Asp Asp Glu Ala Asp Tyr Tyr Cys
             85                  90                  95

Val Ala Trp Asp Ser Ser Ser Glu
            100

<210> SEQ ID NO 331
<211> LENGTH: 96
<212> TYPE: PRT
<213> ORGANISM: Llama glama

<400> SEQUENCE: 331

Gln Pro Val Gly Thr Gln Leu Pro Ser Phe Ser Ala Pro Leu Gly Ala
1               5                   10                  15

Ser Ala Arg Leu Thr Cys Thr Leu Ser Ser Gly Asn Ser Val Gly Ser
            20                  25                  30

Tyr Asp Ile Ser Trp Tyr Gln His Lys Ala Gly Ser Pro Pro Arg Tyr
        35                  40                  45

Leu Leu Tyr Tyr Tyr Thr Asp Ser Asp Lys Gln Gln Gly Ser Gly Val
    50                  55                  60

Pro Ser Arg Phe Ser Gly Ser Lys Asp Ala Ser Ala Asn Ser Gly Leu
65                  70                  75                  80

Leu Leu Ile Ser Val Leu Gln Pro Glu Asp Glu Ala Asp Tyr Tyr Cys
                85                  90                  95

<210> SEQ ID NO 332
<211> LENGTH: 104
<212> TYPE: PRT
<213> ORGANISM: Homo sapiens

<400> SEQUENCE: 332

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Ser
            100

<210> SEQ ID NO 333
<211> LENGTH: 104
<212> TYPE: PRT
<213> ORGANISM: Camelus ferus

<400> SEQUENCE: 333

Gln Pro Val Leu Thr Gln Pro Pro Phe Leu Ala Glu Ser Pro Ser Ala
1               5                   10                  15

Ser Thr Arg Leu Thr Cys Thr Leu Ser Asn Gly Asn Ser Ala Gly Ser
            20                  25                  30

Cys Ile Ile Ser Cys Tyr Gln Gln Lys Ala Gly Ser Pro Pro Arg Tyr
        35                  40                  45

```
Leu Leu Ser Tyr Tyr Ser Asp Pro Ile Lys Arg Gln Gly Ser Gly Val
        50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Asp Cys
                85                  90                  95

Ser Ala Val Ser Ser Ser Gly Asn
            100
```

<210> SEQ ID NO 334
<211> LENGTH: 104
<212> TYPE: PRT
<213> ORGANISM: Llama pacos

<400> SEQUENCE: 334

```
Gln Pro Val Leu Thr Gln Leu Pro Phe Leu Ala Glu Ser Pro Gly Ala
 1               5                  10                  15

Ser Thr Arg Leu Thr Cys Thr Leu Ser Asn Gly Asn Ser Ala Gly Ser
                20                  25                  30

Cys Ile Ile Ser Trp Tyr Gln His Lys Ala Gly Ser Pro Pro Arg Tyr
                35                  40                  45

Leu Leu Ser Tyr Tyr Ser Gly Ala Ile Lys Arg Gln Gly Ser Gly Val
        50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                85                  90                  95

Ser Ala Val Ser Ser Ser Ser Asn
            100
```

<210> SEQ ID NO 335
<211> LENGTH: 104
<212> TYPE: PRT
<213> ORGANISM: Llama pacos

<400> SEQUENCE: 335

```
Gln Leu Val Val Thr Gln Pro Pro Phe Leu Ala Glu Ser Pro Gly Ala
 1               5                  10                  15

Ser Thr Arg Leu Thr Cys Thr Leu Ser Asn Gly Asn Ser Ala Gly Ser
                20                  25                  30

Cys Ile Ile Ser Trp Tyr Gln His Lys Ala Gly Ser Pro Pro Arg Tyr
                35                  40                  45

Leu Leu Ser Tyr Tyr Ser Gly Pro Ile Lys Arg Gln Gly Ser Gly Val
        50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                85                  90                  95

Ser Ala Val Ser Ser Ser Ser Asn
            100
```

<210> SEQ ID NO 336
<211> LENGTH: 99
<212> TYPE: PRT
<213> ORGANISM: Camelus ferus

<400> SEQUENCE: 336

Gln Leu Val Glu Thr Gln Leu Pro Phe Val Ser Glu Phe Pro Gly Ala
1               5                   10                  15

Ser Ser Ile Leu Thr Cys Thr Leu Thr Ser Gly Lys Ser Val Gly Ser
            20                  25                  30

His Tyr Ile Ser Asn Gln Gln Lys Ala Gly Ser Pro Pro Gln Tyr Leu
            35                  40                  45

Leu Tyr Tyr Tyr Ser Asp Ser Ser Lys His Gln Gly Ser Gly Val Gln
    50                  55                  60

Ser His Phe Ser Gly Ser Arg Asp Ala Ser Ala Asn Ala Gly Leu Leu
65                  70                  75                  80

Leu Ile Ser Gly Leu Gln Pro Glu Asp Glu Ala Ile Thr Ala Leu His
                85                  90                  95

Ile Arg Ala

<210> SEQ ID NO 337
<211> LENGTH: 100
<212> TYPE: PRT
<213> ORGANISM: Llama pacos

<400> SEQUENCE: 337

Gln Leu Val Glu Thr Gln Leu Ser Phe Val Ser Glu Phe Pro Gly Ala
1               5                   10                  15

Ser Ser Ile Leu Thr Cys Thr Leu Thr Ser Gly Asn Ser Val Gly Ser
            20                  25                  30

His Tyr Ile Ser Trp Asn Gln Gln Lys Ala Gly Ser Pro Pro Arg Tyr
            35                  40                  45

Leu Leu Tyr Tyr Tyr Ser Asp Ser Ser Lys His Gln Gly Ser Gly Val
    50                  55                  60

Gln Ser Cys Phe Ser Gly Ser Lys Asp Ala Ser Ala Asn Ala Gly Leu
65                  70                  75                  80

Leu Leu Ile Ser Gly Leu Gln Pro Glu Asp Glu Ala Ile Thr Ala Leu
                85                  90                  95

His Ile Arg Ala
            100

<210> SEQ ID NO 338
<211> LENGTH: 96
<212> TYPE: PRT
<213> ORGANISM: Llama glama

<400> SEQUENCE: 338

Gln Leu Val Glu Thr Gln Leu Ser Phe Val Ser Glu Phe Pro Gly Ala
1               5                   10                  15

Ser Ser Ile Leu Thr Cys Thr Leu Thr Ser Gly Asn Ser Val Gly Ser
            20                  25                  30

His Tyr Ile Ser Trp Asn Gln Gln Lys Ala Gly Ser Pro Pro Arg Tyr
            35                  40                  45

Leu Leu Tyr Tyr Tyr Ser Asp Ser Ser Lys His Gln Gly Ser Gly Val
    50                  55                  60

Gln Ser Cys Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

<210> SEQ ID NO 339
<211> LENGTH: 96
<212> TYPE: PRT

<213> ORGANISM: Llama pacos

<400> SEQUENCE: 339

Gln Pro Val Leu Thr Gln Pro Ser Leu Ser Gly Ser Leu Gly Ala
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Lys Ala Gly Ser Pro Pro Arg Tyr
        35                  40                  45

Leu Leu Asp Tyr Tyr Ser Asp Ser Ser Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

<210> SEQ ID NO 340
<211> LENGTH: 96
<212> TYPE: PRT
<213> ORGANISM: Llama glama

<400> SEQUENCE: 340

Gln His Val Val Thr Gln Pro Ser Leu Ala Ser Leu Gly Ser
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Lys Ala Gly Ser Pro Pro Arg Tyr
        35                  40                  45

Leu Leu Tyr Tyr Tyr Ser Asp Ser Ser Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

<210> SEQ ID NO 341
<211> LENGTH: 96
<212> TYPE: PRT
<213> ORGANISM: Llama glama

<400> SEQUENCE: 341

Gln Pro Val Leu Thr Gln Pro Ser Leu Ser Gly Ser Leu Gly Ala
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Lys Ala Gly Ser Pro Pro Arg Tyr
        35                  40                  45

Leu Leu Asp Tyr Tyr Ser Asp Ser Ser Lys His Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Glu Asp Glu Ala Asp Tyr Tyr Cys
                85                  90                  95

<210> SEQ ID NO 342
<211> LENGTH: 103
<212> TYPE: PRT
<213> ORGANISM: Camelus ferus

<400> SEQUENCE: 342

Gln His Val Leu Thr Gln Leu Pro Ser Leu Ser Glu Ser Pro Glu Ala
1               5                   10                  15

Ser Ala Arg Leu Thr Cys Thr Leu Ser Ser Gly Asn Ser Val Gly Ser
            20                  25                  30

Ser Ala Ile Ser Trp Tyr Arg Gln Lys Ala Gly Ser Pro Pro Trp Tyr
        35                  40                  45

Leu Leu Tyr Tyr His Arg Asp Ser Ser Lys His Gln Gly Ser Gly Val
    50                  55                  60

Pro Ser Arg Phe Ser Gly Ser Lys Asp Ala Leu Thr Asn Ala Gly Leu
65                  70                  75                  80

Leu Leu Ile Ser Gly Leu Gln Pro Glu Asp Glu Ala His Tyr Tyr Cys
                85                  90                  95

Val Ala Trp Asp Gly Asn Asn
            100

<210> SEQ ID NO 343
<211> LENGTH: 103
<212> TYPE: PRT
<213> ORGANISM: Camelus ferus

<400> SEQUENCE: 343

Gln Leu Val Leu Thr Gln Pro Pro Ser Leu Ser Glu Thr Pro Gly Ala
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Thr Ala Gly Ser Pro Pro Arg Tyr
        35                  40                  45

Leu Leu Tyr Tyr Tyr Ser Asp Ser Asp Lys Gln Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Lys Asp Glu Ala Asp Tyr Tyr Cys
                85                  90                  95

Ala Ala Val Asp Ser Ser Ser
            100

<210> SEQ ID NO 344
<211> LENGTH: 103
<212> TYPE: PRT
<213> ORGANISM: Camelus ferus

<400> SEQUENCE: 344

Gln Leu Val Leu Thr Gln Pro Pro Ser Leu Ser Glu Thr Pro Gly Ala
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Thr Ala Gly Ser Pro Pro Arg Tyr
        35                  40                  45

Leu Leu Tyr Tyr Tyr Ser Asp Ser Asp Lys Gln Gln Gly Ser Gly Val
    50                  55                  60

Pro Ser Arg Phe Ser Gly Ser Lys Asp Ala Ser Ala Asn Ala Gly Leu
65                  70                  75                  80

Leu Leu Ile Ser Gly Leu Gln Pro Lys Asp Glu Ala Asp Tyr Tyr Cys
                85                  90                  95

Ala Ala Val Asp Ser Ser Ser
            100

<210> SEQ ID NO 345
<211> LENGTH: 103
<212> TYPE: PRT
<213> ORGANISM: Camelus ferus

<400> SEQUENCE: 345

Gln Pro Val Leu Thr Gln Pro Pro Ser Leu Ser Gly Ser Leu Gly Ser
1               5                   10                  15

Ser Ala Arg Leu Thr Cys Thr Leu Ser Ser Gly Asn Asn Val Gly Gly
            20                  25                  30

Tyr Thr Val Tyr Trp Tyr Gln Gln Asn Ala Gly Ser Pro Pro Arg Tyr
        35                  40                  45

Leu Val Tyr Tyr Tyr Ser Asp Ser Ser Lys His Gln Gly Ser Gly Val
    50                  55                  60

Pro Ser Cys Phe Ser Gly Ser Lys Asp Ala Ser Ala Asn Thr Gly Leu
65                  70                  75                  80

Leu Leu Ile Ser Gly Leu Gln Pro Glu Asp Glu Ala Asp Tyr Tyr Cys
                85                  90                  95

Gly Thr Leu His Gly Asn Gly
            100

<210> SEQ ID NO 346
<211> LENGTH: 102
<212> TYPE: PRT
<213> ORGANISM: Camelus ferus

<400> SEQUENCE: 346

Gln Pro Val Leu Thr Pro Pro Ser Leu Ser Ala Ser Leu Gly Ala Ser
1               5                   10                  15

Val Arg Leu Thr Cys Thr Leu Ser Ser Gly Asn Ser Val Gly Ser Tyr
            20                  25                  30

Asp Leu Ser Trp Tyr Gln Gly Lys Ala Gly Ser Pro Pro Arg Tyr Leu
        35                  40                  45

Leu Tyr Tyr Tyr Ser Asp Ser Lys His Gln Gly Ser Arg Val Pro
    50                  55                  60

Ser Cys Phe Ser Gly Ser Lys Asp Ala Leu Ala Asn Ser Gly Leu Leu
65                  70                  75                  80

His Ile Ser Arg Leu Gln Pro Glu Asp Glu Ala Asp Cys Tyr Cys Phe
                85                  90                  95

Ala Tyr Lys Asn His Ser
            100

<210> SEQ ID NO 347
<211> LENGTH: 103
<212> TYPE: PRT
<213> ORGANISM: Llama pacos

<400> SEQUENCE: 347

Gln Pro Val Val Thr Gln Pro Pro Ser Leu Ser Ala Ser Pro Gly Ser
1               5                   10                  15

Ser Val Arg Leu Thr Cys Thr Leu Ser Ser Gly Asn Ser Val Gly Ser
            20                  25                  30

Tyr Asp Ile Ser Trp Tyr Gln Gln Lys Ala Gly Ser Pro Pro Arg Tyr
        35                  40                  45

Leu Leu Tyr Tyr Tyr Ser Asp Ser Ser Lys His Gln Gly Ser Gly Val

```
                    50                  55                  60
Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95

Ser Ala Tyr Lys Ser Gly Tyr
            100
```

<210> SEQ ID NO 348
<211> LENGTH: 96
<212> TYPE: PRT
<213> ORGANISM: Llama glama

<400> SEQUENCE: 348

```
Gln Leu Val Val Thr Gln Pro Pro Ser Leu Ser Ala Ser Pro Gly Ser
 1               5                  10                  15

Ser Val Arg Leu Thr Cys Thr Leu Ser Ser Gly Asn Ser Val Gly Ser
                20                  25                  30

Tyr Asp Ile Ser Trp Tyr Gln Gln Lys Ala Gly Ser Pro Pro Arg Tyr
            35                  40                  45

Leu Leu Tyr Tyr Tyr Ser Asp Ser Ser Lys His Gln Gly Ser Gly Val
        50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95
```

<210> SEQ ID NO 349
<211> LENGTH: 96
<212> TYPE: PRT
<213> ORGANISM: Llama glama

<400> SEQUENCE: 349

```
Gln Leu Val Leu Thr Gln Pro Pro Ser Leu Ser Ala Ser Pro Gly Ser
 1               5                  10                  15

Ser Val Arg Leu Thr Cys Thr Leu Ser Ser Gly Asn Ser Val Gly Ser
                20                  25                  30

Tyr Tyr Ile Ser Trp Tyr Gln Gln Lys Ala Gly Ser Pro Pro Arg Tyr
            35                  40                  45

Leu Leu Tyr Tyr Tyr Ser Asp Ser Asp Lys His Gln Gly Ser Gly Val
        50                  55                  60

Pro Ser Arg Phe Ser Gly Ser Asn Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95
```

<210> SEQ ID NO 350
<211> LENGTH: 96
<212> TYPE: PRT
<213> ORGANISM: Llama glama

<400> SEQUENCE: 350

```
Gln Leu Val Val Thr Gln Ala Pro Ser Leu Ser Ala Ser Pro Gly Ser
 1               5                  10                  15

Ser Val Arg Leu Thr Cys Thr Leu Ser Ser Gly Asn Ser Val Gly Ser
                20                  25                  30

Tyr Tyr Ile Ser Trp Tyr Gln Gln Lys Ala Gly Ser Pro Pro Arg Tyr
            35                  40                  45
```

```
Leu Leu Tyr Tyr Tyr Ser Asp Ser Asp Lys Gln Gln Gly Ser Gly Val
            50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                85                  90                  95

<210> SEQ ID NO 351
<211> LENGTH: 96
<212> TYPE: PRT
<213> ORGANISM: Llama glama

<400> SEQUENCE: 351

Gln Leu Val Leu Thr Gln Pro Pro Ser Leu Ser Ala Ser Pro Gly Ser
 1               5                  10                  15

Ser Val Arg Leu Thr Cys Thr Leu Ser Ser Gly Asn Ser Val Gly Ser
                20                  25                  30

Tyr Tyr Ile Ser Trp Tyr Gln Gln Lys Ala Gly Ser Pro Pro Gln Tyr
                35                  40                  45

Leu Leu Ser Tyr Tyr Ser Asp Ser Tyr Lys His Gln Gly Ser Gly Val
            50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                85                  90                  95

<210> SEQ ID NO 352
<211> LENGTH: 96
<212> TYPE: PRT
<213> ORGANISM: Llama pacos

<400> SEQUENCE: 352

Gln Leu Val Leu Thr Gln Pro Pro Ser Leu Ser Ala Ser Leu Gly Ser
 1               5                  10                  15

Ser Val Arg Leu Thr Cys Thr Leu Ser Ser Gly Asn Ser Val Gly Ser
                20                  25                  30

Tyr Tyr Ile Ser Trp Tyr Gln Gln Lys Ala Gly Ser Pro Pro Gln Tyr
                35                  40                  45

Leu Leu Ser Tyr Tyr Ser Asp Ser Tyr Lys His Gln Gly Ser Gly Val
            50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                85                  90                  95

<210> SEQ ID NO 353
<211> LENGTH: 103
<212> TYPE: PRT
<213> ORGANISM: Llama pacos

<400> SEQUENCE: 353

Gln His Val Val Thr Gln Pro Pro Ser Leu Ser Ala Ser Leu Gly Ser
 1               5                  10                  15

Ser Ala Arg Leu Thr Cys Thr Leu Ser Ser Gly Asn Ser Val Gly Ser
                20                  25                  30

Tyr Tyr Ile Ser Trp Tyr Gln Gln Lys Ala Gly Ser Pro Pro Arg Tyr
                35                  40                  45
```

```
Leu Leu Tyr Tyr Tyr Ser Asp Ser Tyr Lys Gln Gln Gly Ser Gly Val
 50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95

Val Ala Tyr Lys Ser Lys Tyr
                100

<210> SEQ ID NO 354
<211> LENGTH: 96
<212> TYPE: PRT
<213> ORGANISM: Llama pacos

<400> SEQUENCE: 354

Gln His Val Val Thr Gln Pro Pro Ser Leu Ser Ala Ser Leu Gly Ser
 1               5                  10                  15

Ser Ala Arg Leu Thr Cys Thr Leu Ser Ser Gly Asn Ser Val Gly Ser
                 20                  25                  30

Tyr Tyr Ile Ser Trp Tyr Gln Gln Lys Ala Gly Ser Pro Pro Arg Tyr
                 35                  40                  45

Leu Leu Tyr Tyr Tyr Ser Asp Ser Tyr Lys Gln Gln Gly Ser Gly Val
 50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95

<210> SEQ ID NO 355
<211> LENGTH: 96
<212> TYPE: PRT
<213> ORGANISM: Llama glama

<400> SEQUENCE: 355

Gln His Val Val Thr Gln Pro Pro Ser Leu Ser Ala Ser Leu Gly Ser
 1               5                  10                  15

Ser Ala Arg Leu Thr Cys Thr Leu Ser Ser Gly Asn Ser Val Gly Ser
                 20                  25                  30

Tyr Tyr Ile Ser Trp Tyr Gln Gln Lys Ala Gly Ser Pro Pro Arg Tyr
                 35                  40                  45

Leu Leu Tyr Tyr Tyr Ser Asp Ser Tyr Lys Gln Gln Gly Ser Gly Val
 50                  55                  60

Pro Ser Arg Phe Ser Gly Ser Lys Asp Ala Ser Ala Asn Ala Gly Leu
 65                  70                  75                  80

Leu Leu Ile Ser Gly Leu Gln Pro Glu Asp Glu Ala Asp Tyr Tyr Cys
                 85                  90                  95

<210> SEQ ID NO 356
<211> LENGTH: 96
<212> TYPE: PRT
<213> ORGANISM: Llama glama

<400> SEQUENCE: 356

Gln Leu Val Leu Thr Gln Pro Pro Ser Leu Ser Ala Ser Pro Gly Ser
 1               5                  10                  15

Ser Val Arg Leu Thr Cys Thr Leu Ser Ser Gly Asn Ser Val Gly Ser
                 20                  25                  30

Tyr Tyr Ile Ser Trp Tyr Gln Gln Lys Ala Gly Ser Pro Pro Arg Tyr
```

```
                35                  40                  45
Leu Leu Tyr Tyr Tyr Ser Asp Ser Tyr Lys Gln Gln Gly Ser Gly Val
        50                  55                  60
Pro Ser Arg Phe Ser Gly Ser Lys Asp Ala Ser Ala Asn Ala Gly Leu
65                  70                  75                  80
Leu Leu Ile Ser Gly Leu Gln Pro Glu Asp Glu Ala Asp Tyr Tyr Cys
                85                  90                  95
```

<210> SEQ ID NO 357
<211> LENGTH: 95
<212> TYPE: PRT
<213> ORGANISM: Llama glama

<400> SEQUENCE: 357

```
Gln Leu Val Leu Thr Gln Leu Pro Ser Leu Phe Thr Ser Pro Gly Ser
1               5                   10                  15
Ser Val Arg Leu Thr Cys Thr Leu Ser Ser Gly Asn Ser Val Gly Ser
                20                  25                  30
Tyr Tyr Ile Ser Trp Tyr Gln Gln Lys Ala Gly Ser Pro Pro Trp Tyr
                35                  40                  45
Leu Leu Tyr Tyr Ser Asp Ser Tyr Lys Gln Gln Gly Ser Gly Val Pro
        50                  55                  60
Ser Arg Phe Ser Gly Ser Lys Asp Ala Ser Ala Asn Ala Gly Leu Leu
65                  70                  75                  80
Leu Ile Ser Gly Leu Gln Pro Glu Asp Glu Ala Asp Tyr Tyr Cys
                85                  90                  95
```

<210> SEQ ID NO 358
<211> LENGTH: 103
<212> TYPE: PRT
<213> ORGANISM: Camelus ferus

<400> SEQUENCE: 358

```
Gln Leu Val Leu Thr Gln Pro Pro Ser Leu Ser Glu Ser Pro Gly Ala
1               5                   10                  15
Ser Ala Arg Leu Thr Cys Thr Leu Ser Ser Gly Asn Ser Val Gly Ser
                20                  25                  30
Tyr Tyr Ile Ser Trp Tyr Gln Gln Lys Ala Gly Ser Pro Pro Arg Tyr
                35                  40                  45
Leu Leu Tyr Tyr Tyr Ser Asp Ser Asp Lys Gln Gln Gly Ser Gly Val
        50                  55                  60
Leu Ser Arg Phe Ser Gly Ser Lys Asp Ala Ser Ala Asn Ala Gly Leu
65                  70                  75                  80
Leu Leu Ile Ser Gly Leu Gln Pro Lys Gly Gly Thr Arg Glu Leu Ala
                85                  90                  95
Val Gly Thr Val Leu Ala Ala
                100
```

<210> SEQ ID NO 359
<211> LENGTH: 94
<212> TYPE: PRT
<213> ORGANISM: Llama glama

<400> SEQUENCE: 359

```
Gln Leu Val Leu Thr Gln Pro Pro Ser Leu Ser Ala Ser Pro Gly Ser
1               5                   10                  15
Ser Val Arg Leu Thr Cys Thr Leu Ser Ser Gly Asn Ser Val Gly Ser
                20                  25                  30
```

Tyr Tyr Ile Ser Trp Tyr Gln Gln Lys Ala Gly Ser Pro Arg Tyr
            35                  40                  45

Leu Leu Tyr Tyr Tyr Ser Asp Ser Ser Lys His Gln Gly Ser Gly Val
 50                  55                  60

Pro Ser Arg Phe Ser Gly Ser Asn Asp Ala Ser Asn Ala Gly Leu
 65                  70                  75                  80

Leu Leu Ile Ser Gly Leu Cys Arg Gly Arg Gly Leu Leu Leu
                85                  90

<210> SEQ ID NO 360
<211> LENGTH: 102
<212> TYPE: PRT
<213> ORGANISM: Homo sapiens

<400> SEQUENCE: 360

Gln Pro Val Leu Thr Gln Pro Thr Ser Leu Ser Ala Ser Pro Gly Ala
 1               5                  10                  15

Ser Ala Arg Phe Thr Cys Thr Leu Arg Ser Gly Ile Asn Val Gly Thr
                20                  25                  30

Tyr Arg Ile Tyr Trp Tyr Gln Gln Asn Pro Gly Ser Leu Pro Arg Tyr
            35                  40                  45

Leu Leu Arg Tyr Lys Ser Asp Ser Asp Lys Gln Gln Gly Ser Gly Val
 50                  55                  60

Pro Ser Arg Phe Ser Gly Ser Lys Asp Ala Ser Thr Asn Ala Gly Leu
 65                  70                  75                  80

Leu Leu Ile Ser Gly Leu Gln Ser Glu Asp Glu Ala Asp Tyr Tyr Cys
                85                  90                  95

Ala Ile Trp Tyr Ser Ser
            100

<210> SEQ ID NO 361
<211> LENGTH: 102
<212> TYPE: PRT
<213> ORGANISM: Homo sapiens

<400> SEQUENCE: 361

Gln Pro Val Leu Thr Gln Pro Thr Ser Leu Ser Ala Ser Pro Gly Ala
 1               5                  10                  15

Ser Ala Arg Leu Thr Cys Thr Leu Arg Ser Gly Ile Asn Leu Gly Ser
                20                  25                  30

Tyr Arg Ile Phe Trp Tyr Gln Gln Lys Pro Glu Ser Pro Pro Arg Tyr
            35                  40                  45

Leu Leu Ser Tyr Tyr Ser Asp Ser Ser Lys His Gln Gly Ser Gly Val
 50                  55                  60

Pro Ser Arg Phe Ser Gly Ser Lys Asp Ala Ser Ser Asn Ala Gly Ile
 65                  70                  75                  80

Leu Val Ile Ser Gly Leu Gln Ser Glu Asp Glu Ala Asp Tyr Tyr Cys
                85                  90                  95

Met Ile Trp His Ser Ser
            100

<210> SEQ ID NO 362
<211> LENGTH: 68
<212> TYPE: PRT
<213> ORGANISM: Llama pacos

<400> SEQUENCE: 362

Ile Ser Trp Tyr Gln Gln Lys Ala Gly Ser Pro Pro Arg Tyr Leu Leu
1               5                   10                  15

Asp Tyr Tyr Ser Asp Ser Ser Lys His Gln Gly Ser Gly Val Pro Ser
            20                  25                  30

Arg Phe Ser Gly Ser Lys Asp Ala Ser Ala Asn Ala Gly Leu Leu Leu
        35                  40                  45

Ile Ser Gly Leu Gln Pro Glu Asp Glu Ala Tyr Tyr Cys Ala Ala
50                  55                  60

Gly Asp Ser Ser
65

<210> SEQ ID NO 363
<211> LENGTH: 93
<212> TYPE: PRT
<213> ORGANISM: Llama pacos

<400> SEQUENCE: 363

Val Cys Arg Val Pro Leu Pro Ala Ser Ala Asp Ser Ala Ala Leu Gln
1               5                   10                  15

Gln Leu Asp Ser Pro Ala Pro Ala Val Gly Thr Val Gly Ser Tyr Arg
            20                  25                  30

Ile Ser Trp Tyr Gln Gln Lys Ala Gly Ser Pro Pro Gln Tyr Leu Leu
        35                  40                  45

Asp Tyr Tyr Ser Gly Ser Asp Lys Gln Gln Gly Ser Ser Val Pro Thr
50                  55                  60

Gly Phe Ser Gly Ser Lys Asp Pro Ser Ala Asn Ala Gly Leu Pro Leu
65                  70                  75                  80

Ile Ser Gly Leu Gln Pro Glu Asp Glu Ala Val Tyr His
                85                  90

<210> SEQ ID NO 364
<211> LENGTH: 100
<212> TYPE: PRT
<213> ORGANISM: Camelus ferus

<400> SEQUENCE: 364

Pro Ser Phe Cys Leu Ser Arg Pro Pro Ser Leu Ser Leu Arg Glu Gln
1               5                   10                  15

Gln Leu Asp Ser Pro Ala Pro Ala Val Gly Thr Val Asp Ser Leu Arg
            20                  25                  30

Ile Ser Trp Phe Gln Gln Lys Ala Gly Ser Pro Pro Gln Tyr Leu Leu
        35                  40                  45

Asn Tyr Tyr Ser Gly Ser Asn Lys His His Gly Ser Gly Val Pro Ile
50                  55                  60

Gly Phe Ser Gly Ser Lys Asp Ala Ser Ala Asn Val Gly Leu Pro Leu
65                  70                  75                  80

Ile Ser Gly Leu Gln Pro Glu Asp Glu Ala Asp Tyr Tyr Cys Ala Ala
                85                  90                  95

Trp Asp Gly Ser
            100

<210> SEQ ID NO 365
<211> LENGTH: 99
<212> TYPE: PRT
<213> ORGANISM: Camelus ferus

<400> SEQUENCE: 365

Ser Leu Cys Leu Ser Cys Pro Pro Ser Leu Ser Leu Leu Lys His Gln

```
1               5                   10                  15
Pro Glu Ala Ala Ala Pro Ser Met Gly Thr Val Leu Ala Ala Thr Thr
            20                  25                  30

Ser Trp Tyr Gln Gln Lys Ala Gly Ser Pro Pro Gln Tyr Leu Leu Asn
        35                  40                  45

Tyr Tyr Ser Asp Ser Ser Lys Gln Gln Gly Phe Gly Val Pro Ser Cys
        50                  55                  60

Phe Ser Gly Ser Val Asp Pro Leu Ala Asn Ala Gly Leu Gln Leu Ile
65                  70                  75                  80

Ser Gly Leu Gln Pro Glu Asp Glu Ala Asp Tyr Tyr Cys Ala Glu Tyr
                85                  90                  95

His Gly Asn

<210> SEQ ID NO 366
<211> LENGTH: 99
<212> TYPE: PRT
<213> ORGANISM: Llama pacos

<400> SEQUENCE: 366

Gln Leu Val Leu Thr Gln Pro Pro Ser Leu Ser Ala Ser Leu Gly Ala
1               5                   10                  15

Ser Thr Arg Leu Thr Cys Thr Leu Ser Ser Gly Ile Ser Val Gly Ser
            20                  25                  30

Tyr Tyr Ile Ser Trp Asn Gln Lys Ala Gly Ser Pro Gln Tyr
        35                  40                  45

Leu Leu Tyr Asp Tyr Thr Asp Ser Ser Lys Gln Gln Asp Ser Trp Val
        50                  55                  60

Pro Ser Arg Phe Ser Gly Ser Ser Ala Asn Ala Gly Leu Leu Leu Ile
65                  70                  75                  80

Ser Gly Leu Gln Pro Glu Asp Glu Ser Glu Tyr Tyr Cys Ser Ala Tyr
                85                  90                  95

Ile Ser Gly

<210> SEQ ID NO 367
<211> LENGTH: 102
<212> TYPE: PRT
<213> ORGANISM: Camelus ferus

<400> SEQUENCE: 367

Gln Pro Val Leu Thr Gln Pro Pro Ser Leu Ser Ala Ser Leu Gly Ala
1               5                   10                  15

Ser Ala Arg Leu Thr Cys Thr Leu Ser Ser Gly Asn Ser Val Gly Ser
            20                  25                  30

Tyr Ala Ile Ser Trp Tyr Gln Gln Thr Ala Gly Ser Pro Pro Arg Tyr
        35                  40                  45

Leu Leu Asp Tyr Tyr Ser His Ser Ser Lys His Gly Thr Ser Cys Thr
        50                  55                  60

Thr Thr Gln Thr Leu Ile Ser Ser Arg Ala Pro Gly Ser Arg Ala Ala
65                  70                  75                  80

Ser Leu Gly Pro Lys Met Pro Arg Pro Met Gln Gly Phe Cys Ser Ser
                85                  90                  95

Leu Gly Cys Ser Pro Arg
            100

<210> SEQ ID NO 368
<211> LENGTH: 91
```

<212> TYPE: PRT
<213> ORGANISM: Camelus ferus

<400> SEQUENCE: 368

Gln Leu Val Leu Thr Gln Pro Pro Ser Leu Ser Ala Ser Leu Gly Ala
1               5                   10                  15

Ser Ala Arg Leu Thr Cys Thr Leu Ser Ser Gly Ile Ser Val Gly Ser
            20                  25                  30

Tyr Tyr Ile Ser Trp Asn Gln Gln Lys Ala Gly Ser Pro Pro Trp Tyr
        35                  40                  45

Leu Leu Tyr Tyr Tyr Ser Pro Val Asn Thr Arg Val Pro Gly Ser Arg
    50                  55                  60

Ala Ala Ser Leu Gly Pro Arg Met Pro Gln Pro Met Gln Gly Cys Asn
65                  70                  75                  80

Pro Arg Thr Ser Leu Ser Ile Thr Ala Leu His
                85                  90

<210> SEQ ID NO 369
<211> LENGTH: 91
<212> TYPE: PRT
<213> ORGANISM: Llama glama

<400> SEQUENCE: 369

Gln Leu Val Leu Thr Gln Pro Pro Ser Leu Ser Glu Cys Pro Glu Glu
1               5                   10                  15

Ser Ala Arg Leu Thr Cys Thr Leu Ser Ser Gly Asn Ser Val Gly Ser
            20                  25                  30

Tyr Tyr Lys Leu Val Pro Gly Glu Ala Phe Pro Ser Thr Ser Thr Thr
        35                  40                  45

Thr Gln Ile Pro Val Arg Ser Arg Ala Pro Gly Ser Arg Ala Ala Ser
    50                  55                  60

Leu Gly Pro Ile Pro Arg Pro Val His Gly Phe Gly Ser Ser Leu Gly
65                  70                  75                  80

Tyr Arg Leu Arg Thr Arg Leu Thr Ile Thr Val
                85                  90

<210> SEQ ID NO 370
<211> LENGTH: 91
<212> TYPE: PRT
<213> ORGANISM: Llama pacos

<400> SEQUENCE: 370

Gln Leu Val Val Thr Gln Pro Pro Ser Leu Ser Glu Cys Leu Glu Glu
1               5                   10                  15

Ser Ala Arg Leu Thr Cys Thr Leu Ser Ser Gly Asn Ser Asp Gly Ser
            20                  25                  30

Tyr Tyr Lys Leu Val Pro Gly Glu Ala Phe Pro Ser Thr Ser Trp Thr
        35                  40                  45

Thr Thr Gln Ile Pro Val Ser Arg Ala Pro Gly Ser Arg Ala Ala
    50                  55                  60

Ser Leu Gly Pro Ile Pro Arg Pro Val His Ser Phe Gly Ser Ser Leu
65                  70                  75                  80

Gly Cys Arg Leu Arg Thr Arg Leu Thr Ile Thr
                85                  90

<210> SEQ ID NO 371
<211> LENGTH: 94
<212> TYPE: PRT

<213> ORGANISM: Llama glama

<400> SEQUENCE: 371

Gln Pro Val Leu Thr Gln Pro Ser Leu Ser Gly Ser Leu Gly Ser
1               5                   10                  15

Pro Asp Ser Pro Ala Pro Ala Val Gly Thr Met Leu Glu Ala Thr Gln
            20                  25                  30

Tyr Thr Gly Thr Ser Arg Arg Gln Gly Ala Leu Pro Gly Thr Ser Cys
        35                  40                  45

Thr Thr Thr Gln Thr Pro Val Asn Ile Arg Ala Pro Gly Phe Gln Ala
    50                  55                  60

Ala Ser Leu Gly Pro Lys Met Pro Gln Pro Met Gln Gly Phe Cys Ser
65                  70                  75                  80

Ser Leu Gly Cys Ser Pro Arg Thr Arg Leu Thr Ile Thr Val
                85                  90

<210> SEQ ID NO 372
<211> LENGTH: 94
<212> TYPE: PRT
<213> ORGANISM: Llama glama

<400> SEQUENCE: 372

Gln Leu Val Leu Thr Gln Ser Pro Ser Leu Ser Gly Ser Leu Gly Ser
1               5                   10                  15

Pro Asp Ser Pro Ala Pro Ala Val Gly Thr Met Leu Glu Ala Thr Gln
            20                  25                  30

Tyr Thr Gly Thr Ser Arg Arg Gln Gly Ala Leu Pro Gly Thr Ser Cys
        35                  40                  45

Thr Thr Thr Gln Thr Pro Val Asn Ile Arg Ala Pro Gly Phe Gln Ala
    50                  55                  60

Ala Ser Leu Gly Pro Lys Met Pro Gln Pro Met Gly Gly Phe Cys Ser
65                  70                  75                  80

Ser Leu Gly Cys Ser Pro Arg Met Arg Leu Thr Ile Thr Val
                85                  90

<210> SEQ ID NO 373
<211> LENGTH: 94
<212> TYPE: PRT
<213> ORGANISM: Llama glama

<400> SEQUENCE: 373

Gln Pro Val Leu Thr Gln Pro Ser Leu Ser Gly Ser Leu Gly Ser
1               5                   10                  15

Pro Asp Ser Pro Ala Pro Ala Val Gly Thr Met Leu Glu Ala Thr Gln
            20                  25                  30

Tyr Thr Gly Thr Ser Arg Arg Gln Gly Ala Leu Pro Gly Thr Ser Cys
        35                  40                  45

Thr Thr Thr Gln Thr Pro Val Asn Ile Arg Ala Pro Gly Phe Gln Ala
    50                  55                  60

Ala Ser Leu Gly Pro Lys Met Pro Gln Pro Met Gly Gly Phe Cys Ser
65                  70                  75                  80

Ser Leu Gly Cys Ser Pro Arg Met Arg Leu Thr Ile Thr Val
                85                  90

<210> SEQ ID NO 374
<211> LENGTH: 100
<212> TYPE: PRT
<213> ORGANISM: Llama pacos

<400> SEQUENCE: 374

Gln Pro Val Leu Thr Gln Pro Pro Ser Leu Ser Gly Ser Leu Gly Ser
1               5                   10                  15

Pro Asp Ser Pro Ala Pro Ala Val Gly Thr Met Leu Glu Ala Thr Gln
            20                  25                  30

Tyr Thr Gly Thr Ser Arg Arg Gln Gly Ala Leu Pro Gly Thr Ser Cys
        35                  40                  45

Thr Thr Thr Gln Thr Pro Val Asn Ile Arg Ala Pro Gly Phe Gln Ala
50                  55                  60

Ala Ser Leu Gly Pro Lys Met Pro Gln Pro Met Gln Gly Phe Cys Ser
65                  70                  75                  80

Ser Leu Gly Cys Ser Pro Arg Thr Arg Leu Thr Ile Thr Val Leu Cys
                85                  90                  95

Phe Ser Ala Thr
            100

<210> SEQ ID NO 375
<211> LENGTH: 90
<212> TYPE: PRT
<213> ORGANISM: Llama glama

<400> SEQUENCE: 375

Gln Leu Leu Leu Thr Gln Pro Pro Ser Ser Asn Ser Gln Thr His Leu
1               5                   10                  15

His Pro Glu Gln Trp Glu Gln Leu Ala Ala Thr Gly Tyr Pro Gly Thr
            20                  25                  30

Ser Arg Arg Gln Gly Ala Leu Pro Gly Thr Ser Trp Thr Thr Thr Gln
        35                  40                  45

Ala Pro Ile Ser Ser Arg Ala Pro Val Ser Arg Leu Ala Ser Leu Asp
    50                  55                  60

Pro Lys Ile Leu Arg Pro Met Gln Gly Phe His Ser Ser Leu Gly Cys
65                  70                  75                  80

Ser Pro Arg Thr Arg Leu Thr Ile Thr Val
                85                  90

<210> SEQ ID NO 376
<211> LENGTH: 89
<212> TYPE: PRT
<213> ORGANISM: Llama glama

<400> SEQUENCE: 376

Gln Leu Leu Leu Thr Gln Pro Pro Ser Ser Asn Ser Thr His Leu His
1               5                   10                  15

Pro Glu Gln Trp Glu Gln Leu Ala Ala Thr Gly Tyr Pro Gly Thr Ser
            20                  25                  30

Arg Arg Gln Gly Ala Leu Pro Gly Thr Ser Trp Thr Thr Thr Gln Ala
        35                  40                  45

Leu Ile Ser Ser Arg Ala Pro Val Ser Arg Leu Ala Ser Leu Asp Pro
    50                  55                  60

Lys Ile Pro Arg Pro Met Gln Gly Phe His Ser Ser Leu Gly Cys Ser
65                  70                  75                  80

Pro Arg Thr Arg Leu Thr Ile Thr Val
            85

<210> SEQ ID NO 377
<211> LENGTH: 89

<212> TYPE: PRT
<213> ORGANISM: Llama glama

<400> SEQUENCE: 377

Gln Leu Leu Leu Thr Gln Pro Ser Ser Asn Ser Thr His Leu His
1               5                   10                  15

Pro Glu Gln Trp Glu Gln Leu Ala Ala Thr Gly Tyr Pro Gly Thr Ser
            20                  25                  30

Arg Arg Gln Gly Ala Leu Pro Gly Ile Ser Cys Thr Thr Thr Gln Thr
        35                  40                  45

His Thr Ser Ser Arg Ala Pro Gly Ser Arg Ala Ala Ser Leu Asp Pro
    50                  55                  60

Lys Met Pro Gln Pro Met Gln Gly Phe Cys Ser Ser Leu Gly Cys Ser
65                  70                  75                  80

Leu Arg Thr Arg Leu Thr Ile Thr Val
                85

<210> SEQ ID NO 378
<211> LENGTH: 102
<212> TYPE: PRT
<213> ORGANISM: Camelus ferus

<400> SEQUENCE: 378

Ala Pro Ser Val Cys Val Cys Lys Val Pro Leu Pro Ala Cys Ala Asp
1               5                   10                  15

Ser Ala Ala Leu Pro Leu Ser Ile Thr Gly Ser Ile Ser Gln Thr His
            20                  25                  30

Leu His Pro Glu Gln Trp Asp Gln Cys Trp Gln Leu His Ile Leu
        35                  40                  45

Glu Pro Ala Glu Gly Arg Glu Pro Ser Leu Val Ser Pro Val Leu Leu
    50                  55                  60

Leu Ser Ser Lys His Gln Gly Ser Gly Val Gln Ser Cys Phe Ser Gly
65                  70                  75                  80

Ser Lys Asp Ala Ser Ala Asn Ala Gly Leu Gln Pro Glu Asp Glu Ser
                85                  90                  95

Glu Tyr Tyr Cys Ser Ala
            100

<210> SEQ ID NO 379
<211> LENGTH: 97
<212> TYPE: PRT
<213> ORGANISM: Llama pacos

<400> SEQUENCE: 379

Ala Pro Cys Val Cys Val Cys Arg Val Pro Leu Pro Ala Cys Gly Asp
1               5                   10                  15

Ser Ala Ala Leu Pro Leu Val Ser Arg Ile Ser Gln Thr His Leu His
            20                  25                  30

Thr Gln Trp Glu Gln Trp Gln Leu Leu Gln Val Gly Thr Arg Arg Ser
        35                  40                  45

Leu Pro Gln Tyr Leu Leu Asp Tyr Tyr Ser Asp Ser Ser Lys Gln Gln
    50                  55                  60

Gly Ser Gly Val Pro Ser Cys Phe Ser Gly Ser Val Asp Pro Ser Ala
65                  70                  75                  80

Ser Ala Gln Leu Arg Leu Ile Ser Gly Leu Gln Ala Glu Asp Glu Ala
                85                  90                  95

Asp

```
<210> SEQ ID NO 380
<211> LENGTH: 100
<212> TYPE: PRT
<213> ORGANISM: Camelus ferus

<400> SEQUENCE: 380

Ser Pro Ser Val Gly Thr Arg Gly Leu Ala Pro Trp Pro Gly Leu Leu
1               5                   10                  15

Ser Cys Ser Cys Phe Ser Leu Thr Ala Gln Val Gly Met Gly Leu Gly
                20                  25                  30

Asp His Ile Ser Val Pro Cys Leu Gln Gln Pro Trp Leu Arg Leu Trp
            35                  40                  45

Lys Cys Phe Leu Gln Val Pro Lys His Gln Asp Ser Gly Val Pro Ser
50                  55                  60

Arg Phe Ser Gly Ser Lys Asp Ala Ser Ala Asn Ala Gly Leu Leu Leu
65                  70                  75                  80

Ile Ser Gly Leu Gln Pro Glu Asp Glu Ala Asp Tyr Tyr Cys Ala Ala
                85                  90                  95

Val Asp Ser Ser
            100

<210> SEQ ID NO 381
<211> LENGTH: 100
<212> TYPE: PRT
<213> ORGANISM: Camelus ferus

<400> SEQUENCE: 381

Pro Ala Tyr Cys Asp Ala Ser Leu Pro Leu Val Ser Arg Ser Ile Ser
1               5                   10                  15

Gln Thr His Leu His Pro Glu Gln Arg Glu Gln Cys Trp Gln Leu Tyr
                20                  25                  30

Tyr Lys Leu Val Pro Gln Lys Ala Gly Ser Pro Pro Arg Tyr Leu Leu
            35                  40                  45

Asp Tyr Tyr Ser Asp Ser Ile Lys His Gln Asp Ser Gly Val Pro Ser
50                  55                  60

Arg Phe Ser Gly Ser Lys Asp Ala Ser Ala Asn Ala Gly Leu Leu Leu
65                  70                  75                  80

Ile Ser Gly Leu Gln Pro Glu Asp Glu Ala Asp Tyr Tyr Cys Ala Ala
                85                  90                  95

Val Asp Ser Ser
            100

<210> SEQ ID NO 382
<211> LENGTH: 55
<212> TYPE: PRT
<213> ORGANISM: Llama pacos

<400> SEQUENCE: 382

Ser Pro Ser Val Gly Thr Arg Gly Leu Ala Pro Trp Pro Gly Leu Leu
1               5                   10                  15

Ser Cys Ser Cys Ser Ser Leu Thr Ala Gln Val Gly Thr Gly Leu Arg
                20                  25                  30

Asp Trp Val Ser Val Pro His Leu Gln Gln Pro Leu Trp Leu Arg Leu
            35                  40                  45

Glu Cys Phe Leu Gln Ile Pro
50                  55
```

-continued

<210> SEQ ID NO 383
<211> LENGTH: 58
<212> TYPE: PRT
<213> ORGANISM: Llama pacos

<400> SEQUENCE: 383

Ala Trp Pro Pro Ala Thr Val Pro Ala Glu Ile Leu Leu Pro Leu Arg
1               5                   10                  15

Gln Glu Pro Gly Pro Gln Gly Pro Ser Ser Leu Leu Trp Ile Gln Arg
            20                  25                  30

His Gly Gln Glu His Gly Leu Phe Glu His Leu Ala Ser Ala Gly Gly
        35                  40                  45

Gly Cys Val Leu Leu Cys Cys Gly Gly Pro
    50                  55

<210> SEQ ID NO 384
<211> LENGTH: 97
<212> TYPE: PRT
<213> ORGANISM: Homo sapiens

<400> SEQUENCE: 384

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser

<210> SEQ ID NO 385
<211> LENGTH: 97
<212> TYPE: PRT
<213> ORGANISM: Camelus ferus

<400> SEQUENCE: 385

Gly Gln Arg Leu Cys Leu Ser Pro Ala Leu Cys Trp Gly Leu Leu Gly
1               5                   10                  15

Arg Arg Ser Pro Ser Pro Ala Pro Ala Ala Ala Thr Leu Gly Ile
            20                  25                  30

Val Pro Ser Tyr Gln Gln Arg Pro Gly Ser Ala Leu Thr Thr Val Ile
        35                  40                  45

Tyr Lys Asp Asp Glu Arg Pro Ser Glu Val Pro Ala Arg Phe Ser Gly
    50                  55                  60

Ser Ile Asp Thr Ser Ser Ser Ala Ala Ser Leu Thr Ile Ser Gly Leu
65                  70                  75                  80

Lys Pro Lys Asp Glu Ala Asp Tyr Cys Cys Gln Ser Asp Ser Tyr Asp Ser
                85                  90                  95

Ser

<210> SEQ ID NO 386
<211> LENGTH: 96

```
<212> TYPE: PRT
<213> ORGANISM: Llama glama

<400> SEQUENCE: 386

Gly Gln Arg Leu Cys Leu Ser Pro Ala Leu Cys Arg Gly Leu Leu Gly
1               5                   10                  15

Arg Arg Ser Pro Ser Pro Val Pro Ala Ala Thr Thr Leu Gly Ile
            20                  25                  30

Val His Cys Tyr Gln Gln Arg Pro Gly Ser Ala Pro Thr Thr Val Ile
        35                  40                  45

Tyr Lys Asp Asp Glu Arg Pro Ser Glu Val Pro Ala Arg Phe Pro Asp
    50                  55                  60

Ser Thr Asp Thr Ser Ser Ala Ala Ser Leu Thr Ile Ser Gly Leu
65                  70                  75                  80

Lys Pro Glu Asp Glu Ala Asp Tyr Cys Cys Gln Ser Gly Tyr Asp Ser
                85                  90                  95

<210> SEQ ID NO 387
<211> LENGTH: 97
<212> TYPE: PRT
<213> ORGANISM: Llama pacos

<400> SEQUENCE: 387

Gly Gln Arg Leu Cys Leu Ser Pro Ala Leu Cys Arg Gly Leu Leu Gly
1               5                   10                  15

Arg Arg Ser Pro Ser Pro Val Pro Ala Ala Thr Thr Leu Gly Ile
            20                  25                  30

Val His Cys Tyr Gln Gln Arg Pro Gly Ser Ala Pro Thr Thr Val Ile
        35                  40                  45

Tyr Lys Asp Asp Glu Arg Pro Ser Glu Val Pro Ala Arg Phe Pro Asp
    50                  55                  60

Ser Thr Asp Thr Ser Ser Ala Ala Ser Leu Thr Ile Ser Gly Leu
65                  70                  75                  80

Lys Pro Glu Asp Glu Ala Asp Tyr Cys Cys Gln Ser Gly Tyr Asp Ser
                85                  90                  95

Ser

<210> SEQ ID NO 388
<211> LENGTH: 98
<212> TYPE: PRT
<213> ORGANISM: Homo sapiens

<400> SEQUENCE: 388

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

His Tyr Pro Tyr Trp Phe Gln Gln Lys Pro Gly Gln Ala Pro Arg Thr
        35                  40                  45

Leu Ile Tyr Asp Thr Ser Asn Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Leu Leu Ser Tyr Ser Gly
                85                  90                  95

Ala Arg
```

<210> SEQ ID NO 389
<211> LENGTH: 98
<212> TYPE: PRT
<213> ORGANISM: Camelus ferus

<400> SEQUENCE: 389

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Tyr Gln Gln Lys Pro Gly Gln Ser Leu Arg Thr
        35                  40                  45

Leu Ile Tyr Ser Thr Asn Ser Arg His Ser Gly Val Pro Asn Arg Phe
    50                  55                  60

Ser Gly Ser Ile Ser Gly Lys Lys Ala Ala Leu Thr Ile Thr Gly Ala
65                  70                  75                  80

Gln Pro Glu Asp Glu Ala Asp Tyr Tyr Cys Ala Leu Asp Thr Gly Ser
                85                  90                  95

Gly Gly

<210> SEQ ID NO 390
<211> LENGTH: 90
<212> TYPE: PRT
<213> ORGANISM: Llama glama

<400> SEQUENCE: 390

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Lys Pro Gly Gln Ala Pro Arg Thr
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Glu Tyr Tyr Cys
                85                  90

<210> SEQ ID NO 391
<211> LENGTH: 99
<212> TYPE: PRT
<213> ORGANISM: Homo sapiens

<400> SEQUENCE: 391

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Ser
            20                  25                  30

Tyr Tyr Pro Ser Trp Tyr Gln Gln Thr Pro Gly Gln Ala Pro Arg Thr
        35                  40                  45

Leu Ile Tyr Ser Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Val Leu Tyr Met Gly Ser
                85                  90                  95

Gly Ile Ser

<210> SEQ ID NO 392
<211> LENGTH: 99
<212> TYPE: PRT
<213> ORGANISM: Llama pacos

<400> SEQUENCE: 392

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Gly Trp Tyr Gln Gln Thr Pro Gly Gln Ala Pro Arg Thr
        35                  40                  45

Leu Ile Tyr Asn Thr Asn Ser Arg Tyr Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Val Tyr Ile Gly Ser
                85                  90                  95

Gly Ser Tyr

<210> SEQ ID NO 393
<211> LENGTH: 99
<212> TYPE: PRT
<213> ORGANISM: Camelus ferus

<400> SEQUENCE: 393

Gln Thr Val Val Thr Gln Glu Pro Ser Leu Ser Val Ser Pro Gly Gly
1               5                   10                  15

Thr Val Thr Leu Thr Cys Gly Leu Ser Thr Gly Ser Val Thr Ser Ser
            20                  25                  30

Asn Tyr Pro Ser Trp Tyr Gln Gln Thr Pro Gly Gln Ser Pro Gln Leu
        35                  40                  45

Leu Ile Tyr Lys Thr Asn Ser Arg His Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Asp Tyr Tyr Cys Ala Leu Tyr Met Gly Ser
                85                  90                  95

Gly Ser Tyr

<210> SEQ ID NO 394
<211> LENGTH: 99
<212> TYPE: PRT
<213> ORGANISM: Llama pacos

<400> SEQUENCE: 394

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Ser Trp Tyr Gln Gln Thr Pro Gly Gln Ala Pro Arg Ala
        35                  40                  45

Leu Ile Tyr Ser Thr Asn Ser Arg His Ser Gly Val Pro Ser Arg Phe
    50                  55                  60

```
Ser Gly Ser Ile Ser Gly Asn Lys Ala Thr Leu Thr Ile Ser Gly Ala
 65                  70                  75                  80

Gln Pro Glu Asp Glu Ala Asp Phe Tyr Cys Ala Leu Ser Arg Val Ser
                 85                  90                  95

Gly Thr Tyr

<210> SEQ ID NO 395
<211> LENGTH: 99
<212> TYPE: PRT
<213> ORGANISM: Llama pacos

<400> SEQUENCE: 395

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Thr Ser
                20                  25                  30

Asn Tyr Pro Gly Trp Phe Gln Gln Thr Thr Gly Gln Ala Pro Arg Ala
             35                  40                  45

Leu Ile Tyr Ser Thr Asn Ser Arg His Ser Gly Val Pro Ser Ser Phe
         50                  55                  60

Ser Gly Ser Ile Ser Gly Asn Lys Ala Ala Leu Thr Ile Thr Gly Ala
 65                  70                  75                  80

Gln Pro Lys Asp Glu Ala Asn Tyr Asp Cys Ser Leu Tyr Pro Gly Ser
                 85                  90                  95

Tyr Pro Asp

<210> SEQ ID NO 396
<211> LENGTH: 99
<212> TYPE: PRT
<213> ORGANISM: Camelus ferus

<400> SEQUENCE: 396

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ser Ser
                20                  25                  30

Asn Tyr Pro Arg Trp Tyr Gln Gln Thr Thr Gly Gln Ala Pro Arg Thr
             35                  40                  45

Leu Ile Tyr Asn Thr Asn Ser Arg His Ser Gly Val Ser Ser Cys Phe
         50                  55                  60

Ser Gly Ser Ile Ser Gly Asn Lys Ala Ala Leu Thr Ile Thr Gly Ala
 65                  70                  75                  80

Gln Pro Glu Asp Glu Asp Asp Tyr Tyr Cys Ala Leu Tyr Val Ser Ser
                 85                  90                  95

Gly Ser Tyr

<210> SEQ ID NO 397
<211> LENGTH: 90
<212> TYPE: PRT
<213> ORGANISM: Llama glama

<400> SEQUENCE: 397

Gln Thr Val Val Thr Gln Glu Pro Ser Leu Ser Val Ser Pro Gly Gly
 1               5                  10                  15

Thr Val Thr Leu Thr Cys Gly Leu Ser Ser Gly Ser Val Thr Ser Ser
                20                  25                  30

Asn Tyr Pro Gly Trp Phe Gln Gln Thr Pro Gly Gln Ala Pro Arg Thr
```

```
                    35                  40                  45

Leu Ile Tyr Asn Thr Asn Ser Arg His Ser Gly Val Pro Ser Arg Phe
            50                  55                  60

Ser Gly Ser Ile Ser Gly Asn Lys Ala Ala Leu Thr Ile Thr Gly Ala
 65                  70                  75                  80

Gln Pro Glu Asp Glu Ala Glu Tyr Tyr Cys
                85                  90

<210> SEQ ID NO 398
<211> LENGTH: 99
<212> TYPE: PRT
<213> ORGANISM: Camelus ferus

<400> SEQUENCE: 398

Gln Thr Val Val Thr Gln Glu Pro Ser Leu Ser Val Ser Pro Gly Gly
  1               5                  10                  15

Thr Val Thr Leu Thr Cys Gly Leu Ser Ser Gly Ser Val Thr Thr Ser
                20                  25                  30

Asn Tyr Pro Gly Trp Tyr Gln Gln Thr Pro Gly Gln Ala Pro Arg Ala
            35                  40                  45

Leu Ile Tyr Asn Thr Asn Ser Arg Pro Ser Gly Val Pro Ser Arg Phe
            50                  55                  60

Ser Gly Ser Ile Ser Gly Lys Lys Ala Ala Leu Thr Ile Thr Gly Ala
 65                  70                  75                  80

Gln Pro Glu Asp Glu Ala Glu Tyr Tyr Cys Ala Leu Tyr Met Gly Ser
                85                  90                  95

Gly Ser Tyr

<210> SEQ ID NO 399
<211> LENGTH: 99
<212> TYPE: PRT
<213> ORGANISM: Llama pacos

<400> SEQUENCE: 399

Gln Thr Val Val Thr Gln Glu Pro Ser Leu Ser Val Ser Pro Gly Gly
  1               5                  10                  15

Thr Val Thr Leu Thr Cys Gly Leu Ser Ser Gly Ser Val Thr Ser Ser
                20                  25                  30

Asn Tyr Pro Gly Trp Tyr Gln Gln Thr Pro Gly Gln Ala Pro Arg Ala
            35                  40                  45

Leu Ile Tyr Asn Thr Asn Ser Arg His Ser Gly Val Pro Ser Arg Phe
            50                  55                  60

Ser Gly Ser Ile Ser Gly Asn Lys Ala Thr Leu Thr Ile Ser Gly Ala
 65                  70                  75                  80

Gln Pro Glu Asp Glu Ala Asp Phe Tyr Cys Ala Leu Ser Arg Val Ser
                85                  90                  95

Gly Thr Tyr

<210> SEQ ID NO 400
<211> LENGTH: 99
<212> TYPE: PRT
<213> ORGANISM: Llama pacos

<400> SEQUENCE: 400

Gln Thr Val Val Thr Gln Glu Pro Ser Leu Ser Val Ser Pro Gly Gly
  1               5                  10                  15

Thr Val Thr Leu Thr Cys Gly Leu Ser Ser Gly Ser Val Thr Ser Ser
```

-continued

```
                20                  25                  30

Asn Tyr Pro Gly Trp Tyr Gln Gln Thr Pro Gly Gln Ala Pro Arg Ala
            35                  40                  45

Leu Ile Tyr Asn Thr Asn Ser Arg His Ser Gly Val Pro Ser Arg Tyr
 50                  55                  60

Ser Gly Ser Ile Ser Gly Asn Lys Ala Ala Leu Thr Ile Thr Gly Ala
 65                  70                  75                  80

Glu Pro Glu Asp Glu Ala Asp Tyr Tyr Cys Ala Leu His Lys Gly Ser
                85                  90                  95

Tyr Thr Asp

<210> SEQ ID NO 401
<211> LENGTH: 99
<212> TYPE: PRT
<213> ORGANISM: Llama pacos

<400> SEQUENCE: 401

Gln Thr Val Val Thr Gln Glu Pro Ser Met Ser Val Ser Pro Gly Gly
 1               5                  10                  15

Thr Val Thr Leu Thr Cys Gly Leu Ser Ser Gly Ser Val Thr Thr Ser
                20                  25                  30

Asn Tyr Pro Gly Trp Phe Gln Gln Thr Pro Gly Gln Ala Pro Arg Thr
            35                  40                  45

Leu Ile Tyr Arg Thr Ser Asn Arg Leu Ser Gly Val Pro Ser Arg Phe
 50                  55                  60

Ser Gly Ser Ile Ser Gly Asn Lys Ala Ala Leu Thr Ile Met Gly Ala
 65                  70                  75                  80

Gln Pro Glu Asp Glu Ala Glu Tyr Tyr Cys Ala Val Tyr Val Gly Ser
                85                  90                  95

Gly Ser Tyr

<210> SEQ ID NO 402
<211> LENGTH: 90
<212> TYPE: PRT
<213> ORGANISM: Llama glama

<400> SEQUENCE: 402

Gln Thr Val Val Thr Gln Glu Pro Ser Met Ser Val Ser Pro Gly Gly
 1               5                  10                  15

Thr Val Thr Leu Thr Cys Gly Leu Ser Ser Gly Ser Val Thr Thr Ser
                20                  25                  30

Asn Tyr Pro Gly Trp Phe Gln Gln Thr Pro Gly Gln Ala Pro Arg Thr
            35                  40                  45

Leu Ile Tyr Arg Thr Ser Asn Arg Leu Ser Gly Val Pro Ser Arg Phe
 50                  55                  60

Ser Gly Ser Ile Ser Gly Asn Lys Ala Ala Leu Thr Ile Met Gly Ala
 65                  70                  75                  80

Gln Pro Glu Asp Glu Ala Glu Tyr Tyr Cys
                85                  90

<210> SEQ ID NO 403
<211> LENGTH: 99
<212> TYPE: PRT
<213> ORGANISM: Llama pacos

<400> SEQUENCE: 403

Gln Thr Val Val Thr Gln Glu Pro Ser Met Ser Val Ser Pro Gly Gly
```

```
                1               5                  10                 15
              Thr Val Thr Leu Thr Cys Gly Leu Ser Ser Gly Ser Val Thr Thr Ser
                              20                  25                 30

Asn Tyr Pro Gly Trp Phe Gln Gln Thr Pro Gly Gln Ala Pro Arg Thr
                              35                  40                 45

Leu Ile Tyr Arg Thr Ser Asn Arg Leu Ser Gly Val Pro Ser Arg Phe
                              50                  55                 60

Ser Gly Ser Ile Ser Gly Asn Lys Ala Ala Leu Thr Ile Met Gly Ala
               65                 70                  75                 80

Gln Pro Glu Asp Glu Ala Glu Tyr Tyr Cys Ala Val Tyr Val Gly Ser
                                  85                  90                 95

Gly Ser Tyr

<210> SEQ ID NO 404
<211> LENGTH: 99
<212> TYPE: PRT
<213> ORGANISM: Camelus ferus

<400> SEQUENCE: 404

Gln Thr Val Val Thr Gln Glu Pro Ser Met Ser Val Ser Pro Gly Gly
               1               5                  10                 15

Thr Val Thr Leu Thr Cys Gly Leu Ser Ser Gly Ser Val Thr Thr Ser
                              20                  25                 30

Asn Tyr Pro Gly Trp Ile Gln Gln Thr Pro Gly Gln Ala Pro Ser Thr
                              35                  40                 45

Leu Ile Tyr Arg Thr Ser Asn Arg Leu Ser Gly Val Pro Ser Arg Phe
                              50                  55                 60

Ser Gly Ser Ile Ser Gly Asn Lys Ala Ala Leu Thr Ile Thr Gly Ala
               65                 70                  75                 80

Gln Pro Glu Asp Glu Ala Asp Tyr Tyr Cys Ala Val Tyr Met Gly Ser
                                  85                  90                 95

Gly Ser Tyr

<210> SEQ ID NO 405
<211> LENGTH: 99
<212> TYPE: PRT
<213> ORGANISM: Camelus ferus

<400> SEQUENCE: 405

Gln Thr Val Val Thr Gln Glu Pro Ser Leu Ser Val Ser Pro Gly Gly
               1               5                  10                 15

Thr Val Thr Leu Thr Cys Gly Leu Ser Ser Gly Ser Val Thr Thr Ser
                              20                  25                 30

Tyr Tyr Pro Gly Trp Tyr Gln Gln Thr Pro Gly Arg Ala Pro Arg Ala
                              35                  40                 45

Leu Ile Tyr Ser Thr Ser Ser Arg Tyr Ser Gly Val Pro Ser Arg Phe
                              50                  55                 60

Ser Gly Ser Ile Ser Gly Asn Lys Ala Ala Leu Thr Ile Thr Gly Ala
               65                 70                  75                 80

Gln Pro Lys Glu Glu Ala Asp Tyr Asp Cys Ser Leu Tyr His Gly Ser
                                  85                  90                 95

Tyr Pro Asp

<210> SEQ ID NO 406
<211> LENGTH: 99
<212> TYPE: PRT
```

<213> ORGANISM: Llama pacos

<400> SEQUENCE: 406

Gln Thr Val Val Thr Gln Glu Pro Ser Leu Ser Ala Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Phe Gln Gln Thr Pro Gly Gln Ala Pro Arg Thr
        35                  40                  45

Leu Ile Tyr Ser Thr Ser Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Asp Ile Gly Ser
                85                  90                  95

Tyr Thr Asp

<210> SEQ ID NO 407
<211> LENGTH: 99
<212> TYPE: PRT
<213> ORGANISM: Camelus ferus

<400> SEQUENCE: 407

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Ser Ser Ser
            20                  25                  30

Asn Tyr Pro Gly Trp Ile Gln Gln Thr Pro Gly Gln Val Pro Arg Thr
        35                  40                  45

Leu Ile Tyr Ser Thr Ser Ser Arg Pro Ser Gly Ile Pro Ser Arg Phe
    50                  55                  60

Ala Gly Thr Ile Ser Gly Asn Lys Ala Thr Leu Thr Ile Thr Gly Ala
65                  70                  75                  80

Gln Pro Glu Asp Glu Ala Asp Tyr Tyr Cys Ala Leu Tyr Pro Gly Ser
                85                  90                  95

Tyr Leu Asp

<210> SEQ ID NO 408
<211> LENGTH: 99
<212> TYPE: PRT
<213> ORGANISM: Camelus ferus

<400> SEQUENCE: 408

Pro Thr Val Val Thr Gln Glu Pro Ser Leu Ser Val Ser Pro Gly Trp
1               5                   10                  15

Thr Val Thr Leu Thr Cys Gly Leu Ser Ser Gly Ser Val Thr Thr Ser
            20                  25                  30

Asn Asp Pro Gly Trp Ile Gln Gln Thr Pro Gly Gln Val Pro Arg Thr
        35                  40                  45

Leu Ile Tyr Arg Thr Ser Ser His Leu Ser Gly Val Pro Ser Arg Phe
    50                  55                  60

Phe Arg Ser Ile Ser Gly Asn Lys Ala Ala Leu Thr Ile Met Gly Ala
65                  70                  75                  80

Gln Pro Lys Asp Glu Ala Asp Tyr Tyr Cys Ala Leu Asp Met Gly Ser
                85                  90                  95

Gly Ser Tyr

<210> SEQ ID NO 409
<211> LENGTH: 99
<212> TYPE: PRT
<213> ORGANISM: Llama pacos

<400> SEQUENCE: 409

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Asp Tyr Tyr Cys Ala Leu Tyr Met Gly Ser
                85                  90                  95

Gly Ser Asn
```

<210> SEQ ID NO 410
<211> LENGTH: 90
<212> TYPE: PRT
<213> ORGANISM: Llama glama

<400> SEQUENCE: 410

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Glu Tyr Tyr Cys
                85                  90
```

<210> SEQ ID NO 411
<211> LENGTH: 89
<212> TYPE: PRT
<213> ORGANISM: Llama pacos

<400> SEQUENCE: 411

```
Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Leu
        35                  40                  45

Leu Ile Tyr Asn Thr Asn Ser Arg His Ser Gly Val Pro Ser Arg Phe
    50                  55                  60

Ser Gly Ser Ile Ser Gly Asn Lys Ala Ala Leu Thr Ile Thr Gly Ala
65                  70                  75                  80

Pro Glu Asp Glu Ala Asp Tyr Tyr Cys
```

<210> SEQ ID NO 412
<211> LENGTH: 90
<212> TYPE: PRT
<213> ORGANISM: Llama glama

<400> SEQUENCE: 412

Gln Thr Val Val Thr Gln Glu Pro Ser Leu Ser Val Ser Pro Gly Gly
1               5                   10                  15

Thr Val Thr Leu Thr Cys Gly Leu Ser Ser Gly Ser Val Thr Ser Ser
            20                  25                  30

Asn Tyr Pro Asp Trp Tyr Gln Gln Thr Pro Gly Gln Ala Pro Arg Ala
        35                  40                  45

Leu Ile Tyr Ser Thr Asn Ser Arg His Ser Gly Val Pro Asn Arg Phe
    50                  55                  60

Ser Gly Ser Ile Ser Gly Asn Lys Ala Ala Leu Thr Ile Thr Gly Ala
65                  70                  75                  80

Gln Pro Glu Asp Glu Ala Glu Tyr Tyr Cys
                85                  90

<210> SEQ ID NO 413
<211> LENGTH: 99
<212> TYPE: PRT
<213> ORGANISM: Llama pacos

<400> SEQUENCE: 413

Gln Thr Val Val Thr Gln Lys Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Ile Gln Gln Thr Pro Gly Gln Val Leu His Thr
        35                  40                  45

Leu Ile Tyr Ser Thr Ser Ser Cys Leu Ser Gly Val Pro Ser Arg Phe
    50                  55                  60

Ser Gly Ser Ile Ser Gly Asn Lys Thr Thr Leu Thr Ile Thr Gly Ala
65                  70                  75                  80

Gln Pro Glu Asp Glu Ala Asp Tyr Tyr Cys Ala Val Tyr Ile Trp Val
                85                  90                  95

Val Ala Val

<210> SEQ ID NO 414
<211> LENGTH: 99
<212> TYPE: PRT
<213> ORGANISM: Llama pacos

<400> SEQUENCE: 414

Gln Thr Val Val Thr Gln Lys Pro Ser Leu Ser Val Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Gly Trp Ile Gln Gln Thr Pro Gly Gln Val Leu His Thr
        35                  40                  45

Leu Ile Tyr Ser Thr Ser Ser Cys Leu Ser Gly Val Pro Ser Arg Phe
    50                  55                  60

Ser Gly Ser Ile Ser Gly Asn Lys Thr Thr Leu Thr Ile Thr Gly Ala
65                  70                  75                  80

```
Gln Pro Glu Asp Glu Ala Asp Tyr Tyr Cys Ala Val Tyr Ile Trp Val
                85                  90                  95

Val Ala Val

<210> SEQ ID NO 415
<211> LENGTH: 96
<212> TYPE: PRT
<213> ORGANISM: Camelus ferus

<400> SEQUENCE: 415

Lys Thr Val Val Thr Gln Glu Pro Ser Leu Ser Val Ser Pro Gly Gly
1               5                   10                  15

Thr Val Thr Phe Thr Cys Gly Leu Ser Pro Gly Ser Val Thr Ile Ser
                20                  25                  30

Asp Tyr His Ser Trp Tyr Gln Gln Thr Pro Gly Gln Ala Pro Ala Leu
            35                  40                  45

Ile Tyr Ser Thr Ser Ser His Tyr Ser Gly Val Pro Asn Gln Phe Ser
        50                  55                  60

Gly Ser Ile Ser Gly Asn Lys Ala Ala Leu Thr Ile Thr Gly Ala Gln
65                  70                  75                  80

Pro Glu Asp Glu Ala Asp Tyr Asp Cys Ala Leu His Thr Gly Ser Tyr
                85                  90                  95

<210> SEQ ID NO 416
<211> LENGTH: 96
<212> TYPE: PRT
<213> ORGANISM: Camelus ferus

<400> SEQUENCE: 416

Lys Thr Val Val Thr Gln Glu Pro Ser Leu Ser Val Ser Pro Gly Gly
1               5                   10                  15

Thr Val Thr Phe Thr Cys Gly Leu Ser Pro Gly Ser Val Thr Ile Ser
                20                  25                  30

Asp Tyr His Ser Trp Tyr Gln Gln Thr Pro Gly Gln Ala Pro Ala Leu
            35                  40                  45

Ile Tyr Ser Thr Ser Ser His Tyr Ser Gly Val Pro Asn Gln Phe Ser
        50                  55                  60

Gly Ser Ile Ser Gly Asn Lys Ala Ala Leu Thr Ile Thr Gly Ala Gln
65                  70                  75                  80

Pro Glu Asp Glu Ala Asp Tyr Asp Cys Ala Leu His Thr Gly Ser Tyr
                85                  90                  95

<210> SEQ ID NO 417
<211> LENGTH: 96
<212> TYPE: PRT
<213> ORGANISM: Llama pacos

<400> SEQUENCE: 417

Gln Thr Val Val Thr Gln Gln Ser Phe Leu Lys Val Ser Pro Gln Gly
1               5                   10                  15

Thr Phe Thr Leu Thr Cys Gly Leu Ser Pro Gly Thr Val Thr Thr Ser
                20                  25                  30

Asn Tyr Pro Cys Phe Tyr Gln Gln Thr Arg Gly Gln Ala Leu Leu Leu
            35                  40                  45

Ile Tyr Ser Ser Asn Ser Arg Pro Thr Gly Val Pro Ser Arg Ser Ser
        50                  55                  60

Gly Thr Val Ser Gly Asn Lys Ala Ala Leu Thr Ile Thr Arg Ala Gln
65                  70                  75                  80
```

```
Pro Glu Asp Lys Ala Asp Tyr Tyr Cys Ala Leu Glu Met Gly Ser Tyr
            85                  90                  95
```

<210> SEQ ID NO 418
<211> LENGTH: 96
<212> TYPE: PRT
<213> ORGANISM: Llama pacos

<400> SEQUENCE: 418

```
Gln Thr Val Val Thr Gln Gln Ser Phe Leu Lys Val Ser Pro Gln Gly
1               5                   10                  15
Thr Phe Thr Leu Thr Cys Gly Leu Ser Pro Gly Thr Val Thr Thr Ser
            20                  25                  30
Asn Tyr Pro Cys Phe Tyr Gln Gln Thr Arg Gly Gln Ala Leu Leu Leu
        35                  40                  45
Ile Tyr Ser Ser Asn Ser Arg Pro Thr Gly Val Pro Ser Arg Ser Ser
    50                  55                  60
Gly Thr Val Ser Gly Asn Lys Ala Ala Leu Thr Ile Thr Arg Ala Gln
65                  70                  75                  80
Pro Glu Asp Lys Ala Asp Tyr Tyr Cys Ala Leu Glu Met Gly Ser Tyr
            85                  90                  95
```

<210> SEQ ID NO 419
<211> LENGTH: 96
<212> TYPE: PRT
<213> ORGANISM: Llama pacos

<400> SEQUENCE: 419

```
Gln Thr Val Val Thr Gln Val Ser Ser Leu Ser Val Phe Leu Arg Gly
1               5                   10                  15
Thr Val Thr Leu Thr Cys Gly Leu Asn Ser Gly Ser Val Thr Thr Ser
            20                  25                  30
Lys Tyr Ser Ser Trp Tyr Gln Arg Thr Gln Gly Gln Ala Pro Arg Met
        35                  40                  45
Leu Ile Ser Thr Asn Ser Cys Leu Ser Gly Val Leu Asn Arg Leu Ser
    50                  55                  60
Gly Thr Ile Ser Gly Asn Lys Ser Ala Leu Thr Ile Thr Gly Ala Gln
65                  70                  75                  80
Ser Glu Asp Glu Ala Asp Tyr Tyr Cys Ala Leu Asp Thr Gly Ser Tyr
            85                  90                  95
```

<210> SEQ ID NO 420
<211> LENGTH: 89
<212> TYPE: PRT
<213> ORGANISM: Llama glama

<400> SEQUENCE: 420

```
Gln Thr Val Val Thr Gln Val Ser Ser Leu Ser Val Phe Leu Arg Gly
1               5                   10                  15
Thr Val Thr Leu Thr Cys Gly Leu Asn Ser Gly Ser Val Thr Thr Ser
            20                  25                  30
Lys Tyr Ser Ser Trp Tyr Gln Arg Thr Gln Gly Gln Ala Pro Arg Met
        35                  40                  45
Leu Ile Ser Thr Asn Ser Cys Leu Ser Gly Val Leu Asn Arg Leu Ser
    50                  55                  60
Gly Thr Ile Ser Gly Asn Lys Ser Ala Leu Thr Ile Thr Gly Ala Gln
65                  70                  75                  80
```

-continued

Ser Glu Asp Glu Ala Glu Tyr Tyr Cys
                85

<210> SEQ ID NO 421
<211> LENGTH: 89
<212> TYPE: PRT
<213> ORGANISM: Llama glama

<400> SEQUENCE: 421

Gln Thr Val Val Thr Gln Val Ser Ser Leu Ser Val Phe Leu Leu Gly
1               5                   10                  15

Thr Val Thr Leu Thr Cys Gly Leu Asn Ser Gly Ser Val Thr Thr Ser
            20                  25                  30

Lys Tyr Pro Ser Trp Tyr Gln Arg Met Gln Gly Gln Ala Pro Arg Met
        35                  40                  45

Leu Ile Arg Thr Asn Ser Cys Leu Ser Gly Val Leu Asn Arg Leu Ser
    50                  55                  60

Gly Thr Ile Ser Gly Asn Lys Ser Ala Leu Thr Phe Thr Gly Ala Gln
65                  70                  75                  80

Ser Glu Asp Glu Ala Glu Tyr Tyr Cys
                85

<210> SEQ ID NO 422
<211> LENGTH: 89
<212> TYPE: PRT
<213> ORGANISM: Llama glama

<400> SEQUENCE: 422

Gln Thr Leu Val Thr Gln Val Ser Ser Leu Ser Val Phe Leu Leu Gly
1               5                   10                  15

Thr Val Thr Leu Thr Cys Gly Leu Asn Ser Gly Ser Val Thr Thr Ser
            20                  25                  30

Lys Tyr Pro Ser Trp Tyr Gln Arg Met Gln Gly Gln Ala Pro Arg Met
        35                  40                  45

Leu Ile Ser Thr Asn Ser Cys Leu Ser Gly Val Leu Ser Arg Phe Ser
    50                  55                  60

Gly Thr Val Cys Gly Asn Lys Ala Ala Leu Ser Ile Thr Gly Ser Gln
65                  70                  75                  80

Ser Glu Asp Glu Ala Glu Tyr Tyr Cys
                85

<210> SEQ ID NO 423
<211> LENGTH: 96
<212> TYPE: PRT
<213> ORGANISM: Llama pacos

<400> SEQUENCE: 423

Gln Thr Val Met Thr Gln Glu Pro Ser Leu Ser Gly Ser Pro Gly Gly
1               5                   10                  15

Lys Val Thr Leu Thr Cys Gly Leu Ser Ser Gly Ser Val Thr Thr Ser
            20                  25                  30

Asn Tyr Pro Gly Trp Tyr Gln Arg Thr Gln Gly Gln Ala Pro Arg Leu
        35                  40                  45

Leu Ile Ser Thr Asn Ser Cys Leu Ser Gly Val Leu Asn Cys Phe Ser
    50                  55                  60

Gly Thr Val Cys Gly Asn Lys Ala Ala Leu Thr Ile Thr Gly Ala Gln
65                  70                  75                  80

Ser Glu Asp Glu Ala Glu Tyr Tyr Cys Ala Arg Asp Thr Gly Ser Cys 85                  90                  95

<210> SEQ ID NO 424
<211> LENGTH: 96
<212> TYPE: PRT
<213> ORGANISM: Llama pacos

<400> SEQUENCE: 424

Gln Thr Val Met Thr Gln Glu Pro Ser Leu Ser Gly Ser Pro Gly Gly
1               5                   10                  15

Lys Val Thr Leu Thr Cys Gly Leu Ser Ser Gly Ser Val Thr Thr Ser
            20                  25                  30

Asn Tyr Pro Gly Trp Tyr Gln Arg Thr Gln Gly Gln Ala Pro Arg Leu
        35                  40                  45

Leu Ile Ser Thr Asn Ser Cys Leu Ser Gly Val Leu Asn Cys Phe Ser
    50                  55                  60

Gly Thr Val Cys Gly Asn Lys Ala Ala Leu Thr Ile Thr Gly Ala Gln
65                  70                  75                  80

Ser Glu Asp Glu Ala Glu Tyr Tyr Cys Ala Arg Asp Thr Gly Ser Cys
                85                  90                  95

<210> SEQ ID NO 425
<211> LENGTH: 86
<212> TYPE: PRT
<213> ORGANISM: Llama glama

<400> SEQUENCE: 425

Gln Thr Val Met Thr Gln Glu Pro Ser Leu Ser Gly Ser Pro Gly Gly
1               5                   10                  15

Lys Val Thr Leu Thr Cys Gly Leu Ser Ser Gly Ser Val Thr Thr Ser
            20                  25                  30

Asn Tyr Pro Gly Trp Tyr Gln Arg Thr Gln Gly Gln Ala Pro Arg Leu
        35                  40                  45

Leu Ile Arg Thr Asn Ser Cys Leu Ser Gly Val Leu Asn Cys Phe Ser
    50                  55                  60

Gly Thr Val Cys Arg Asn Lys Ala Ala Leu Thr Ile Thr Gly Ala Gln
65                  70                  75                  80

Ser Glu Asp Glu Ala Glu
                85

<210> SEQ ID NO 426
<211> LENGTH: 94
<212> TYPE: PRT
<213> ORGANISM: Camelus ferus

<400> SEQUENCE: 426

Gln Thr Val Val Thr Gln Asp Ser Ser Leu Ser Ala Ser Pro Gly Gly
1               5                   10                  15

Thr Val Thr Leu Thr Cys Gly Leu Ser Ser Gly Ser Val Thr Thr Ser
            20                  25                  30

Asn Tyr Pro Ser Trp Tyr Gln Arg Thr Gln Gly Gln Ala Pro Arg Leu
        35                  40                  45

Leu Ile Ser Thr Asn Ser Cys Pro Ser Gly Asn Leu Asn Arg Phe Ser
    50                  55                  60

Gly Thr Ser Pro Arg Met Arg Pro Ser Ile Ile Val Leu Trp Thr Gln
65                  70                  75                  80

Val Val Thr Ile Thr Gln Cys Asn Leu Thr Gly Lys Cys Phe
                85                  90

<210> SEQ ID NO 427
<211> LENGTH: 98
<212> TYPE: PRT
<213> ORGANISM: Camelus ferus

<400> SEQUENCE: 427

Gln Thr Val Val Ile Gln Asn Ser Ser Leu Thr Leu Ser Pro Gly Glu
1               5                   10                  15

Thr Val Thr Leu Thr Cys Gly Pro Ser Ser Gly Ser Val Thr Thr Ser
            20                  25                  30

Asn Tyr Pro Ser Trp Tyr Gln Gln Thr Pro Gly Gln Ala Pro Gln Val
        35                  40                  45

Leu Pro Ile Ala Glu Ala Ala Glu Gly Pro Gln Ser Gly Val Pro Ser
    50                  55                  60

Arg Leu Ser Gly Ser Ile Ser Gly Ile Lys Ala Thr Leu Thr Asn Thr
65                  70                  75                  80

Glu Ala Leu Pro Lys Asp Lys Ala Asp Tyr Tyr Cys Ala Leu Tyr Pro
                85                  90                  95

Gly Ser

<210> SEQ ID NO 428
<211> LENGTH: 98
<212> TYPE: PRT
<213> ORGANISM: Llama pacos

<400> SEQUENCE: 428

Gln Thr Val Val Thr Gln Glu Pro Ser Leu Ser Val Ser Pro Gly Glu
1               5                   10                  15

Met Val Thr Leu Thr Cys Gly Pro Ser Ser Gly Ser Val Thr Thr Ser
            20                  25                  30

Asn Tyr Pro Ser Trp Tyr Gln Gln Thr Pro Gly Gln Ala Pro Gln Val
        35                  40                  45

Leu Ser Ile Ala Glu Ala Ala Thr Ile Leu Arg Ser Pro Val Ala Cys
    50                  55                  60

Leu Asp Pro Ser Leu Gly Ser Lys Pro Pro Ser Pro Leu Arg Pro
65                  70                  75                  80

Cys Pro Arg Thr Arg Pro Thr Ile Thr Val Leu Cys Thr Leu Val Val
                85                  90                  95

Thr Val

<210> SEQ ID NO 429
<211> LENGTH: 98
<212> TYPE: PRT
<213> ORGANISM: Llama pacos

<400> SEQUENCE: 429

Gln Thr Val Val Thr Gln Glu Pro Ser Leu Ser Val Ser Pro Gly Glu
1               5                   10                  15

Met Val Thr Leu Thr Cys Gly Pro Ser Ser Gly Ser Val Thr Thr Ser
            20                  25                  30

Asn Tyr Pro Ser Trp Tyr Gln Gln Thr Pro Gly Gln Ala Pro Gln Val
        35                  40                  45

Leu Ser Ile Ala Glu Ala Ala Thr Ile Leu Arg Ser Pro Val Ala Cys
    50                  55                  60

Leu Asp Pro Ser Leu Gly Ser Lys Pro Pro Ser Pro Pro Leu Arg Pro
65                  70                  75                  80

-continued

```
Cys Pro Arg Thr Arg Pro Thr Ile Thr Val Leu Cys Thr Leu Val Val
                85                  90                  95
Thr Val

<210> SEQ ID NO 430
<211> LENGTH: 99
<212> TYPE: PRT
<213> ORGANISM: Homo sapiens

<400> SEQUENCE: 430

Gln Pro Val Leu Thr Gln Pro Ser Ala Ser Ala Ser Leu Gly Ala
1               5                   10                  15

Ser Val Thr Leu Thr Cys Thr Leu Ser Ser Gly Tyr Ser Asn Tyr Lys
                20                  25                  30

Val Asp Trp Tyr Gln Gln Arg Pro Gly Lys Pro Arg Phe Val Met
            35                  40                  45

Arg Val Gly Thr Gly Gly Ile Val Gly Ser Lys Gly Asp Gly Ile Pro
50                  55                  60

Asp Arg Phe Ser Val Leu Gly Ser Gly Leu Asn Arg Tyr Leu Thr Ile
65                  70                  75                  80

Lys Asn Ile Gln Glu Glu Asp Glu Ser Asp Tyr His Cys Gly Ala Asp
                85                  90                  95

His Gly Ser

<210> SEQ ID NO 431
<211> LENGTH: 99
<212> TYPE: PRT
<213> ORGANISM: Llama pacos

<400> SEQUENCE: 431

Gln Pro Val Leu Met Gln Pro Ser Ala Ser Ala Ser Leu Gly Ala
1               5                   10                  15

Leu Ala Met Ile Thr Cys Thr Pro Arg Thr Gly Tyr Ile Cys Tyr Tyr
                20                  25                  30

Val Asp Trp Tyr Gln Gln Asp Pro Gly Asn Gly Pro Arg Phe Glu Met
            35                  40                  45

Gly Ala Gly Thr Ser Gly Gly Val Gly Ser Lys Gly Asp Gly Val Ser
50                  55                  60

Asp Arg Phe Ser Gly Leu Gly Ser Gly Leu Glu His Ser Val Asn Ile
65                  70                  75                  80

Gln Asn Val Arg Glu Glu Asp Lys Ser Asp Tyr Ile Cys Gly Ala Asp
                85                  90                  95

His Gly Ser

<210> SEQ ID NO 432
<211> LENGTH: 93
<212> TYPE: PRT
<213> ORGANISM: Llama glama

<400> SEQUENCE: 432

Gln Pro Val Leu Met Gln Pro Ser Ala Ser Ala Ser Leu Gly Ala
1               5                   10                  15

Leu Ala Met Ile Thr Cys Thr Pro Arg Thr Gly Tyr Ile Cys Tyr Tyr
                20                  25                  30

Val Asp Trp Tyr Gln Gln Asp Pro Gly Asn Gly Pro Arg Phe Glu Met
            35                  40                  45
```

```
Gly Ala Gly Thr Ser Gly Gly Val Gly Ser Lys Gly Asp Gly Val Ser
        50                  55                  60

Asp Arg Phe Ser Gly Leu Gly Ser Gly Leu Glu His Ser Val Asn Ile
 65                  70                  75                  80

Gln Asn Val Arg Glu Glu Asp Lys Ser Asp Tyr Ile Cys
                 85                  90

<210> SEQ ID NO 433
<211> LENGTH: 93
<212> TYPE: PRT
<213> ORGANISM: Llama glama

<400> SEQUENCE: 433

Gln Pro Val Leu Met Gln Pro Ser Ala Ser Ala Ser Leu Gly Ala
 1               5                  10                  15

Leu Ala Met Ile Thr Cys Thr Leu Arg Thr Gly Tyr Ile Cys Tyr Tyr
                 20                  25                  30

Val Asp Trp Tyr Gln Gln Asp Pro Gly Asn Gly Pro Arg Phe Glu Met
             35                  40                  45

Gly Ala Ala Thr Ser Gly Gly Val Ser Lys Gly Asp Gly Val Ser
        50                  55                  60

Asp His Phe Ser Ser Val Gly Ser Gly Leu Glu His Ser Val Asn Ile
 65                  70                  75                  80

Gln Asn Val Arg Glu Glu Asp Lys Ser Asp Tyr Ile Cys
                 85                  90

<210> SEQ ID NO 434
<211> LENGTH: 95
<212> TYPE: PRT
<213> ORGANISM: Llama glama

<400> SEQUENCE: 434

Gln Pro Val Pro Thr Gln Ser Pro Ser Ala Ser Ala Ser Leu Gly Ala
 1               5                  10                  15

Ser Ser Lys Leu Thr Cys Thr Leu Ser Ser Gly His Ser Gly Tyr Val
                 20                  25                  30

Asp Tyr Gln Gln Asp Pro Gly Asn Gly Ser Phe Glu Met Gly Val Gly
             35                  40                  45

Thr Ser Ser Val Leu Glu Ser Lys Gly Asp Gly Val Ser Asp Ser Phe
        50                  55                  60

Ser Gly Ser Gly Ser Pro Glu Arg Tyr Leu Thr Ile Gln Asn Val Leu
 65                  70                  75                  80

Glu Glu Asp Glu Ala Asp Ile Cys Gly Ala Asp His Gly Ser
                 85                  90                  95

<210> SEQ ID NO 435
<211> LENGTH: 97
<212> TYPE: PRT
<213> ORGANISM: Llama glama

<400> SEQUENCE: 435

Gln Pro Met Leu Thr Gln Ser Ser Pro Ala Ser Ala Ser Leu Gly Ala
 1               5                  10                  15

Ser Ala Lys Leu Thr Cys Thr Leu Ser Ser Gly Tyr Ser Gly Phe Tyr
                 20                  25                  30

Met Asp Tyr Gln Gln Asp Pro Gly Lys Gly Thr Gln Phe Glu Met Gly
             35                  40                  45

Val Gly Ile Ser Gly Val Val Glu Ser Met Arg Asp Gly Val Ser Asp
```

```
                  50                  55                  60

Arg Phe Ser Gly Ser Gly Pro Gly Pro Glu His Asp Leu Thr Ile Asn
 65                  70                  75                  80

Val Leu Glu Glu Asp Glu Ala Asp Tyr Ile Cys Gly Pro Asp His Gly
                 85                  90                  95

Ser

<210> SEQ ID NO 436
<211> LENGTH: 96
<212> TYPE: PRT
<213> ORGANISM: Llama glama

<400> SEQUENCE: 436

Gln Pro Val Leu Thr Gln Thr Pro Ser Ala Ser Ala Ser Leu Gly Ala
 1               5                  10                  15

Ser Gly Ser Ser Pro Ala Pro Ala Val Ala Thr Val Val Phe Thr Trp
                 20                  25                  30

Thr Ser Thr Ser Lys Thr Gln Gly Lys Gly Pro Gln Phe Glu Val Gly
                 35                  40                  45

Val Gly Thr Gly Val Val Glu Ser Arg Tyr Arg Val Ser Asp Arg
             50                  55                  60

Phe Ser Gly Ser Gly Pro Gly Glu Cys Tyr Leu Thr Ile Asn Val
 65                  70                  75                  80

Leu Glu Glu Asp Glu Ala Asp Tyr Ile Cys Gly Pro Asp His Asp Ser
                 85                  90                  95

<210> SEQ ID NO 437
<211> LENGTH: 98
<212> TYPE: PRT
<213> ORGANISM: Camelus ferus

<400> SEQUENCE: 437

Gln Pro Val Leu Thr Gln Ser Pro Ser Ala Ser Ser Leu Arg Ala
 1               5                  10                  15

Ser Ala Lys Phe Thr Thr Leu Ser Asn Gly Tyr Ser Gly Cys Tyr Val
                 20                  25                  30

Asp Trp Tyr Gln Gln Asp Pro Gly Asn Gly Pro Gln Phe Glu Met Gly
                 35                  40                  45

Val Gly Thr Ser Val Val Glu Ser Lys Glu Asp Gly Val Ser Asp
             50                  55                  60

Arg Phe Ala Gly Ser Gly Ser Cys Pro Glu Cys Tyr Leu Thr Ile Gln
 65                  70                  75                  80

Asn Val Trp Glu Glu Ala Lys Thr Asp Tyr Ile Cys Gly Ala Asp Arg
                 85                  90                  95

Gly Ser

<210> SEQ ID NO 438
<211> LENGTH: 98
<212> TYPE: PRT
<213> ORGANISM: Camelus ferus

<400> SEQUENCE: 438

Gln Pro Val Leu Thr Gln Ser Pro Ser Ala Ser Ser Leu Arg Ala
 1               5                  10                  15

Ser Ala Lys Phe Thr Thr Leu Ser Asn Gly Tyr Ser Gly Cys Tyr Val
                 20                  25                  30

Asp Trp Tyr Gln Gln Asp Pro Gly Asn Gly Pro Gln Phe Glu Met Gly
```

35                  40                  45

Val Gly Thr Ser Gly Val Val Glu Ser Lys Glu Asp Gly Asp Ser Asn
         50                  55                  60

Arg Phe Ser Val Ser Gly Ser Arg Glu Arg Tyr Leu Thr Ile Gln
 65                  70                  75                  80

Met Phe Gln Glu Asp Asp Arg Leu Thr Thr Ser Val Gly Gln Thr Met
                 85                  90                  95

Ala Ala

<210> SEQ ID NO 439
<211> LENGTH: 97
<212> TYPE: PRT
<213> ORGANISM: Camelus ferus

<400> SEQUENCE: 439

Gln Pro Val Leu Met Gln Leu Pro Phe Ala Phe Ala Ser Leu Gly Ala
 1               5                  10                  15

Ser Ala Lys Leu Thr Cys Thr Leu Ser Ser Gly Tyr Ser Gly Tyr Tyr
                20                  25                  30

Val Asp Trp Tyr Glu Gln Asp Pro Gly Asn Gly Ser Gln Phe Glu Met
                35                  40                  45

Gly Gly Ser Thr Ser Gly Ile Thr Gly Tyr Lys Glu Asp Gly Val Ser
         50                  55                  60

Asp His Phe Ser Gly Ser Gly Ser Leu Glu His Tyr Leu Thr Ile
 65                  70                  75                  80

Asn Val Glu Glu Asp Lys Ala Gly Tyr Ile Cys Gly Thr Asp His Gly
                 85                  90                  95

Ser

<210> SEQ ID NO 440
<211> LENGTH: 97
<212> TYPE: PRT
<213> ORGANISM: Homo sapiens

<400> SEQUENCE: 440

Gln Ala Gly Leu Thr Gln Pro Pro Ser Val Ser Lys Gly Leu Arg Gln
 1               5                  10                  15

Thr Ala Thr Leu Thr Cys Thr Gly Asn Ser Asn Ile Val Gly Asn Gln
                20                  25                  30

Gly Ala Ala Trp Leu Gln Gln His Gln Gly His Pro Pro Lys Leu Leu
                35                  40                  45

Ser Tyr Arg Asn Asn Asn Arg Pro Ser Gly Ile Ser Glu Arg Phe Ser
         50                  55                  60

Ala Ser Arg Ser Gly Asn Thr Ala Ser Leu Thr Ile Thr Gly Leu Gln
 65                  70                  75                  80

Pro Glu Asp Glu Ala Asp Tyr Tyr Cys Ser Ala Leu Asp Ser Ser Leu
                 85                  90                  95

Ser

<210> SEQ ID NO 441
<211> LENGTH: 97
<212> TYPE: PRT
<213> ORGANISM: Camelus ferus

<400> SEQUENCE: 441

Gln Ala Trp Leu Thr Gln Pro Gln Ser Val Thr Gly Ser Leu Gly Gln
 1               5                  10                  15

Thr Ala Thr Leu Thr Cys Thr Gly Asn Val His Ser Ile Gly Asn Glu
            20                  25                  30

Gly Pro Ala Trp Leu Gln Gln His Gln Gly Gln Ala Pro Arg Leu Leu
        35                  40                  45

Thr Leu Arg Asn Asn His Gln Pro Ser Gly Leu Ser Glu Arg Phe Leu
    50                  55                  60

Gly Ser Arg Ser Gly Ser Met Ala Thr Leu Ser Ile Ser Gly Leu Gln
65                  70                  75                  80

Ala Glu Asp Glu Ala Asp Tyr Tyr Cys Ser Ala Trp Asp Ser Ser Leu
                85                  90                  95

Ser

<210> SEQ ID NO 442
<211> LENGTH: 97
<212> TYPE: PRT
<213> ORGANISM: Llama pacos

<400> SEQUENCE: 442

Gln Ala Arg Leu Thr Gln Pro Arg Ser Val Thr Ala Ser Pro Gly Gln
1               5                   10                  15

Thr Ala Thr Leu Thr Cys Thr Gly Asp Ser His Ser Val Gly Asn Glu
            20                  25                  30

Gly Ala Ala Trp Leu Gln Gln His Pro Gly Gln Ala Pro Arg Leu Leu
        35                  40                  45

Thr Leu Arg Asn Asn Gln Arg Pro Ser Gly Val Ser Glu Arg Phe Ser
    50                  55                  60

Gly Ser Arg Ser Gly Ser Thr Ala Thr Leu Ser Ile Ser Gly Leu Gln
65                  70                  75                  80

Ala Glu Asp Glu Ala Asp Tyr Tyr Cys Ser Ala Trp Asp Ser Ser Leu
                85                  90                  95

Ser

<210> SEQ ID NO 443
<211> LENGTH: 89
<212> TYPE: PRT
<213> ORGANISM: Llama glama

<400> SEQUENCE: 443

Gln Ala Trp Leu Thr Gln Pro Gln Ser Val Thr Ala Ser Pro Gly Gln
1               5                   10                  15

Thr Ala Thr Leu Thr Cys Thr Gly Asp Gly His Ser Val Gly Asn Glu
            20                  25                  30

Gly Ala Ala Trp Leu Gln Gln His Pro Gly Gln Ala Pro Arg Leu Leu
        35                  40                  45

Thr Leu Gly Asn Asn Gln Arg Pro Ser Gly Val Ser Glu Arg Phe Ser
    50                  55                  60

Gly Ser Arg Ser Gly Ser Thr Ala Thr Leu Ser Ile Ser Gly Leu Gln
65                  70                  75                  80

Ala Glu Asp Glu Ala Asp Tyr Tyr Cys
                85

<210> SEQ ID NO 444
<211> LENGTH: 96
<212> TYPE: PRT
<213> ORGANISM: Homo sapiens

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Pro
                85                  90                  95

<210> SEQ ID NO 445
<211> LENGTH: 96
<212> TYPE: PRT
<213> ORGANISM: Llama pacos

<400> SEQUENCE: 445

Ala Thr Gln Val Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
            20                  25                  30

Leu Ala Trp Tyr Gln Gln Lys Pro Gly Gln Ala Pro Lys Leu Leu Ile
        35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65              70                  75                  80

Glu Asp Ala Gly Thr Tyr Tyr Cys Leu Gln His Lys Leu Pro Ser His
                85                  90                  95

<210> SEQ ID NO 446
<211> LENGTH: 96
<212> TYPE: PRT
<213> ORGANISM: Camelus ferus

<400> SEQUENCE: 446

Ala Thr Gln Met Thr Gln Ser Pro Ser Ser Leu Ser Ala Ser Leu Gly
1               5                   10                  15

Asp Thr Val Thr Ile Thr Cys Gln Ala Ser Gln Ser Ile Ser Ser Tyr
            20                  25                  30

Leu Ala Trp His Gln Gln Lys Pro Gly Gln Ala Pro Lys Leu Leu Ile
        35                  40                  45

Tyr Gly Ala Ser Ser Leu His Thr Gly Phe Pro Ser Arg Phe Ser Gly
    50                  55                  60

Ser Gly Ser Gly Thr Ser Phe Thr Leu Thr Ile Ser Gly Val Glu Ala
65              70                  75                  80

Glu Asp Val Gly Thr Tyr Tyr Cys Leu Gln His Asn Ser Tyr Pro Pro
                85                  90                  95

<210> SEQ ID NO 447
<211> LENGTH: 96
<212> TYPE: PRT
<213> ORGANISM: Llama pacos

<400> SEQUENCE: 447

Ala Thr Gln Met Thr Gln Ser Pro Ser Ser Leu Ser Ala Ser Leu Gly
1               5                   10                  15

Asp Arg Val Thr Ile Thr Cys Gln Ala Ser Gln Ser Ile Ser Ser Tyr
                20                  25                  30

Leu Ala Trp Tyr Gln Gln Lys Pro Gly Gln Ala Pro Lys Leu Leu Ile
            35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Tyr Ser Ala Pro Pro
                85                  90                  95

<210> SEQ ID NO 448
<211> LENGTH: 96
<212> TYPE: PRT
<213> ORGANISM: Camelus ferus

<400> SEQUENCE: 448

Ala Thr Gln Val Thr Gln Ser Pro Ser Ser Leu Ser Ala Ser Leu Gly
1               5                   10                  15

Asp Thr Val Thr Ile Thr Cys Gln Ala Ser Gln Ser Ile Ser Ser Tyr
                20                  25                  30

Leu Ala Trp Tyr Gln Gln Lys Pro Gly Gln Val Pro Lys Leu Leu Ile
            35                  40                  45

Tyr Asp Ala Ser Ser Leu Tyr Thr Gly Val Pro Ser Arg Phe Ser Gly
    50                  55                  60

Ser Gly Ser Gly Thr Ser Phe Thr Leu Thr Ile Ser Gly Val Glu Ala
65                  70                  75                  80

Glu Asp Val Gly Thr Tyr Tyr Cys Gln Gln Tyr Asn Ser Ala Pro Pro
                85                  90                  95

<210> SEQ ID NO 449
<211> LENGTH: 96
<212> TYPE: PRT
<213> ORGANISM: Homo sapiens

<400> SEQUENCE: 449

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Pro
                85                  90                  95

<210> SEQ ID NO 450
<211> LENGTH: 96
<212> TYPE: PRT
<213> ORGANISM: Llama pacos

<400> SEQUENCE: 450

Ala Thr Gln Met Thr Gln Ser Pro Ser Ser Ser Leu Ser Ala Ser Leu Gly

```
                1               5                  10                  15
Asp Arg Val Thr Ile Thr Cys Gln Ala Ser Gln Ser Ile Ser Asn Glu
            20                  25                  30

Leu Ser Trp His Gln Gln Lys Pro Gly Gln Thr Pro Lys Leu Leu Ile
            35                  40                  45

Tyr Gly Ala Ser Arg Leu Gln Thr Gly Val Pro Ser Thr Phe Ser Gly
            50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Tyr Ser Ala Pro Pro
                85                  90                  95
```

<210> SEQ ID NO 451
<211> LENGTH: 96
<212> TYPE: PRT
<213> ORGANISM: Llama pacos

<400> SEQUENCE: 451

```
Ala Thr Gln Met Thr Gln Ser Ser Ser Leu Ser Ala Ser Leu Gly
1               5                  10                  15

Asp Arg Val Thr Ile Thr Cys Gln Ala Ser Gln Ser Ile Ser Asn Glu
            20                  25                  30

Leu Ser Trp His Gln Gln Lys Pro Gly Gln Thr Pro Lys Leu Leu Ile
            35                  40                  45

Tyr Gly Ala Ser Arg Leu Gln Thr Gly Val Pro Ser Arg Phe Ser Gly
            50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys Gln Gln Tyr Tyr Ser Ala Pro Pro
                85                  90                  95
```

<210> SEQ ID NO 452
<211> LENGTH: 88
<212> TYPE: PRT
<213> ORGANISM: Llama glama

<400> SEQUENCE: 452

```
Ala Thr Gln Met Thr Gln Ser Ser Ser Leu Ser Ala Ser Leu Gly
1               5                  10                  15

Asp Arg Val Thr Ile Thr Cys Gln Ala Ser Gln Ser Ile Ser Asn Glu
            20                  25                  30

Leu Ser Trp His Gln Gln Lys Pro Gly Gln Thr Pro Lys Leu Leu Ile
            35                  40                  45

Tyr Gly Ala Ser Arg Leu Gln Thr Gly Val Pro Ser Arg Phe Ser Gly
            50                  55                  60

Ser Gly Ser Gly Thr Ser Phe Thr Leu Thr Ile Ser Gly Leu Glu Ala
65                  70                  75                  80

Glu Asp Ala Gly Thr Tyr Tyr Cys
                85
```

<210> SEQ ID NO 453
<211> LENGTH: 96
<212> TYPE: PRT
<213> ORGANISM: Llama pacos

<400> SEQUENCE: 453

```
Ala Thr Gln Met Thr Gln Ser Pro Ser Ser Leu Ser Ala Ser Leu Gly
1               5                  10                  15
```

Asp Arg Val Thr Ile Thr Cys Gln Ala Ser Gln Ser Ile Ser Thr Glu
            20                  25                  30

Leu Ser Trp Tyr Gln Gln Lys Pro Gly Gln Thr Pro Lys Leu Leu Ile
            35                  40                  45

Tyr Gly Ala Ser Arg Leu Gln Thr Gly Val Pro Ser Arg Phe Ser Gly
    50                  55                  60

Ser Gly Ser Gly Thr Ser Phe Thr Leu Thr Ile Ser Gly Leu Glu Ala
65                  70                  75                  80

Glu Asp Leu Ala Thr Tyr Tyr Cys Leu Gln Asp Tyr Ser Trp Pro Pro
                85                  90                  95

<210> SEQ ID NO 454
<211> LENGTH: 96
<212> TYPE: PRT
<213> ORGANISM: Camelus ferus

<400> SEQUENCE: 454

Ala Thr Gln Met Thr Gln Ser Pro Ser Ser Leu Ser Ala Ser Leu Gly
1               5                   10                  15

Asp Thr Val Thr Ile Thr Cys Arg Ala Ser Gln Ser Ile Ser Asn Glu
            20                  25                  30

Leu Ser Trp Tyr Gln Gln Lys Pro Gly Gln Ala Pro Lys Leu Leu Ile
            35                  40                  45

Tyr Asp Ala Ser Ser Leu His Thr Gly Val Pro Ser Lys Phe Ser Gly
    50                  55                  60

Ser Gly Ser Gly Thr Ser Phe Thr Leu Thr Ile Ser Gly Val Glu Ala
65                  70                  75                  80

Glu Asp Ala Gly Thr Tyr Tyr Ser Gln Gln Tyr Tyr Arg Ala Pro Pro
                85                  90                  95

<210> SEQ ID NO 455
<211> LENGTH: 88
<212> TYPE: PRT
<213> ORGANISM: Camelus ferus

<400> SEQUENCE: 455

Ala Thr Gln Met Thr Gln Ser Pro Ser Ser Leu Ser Ala Ser Leu Gly
1               5                   10                  15

Asp Thr Val Thr Ile Thr Cys Gln Ala Ser Gln Ser Ile Ser Ser Tyr
            20                  25                  30

Leu Ala Trp His Gln Gln Lys Pro Gly Gln Ala Pro Lys Leu Leu Ile
            35                  40                  45

Tyr Gly Ala Ser Ser Leu His Thr Gly Phe Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 456
<211> LENGTH: 86
<212> TYPE: PRT
<213> ORGANISM: Camelus ferus

<400> SEQUENCE: 456

Ala Thr Gln Met Thr Gln Ser Pro Ser Ser Leu Ser Ala Ser Leu Gly
1               5                   10                  15

Asp Thr Val Thr Ile Thr Cys Gln Ala Ser Gln Ser Ile Ser Ser Tyr
            20                  25                  30

Leu Ala Trp His Gln Gln Lys Pro Gly Gln Ala Pro Lys Leu Leu Ile
        35                  40                  45

Tyr Gly Ala Ser Ser Leu His Thr Gly Phe Pro Ser Arg Phe Ser Gly
    50                  55                  60

Ser Gly Ser Gly Thr Ser Phe Thr Leu Thr Ile Arg Asp Arg Thr Asn
65                  70                  75                  80

Lys Ile Ala Ala Ala Val
                85

<210> SEQ ID NO 457
<211> LENGTH: 86
<212> TYPE: PRT
<213> ORGANISM: Llama pacos

<400> SEQUENCE: 457

Glu Ile Val Leu Thr Gln Ser Pro Ala Ser Lys Ala Val Ser Gln Gly
1               5                   10                  15

Glu Arg Val Thr Ile Thr Cys Ser Ala Ser Ser Ser Val Ser Thr Cys
            20                  25                  30

Tyr Leu Thr Leu Val Pro Thr Glu Ala Gln Ser Pro Ser Gln Ala Pro
        35                  40                  45

Tyr Phe His Ile Gln Pro Gly Phe Trp Gly Pro Ile Pro Leu Gln Trp
    50                  55                  60

Gln Trp Ile Trp Asp Leu Leu Leu Ser His His Gln Gln Arg Gly Gly
65                  70                  75                  80

Arg Cys Cys Arg Leu Leu
                85

<210> SEQ ID NO 458
<211> LENGTH: 86
<212> TYPE: PRT
<213> ORGANISM: Llama pacos

<400> SEQUENCE: 458

Glu Ile Val Leu Thr Gln Ser Pro Ala Ser Lys Ala Val Ser Gln Glu
1               5                   10                  15

Glu Arg Val Thr Ile Thr Cys Ser Ala Ser Ser Ser Val Ser Thr Cys
            20                  25                  30

Tyr Leu Thr Leu Val Pro Thr Glu Ala Gln Ser Pro Ser Gln Ala Pro
        35                  40                  45

Tyr Phe His Ile Gln Pro Gly Phe Trp Gly Pro Ile Pro Leu Gln Trp
    50                  55                  60

Gln Trp Ile Trp Asp Leu Leu Leu Ser His His Gln Gln Arg Gly Gly
65                  70                  75                  80

Arg Cys Cys Arg Leu Leu
                85

<210> SEQ ID NO 459
<211> LENGTH: 86
<212> TYPE: PRT
<213> ORGANISM: Camelus ferus

<400> SEQUENCE: 459

Glu Ile Val Leu Thr Gln Ser Pro Ala Ser Lys Ala Val Ser Gln Gly
1               5                   10                  15

Glu Arg Val Thr Ile Thr Cys Ser Ala Ser Ser Ser Val Ser Thr Cys

```
                      20                  25                  30

Tyr Leu Thr Leu Leu Pro Thr Glu Ala Arg Ser Pro Ser Gln Ala Pro
            35                  40                  45

Tyr Leu His Ile Gln Pro Gly Leu Trp Gly Pro Ile Pro Leu Gln Trp
        50                  55                  60

Gln Trp Ile Trp Asp Leu Leu Ser His His Gln Gln Arg Gly Gly
 65                  70                  75                  80

Arg Tyr Cys Arg Leu Leu
                85

<210> SEQ ID NO 460
<211> LENGTH: 100
<212> TYPE: PRT
<213> ORGANISM: Homo sapiens

<400> SEQUENCE: 460

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                85                  90                  95

Ile Gln Leu Pro
            100

<210> SEQ ID NO 461
<211> LENGTH: 100
<212> TYPE: PRT
<213> ORGANISM: Llama pacos

<400> SEQUENCE: 461

Asp Val Val Leu Thr Gln Thr Pro Gly Ser Leu Ser Val Pro Gly
 1               5                  10                  15

Glu Ser Ala Ser Ile Ser Cys Lys Ala Ser Gln Ser Leu Val His Thr
            20                  25                  30

Asp Gly Lys Thr Tyr Leu Tyr Trp Leu Leu Gln Lys Pro Gly Gln Ser
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
 65                  70                  75                  80

Ser Gly Val Lys Ala Glu Asp Ala Gly Val Tyr Tyr Cys Ala Gln Ala
                85                  90                  95

Ile Tyr Asp Pro
            100

<210> SEQ ID NO 462
<211> LENGTH: 100
<212> TYPE: PRT
<213> ORGANISM: Llama pacos

<400> SEQUENCE: 462
```

Asp Val Val Leu Thr Gln Thr Pro Gly Ser Leu Ser Val Ile Pro Gly
1               5                   10                  15

Glu Ser Ala Ser Ile Ser Cys Lys Ala Ser Gln Ser Leu Val His Ser
                20                  25                  30

Asp Gly Lys Thr Tyr Leu Tyr Trp Leu Leu Gln Lys Pro Gly Gln Ser
            35                  40                  45

Pro Gln Arg Leu Ile Tyr Gln Val Ser Asn Arg Gly Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Ile Tyr Asp Pro
            100

<210> SEQ ID NO 463
<211> LENGTH: 98
<212> TYPE: PRT
<213> ORGANISM: Llama pacos

<400> SEQUENCE: 463

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
                20                  25                  30

Asp Gly Lys Thr Tyr Leu Tyr Trp Leu Leu Gln Lys Pro Gly Gln Ser
            35                  40                  45

Pro Gln Arg Leu Ile Tyr Gln Val Ser Asn Arg Gly Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Ile Tyr

<210> SEQ ID NO 464
<211> LENGTH: 93
<212> TYPE: PRT
<213> ORGANISM: Llama glama

<400> SEQUENCE: 464

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
                20                  25                  30

Asp Gly Lys Thr Tyr Leu Tyr Trp Leu Leu Gln Lys Pro Gly Gln Ser
            35                  40                  45

Pro Gln Arg Leu Ile Tyr Gln Val Ser Asn Arg Gly Ser Gly Val Pro
        50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys
                85                  90

<210> SEQ ID NO 465
<211> LENGTH: 93

<212> TYPE: PRT
<213> ORGANISM: Llama glama

<400> SEQUENCE: 465

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Ser
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys
            85                  90

<210> SEQ ID NO 466
<211> LENGTH: 100
<212> TYPE: PRT
<213> ORGANISM: Camelus ferus

<400> SEQUENCE: 466

Glu Val Val Leu Thr Gln Thr Pro Gly Pro Leu Ser Val Thr Pro Gly
1               5                   10                  15

Glu Pro Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Pro
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
            85                  90                  95

Thr Arg Asp Arg
            100

<210> SEQ ID NO 467
<211> LENGTH: 99
<212> TYPE: PRT
<213> ORGANISM: Camelus ferus

<400> SEQUENCE: 467

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Arg Gln Lys Pro Gly Gln Ser
        35                  40                  45

Pro Gln Leu Ile Tyr Gln Val Ser Lys Arg Gly Ser Gly Val Pro Asp
    50                  55                  60

Arg Phe Thr Gly Ser Gly Ser Gly Thr Asp Phe Thr Leu Lys Ile Ser
65                  70                  75                  80

Gly Val Lys Ala Glu Asp Ala Gly Val His Tyr Cys Ala Gln Ala Thr
            85                  90                  95

Gln Ser Pro

<210> SEQ ID NO 468
<211> LENGTH: 93
<212> TYPE: PRT
<213> ORGANISM: Llama glama

<400> SEQUENCE: 468

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Val His Ser
            20                  25                  30

Asp Gly Lys Thr Tyr Leu Tyr Trp Leu Leu Gln Lys Pro Gly Gln Ser
        35                  40                  45

Pro Gln Arg Leu Ile Tyr Gln Val Ser Asn Arg Gly Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys
                85                  90

<210> SEQ ID NO 469
<211> LENGTH: 98
<212> TYPE: PRT
<213> ORGANISM: Llama pacos

<400> SEQUENCE: 469

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Ile His Thr
            20                  25                  30

Asp Gly Lys Thr Tyr Leu Tyr Trp Leu Leu Gln Lys Pro Gly Gln Arg
        35                  40                  45

Pro Gln Leu Leu Ile Tyr Gln Val Ser Asn His Glu Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys Ala Gln Ala
                85                  90                  95

Thr Tyr

<210> SEQ ID NO 470
<211> LENGTH: 93
<212> TYPE: PRT
<213> ORGANISM: Llama glama

<400> SEQUENCE: 470

Asp Val Val Leu Thr Gln Thr Pro Gly Ser Leu Ser Val Val Pro Gly
1               5                   10                  15

Glu Ser Ala Ser Ile Ser Cys Lys Ala Ser Gln Ser Leu Ile His Thr
            20                  25                  30

Asp Gly Lys Thr Tyr Leu Tyr Trp Leu Leu Gln Lys Pro Gly Gln Arg
        35                  40                  45

Pro Gln Leu Leu Ile Tyr Gln Val Ser Asn His Glu Ser Gly Val Pro
    50                  55                  60

Asp Arg Phe Thr Gly Ser Gly Ser Gly Thr Asp Phe Thr Leu Lys Ile
65                  70                  75                  80

Ser Gly Val Lys Ala Glu Asp Ala Gly Val Tyr Tyr Cys

```
                              85                  90

<210> SEQ ID NO 471
<211> LENGTH: 100
<212> TYPE: PRT
<213> ORGANISM: Llama pacos

<400> SEQUENCE: 471

Asp Leu Val Leu Thr Gln Ile Pro Gly Ser Leu Ser Val Thr Pro Gly
1               5                   10                  15

Glu Pro Ala Ser Ile Ser Cys Arg Ser Thr Glu Asn Leu Glu Asp Ser
            20                  25                  30

Glu Gly Asp Thr Tyr Leu Ser Trp Tyr Leu Gln Lys Pro Gly Gln Ser
        35                  40                  45

Pro Gln Met Leu Ile Phe Ala Gly Ser Arg Ala Pro Gly Ile Pro
    50                  55                  60

Asp Arg Phe Thr Gly Ser Gly Ser Glu Thr Ala Phe Thr Leu Lys Ile
65                  70                  75                  80

Ser Gly Val Lys Ala Glu Asp Ala Gly Val Tyr Tyr Cys Ala Gln Ser
                85                  90                  95

Leu Pro Thr Val
            100

<210> SEQ ID NO 472
<211> LENGTH: 101
<212> TYPE: PRT
<213> ORGANISM: Homo sapiens

<400> SEQUENCE: 472

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
        35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 473
<211> LENGTH: 101
<212> TYPE: PRT
<213> ORGANISM: Llama pacos

<400> SEQUENCE: 473

Asn Ile Val Leu Thr Arg Phe Leu Ala Ser Val Ile Ala Ser Pro Gly
1               5                   10                  15

Glu Leu Ala Thr Ile Ser Cys Arg Ala Ser Arg Val Ser Gly Ile
            20                  25                  30

Leu Gly Ile Ile Ile Leu Val Asn Trp Cys Lys Gln Lys Pro Gly Gln
        35                  40                  45

Pro Pro Lys Leu Leu Ile Cys Ala Ala Thr Arg Arg Ala Pro Gly Val
    50                  55                  60
```

Pro Ala Arg Phe Arg Gly Ser Gly Ser Gly Thr Asp Phe Thr Leu Thr
65                  70                  75                  80

Ile His Pro Val Glu Ala Asp Asp Ala Glu Glu Asp Phe Cys Gln His
                85                  90                  95

Ser Lys Glu Asp Pro
            100

<210> SEQ ID NO 474
<211> LENGTH: 101
<212> TYPE: PRT
<213> ORGANISM: Llama pacos

<400> SEQUENCE: 474

Asn Ile Val Leu Thr Arg Phe Leu Ala Ser Val Ile Ala Ser Pro Gly
1               5                   10                  15

Glu Leu Ala Thr Ile Ser Cys Arg Ala Ser Arg Val Ser Val Ile
            20                  25                  30

Leu Gly Ile Ile Ile Leu Val Asn Trp Cys Lys Gln Lys Pro Gly Gln
            35                  40                  45

Pro Pro Lys Leu Leu Ile Cys Ala Ala Thr Arg Ala Pro Gly Val
        50                  55                  60

Pro Ala Arg Phe Arg Gly Ser Gly Ser Gly Thr Asp Phe Thr Leu Thr
65                  70                  75                  80

Ile His Pro Val Glu Ala Asp Asp Ala Glu Glu Asp Phe Cys Gln His
                85                  90                  95

Ser Lys Glu Asp Pro
            100

<210> SEQ ID NO 475
<211> LENGTH: 100
<212> TYPE: PRT
<213> ORGANISM: Camelus ferus

<400> SEQUENCE: 475

Asn Ile Val Leu Thr Arg Phe Leu Ala Ser Val Ile Ala Ser Pro Gly
1               5                   10                  15

Glu Ala Thr Ile Ser Cys Arg Ala Ser Arg Arg Val Ser Gly Ile Leu
            20                  25                  30

Gly Ile Ile Ile Leu Val Asn Trp Cys Lys Gln Lys Pro Gly Gln Pro
            35                  40                  45

Pro Lys Leu Leu Ile Cys Ala Ala Thr Cys Arg Ala Pro Gly Val Pro
        50                  55                  60

Ala Arg Phe Cys Ser Ser Gly Ser Gly Thr Asp Phe Thr Leu Thr Ile
65                  70                  75                  80

His Pro Val Glu Ala Asp Asp Ala Glu Glu Asp Phe Cys Gln His Ser
                85                  90                  95

Lys Glu Asp Pro
            100

<210> SEQ ID NO 476
<211> LENGTH: 94
<212> TYPE: PRT
<213> ORGANISM: Llama glama

<400> SEQUENCE: 476

Asn Ile Val Leu Thr Arg Phe Leu Ala Ser Val Ile Ala Ser Pro Gly
1               5                   10                  15

```
Glu Leu Ala Thr Ile Ser Cys Arg Ala Ser Arg Val Ser Gly Ile
                20                  25                  30

Leu Gly Ile Ile Ile Leu Val Asn Trp Cys Lys Gln Lys Pro Gly Gln
         35                  40                  45

Pro Pro Lys Leu Leu Ile Cys Ala Ala Thr Arg Leu Ala Pro Gly Val
 50                  55                  60

Pro Ala Arg Phe Arg Gly Ser Gly Ser Gly Thr Asp Phe Thr Leu Thr
 65                  70                  75                  80

Ile His Pro Val Glu Ala Asp Asp Ala Glu Glu Asp Phe Cys
                85                  90
```

<210> SEQ ID NO 477
<211> LENGTH: 96
<212> TYPE: PRT
<213> ORGANISM: Homo sapiens

<400> SEQUENCE: 477

```
Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                85                  90                  95
```

<210> SEQ ID NO 478
<211> LENGTH: 96
<212> TYPE: PRT
<213> ORGANISM: Camelus ferus

<400> SEQUENCE: 478

```
Ser Ala Val Leu Thr Gln Thr Pro Ala Ile Leu Ser Val Ser Leu Arg
 1               5                  10                  15

Glu Ser Ile Ser Ile Thr Cys Thr Ala Asn Glu Ser Val Ser Asp Tyr
                20                  25                  30

Val Ser Trp Tyr Gln Gln Lys Pro Gly Gln Ala Pro Arg Leu Leu Ile
         35                  40                  45

Tyr Asp Ala Asp Asp Arg Tyr Pro Gly Val Pro Asp Arg Phe Val Gly
 50                  55                  60

Leu Gln Ser Gly Thr Gln Phe Ile Leu Thr Ile Asn Lys Val Glu Ala
 65                  70                  75                  80

Asp Asp Ala Ala Ser Tyr Tyr Cys Gln Gln Gly Tyr Thr Val Pro Pro
                85                  90                  95
```

<210> SEQ ID NO 479
<211> LENGTH: 96
<212> TYPE: PRT
<213> ORGANISM: Llama pacos

<400> SEQUENCE: 479

```
Ser Ala Glu Leu Thr Gln Thr Pro Ala Ile Leu Ser Val Ser Leu Arg
 1               5                  10                  15

Glu Ser Ile Ser Ile Thr Cys Thr Ala Ser Glu Ser Val Ser Asp Tyr
```

```
                    20                  25                  30

Val Ser Trp Tyr Gln Gln Lys Pro Gly Gln Ala Pro Arg Leu Leu Ile
            35                  40                  45

Tyr Asp Thr Asp Arg Tyr Ser Gly Val Pro Asp Arg Phe Val Gly
    50                  55                  60

Leu Gln Ser Gly Thr Gln Phe Ile Leu Thr Ile Asn Asn Val Glu Ala
65                  70                  75                  80

Asp Asp Thr Ala Ser Tyr Tyr Cys Phe His Asp Tyr Thr Val Pro Pro
                85                  90                  95

<210> SEQ ID NO 480
<211> LENGTH: 96
<212> TYPE: PRT
<213> ORGANISM: Camelus ferus

<400> SEQUENCE: 480

Gln Ile Ala Leu Thr Gln Phe Pro Glu Ser Leu Ala Ala Ser His Gly
1               5                   10                  15

Ser Leu Val Ser Ile Thr Cys Arg Ser Ser Ile Glu Val Gly Thr Ser
                20                  25                  30

Met Ala Trp Tyr Gln Gln Lys Pro Lys Glu Ala Pro Arg Leu Leu Ile
            35                  40                  45

Phe Gly Ala Ser Ala Arg Ala Ser Gly Thr Pro Ser Arg Phe Ser Gly
    50                  55                  60

Ser Gly Ser Gly Ser Asp Phe Ser Leu Ala Ile His Gly Val Glu Ala
65                  70                  75                  80

Glu Asp Val Gly Val Tyr Tyr Cys Gln Gln His Ala Ser Leu Pro Leu
                85                  90                  95

<210> SEQ ID NO 481
<211> LENGTH: 96
<212> TYPE: PRT
<213> ORGANISM: Llama pacos

<400> SEQUENCE: 481

Gln Ile Ala Leu Thr Gln Phe Pro Glu Ser Leu Ala Ala Ser His Gly
1               5                   10                  15

Ser Leu Val Ser Ile Thr Cys Arg Ser Ser Met Glu Val Gly Thr Ser
                20                  25                  30

Met Ala Trp Tyr Gln Gln Lys Pro Lys Glu Ala Pro Arg Leu Leu Ile
            35                  40                  45

Phe Gly Ala Ser Ala Arg Ala Ser Gly Thr Pro Ser Arg Phe Ser Gly
    50                  55                  60

Ser Gly Ser Gly Ser Asp Phe Ser Leu Ala Ile His Gly Val Glu Ala
65                  70                  75                  80

Glu Asp Val Gly Val Tyr Tyr Cys Gln Gln His Ile Ser Leu Pro Leu
                85                  90                  95

<210> SEQ ID NO 482
<211> LENGTH: 102
<212> TYPE: PRT
<213> ORGANISM: Homo sapiens

<400> SEQUENCE: 482

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30
```

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
             85                  90                  95

Tyr Tyr Ser Thr Pro Pro
            100

<210> SEQ ID NO 483
<211> LENGTH: 102
<212> TYPE: PRT
<213> ORGANISM: Llama pacos

<400> SEQUENCE: 483

Asp Ile Val Met Thr Gln Ser Pro Ser Ser Val Thr Ala Ser Ala Gly
 1               5                  10                  15

Glu Lys Val Thr Ile Asn Cys Lys Ser Ser Gln Ser Val Leu Tyr Ser
             20                  25                  30

Ser Asn Gln Lys Asn Tyr Leu Ala Trp Tyr Gln Gln Arg Pro Gly Gln
         35                  40                  45

Ser Pro Arg Leu Leu Ile Tyr Trp Ala Ser Thr Arg Glu Ser Gly Val
 50                  55                  60

Pro Asp Arg Phe Ser Ser Ser Gly Ser Thr Thr Asp Phe Thr Leu Thr
 65                  70                  75                  80

Ile Ser Ser Phe Gln Pro Glu Asp Val Ala Val Tyr Tyr Cys Gln Gln
             85                  90                  95

Ala Tyr Ser Ala Pro Pro
            100

<210> SEQ ID NO 484
<211> LENGTH: 94
<212> TYPE: PRT
<213> ORGANISM: Llama glama

<400> SEQUENCE: 484

Asp Ile Val Met Thr Gln Ser Pro Ser Ser Val Thr Ala Ser Ala Gly
 1               5                  10                  15

Glu Lys Val Thr Ile Asn Cys Lys Ser Ser Gln Ser Val Leu Tyr Ser
             20                  25                  30

Ser Asn Gln Lys Asn Tyr Leu Ala Trp Tyr Gln Gln Arg Leu Gly Gln
         35                  40                  45

Ser Pro Arg Leu Leu Ile Tyr Trp Ala Ser Thr Arg Glu Ser Gly Val
 50                  55                  60

Pro Asp Arg Phe Ser Gly Ser Gly Ser Thr Thr Asp Phe Thr Leu Thr
 65                  70                  75                  80

Ile Ser Ser Phe Gln Pro Glu Asp Val Ala Val Tyr Tyr Cys
             85                  90

<210> SEQ ID NO 485
<211> LENGTH: 102
<212> TYPE: PRT
<213> ORGANISM: Camelus ferus

<400> SEQUENCE: 485

```
Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Leu Ser Ser
            20                  25                  30

Ser Asn Gln Lys Ser Tyr Leu Ala Trp Tyr Gln Gln Arg Pro Gly Gln
        35                  40                  45

Ser Pro Arg Leu Leu Ile Tyr Tyr Ala Ser Thr Arg Glu Ser Gly Val
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Ser
            100

<210> SEQ ID NO 486
<211> LENGTH: 102
<212> TYPE: PRT
<213> ORGANISM: Camelus ferus

<400> SEQUENCE: 486

Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Phe Ser Ser
            20                  25                  30

Ser Ser Gln Lys Ser Leu Leu Ala Trp His Gln Gln Arg Asn Gly Gln
        35                  40                  45

Ser Pro Arg Arg Leu Ile Tyr Tyr Ala Ser Thr Arg Ala Ser Gly Val
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Pro
            100

<210> SEQ ID NO 487
<211> LENGTH: 102
<212> TYPE: PRT
<213> ORGANISM: Llama pacos

<400> SEQUENCE: 487

Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Val Ser Gly
            20                  25                  30

Ser Asn Gln Lys Ser Tyr Leu Asn Trp Tyr Gln Gln Arg Pro Gly Gln
        35                  40                  45

Ser Pro Arg Leu Leu Ile Tyr Tyr Ala Ser Thr Gln Glu Ser Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Ser
            100
```

<210> SEQ ID NO 488
<211> LENGTH: 102
<212> TYPE: PRT
<213> ORGANISM: Llama pacos

<400> SEQUENCE: 488

Asp Ile Val Met Thr Gln Ser Pro Ser Ser Val Thr Ala Ser Val Gly
1               5                   10                  15

Glu Lys Val Thr Ile Asn Cys Lys Ser Ser Gln Ser Val Ser Gly
            20                  25                  30

Ser Asn Gln Lys Ser Tyr Leu Asn Trp Tyr Gln Gln Arg Pro Gly Gln
        35                  40                  45

Ser Pro Arg Leu Leu Ile Tyr Tyr Ala Ser Thr Gln Glu Leu Gly Ile
    50                  55                  60

Pro Asp Arg Phe Ser Gly Ser Gly Ser Thr Thr Asp Phe Thr Leu Thr
65                  70                  75                  80

Ile Ser Ser Val Gln Pro Glu Asp Ala Ala Val Tyr Tyr Cys Gln Gln
                85                  90                  95

Ala Tyr Ser Ala Pro Ser
            100

<210> SEQ ID NO 489
<211> LENGTH: 96
<212> TYPE: PRT
<213> ORGANISM: Homo sapiens

<400> SEQUENCE: 489

Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Leu
                85                  90                  95

<210> SEQ ID NO 490
<211> LENGTH: 96
<212> TYPE: PRT
<213> ORGANISM: Camelus ferus

<400> SEQUENCE: 490

Glu Thr Val Leu Thr Gln Ser Pro Ala Leu Val Ser Ala Thr Pro Gly
1               5                   10                  15

Asp Lys Val Thr Leu Thr Cys Lys Ala Ser Gln Asp Ile Asp Asp Asp
            20                  25                  30

Ile Met Trp Tyr Gln Gln Lys Pro Gly Gln Ala Pro Arg Leu Ile Ile
        35                  40                  45

Lys Tyr Val Ser Thr Leu Ile Ser Gly Val Pro Ser Arg Phe Ser Gly
    50                  55                  60

Ser Gly Tyr Gly Thr Asp Phe Asn Leu Thr Ile Asp Asn Met Lys Ser
65                  70                  75                  80

Glu Asp Ala Ala Tyr Tyr Phe Cys Gln Gln Asp Asp Asn Thr Pro Leu

```
                85                  90                  95

<210> SEQ ID NO 491
<211> LENGTH: 96
<212> TYPE: PRT
<213> ORGANISM: Llama pacos

<400> SEQUENCE: 491

Glu Thr Val Pro Thr Gln Ser Pro Ala Leu Ala Ser Ala Thr Pro Gly
1               5                   10                  15

Asp Lys Val Thr Leu Thr Cys Lys Val Ser Gln Asp Thr Asp Asp Asp
            20                  25                  30

Ile Met Trp Tyr Gln Gln Lys Pro Gly Gln Ala Pro Arg Leu Ile Thr
        35                  40                  45

Lys Tyr Asp Ser Thr Val Ile Ser Gly Leu Pro Ser Arg Phe Ser Gly
    50                  55                  60

Ser Gly Tyr Gly Thr Asp Phe Thr Leu Thr Ile Asp Asn Met Lys Ser
65                  70                  75                  80

Glu Asp Ala Ala Tyr Tyr Phe Cys Gln Gln Asp Asn Ile Pro Leu
                85                  90                  95

<210> SEQ ID NO 492
<211> LENGTH: 88
<212> TYPE: PRT
<213> ORGANISM: Llama glama

<400> SEQUENCE: 492

Glu Thr Val Pro Ile Gln Ser Pro Ala Leu Ala Ser Ala Thr Pro Gly
1               5                   10                  15

Asp Lys Val Thr Leu Thr Cys Lys Ala Ser Gln Asp Thr Asp Asp Asp
            20                  25                  30

Ile Met Trp Tyr Gln Gln Lys Pro Gly Gln Ala Pro Arg Leu Ile Ile
        35                  40                  45

Lys Tyr Asp Ser Thr Leu Ile Ser Gly Val Pro Ser Arg Phe Ser Gly
    50                  55                  60

Ser Gly Tyr Gly Thr Asp Phe Thr Leu Thr Ile Asp Asn Met Lys Ser
65                  70                  75                  80

Glu Asp Ala Ala Tyr Tyr Phe Cys
                85

<210> SEQ ID NO 493
<211> LENGTH: 95
<212> TYPE: PRT
<213> ORGANISM: Homo sapiens

<400> SEQUENCE: 493

Asp Val Val Met Thr Gln Ser Pro Ala Phe Leu Ser Val Thr Pro Gly
1               5                   10                  15

Glu Lys Val Thr Ile Thr Cys Gln Ala Ser Glu Gly Ile Gly Asn Tyr
            20                  25                  30

Leu Tyr Trp Tyr Gln Gln Lys Pro Asp Gln Ala Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Lys His Pro
                85                  90                  95
```

<210> SEQ ID NO 494
<211> LENGTH: 95
<212> TYPE: PRT
<213> ORGANISM: Camelus ferus

<400> SEQUENCE: 494

Ala Thr Val Leu Thr Gln Ser Pro Ala Leu Leu Ser Lys Ala Pro Gly
1               5                   10                  15

Asp Lys Ala Thr Ile Thr Cys Arg Ala Ser Gln Ser Val Ser Asn Tyr
            20                  25                  30

Leu Arg Trp Tyr Lys Gln Lys Pro Asn Gln Pro Pro Lys Leu Leu Ile
        35                  40                  45

Gln Tyr Thr Ser Gln Thr Phe Ser Gly Val Pro Ala Arg Phe Ile Gly
    50                  55                  60

Ser Gly Ser Gly Thr Asp Phe Thr Leu Thr Ile Ser Ser Leu Glu Ala
65                  70                  75                  80

Glu Asp Ala Ala Lys Tyr Tyr Cys Gln Gln Gly Tyr Ser Ser
                85                  90                  95

<210> SEQ ID NO 495
<211> LENGTH: 95
<212> TYPE: PRT
<213> ORGANISM: Llama pacos

<400> SEQUENCE: 495

Ala Thr Met Leu Thr Gln Ser Pro Ala Leu Leu Ser Lys Ala Pro Gly
1               5                   10                  15

Asp Lys Ala Thr Ile Thr Cys Arg Ala Ser Gln Ser Ile Ser Thr Ser
            20                  25                  30

Leu His Trp Tyr Gln Gln Lys Pro Asn Gln Pro Pro Lys Leu Leu Ile
        35                  40                  45

Gln His Ala Ser Gln Thr Phe Ser Gly Val Pro Thr Arg Phe Ser Gly
    50                  55                  60

Ser Gly Ser Gly Thr Asp Phe Thr Leu Thr Ile Ser Ser Leu Glu Ala
65                  70                  75                  80

Glu Asp Ala Ala Lys Cys Tyr Cys Gln Gln Gly Tyr Ser Tyr Ser
                85                  90                  95

<210> SEQ ID NO 496
<211> LENGTH: 88
<212> TYPE: PRT
<213> ORGANISM: Llama glama

<400> SEQUENCE: 496

Ala Thr Met Leu Thr Gln Ser Pro Ala Leu Leu Ser Lys Ala Pro Gly
1               5                   10                  15

Asp Lys Ala Thr Ile Thr Cys Arg Ala Ser Gln Ser Ile Ser Thr Ser
            20                  25                  30

Leu His Trp Tyr Gln Gln Lys Pro Asn Gln Pro Pro Lys Leu Leu Ile
        35                  40                  45

Gln His Ala Ser Gln Thr Phe Ser Gly Val Pro Thr Arg Phe Ser Gly
    50                  55                  60

Ser Gly Ser Gly Thr Asp Phe Thr Leu Thr Ile Ser Ser Leu Glu Ala
65                  70                  75                  80

Glu Asp Ala Ala Lys Cys Tyr Cys
                85

```
<210> SEQ ID NO 497
<211> LENGTH: 23
<212> TYPE: DNA
<213> ORGANISM: Llama pacos

<400> SEQUENCE: 497
caggtccagc tggtgcagtc agg                                             23

<210> SEQ ID NO 498
<211> LENGTH: 23
<212> TYPE: DNA
<213> ORGANISM: Camel ferus

<400> SEQUENCE: 498
caggtccagc tggtgcagtc tgg                                             23

<210> SEQ ID NO 499
<211> LENGTH: 23
<212> TYPE: DNA
<213> ORGANISM: Camel ferus

<400> SEQUENCE: 499
caggtccagc tgctgcagtc tgg                                             23

<210> SEQ ID NO 500
<211> LENGTH: 294
<212> TYPE: DNA
<213> ORGANISM: Homo sapiens

<400> SEQUENCE: 500
gaggttgtgc tgactcagcc cagctctgtg tcggggtctc ctgggcagaa ggtcaccatc     60
tcctgtgccc gcagcagcga caacactggg gattgtgcac tgctaccagc agcgcccagg   120
cagtgccccc accactgtaa tctacaaaga tgatgaaaga ccctctgagg ttcccgctcg   180
gttccctgac tccactgaca cctcctccag tgctgcctcc ctgaccatct ctgggctgaa   240
gcccgaggac gaggccgact actgttgtca gtctggttat gacagcagta agaa         294

<210> SEQ ID NO 501
<211> LENGTH: 91
<212> TYPE: PRT
<213> ORGANISM: Homo sapiens

<400> SEQUENCE: 501

Glu Val Val Leu Thr Gln Pro Ser Ser Val Ser Gly Ser Pro Gly Gln
1               5                   10                  15

Lys Val Thr Ile Ser Cys Ala Arg Ser Ser Asp Asn Thr Gly Asp Cys
            20                  25                  30

Ala Leu Leu Pro Ala Ala Pro Arg Gln Cys Pro His His Cys Asn Leu
        35                  40                  45

Gln Arg Lys Thr Leu Gly Ser Arg Ser Val Pro Leu His His Leu Leu
    50                  55                  60

Gln Cys Cys Leu Pro Asp His Leu Trp Ala Glu Ala Arg Gly Arg Gly
65                  70                  75                  80

Arg Leu Leu Leu Ser Val Trp Leu Gln Gln Glu
                85                  90

<210> SEQ ID NO 502
<211> LENGTH: 96
<212> TYPE: PRT
<213> ORGANISM: Homo sapiens
```

-continued

<400> SEQUENCE: 502

Arg Leu Cys Leu Ser Pro Ala Leu Cys Arg Gly Leu Gly Arg Arg
1               5                   10                  15

Ser Pro Ser Pro Val Pro Ala Ala Thr Thr Leu Gly Ile Val His
            20                  25                  30

Cys Tyr Gln Gln Arg Pro Gly Ser Ala Pro Thr Thr Val Ile Tyr Lys
                35                  40                  45

Asp Asp Glu Arg Pro Ser Glu Val Pro Ala Arg Phe Pro Asp Ser Thr
            50                  55                  60

Asp Thr Ser Ser Ala Ala Ser Leu Thr Ile Ser Gly Leu Lys Pro
65                  70                  75                  80

Glu Asp Glu Ala Asp Tyr Cys Cys Gln Ser Gly Tyr Asp Ser Ser Lys
                85                  90                  95

<210> SEQ ID NO 503
<211> LENGTH: 94
<212> TYPE: PRT
<213> ORGANISM: Homo sapiens

<400> SEQUENCE: 503

Gly Cys Ala Asp Ser Ala Gln Leu Cys Val Gly Val Ser Trp Ala Glu
1               5                   10                  15

Gly His His Leu Leu Cys Pro Gln Gln Arg Gln His Trp Gly Leu Cys
            20                  25                  30

Thr Ala Thr Ser Ser Ala Gln Ala Val Pro Pro Leu Ser Thr Lys
                35                  40                  45

Met Met Lys Asp Pro Leu Arg Phe Pro Leu Gly Ser Leu Thr Pro Leu
            50                  55                  60

Thr Pro Pro Pro Val Leu Pro Pro Ser Leu Gly Ser Pro Arg Thr
65                  70                  75                  80

Arg Pro Thr Thr Val Val Ser Leu Val Met Thr Ala Val Arg
                85                  90

<210> SEQ ID NO 504
<211> LENGTH: 94
<212> TYPE: PRT
<213> ORGANISM: Homo sapiens

<400> SEQUENCE: 504

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
                35                  40                  45

Glu Asp Ser Lys Arg Pro Ser Gly Ile Pro Glu Arg Phe Ser Gly Ser
            50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Gly
                85                  90

<210> SEQ ID NO 505
<211> LENGTH: 94
<212> TYPE: PRT
<213> ORGANISM: Homo sapiens

<400> SEQUENCE: 505

```
Ser Tyr Glu Leu Thr Gln Pro Pro Ser Val Ser Val Ser Leu Gly Gln
1               5                   10                  15

Met Ala Arg Ile Thr Cys Ser Gly Glu Ala Leu Pro Lys Lys Tyr Ala
                20                  25                  30

Tyr Trp Tyr Gln Gln Lys Pro Gly Gln Phe Pro Val Leu Val Ile Tyr
            35                  40                  45

Lys Asp Ser Glu Arg Pro Ser Gly Ile Pro Glu Arg Phe Ser Gly Ser
    50                  55                  60

Ser Ser Gly Thr Ile Val Thr Leu Thr Ile Ser Gly Tyr Gln Val Glu
65                  70                  75                  80

Asp Glu Ala Asp Tyr Tyr Cys Leu Ser Ala Asp Ser Ser Gly
                85                  90
```

<210> SEQ ID NO 506
<211> LENGTH: 94
<212> TYPE: PRT
<213> ORGANISM: Homo sapiens

<400> SEQUENCE: 506

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly
                85                  90
```

<210> SEQ ID NO 507
<211> LENGTH: 94
<212> TYPE: PRT
<213> ORGANISM: Homo sapiens

<400> SEQUENCE: 507

```
Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
                20                  25                  30

Asn Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser
                85                  90
```

<210> SEQ ID NO 508
<211> LENGTH: 94
<212> TYPE: PRT
<213> ORGANISM: Homo sapiens

<400> SEQUENCE: 508

Ser Tyr Glu Leu Thr Gln Leu Pro Ser Val Ser Val Ser Pro Gly Gln
1               5                   10                  15

Thr Ala Arg Ile Thr Cys Ser Gly Asp Val Leu Gly Glu Asn Tyr Ala
            20                  25                  30

Asp Trp Tyr Gln Gln Lys Pro Gly Gln Ala Pro Glu Leu Val Ile Tyr
        35                  40                  45

Glu Asp Ser Glu Arg Tyr Pro Gln Ile Pro Glu Arg Phe Ser Gly Ser
    50                  55                  60

Thr Ser Gly Asn Thr Thr Thr Leu Thr Ile Ser Arg Val Leu Thr Glu
65                  70                  75                  80

Asp Glu Ala Asp Tyr Tyr Cys Leu Ser Gly Asp Glu Asp Asn
            85                  90

<210> SEQ ID NO 509
<211> LENGTH: 94
<212> TYPE: PRT
<213> ORGANISM: Homo sapiens

<400> SEQUENCE: 509

Ser Tyr Glu Leu Met Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Val Gly Ala Glu
65                  70                  75                  80

Asp Glu Ala Asp Tyr Tyr Cys Gln Ser Ala Asp Ser Ser Gly
            85                  90

<210> SEQ ID NO 510
<211> LENGTH: 94
<212> TYPE: PRT
<213> ORGANISM: Homo sapiens

<400> SEQUENCE: 510

Ser Tyr Glu Leu Thr Gln Pro Ser Ser Val Ser Val Ser Pro Gly Gln
1               5                   10                  15

Thr Ala Arg Ile Thr Cys Ser Gly Asp Val Leu Ala Lys Lys Tyr Ala
            20                  25                  30

Arg Trp Phe Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Thr Ile Ser Gly Ala Gln Val Glu
65                  70                  75                  80

Asp Glu Ala Asp Tyr Tyr Cys Tyr Ser Ala Ala Asp Asn Asn
            85                  90

<210> SEQ ID NO 511
<211> LENGTH: 99
<212> TYPE: PRT
<213> ORGANISM: Homo sapiens

<400> SEQUENCE: 511

```
Leu Pro Val Leu Thr Gln Pro Pro Ser Ala Ser Ala Leu Leu Gly Ala
1               5                   10                  15

Ser Ile Lys Leu Thr Cys Thr Leu Ser Ser Glu His Ser Thr Tyr Thr
            20                  25                  30

Ile Glu Trp Tyr Gln Gln Arg Pro Gly Arg Ser Pro Gln Tyr Ile Met
            35                  40                  45

Lys Val Lys Ser Asp Gly Ser Asn Ser Lys Gly Asp Gly Ile Pro Asp
50                  55                  60

Arg Phe Met Gly Ser Ser Gly Ala Asp Arg Tyr Leu Thr Phe Ser
65                  70                  75                  80

Asn Leu Gln Ser Asp Asp Glu Ala Glu Tyr Asn Cys Gly Glu Ser His
            85                  90                  95

Thr Ile Asp
```

<210> SEQ ID NO 512
<211> LENGTH: 99
<212> TYPE: PRT
<213> ORGANISM: Homo sapiens

<400> SEQUENCE: 512

```
Gln Pro Val Leu Thr Gln Ser Ser Ser Ala Ser Ala Ser Leu Gly Ser
1               5                   10                  15

Ser Val Lys Leu Thr Cys Thr Leu Ser Ser Gly His Ser Ser Tyr Ile
            20                  25                  30

Ile Ala Trp Asn Gln Gln Pro Gly Lys Ala Pro Arg Tyr Leu Met
            35                  40                  45

Lys Leu Glu Gly Ser Gly Ser Tyr Asn Lys Gly Ser Gly Val Pro Asp
50                  55                  60

Arg Phe Ser Gly Ser Ser Gly Ala Asp Arg Tyr Leu Thr Ile Ser
65                  70                  75                  80

Asn Leu Gln Leu Glu Asp Glu Ala Asp Tyr Tyr Cys Glu Thr Trp Asp
            85                  90                  95

Ser Asn Thr
```

<210> SEQ ID NO 513
<211> LENGTH: 99
<212> TYPE: PRT
<213> ORGANISM: Homo sapiens

<400> SEQUENCE: 513

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Ser Tyr Ala
            20                  25                  30

Ile Ala Trp His Gln Gln Pro Glu Lys Gly Pro Arg Tyr Leu Met
            35                  40                  45

Lys Leu Asn Ser Asp Gly Ser His Ser Lys Gly Asp Gly Ile Pro Asp
50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
            85                  90                  95

Thr Gly Ile
```

<210> SEQ ID NO 514
<211> LENGTH: 103

<212> TYPE: PRT
<213> ORGANISM: Homo sapiens

<400> SEQUENCE: 514

Gln Pro Val Leu Thr Gln Pro Ser Ser Ser Ala Ser Pro Gly Glu
1               5                   10                  15

Ser Ala Arg Leu Thr Cys Thr Leu Pro Ser Asp Ile Asn Val Gly Ser
            20                  25                  30

Tyr Asn Ile Tyr Trp Tyr Gln Gln Lys Pro Gly Ser Pro Pro Arg Tyr
                35                  40                  45

Leu Leu Tyr Tyr Tyr Ser Asp Ser Asp Lys Gly Gln Gly Ser Gly Val
        50                  55                  60

Pro Ser Arg Phe Ser Gly Ser Lys Asp Ala Ser Ala Asn Thr Gly Ile
65                  70                  75                  80

Leu Leu Ile Ser Gly Leu Gln Ser Glu Asp Glu Ala Asp Tyr Tyr Cys
                85                  90                  95

Met Ile Trp Pro Ser Asn Ala
            100

<210> SEQ ID NO 515
<211> LENGTH: 103
<212> TYPE: PRT
<213> ORGANISM: Homo sapiens

<400> SEQUENCE: 515

Gln Ala Val Leu Thr Gln Pro Ala Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
                35                  40                  45

Leu Leu Arg Tyr Lys Ser Asp Ser Asp Lys Gln Gln Gly Ser Gly Val
        50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala
            100

<210> SEQ ID NO 516
<211> LENGTH: 103
<212> TYPE: PRT
<213> ORGANISM: Homo sapiens

<400> SEQUENCE: 516

Gln Pro Val Leu Thr Gln Pro Ser Ser His Ser Ala Ser Ser Gly Ala
1               5                   10                  15

Ser Val Arg Leu Thr Cys Met Leu Ser Ser Gly Phe Ser Tyr Gly Asp
            20                  25                  30

Phe Trp Ile Arg Trp Tyr Gln Gln Lys Pro Gly Asn Pro Pro Arg Tyr
                35                  40                  45

Leu Leu Tyr Tyr His Ser Asp Ser Asn Lys Gly Gln Gly Ser Gly Val
        50                  55                  60

Pro Ser Arg Phe Ser Gly Ser Asn Asp Ala Ser Ala Asn Ala Gly Ile
65                  70                  75                  80

Leu Arg Ile Ser Gly Leu Gln Pro Glu Asp Glu Ala Asp Tyr Tyr Cys

```
                      85                  90                  95
Gly Thr Trp His Ser Asn Ser
                100

<210> SEQ ID NO 517
<211> LENGTH: 98
<212> TYPE: PRT
<213> ORGANISM: Homo sapiens

<400> SEQUENCE: 517

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
                20                  25                  30

Tyr Val Gln Trp Tyr Gln Gln Arg Pro Gly Ser Ser Pro Thr Thr Val
            35                  40                  45

Ile Tyr Glu Asp Asn Gln Arg Pro Ser Gly Val Pro Asp Arg Phe Ser
        50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 518
<211> LENGTH: 98
<212> TYPE: PRT
<213> ORGANISM: Homo sapiens

<400> SEQUENCE: 518

Gln Thr Val Val Thr Gln Glu Pro Ser Leu Thr Val Gly Pro Gly Gly
1               5                   10                  15

Thr Val Thr Leu Thr Cys Ala Gly Ser Thr Gly Ala Val Thr Ser Gly
                20                  25                  30

Tyr Tyr Pro Met Trp Phe Gln Gln Lys Pro Gly Gln Ala Pro Arg Ala
            35                  40                  45

Leu Ile Tyr Ser Thr Ser Asn Lys His Ser Trp Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Leu Leu Ser Tyr Ser Gly
                85                  90                  95

Ala Arg
```